US011684676B2

(12) United States Patent
Zhang et al.

(10) Patent No.: US 11,684,676 B2
(45) Date of Patent: Jun. 27, 2023

(54) SITE-SPECIFIC ANTIBODY-DRUG CONJUGATES BY ADP-RIBOSYL CYCLASES

(71) Applicant: University of Southern California, Los Angeles, CA (US)

(72) Inventors: Yong Zhang, Los Angeles, CA (US); Zhefu Dai, Los Angeles, CA (US); Xiao-Nan Zhang, Los Angeles, CA (US)

(73) Assignee: University of Southern California, Los Angeles, CA (US)

( * ) Notice: Subject to any disclaimer, the term of this patent is extended or adjusted under 35 U.S.C. 154(b) by 0 days.

(21) Appl. No.: 17/996,313

(22) PCT Filed: May 10, 2021

(86) PCT No.: PCT/US2021/031576
§ 371 (c)(1),
(2) Date: Oct. 14, 2022

(87) PCT Pub. No.: WO2021/226584
PCT Pub. Date: Nov. 11, 2021

(65) Prior Publication Data
US 2023/0128344 A1    Apr. 27, 2023

Related U.S. Application Data

(60) Provisional application No. 63/021,975, filed on May 8, 2020.

(51) Int. Cl.
| | |
|---|---|
| *A61K 47/68* | (2017.01) |
| *C12N 9/24* | (2006.01) |
| *C07K 16/28* | (2006.01) |
| *A61K 39/00* | (2006.01) |

(52) U.S. Cl.
CPC ...... *A61K 47/6815* (2017.08); *A61K 47/6807* (2017.08); *A61K 47/6851* (2017.08); *A61K 47/6889* (2017.08); *C07K 16/2851* (2013.01); *C12N 9/2497* (2013.01); *A61K 2039/505* (2013.01); *C07K 2317/90* (2013.01); *C07K 2319/00* (2013.01); *C12Y 302/02006* (2013.01)

(58) Field of Classification Search
CPC ............ A61K 47/6815; A61K 47/6807; A61K 47/6851; A61K 47/6889; A61K 2039/505; C07K 16/2851; C07K 2317/90; C07K 2319/00; C12N 9/2497; C12Y 302/02006
See application file for complete search history.

(56) References Cited

U.S. PATENT DOCUMENTS

2015/0231235 A1    8/2015    Winkel et al.
2020/0040105 A1    2/2020    Elias et al.

FOREIGN PATENT DOCUMENTS

WO    2018227168 A1    12/2018

OTHER PUBLICATIONS

Jiang H et al. Mechanism-Based Small Molecule Probes for Labeling CD38 on Live Cells. J. Am. Chem. Soc. 2009, 131, 1658-1659. (Year: 2009).*
Beck et al., "Strategies and Challenges for the Next Generation of Antibody-Drug Conjugates," Nat Rev Drug Discov., 16(5):315-337, May 2017.
Beerli et al., "Sortase Enzyme-Mediated Generation of Site-Specifically Conjugated Antibody Drug Conjugates with High In Vitro and In Vivo Potency," PLoS One, 10(7):e0131177, Jul. 2015.
Dai et al., "Synthesis of Site-Specific Antibody-Drug Conjugates by ADP-Ribosyl Cyclases," Sci Adv., 6(23): eaba6752, Jun. 2020.
International Search Report and Written Opinion of the ISA/US in PCT/US2021/031576, dated Sep. 14, 2021; 8pgs.
Kern et al., "Discovery of Pyrophosphate Diesters As Tunable, Soluble, and Bioorthogonal Linkers for Site-Specific Antibody—Drug Conjugates," J Am Chem Soc., 138(4):1430-1445, Feb. 2016.
Nanna et al., "Harnessing a Catalytic Lysine Residue for the One-Step Preparation of Homogeneous Antibody-Drug Conjugates," Nat Comm., 8(1):1-9, Dec. 2017.
Tian et al., "A General Approach to Site-Specific Antibody Drug Conjugates," Proc Natl Acad Sci USA, 111(5):1766-1771, Feb. 2014.
Vanbrunt et al., "Genetically Encoded Azide Containing Amino Acid in Mammalian Cells Enables Site-Specific Antibody-Drug Conjugates Using Click Cycloaddition Chemistry," Bioconjug Chem., 26(11):2249-2260, Nov. 2015.
Zhang et al., "A Ribose-Functionalized NAD+ with Unexpected High Activity and Selectivity for Protein Poly-ADP-Ribosylation," Nat Commun., 10(1):4196, Sep. 2019.

* cited by examiner

*Primary Examiner* — Adam Weidner
*Assistant Examiner* — John J Skoko, III
(74) *Attorney, Agent, or Firm* — Haukaas Fortius PLLC; Michael Haukaas

(57) ABSTRACT

Antibody-drug conjugates, compositions thereof, and methods use. The antibody-drug conjugates include a fusion protein comprising an antibody covalently linked to an ADP-ribosyl cyclase protein via a peptide linker moiety at one or more of a C-terminus or N-terminus of a heavy or light chain of the antibody, a NAD or NMN analogue, and a payload such that the NAD or NMN analogue is conjugated to both the payload and the ADP-ribosyl cyclase protein.

25 Claims, 56 Drawing Sheets

Specification includes a Sequence Listing.

E.

F.

A

Gating of Bone Marrow Samples by mCD45 and hCLL-1

B

Gating of Bone Marrow Samples by mCD45 and mCD34

SITE-SPECIFIC ANTIBODY-DRUG CONJUGATES BY ADP-RIBOSYL CYCLASES

RELATED APPLICATIONS

This application is a National Stage filing under 35 U.S.C. § 371 of International Application No. PCT/US2021/031576 filed May 10, 2021, which claims the benefit of U.S. Provisional Patent Application No. 63/021,975, filed May 8, 2020, which applications are incorporated herein by reference.

GOVERNMENT SUPPORT

This invention was made with government support under Grant No. R35GM137901 awarded by the National Institutes of Health and Grant No. W81XWH-19-1-0272 awarded by the Department of Defense. The government has certain rights in the invention.

SEQUENCE LISTING

The instant application contains a Sequence Listing which has been submitted electronically in ASCII format and is hereby incorporated by reference in its entirety. Said ASCII copy, created on Jun. 22, 2021, is named 530_014WO1_SL.txt and is 74,263 bytes in size.

BACKGROUND OF THE INVENTION

Antibody-drug conjugates (ADCs) enable targeted delivery of small-molecule drugs, providing a significantly improved therapeutic index. Owing to their outstanding potency and selectivity, ADCs hold great promise for treatment of a variety of human diseases. Most current ADCs in clinical use or development are generated through nonspecific conjugation to surface cysteine or lysine residues, resulting in heterogeneous ADCs with varied drug-to-antibody ratios (DARs) and distinct pharmacological properties. ADCs with site-specific conjugations show increased stability, pharmacokinetics, and safety profiles. Using engineered amino acids, carbohydrates, or unnatural amino acids, homogeneous ADCs could be generated, but the conjugation processes often require multiple steps or long reaction times due to inefficient chemistries. Although genetic fusions of peptide motifs or engineered enzymes allow more efficient production of site-specific ADCs, the introduced mutations or non-human derived sequences may raise considerable immunogenicity concerns in a subject to which the ADCs are administered. Moreover, despite successes of several types of linkers for attachments and release of cytotoxic payloads, optimal drug linkers remain limited for applying the ADC modality to non-oncology areas.

There remains therefore a great need to develop more targeted and potent therapies for proliferative disorders. The current invention satisfies these needs.

SUMMARY

Antibody-drug conjugates (ADCs) uniquely allow cell-specific delivery of nonselective small-molecule drugs, resulting in significantly improved therapeutic index. Given their outstanding potency and specificity, ADCs have been emerging as an increasingly important class of therapeutics. Here we explore a new concept of transforming CD38 enzymatic activity into a facile approach for generation of site-specific ADCs. This was achieved through coupling bifunctional antibody-CD38 fusion proteins with designer dinucleotide-based covalent inhibitors with stably attached payloads. The resulting ARC-ADC with a defined drug-to-antibody ratio (DAR) of 2 or 4 are rapidly generated through a single-step conjugation step. The generated ARC-ADC targeting human epidermal growth factor receptor 2 (HER2) and C-type lectin-like molecule-1 (CLL-1) display excellent stability and potency against HER2-positive breast cancer and CLL-1 positive acute myeloid leukemia both in vitro and in vivo. This demonstrates a new strategy for production of site-specific ADCs and provides a general approach for the development of a novel class of ADCs with potentially enhanced properties.

Accordingly, certain embodiments of the invention provide an antibody-drug conjugate comprising a fusion protein comprising an antibody covalently linked to an ADP-ribosyl cyclase protein via a linker moiety; a 2'-modified araNAD$^+$ analogue or a 2'-modified araNMN analogue; and a payload wherein the 2'-modified araNAD$^+$ analogue or the 2'-modified araNMN analogue is conjugated to the payload to form a functionalized payload, and the functionalized payload is conjugated to the ADP-ribosyl cyclase protein.

Preferably, the 2'-modified araNAD$^+$ analogue comprises 2'-X-araNAD-N$_3$ wherein X is a fluorine atom, a chlorine atom, or a bromine atom and the 2'-modified araNMN analogue comprises 2'-X-araNMN-PO$_4$ wherein X is a fluorine atom, a chlorine atom, or a bromine atom.

In certain embodiments, the functionalized payload comprises a 2'-modified araNAD$^+$ analogue-payload or a 2'-modified araNMN analogue-payload having a structure disclosed in Scheme 1 or Scheme 2.

In some embodiments, the antibody comprises a monoclonal antibody, polyclonal antibody, a single chain Fv, a bispecific antibody, a multispecific antibody, a Fv fragment, a Fab fragment, and a F(ab)$_2$ fragment.

In some embodiments, the ADP-ribosyl cyclase protein is covalently linked to at least one of the N-terminus or a C-terminus of one or more of the heavy chains or one or more of the light chains of the antibody. In another embodiments, the ADP-ribosyl cyclase protein is covalently linked to the C-terminus of a both heavy chains of the antibody or both light chains of the antibody. In still another embodiment, the ADP-ribosyl cyclase protein is covalently linked to the C-terminus of both heavy chains and both light chains of the antibody. Preferably, the drug-to-antibody ratio (DAR) is 2:1 or 4:1.

Preferably, the 2'-modified araNAD$^+$ analogue or the 2'-modified araNMN analogue is conjugated to glutamate 226 of the catalytic domain of CD38.

The disclosure also provides methods of preparing an antibody-drug conjugate comprising the steps of providing an antibody-linker-ADP-ribosyl cyclase fusion protein, combining a 2'-modified araNAD$^+$ analogue or a 2'-modified araNMN analogue and a payload moiety to form a 2'-modified araNAD$^+$ analogue-payload or a 2'-modified araNMN analogue-payload, and conjugating the antibody-linker-ADP-ribosyl cyclase fusion protein to the 2'-modified araNAD$^+$ analogue-payload or the 2'-modified araNMN analogue-payload to form an antibody-drug conjugate.

In some embodiments, the payload is a chemotoxic agent or a diagnostic agent. Preferably, the chemotoxic agent is auristatin, calicheamicin, maytansine, duocarmycin, a camptothecin analogue such as SN38 or DX-8951, or a benzodiazepine such as pyrrolobenzodiazepine, talirine, tesirine, or indolinobenzodiazepines.

Also provided are methods of treating cancer comprising administering to a subject having cancer or suspected of having cancer a therapeutically effective amount of the antibody-drug conjugate as disclosed herein, thereby inhibiting the growth of cancer cells or killing cancer cells and treating the cancer.

The present invention and its attributes and advantages will be further understood and appreciated with reference to the detailed description below of presently contemplated embodiments, taken in conjunction with the accompanying drawings.

BRIEF DESCRIPTION OF THE DRAWINGS

The following drawings form part of the specification and are included to further demonstrate certain embodiments or various aspects of the invention. In some instances, embodiments of the invention can be best understood by referring to the accompanying drawings in combination with the detailed description presented herein. The description and accompanying drawings may highlight a certain specific example, or a certain aspect of the invention. However, one skilled in the art will understand that portions of the example or aspect may be used in combination with other examples or aspects of the invention.

DETAILED DESCRIPTION

Definitions

Figure 1:
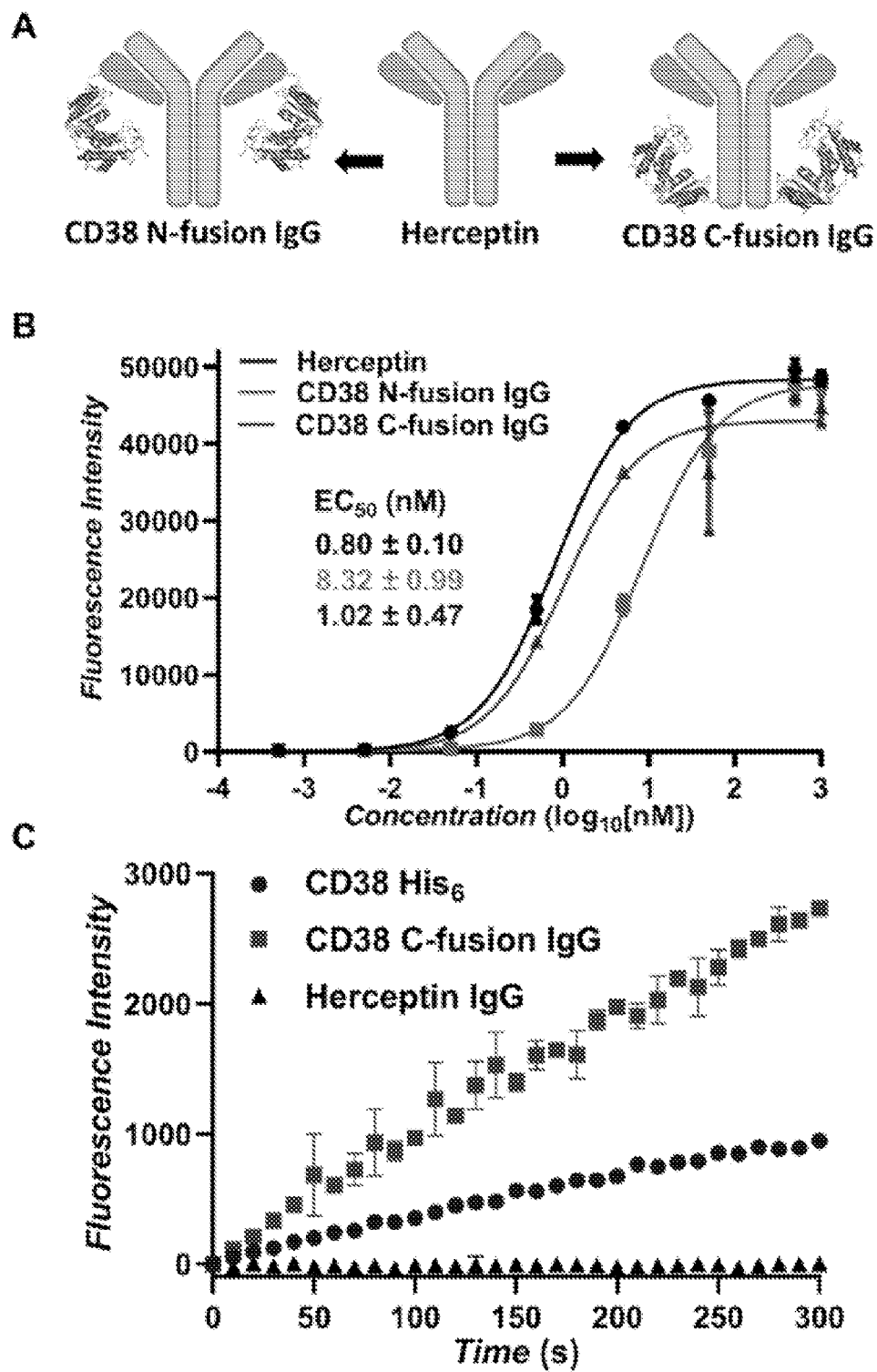
FIG. 1 illustrates the characterization of CD38-antibody fusions and 2'-Cl-araNAD+-N3. (A) Schematic of designed CD38 N-fusion IgG and CD38 C-fusion IgG. (B) Binding to recombinant HER2 extracellular domain by Herceptin and CD38 N- and C-fusion IgGs as analyzed by ELISA. (C) Enzymatic activity of CD38 catalytic domain, CD38 C-fusion IgG, and Herceptin. CD38-His6 (20 nM), CD38 C-fusion IgG (10 nM), and Herceptin (10 nM) were incubated with NGD+ (100 µM) in PBS. The CD38 cyclase activity was monitored based on the formation of fluorescent cyclic GDP-ribose as measured at 410 nm. (D) Chemical structure of 2'-Cl-araNAD+-N3. (E) Inactivation of CD38 C-fusion IgG by 2'-Cl-araNAD+-N3. CD38 C-fusion IgG (2 nM) was incubated with NGD+ (100 µM) in PBS in the presence of various concentrations of 2'-Cl-araNAD+-N3. The enzymatic activity was measured using cyclic GDP-ribose-based fluorescence assays. (F) Stability of Alexa Fluor 488-conjugated CD38 C-fusion IgG in mouse plasma. Using 2'-Cl-araNAD+-N3, CD38 C-fusion IgG was labeled with Alexa Fluor 488 and incubated in mouse plasma at 37° C. for up to 14 days, followed by in-gel fluorescence imaging and Coomassie staining. The quantified fluorescence intensities for intact fusion proteins are shown at the bottom.
Figure 1:
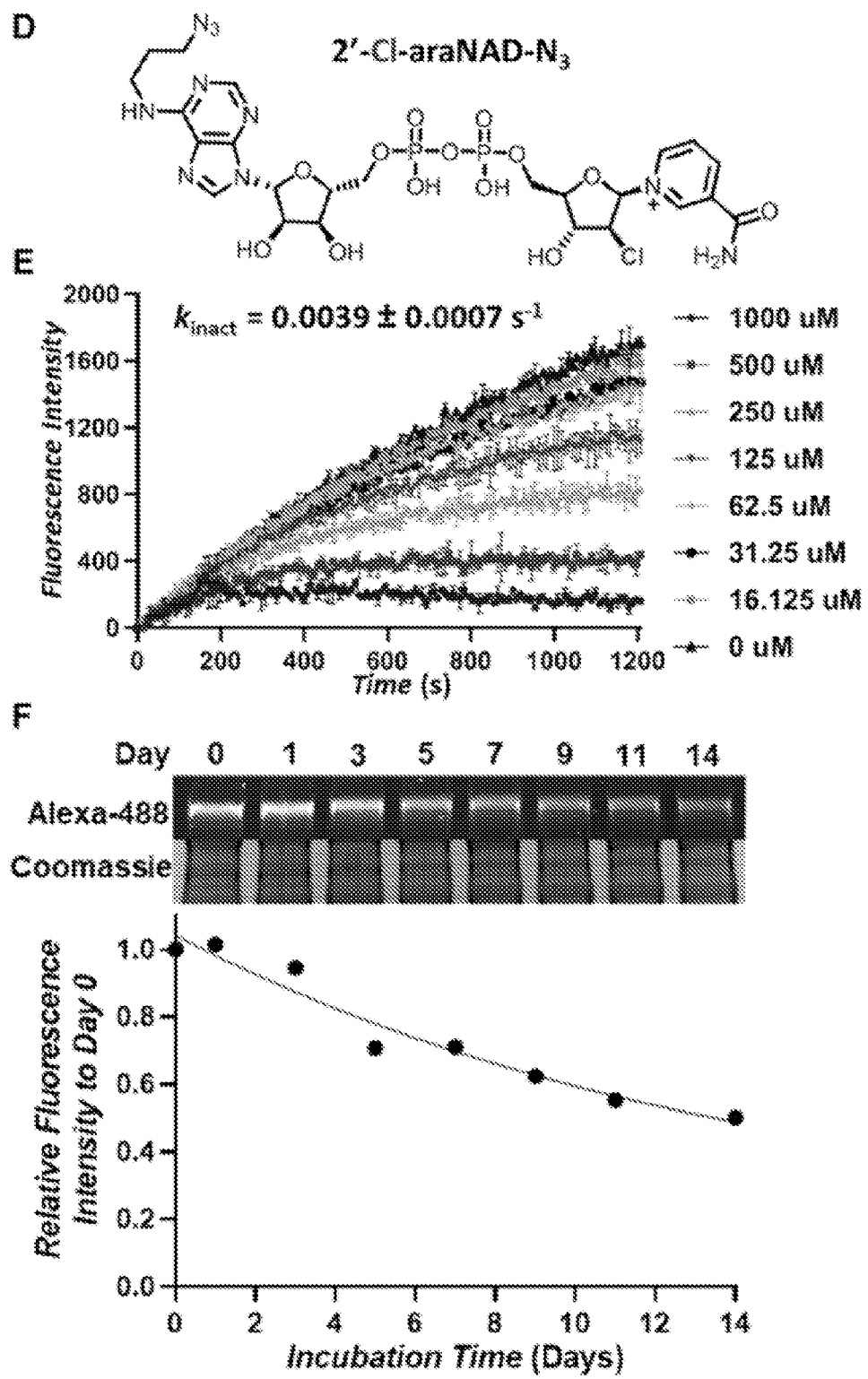

The following definitions are included to provide a clear and consistent understanding of the specification and claims. As used herein, the recited terms have the following meanings. All other terms and phrases used in this specification have their ordinary meanings as one of skill in the art would understand. Such ordinary meanings may be obtained by reference to technical dictionaries, such as *Hawley's Condensed Chemical Dictionary* 14th Edition, by R. J. Lewis, John Wiley & Sons, New York, N.Y., 2001.

References in the specification to "one embodiment", "an embodiment", etc., indicate that the embodiment described may include a particular aspect, feature, structure, moiety, or characteristic, but not every embodiment necessarily includes that aspect, feature, structure, moiety, or characteristic. Moreover, such phrases may, but do not necessarily, refer to the same embodiment referred to in other portions of the specification. Further, when a particular aspect, feature, structure, moiety, or characteristic is described in connection with an embodiment, it is within the knowledge of one skilled in the art to affect or connect such aspect, feature, structure, moiety, or characteristic with other embodiments, whether or not explicitly described.

The singular forms "a," "an," and "the" include plural reference unless the context clearly dictates otherwise. Thus, for example, a reference to "a compound" includes a plurality of such compounds, so that a compound X includes a plurality of compounds X. It is further noted that the claims may be drafted to exclude any optional element. As such, this statement is intended to serve as antecedent basis for the use of exclusive terminology, such as "solely," "only," and the like, in connection with any element described herein, and/or the recitation of claim elements or use of "negative" limitations.

The term "and/or" means any one of the items, any combination of the items, or all of the items with which this term is associated. The phrases "one or more" and "at least one" are readily understood by one of skill in the art, particularly when read in context of its usage. For example, the phrase can mean one, two, three, four, five, six, ten, 100, or any upper limit approximately 10, 100, or 1000 times higher than a recited lower limit. For example, one or more substituents on a phenyl ring refers to one to five, or one to four, for example if the phenyl ring is disubstituted. As will be understood by the skilled artisan, all numbers, including those expressing quantities of ingredients, properties such as molecular weight, reaction conditions, and so forth, are approximations and are understood as being optionally modified in all instances by the term "about." These values can vary depending upon the desired properties sought to be obtained by those skilled in the art utilizing the teachings of the descriptions herein. It is also understood that such values inherently contain variability necessarily resulting from the standard deviations found in their respective testing measurements. When values are expressed as approximations, by use of the antecedent "about," it will be understood that the particular value without the modifier "about" also forms a further aspect.

The term "about" can refer to a variation of ±5%, ±10%, ±20%, or ±25% of the value specified. For example, "about 50" percent can in some embodiments carry a variation from 45 to 55 percent, or as otherwise defined by a particular claim. For integer ranges, the term "about" can include one or two integers greater than and/or less than a recited integer at each end of the range. Unless indicated otherwise herein, the term "about" is intended to include values, e.g., weight percentages, proximate to the recited range that are equivalent in terms of the functionality of the individual ingredient, composition, or embodiment. The term about can also modify the endpoints of a recited range as discussed above in this paragraph.

As will be understood by one skilled in the art, for any and all purposes, particularly in terms of providing a written description, all ranges recited herein also encompass any and all possible sub-ranges and combinations of sub-ranges thereof, as well as the individual values making up the range, particularly integer values. It is therefore understood that each unit between two particular units are also disclosed. For example, if 10 to 15 is disclosed, then 11, 12, 13, and 14 are also disclosed, individually, and as part of a range. A recited range (e.g., weight percentages or carbon groups) includes each specific value, integer, decimal, or identity within the range. Any listed range can be easily recognized as sufficiently describing and enabling the same range being broken down into at least equal halves, thirds, quarters, fifths, or tenths. As a non-limiting example, each range discussed herein can be readily broken down into a lower third, middle third and upper third, etc. As will also be understood by one skilled in the art, all language such as "up to", "at least", "greater than", "less than", "more than", "or more", and the like, include the number recited and such terms refer to ranges that can be subsequently broken down into sub-ranges as discussed above. In the same manner, all ratios recited herein also include all sub-ratios falling within the broader ratio. Accordingly, specific values recited for radicals, substituents, and ranges, are for illustration only; they do not exclude other defined values or other values within defined ranges for radicals and substituents. It will be further understood that the endpoints of each of the ranges are significant both in relation to the other endpoint, and independently of the other endpoint.

One skilled in the art will also readily recognize that where members are grouped together in a common manner, such as in a Markush group, the invention encompasses not only the entire group listed as a whole, but each member of the group individually and all possible subgroups of the main group. Additionally, for all purposes, the invention encompasses not only the main group, but also the main group absent one or more of the group members. The invention therefore envisages the explicit exclusion of any one or more of members of a recited group. Accordingly, provisos may apply to any of the disclosed categories or embodiments whereby any one or more of the recited elements, species, or embodiments, may be excluded from such categories or embodiments, for example, for use in an explicit negative limitation.

The term "contacting" refers to the act of touching, making contact, or of bringing to immediate or close proximity, including at the cellular or molecular level, for example, to bring about a physiological reaction, a chemical reaction, or a physical change, e.g., in a solution, in a reaction mixture, in vitro, or in vivo.

An "effective amount" refers to an amount effective to treat a disease, disorder, and/or condition, or to bring about a recited effect. For example, an effective amount can be an amount effective to reduce the progression or severity of the condition or symptoms being treated. Determination of a therapeutically effective amount is well within the capacity of persons skilled in the art. The term "effective amount" is intended to include an amount of a compound described herein, or an amount of a combination of compounds described herein, e.g., that is effective to treat or prevent a disease or disorder, or to treat the symptoms of the disease or disorder, in a host. Thus, an "effective amount" generally means an amount that provides the desired effect. An appropriate "effective" amount in any individual case may be determined using techniques, such as a dose escalation study.

The terms "treating", "treat" and "treatment" include (i) preventing a disease, pathologic or medical condition from occurring (e.g., prophylaxis); (ii) inhibiting the disease, pathologic or medical condition or arresting its development; (iii) relieving the disease, pathologic or medical condition; and/or (iv) diminishing symptoms associated with the disease, pathologic or medical condition. Thus, the terms "treat", "treatment", and "treating" can extend to prophylaxis and can include prevent, prevention, preventing, lowering, stopping or reversing the progression or severity of the condition or symptoms being treated. As such, the term "treatment" can include medical, therapeutic, and/or prophylactic administration, as appropriate.

The terms "inhibit", "inhibiting", and "inhibition" refer to the slowing, halting, or reversing the growth or progression of a disease, infection, condition, or group of cells. The inhibition can be greater than about 20%, 40%, 60%, 80%, 90%, 95%, or 99%, for example, compared to the growth or progression that occurs in the absence of the treatment or contacting.

The term "antibody" as used herein refers to a polypeptide (or set of polypeptides) of the immunoglobulin family that is capable of binding an antigen non-covalently, reversibly and specifically. For example, a naturally occurring "antibody" of the IgG type is a tetramer comprising at least two heavy (H) chains and two light (L) chains inter-connected by disulfide bonds. Each heavy chain is comprised of a heavy chain variable region (abbreviated herein as $V_H$) and a heavy chain constant region. The heavy chain constant region is comprised of three domains, CHI, CH2 and CH3. Each light chain is comprised of a light chain variable region (abbreviated herein as $V_L$) and a light chain constant region. The light chain constant region is comprised of one domain, CL. The $V_H$ and $V_L$ regions can be further subdivided into regions of hypervariability, termed complementarity determining regions (CDR), interspersed with regions that are more conserved, termed framework regions (FR). Each $V_H$ and $V_L$ is composed of three CDRs and four FRs arranged from amino-terminus to carboxy-terminus in the following order: FR1, CDR1, FR2, CDR2, FR3, CDR3, FR4. The variable regions of the heavy and light chains contain a binding domain that interacts with an antigen, which is sometimes referred to herein as the antigen binding domain. The constant regions of the antibodies may mediate the binding of the immunoglobulin to host tissues or factors, including various cells of the immune system (e.g., effector cells) and the first component (Clq) of the classical complement system. The term "antibody" includes, but is not limited to, monoclonal antibodies, human antibodies, humanized antibodies, camelised antibodies, chimeric antibodies, bispecific or multispecific antibodies and anti-idiotypic (anti-Id) antibodies (including, e.g., anti-Id antibodies to antibodies described herein), single chain variable fragments, and single domain antibodies. The antibodies can be of any isotype/class (e.g., IgG, IgE, IgM, IgD, IgA and IgY) or subclass (e.g., IgGl, IgG2, IgG3, IgG4, IgA1 and IgA2). Both the light and heavy chains are divided into regions of structural and functional homology. The terms "constant" and "variable" are used functionally. In this regard, it will be appreciated that the variable domains of both the light ($V_L$)

and heavy ($V_H$) chain portions determine antigen recognition and specificity. Conversely, the constant domains of the light chain (CL) and the heavy chain (CHI, CH2 or CH3) confer important biological properties such as secretion, transplacental mobility, Fc receptor binding, complement binding, and the like. By convention the numbering of the constant region domains increases as they become more distal from the antigen binding site or amino-terminus of the antibody. The N-terminus is a variable region and at the C-terminus is a constant region; the CH3 and CL domains actually comprise the carboxy-terminus of the heavy and light chain, respectively.

As used herein, "fragment" is defined as at least a portion of the variable region of the immunoglobulin molecule which binds to its target, i.e., the antigen binding region. Some of the constant region of the immunoglobulin may be included.

As used herein, "fused" means to couple directly or indirectly one molecule with another by whatever means, e.g., by covalent bonding, by non-covalent bonding, by ionic bonding, or by non-ionic bonding. Covalent bonding includes bonding by various linkers such as thioether linkers or thioester linkers. Direct fusion involves one molecule attached to the molecule of interest. Indirect fusion involves one molecule attached to another molecule which in turn is attached directly or indirectly to the molecule of interest.

As used herein, the terms "peptide," "polypeptide," and "protein" are used interchangeably, and refer to a compound comprising amino acid residues covalently linked by peptide bonds. A protein or peptide must contain at least two amino acids, and no limitation is placed on the maximum number of amino acids that can comprise a protein's or peptide's sequence. Polypeptides include any peptide or protein comprising two or more amino acids joined to each other by peptide bonds. As used herein, the term refers to both short chains, which also commonly are referred to in the art as peptides, oligopeptides, and oligomers, for example, and to longer chains, which generally are referred to in the art as proteins, of which there are many types. "Polypeptides" include, for example, biologically active fragments, substantially homologous polypeptides, oligopeptides, homodimers, heterodimers, variants of polypeptides, modified polypeptides, derivatives, analogs, fusion proteins, among others. The polypeptides include natural peptides, recombinant peptides, synthetic peptides, or a combination thereof.

By the term "specifically binds," as used herein, is meant a molecule, such as an antibody, which recognizes and binds to another molecule or feature, but does not substantially recognize or bind other molecules or features in a sample.

Th term "CD38" refers to a 46 kDa type II transmembrane glycoprotein (UniProtKB: P28907; Accession No. NM_001775.4). It has a short N-terminal cytoplasmic tail of 20 amino acids, a single transmembrane helix and a long extracellular domain of 256 amino acids. It is expressed on the surface of many immune cells including CD4 and CD8 positive T cells, B cells, NK cells, monocytes, plasma cells and on a significant proportion of normal bone marrow precursor cells. In some instances, the expression of CD38 in lymphocytes may be dependent on the differentiation and activation state of the cell, for example, resting T and B cells may be negative while immature and activated lymphocytes may be predominantly positive for CD38 expression. CD38 mRNA expression has been detected in non-hemopoeitic organs such as the pancreas, brain, spleen and liver (Koguma, T. (1994) Biochim. Biophys. Acta 1223:160).

CD38 is a multifunctional ectoenzyme that is involved in transmembrane signaling and cell adhesion. It is also known as cyclic ADP ribose hydrolase because it can transform NAD+ and NADP+ into cADPR, ADPR and NAADP, depending on extracellular pH. These products induce Ca2+-mobilization inside the cell, which can lead to tyrosine phosphorylation and activation of the cell. CD38 is also a receptor that can interact with a ligand, CD31. Activation of receptor via CD31 leads to intracellular events including Ca2+ mobilization, cell activation, proliferation, differentiation and migration. In some embodiments, the extracellular/catalytic domain of CD38 may include the following mutations: (N100D, N164A, N129D, and N209D).

As used herein, the terms "CLL-1" and "CLL1" are used interchangeably and refer to C-type lectin-like molecule-1, which is an antigenic determinant detectable on leukemia precursor cells and on normal immune cells. C-type lectin-like-1 (CLL-1) is also known as MICL, CLEC12A, CLEC-1, Dendritic Cell-Associated Lectin 1, and DCAL-2. The human and murine amino acid and nucleic acid sequences can be found in a public database, such as GenBank, UniProt and Swiss-Prot. For example, the amino acid sequence of human CLL-1 can be found as UniProt/Swiss-Prot Accession No. Q5QGZ9 and the nucleotide sequence encoding of the human CLL-1 can be found at Accession Nos. NM 001207010.1, NM 138337.5, NM 201623.3, and NM 201625.1.

As used herein, the term "Bst1" refers to Bone marrow stromal antigen 1, also known as ADP-ribosyl cyclase, or cyclic ADP-ribose hydrolase 2, or CD 157. The amino acid sequence of human Bst1 can be found at UniProtKB: Q10588. The nucleotide sequence of human Bst1 can be found at Accession No. NM_004334.3.

Embodiments of the Invention

Certain preferred embodiments of the invention include an antibody-drug conjugate comprising an antibody covalently linked to an ADP-ribosyl cyclase protein via a peptide linker moiety, a 2'-modified araNAD$^+$ analogue or a 2'-modified araNMN analogue, a payload wherein the 2'-modified araNAD$^+$ analogue or the 2'-modified araNMN analogue is conjugated to the payload to form a functionalized payload, and the functionalized payload is conjugated to the ADP-ribosyl cyclase protein to form an antibody-drug conjugate. Also provided are compositions comprising the antibody-drug conjugate and methods of use.

Certain embodiments of the antibody-drug conjugate include a 2'-modified araNAD$^+$ analogue or a 2'-modified araNMN analogue. Scheme 1 discloses preferred embodiments of the 2'-modified araNAD$^+$ analogues that have the structure 2'-X-araNAD-N$_3$ where X is fluorine, chlorine, or bromine, and a functional linker group R is an azido group, alkyne, bicyclo[6.1.0]nonyne (BCN), or Dibenzocyclooctyne (DBCO). Preferably, the functional linker group R is conjugated to a payload such as a chemotoxic agent or a diagnostic agent.

Scheme 1. Formulas I-VI.

(I)

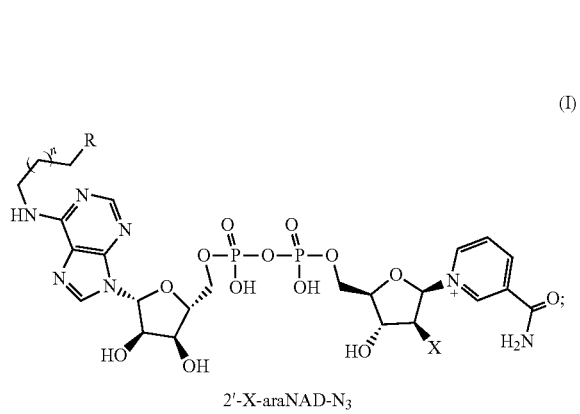

2'-X-araNAD-N₃ wherein R is azido, alkyne, BCN, or DBCO;
X is halo, such as F, Cl, or Br; and
n is 1-8, e.g., 1, 2, 3, 4, 5, 6, 7, or 8.

(II)

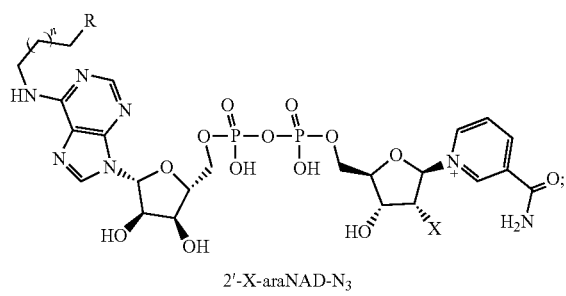

2'-X-araNAD-N₃ wherein R is azido, alkyne, BCN, or DBCO;
X is halo, such as F, Cl, or Br; and
n is 1-8, e.g., 1, 2, 3, 4, 5, 6, 7, or 8.

(III)

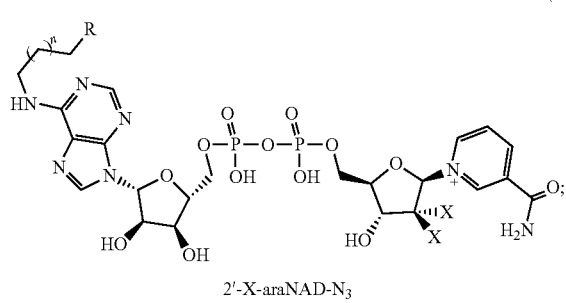

2'-X-araNAD-N₃ wherein R is azido, alkyne, BCN, or DBCO;
X is halo, such as F, Cl, or Br; and
n is 1-8, e.g., 1, 2, 3, 4, 5, 6, 7, or 8.

(IV)

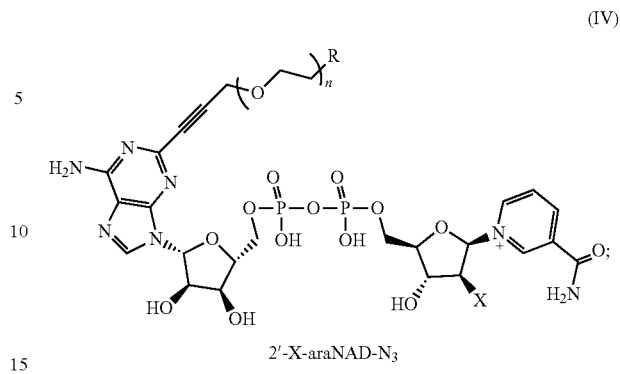

2'-X-araNAD-N₃ wherein R is azido, alkyne, BCN, or DBCO;
X is halo, such as F, Cl, or Br; and
n is 1-5, e.g., 1, 2, 3, 4, or 5.

(V)

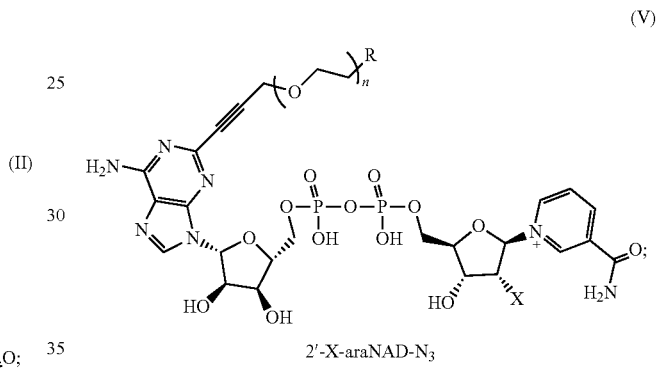

2'-X-araNAD-N₃ wherein R is azido, alkyne, BCN, or DBCO;
X is halo, such as F, Cl, or Br; and
n is 1-5, e.g., 1, 2, 3, 4, or 5.

(VI)

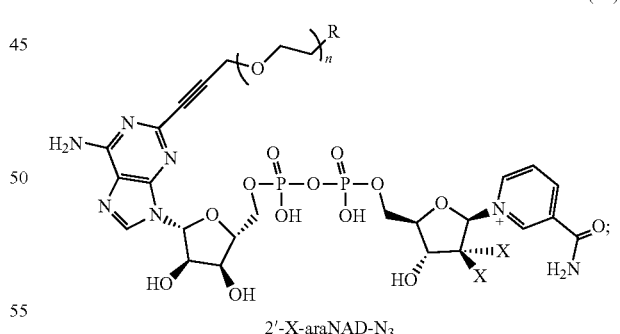

2'-X-araNAD-N₃ wherein R is azido, alkyne, BCN, or DBCO;
X is halo, such as F, Cl, or Br; and
n is 1-5, e.g., 1, 2, 3, 4, or 5.

Preferred embodiments of the invention include a 2'-modified araNAD⁺ analogue having an azido group at N6 of the ADP moiety. Preferably, the 2'-modified araNAD analogue comprises a Chlorine at the 2' position to form 2'-Cl-araNAD⁺. In one certain preferred embodiment, the 2'-modified araNAD⁺ analogue is 6-azido-2'-Cl-araNAD⁺

(2'-Cl-araNAD⁺-N₃). In other preferred embodiments, 2'-modified araNAD⁺ analogue is 2'-F-araNAD⁺ or 2'-F-araNAD⁺-N₃.

Scheme 2 discloses several preferred embodiments of the 2'-modified araNMN analogues that include the structure 2'-X-araNMN-PO₄ where X is a fluorine, chlorine, or bromine atom, and wherein a payload (e.g., a chemotoxic agent) may be conjugated to the PO₄ moiety. In certain preferred embodiments, the 2'-X-araNMN-PO₄ is 2'-F-araNMN-PO₄ or 2'-Cl-araNMN-PO₄. Scheme 2.

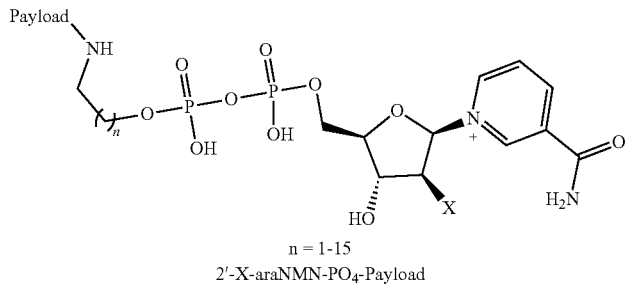

n = 1-15
2'-X-araNMN-PO₄-Payload

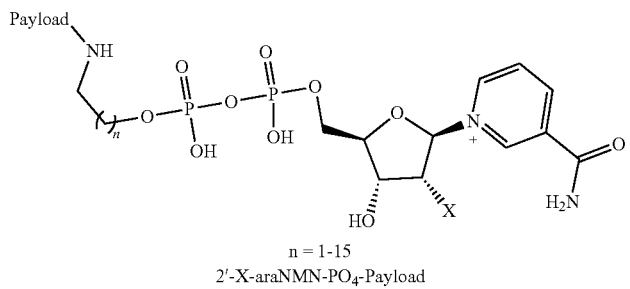

n = 1-15
2'-X-araNMN-PO₄-Payload

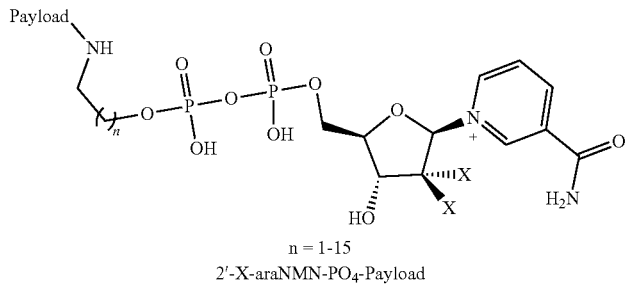

n = 1-15
2'-X-araNMN-PO₄-Payload

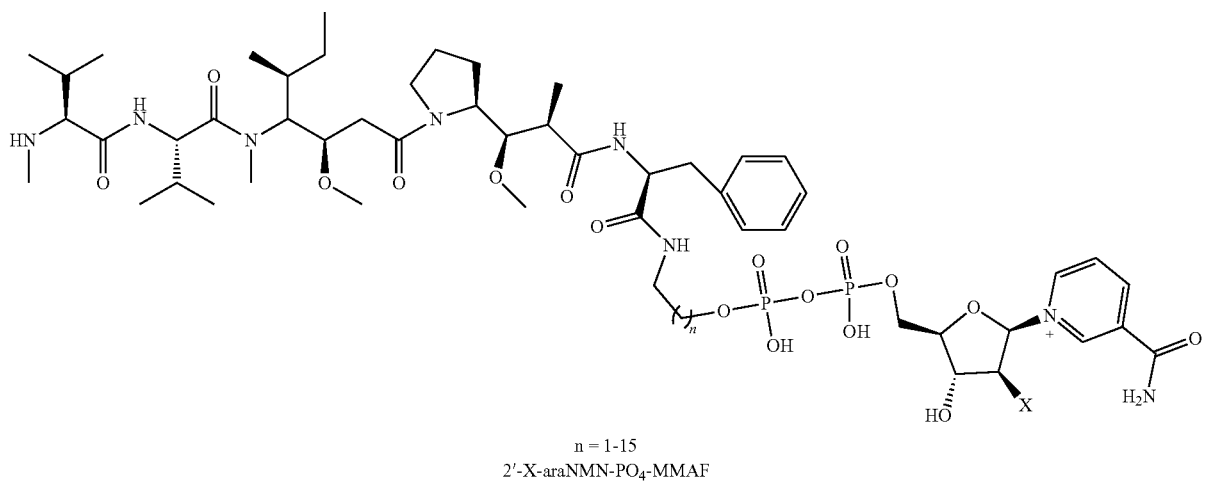

n = 1-15
2'-X-araNMN-PO₄-MMAF

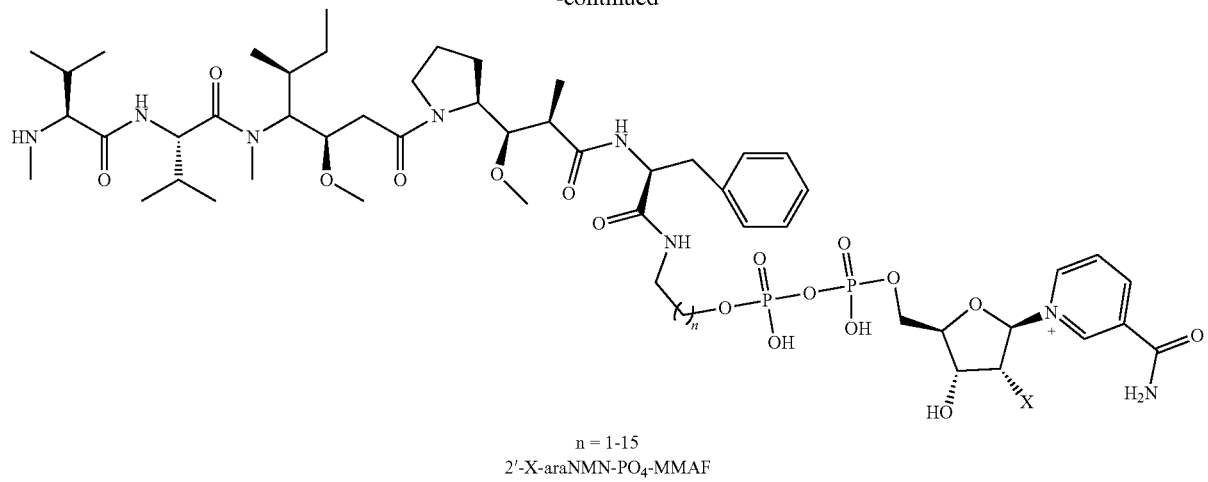

n = 1-15
2'-X-araNMN-PO₄-MMAF

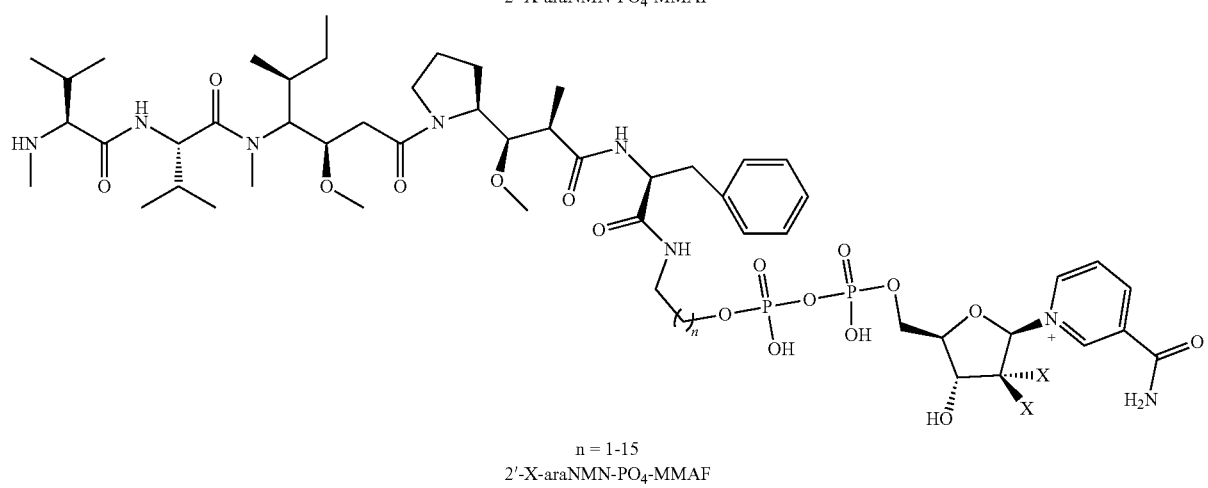

n = 1-15
2'-X-araNMN-PO₄-MMAF wherein X is halo, such as F, Cl, or Br, and n is 0-15 or 1-15.

In certain embodiments, the 2'-modified araNAD$^+$ analogue or a 2'-modified araNMN analogue (with or without payload) is conjugated to glutamate 226 of the catalytic subunit of the ADP-ribosyl cyclase protein CD38.

In certain embodiments of the invention, the antibody may comprise a monoclonal antibody, polyclonal antibody, a single chain Fv, a bispecific antibody, a multispecific antibody, a Fv fragment, a Fab fragment, or a F(ab)₂ fragment. In certain embodiments, the antibody specifically binds to an antigen or epitope of a surface of cancer cell. In some embodiments, the antigen or epitope is human epidermal growth factor receptor 2 (HER2) or human C-type lectin-like-1 (CLL-1). In one certain embodiment, the antibody is Trastuzumab (Herceptin®), another anti-HER2 antibody, or an anti-CLL-1 antibody.

Antibodies (e.g., full length antibodies) generally comprise a variable region heavy chain and a variable region light chain. The antibodies may comprise derivatives or fragments or portions of antibodies that retain the antigen-binding specificity, and also preferably retain most or all of the affinity, of the parent antibody molecule (e.g., for CD38). For example, derivatives may comprise at least one variable region (either a heavy chain or light chain variable region).

Other examples of suitable antibody derivatives and fragments include, without limitation, antibodies with polyepitopic specificity, bispecific antibodies, multi-specific antibodies, diabodies, single-chain molecules, as well as FAb, F(Ab')2, Fd, Fabc, and Fv molecules, single chain (Sc) antibodies, single chain Fv antibodies (scFv), individual antibody light chains, individual antibody heavy chains, fusions between antibody chains and other molecules, heavy chain monomers or timers, light chain monomers or timers, timers consisting of one heavy and one light chain, and other multimers. Single chain Fv antibodies may be multi valent. All antibody isotypes may be used to produce antibody derivatives, fragments, and portions. Antibody derivatives, fragments, and/or portions may be recombinantly produced and expressed by any cell type, prokaryotic or eukaryotic.

In a full-length antibody, each heavy chain is comprised of a heavy chain variable region (abbreviated herein as HCVR or VH) and a heavy chain constant region. The heavy chain constant region is comprised of three domains, CH1, CH2 and CH3. Each light chain is comprised of a light chain variable region (abbreviated herein as LCVR or VL) and a light chain constant region. The light chain constant region is comprised of one domain, CL. The VH and VL regions can be further subdivided into regions of hypervariability, termed complementarity determining regions (CDR), interspersed with regions that are more conserved, termed framework regions (FWR or FR). Each VH and VL is composed of three CDRs and four FWRs, arranged from amino-terminus to carboxy-terminus in the following order: FWR1, CDR1, FWR2, CDR2, FWR3, CDR3, FWR4. Typically, the antigen binding properties of an antibody are less likely to be disturbed by changes to FWR sequences than by changes to the CDR sequences. Immunoglobulin molecules can be of any type (e.g., IgG, IgE, IgM, IgD, IgA and IgY), class (e.g., IgG1, IgG2, IgG3, IgG4, IgA1 and IgA2) or subclass.

The antibodies may be derived from any species. For example, the antibodies may be mouse, rat, goat, horse, swine, bovine, camel, chicken, rabbit, donkey, llama, dromedary, shark, or human antibodies, as well as antibodies from any other animal species. For use in the treatment of humans, non-human derived antibodies may be structurally altered to be less antigenic upon administration to a human patient, including by chimerization or humanization or superhumanization.

In some embodiments, the antibodies are humanized antibodies. Humanized antibodies re those wherein the amino acids directly involved in antigen binding, e.g., the complementarity determining regions (CDR), and in some cases the framework regions (FWR), or portions thereof, of the heavy and/or light chains are not of human origin, while the rest of the amino acids in the antibody are human or otherwise of human origin, e.g., a human antibody scaffold. Humanized antibodies also include antibodies in which one or more residues of the human protein are modified by one or more amino acid substitutions and/or one or more FWR residues of the human protein are replaced by corresponding non-human residues. Humanized antibodies may also comprise residues which are found in neither the human antibody or in the non-human antibody. A humanized antibody may be a super-humanized antibody, e.g., as described in U.S. Pat. No. 7,732,578. The antibodies may be humanized chimeric antibodies.

In highly preferred aspects, the antibodies are fully human. Fully human antibodies are those where the whole molecule is human or otherwise of human origin or includes an amino acid sequence identical to a human form of the antibody. Fully human antibodies include those obtained from a human V gene library, for example, where human genes encoding variable regions of antibodies are recombinantly expressed. Fully human antibodies may be expressed in other organisms (e.g., mice and xenomouse technology) or cells from other organisms transformed with genes encoding human antibodies. Fully human antibodies may nevertheless include amino acid residues not encoded by human sequences, e.g., mutations introduced by random, or site directed mutations.

The antibodies may be full length antibodies of any class, for example, IgG1, IgG2 or IgG4. The constant domains of such antibodies are preferably human. The variable regions of such antibodies may be of non-human origin, or preferably are human in origin or are humanized. Antibody fragments may also be used in place of the full-length antibodies.

The antibodies may be minibodies. Minibodies comprise small versions of whole antibodies, which encode in a single chain the essential elements of a whole antibody. For example, the minibody may be comprised of the VH and VL domains of a native antibody fused to the hinge region and CH3 domain of an immunoglobulin molecule.

In some embodiments, the antibody may comprise non-immunoglobulin derived protein frameworks. For example, reference may be made to (Ku & Schutz, Proc. Nat. Acad. Sci. USA 92: 6552-6556, 1995) which describes a four-helix bundle protein cytochrome b562 having two loops randomized to create CDRs, which have been selected for antigen binding.

Natural sequence variations may exist among heavy and light chains and the genes encoding them, and therefore, persons having ordinary skill in the art would expect to find some level of variation within the amino acid sequences, or the genes encoding them, of the antibodies described and exemplified herein. These variants preferably maintain the unique binding properties (e.g., specificity and affinity) of the parent antibody. Such an expectation is due in part to the degeneracy of the genetic code, as well as to the known evolutionary success of conservative amino acid sequence variations, which do not appreciably alter the nature of the encoded protein. Accordingly, such variants and homologs are considered substantially the same as one another and are included within the scope of the disclosure. The antibodies thus include variants having single or multiple amino acid substitutions, deletions, additions, or replacements that retain the biological properties (e.g., binding specificity and binding affinity) of the parent antibodies. The variants are preferably conservative but may be non-conservative.

Amino acid positions assigned to CDRs and FWRs may be defined according to Kabat Sequences of Proteins of Immunological Interest, National Institutes of Health, Bethesda, Md., 1987 and 1991 (also referred to herein as the Kabat numbering system). In addition, the amino acid positions assigned to CDRs and FWRs may be defined according to the Enhanced Chothia Numbering Scheme (www.bioinfo.org.uk/mdex.html). The heavy chain constant region of an antibody can be defined by the EU numbering system (Edelman, G M et al. (1969), Proc. Natl. Acad. USA, 63, 78-85).

According to the numbering system of Kabat, VH FWRs and CDRs may be positioned as follows: residues 1-30 (FWR1), 31-35 (CDR1), 36-49 (FWR2), 50-65 (CDR2), 6694 (FWR3), 95-102 (CDR3) and 103-113 (FWR4), and VL FWRs and CDRs are positioned as follows: residues 1-23 (FWR1), 24-34 (CDR1), 35-49 (FWR2), 50-56 (CDR2), 57-88 (FWR3), 89-97 (CDR3) and 98-107 (FWR4). In some instances, variable regions may increase in length and according to the Kabat numbering system some amino acids may be designated by a number followed by a letter. This specification is not limited to FWRs and CDRs as defined by the Kabat numbering system, but includes all numbering systems, including the canonical numbering system or of Chothia et al. (1987) J. Mol. Biol. 196:901-17; Chothiaet al. (1989) Nature 342:877-83; and/or Al-Lazikani et al. (1997) J. Mol. Biol. 273:927-48; the numbering system of Honnegher et al. (2001) J. Mol. Biol., 309:657-70; or the IMGT system discussed in Giudicelli et al., (1997) Nucleic Acids Res. 25:206-11. In some embodiments, the CDRs are defined according to the Kabat numbering system.

In some embodiments, for any of the heavy chain CDR2 subdomains described herein, according to the Kabat numbering system, the five C-terminal amino acids may not participate directly in antigen binding, and accordingly, it will be understood that any one or more of these five C-terminal amino acids may be substituted with another naturally occurring amino acid without substantially adversely affecting antigen binding. In some aspects, for any of the light chain CDR1 subdomains described herein, according to the Kabat numbering system, the four N-terminal amino acids may not participate directly in antigen binding, and accordingly, it will be understood that any one or more of these four amino acids may be substituted with another naturally occurring amino acid without substantially adversely affecting antigen binding. For example, as described by Padlan et al. (1995) FASEB J. 9:133-139, the five C terminal amino acids of heavy chain CDR2 and/or the four N-terminal amino acids of light chain CDR1 may not participate in antigen binding. In some embodiments, both the heavy chain CDR2 and the light chain CDR1 do not directly participate in antigen binding.

In some embodiments, an antibody is covalently linked (e.g., a genetic fusion protein) to an ADP-ribosyl cyclase protein. In some embodiments, the ADP-ribosyl cyclase protein is a mammalian ADP-ribosyl cyclase protein. For example, the ADP-ribosyl cyclase protein may include a human ADP-ribosyl cyclase protein, a murine ADP-ribosyl cyclase protein, a porcine ADP-ribosyl cyclase protein, or a bovine ADP-ribosyl cyclase protein. Preferably, the ADP-ribosyl cyclase protein is human, mouse, or bovine CD38 or BST1. Preferably, the CD38 and BST1 protein (UniProtKB: Q10588) are human. More preferably, the ADP-ribosyl cyclase protein is human CD38. In some embodiments, the ADP-ribosyl cyclase protein comprises a catalytic subunit or extracellular domain of CD38 (e.g., V45-I300) (SEQ ID NO: 2 OR SEQ ID NO: 3). Alternatively, the ADP-ribosyl cyclase protein may include a plant ADP-ribosyl cyclase protein (e.g., CD38, BST1).

Embodiments of the invention may include a peptide linker moiety disposed between the antibody and the ADP-ribosyl cyclase protein. More preferably, the peptide linker comprises one or more of a GGS peptide, a $(GGGS)_n$ peptide (SEQ ID NO: 19), or a $(GGGGS)_n$ peptide (SEQ ID NO: 20) wherein n is an integer from 1 to 5. In some embodiments, the peptide linker is GGGGS (SEQ ID NO: 21).

Certain embodiments may include a payload conjugated to the 2'-modified araNAD$^+$ analogue or the 2'-modified araNMN analogue. Preferably, the payload is a chemotoxic agent comprising auristatin, calicheamicin, maytansine, duocarmycin, a camptothecin analogue such as SN38 or DX-8951, or a benzodiazepine such as PBD, talirine, tesirine, or indolinobenzodiazepines. In one preferred embodiment, the auristatin is monomethyl auristatin F.

Other agents that may be used as a payload include, but is not limited to, therapeutic agents of use in combination with the conjugates described herein also include, for example, chemotherapeutic drugs such as *vinca* alkaloids, anthracyclines, epidophyllotoxins, taxanes, antimetabolites, tyrosine kinase inhibitors, alkylating agents, antibiotics, Cox-2 inhibitors, antimitotics, antiangiogenic and proapoptotic agents, particularly doxorubicin, methotrexate, taxol, other camptothecins, and others from these and other classes of anticancer agents, and the like. Other cancer chemotherapeutic drugs include nitrogen mustards, alkyl sulfonates, nitrosoureas, triazenes, folic acid analogs, pyrimidine analogs, purine analogs, platinum coordination complexes, hormones, and the like. Suitable chemotherapeutic agents are described in Remington's Pharmaceutical Sciences, 19th Ed. (Mack Publishing Co. 1995), and in Goodman and Gilman's The Pharmacological Basis of Therapetuics, 7th Ed. (MacMillan Publishing Co. 1985), as well as revised editions of these publications. Other suitable chemotherapeutic agents, such as experimental drugs, are known to those of skill in the art.

Other exemplary active agents include, but are not limited to, 5-fluorouracil, afatinib, aplidin, azaribine, anastrozole, anthracyclines, axitinib, AVL-101, AVL-291, bendamustine, bleomycin, bortezomib, bosutinib, bryostatin-1, busulfan, calicheamycin, camptothecin, carboplatin, 10-hydroxycamptothecin, carmustine, celebrex, chlorambucil, cisplatin (CDDP), Cox-2 inhibitors, irinotecan (CPT-11), SN-38, carboplatin, cladribine, camptothecans, crizotinib, cyclophosphamide, cytarabine, dacarbazine, dasatinib, dinaciclib, docetaxel, dactinomycin, daunorubicin, doxorubicin, 2-pyrrolinodoxorubicine (2P-DOX), cyano-morpholino doxorubicin, doxorubicin glucuronide, epirubicin glucuronide, erlotinib, estramustine, epidophyllotoxin, erlotinib, entinostat, estrogen receptor binding agents, etoposide (VP16), etoposide glucuronide, etoposide phosphate, exemestane, fingolimod, floxuridine (FUdR), 3',5'-O-dioleoyl-FudR (FUdR-dO), fludarabine, flutamide, farnesyl-protein transferase inhibitors, flavopiridol, fostamatinib, ganetespib, GDC-0834, GS-1101, gefitinib, gemcitabine, hydroxyurea, ibrutinib, idarubicin, idelalisib, ifosfamide, imatinib, L-asparaginase, lapatinib, lenolidamide, leucovorin, LFM-A13, lomustine, mechlorethamine, melphalan, mercaptopurine, 6-mercaptopurine, methotrexate, mitoxantrone, mithramycin, mitomycin, mitotane, navelbine, neratinib, nilotinib, nitrosurea, olaparib, plicomycin, procarbazine, paclitaxel, PCI-32765, pentostatin, PSI-341, raloxifene, semustine, sorafenib, streptozocin, SU11248, sunitinib, tamoxifen, temazolomide (an aqueous form of DTIC), transplatinum, thalidomide, thioguanine, thiotepa, teniposide, topotecan, uracil mustard, vatalanib, vinorelbine, vinblastine, vincristine, and ZD1839. Such agents may be part of the conjugates described herein or may alternatively be administered in combination with the described conjugates, either prior to, simultaneously with or after the conjugate.

In certain embodiments, the payload and the 2'-modified araNAD$^+$ analogue (e.g., 6-azido-2'-Cl-araNAD$^+$) may include a functional group or moiety that is capable of undergoing a click chemistry reaction. The click chemistry approach was originally conceived as a method to rapidly generate complex substances by joining small subunits together in a modular fashion. (See, e.g., Evans, R A, 2007, *Aust J Chem* 60(6):384-95.) Multiple variations of click chemistry reaction are known in the art, such as the Huisgen 1,3-dipolar cycloaddition copper catalyzed reaction (Tornoe et al., 2002, *J Org Chem* 67:3057-64). Other alternative reaction mechanisms include cycloaddition reactions such as the Diels-Alder, nucleophilic substitution reactions (especially to small, strained rings like epoxy and aziridine compounds), carbonyl chemistry formation of urea compounds and reactions involving carbon-carbon double bonds, such as alkynes in thiol-yne reactions.

The azide alkyne Huisgen cycloaddition reaction uses a copper catalyst in the presence of a reducing agent to catalyze the reaction of a terminal alkyne group attached to a first molecule. In the presence of a second molecule comprising, for example, an azide moiety, the azide reacts with the activated alkyne to form a 1,4-disubstituted 1,2,3-triazole. Advantageously the copper catalyzed reaction occurs at room temperature and is sufficiently specific that purification of the reaction product is often not required. (Tornoe et al., 2002, *J Org Chem* 67:3057.) Advantageously, the azide and alkyne functional groups are largely inert towards biomolecules in aqueous medium, thus permitting the reaction to occur in complex solutions. The resultant triazole is chemically stable and may not be subject to enzymatic cleavage, making the click chemistry product highly stable in biological systems. And although the copper catalyst is toxic to living cells, the copper-based click chemistry reaction may be used in vitro for immunoconjugate formation.

A copper-free click reaction also has been proposed for covalent modification of biomolecules. (See, e.g., Agard et al., *J. Am. Chem. Soc.* 2004, 126, 46, 15046-15047) In this system, the copper-free reaction uses ring strain in place of the copper catalyst to promote a [3+2] azide-alkyne cycloaddition reaction. For example, cyclooctyne is an 8-carbon ring structure comprising an internal alkyne bond. The closed ring structure induces a substantial bond angle deformation of the acetylene, which is highly reactive with azide groups to form a triazole. Thus, cyclooctyne derivatives may be used for copper-free click reactions.

Another type of copper-free click reaction (Ning et al., Angew Chem Int Ed Engl. 2010 Apr. 12; 49(17): 3065-3068.), is based upon strain-promoted alkyne-nitrone cycloaddition. To address the slow rate of the original cyclooctyne reaction, electron-withdrawing groups are attached adjacent to the triple bond. Examples of such substituted cyclooctynes include difluorinated cyclooctynes, 4-dibenzocyclooctynol and azacyclooctyne. An alternative copper-free reaction involved strain-promoted alkyne-nitrone cycloaddition to give N-alkylated isoxazolines. The reaction was reported to have exceptionally fast reaction kinetics and was used in a one-pot three-step protocol for site-specific modification of peptides and proteins. Nitrones were prepared by the condensation of appropriate aldehydes with N-methylhydroxylamine and the cycloaddition reaction took place in a mixture of acetonitrile and water. These and other known click chemistry reactions may be used to attach carrier moieties to antibodies in vitro.

In some embodiments of the click chemistry reaction, the reactive group comprises an alkyne that can undergo a 1,3-cycloaddition reaction with an azide. Such suitable reactive groups include, but are not limited to, strained alkynes, e.g., those suitable for strain-promoted alkyne-azide cycloadditions (SPAAC), cycloalkynes, e.g., cyclooctynes, benzannulated alkynes, and alkynes capable of undergoing 1,3 cycloaddition reactions with azides in the absence of copper catalysts. Suitable alkynes also include, but are not limited to, substituted alkynes, e.g., fluorinated alkynes, aza-cycloalkynes, BCN, and derivatives thereof. Linker-agent comprising such reactive groups are useful for conjugating antibodies that have been functionalized with azido groups. Such functionalized antibodies include antibodies functionalized with azido-polyethylene glycol groups.

In a preferred embodiment, the antibody binds to an antigen or epitope of an antigen expressed on a cancer or malignant cell. Examples of cancers treatable by the invention disclosed herein include, but are not limited to, lung cancer, breast cancer, ovarian cancer, cervical cancer, gastrointestinal cancers, head and neck cancer, melanoma, sarcoma, esophageal cancer, pancreatic cancer, metastatic pancreatic cancer, metastatic adenocarcinoma of the pancreas, bladder cancer, stomach cancer, fibrotic cancer, glioma, malignant glioma, diffuse intrinsic pontine glioma, recurrent childhood brain neoplasm, renal cell carcinoma, clear-cell metastatic renal cell carcinoma, kidney cancer, prostate cancer, metastatic castration resistant prostate cancer, stage IV prostate cancer, metastatic melanoma, melanoma, malignant melanoma, recurrent melanoma of the skin, melanoma brain metastases, stage IIIA skin melanoma; stage IIIB skin melanoma, stage IIIC skin melanoma; stage IV skin melanoma, malignant melanoma of head and neck, lung cancer, non-small cell lung cancer (NSCLC), squamous cell non-small cell lung cancer, breast cancer, recurrent metastatic breast cancer, hepatocellular carcinoma, richter's syndrome; waldenstrom macroglobulinemia, adult glioblastoma; adult gliosarcoma, recurrent glioblastoma, recurrent childhood rhabdomyosarcoma, recurrent ewing sarcoma/peripheral primitive neuroectodermal tumor, recurrent neuroblastoma; recurrent osteosarcoma, colorectal cancer, MSI positive colorectal cancer; MSI negative colorectal cancer, nasopharyngeal nonkeratinizing carcinoma; recurrent nasopharyngeal undifferentiated carcinoma, cervical adenocarcinoma; cervical adenosquamous carcinoma; cervical squamous cell carcinoma; recurrent cervical carcinoma; stage IVA cervical cancer; stage IVB cervical cancer, anal canal squamous cell carcinoma; metastatic anal canal carcinoma; recurrent anal canal carcinoma, recurrent head and neck cancer; head and neck squamous cell carcinoma (HNSCC), ovarian carcinoma, colon cancer, gastric cancer, advanced GI cancer, gastric adenocarcinoma; gastroesophageal junction adenocarcinoma, bone neoplasms, soft tissue sarcoma; bone sarcoma, thymic carcinoma, urothelial carcinoma, recurrent merkel cell carcinoma; stage III merkel cell carcinoma; stage IV merkel cell carcinoma, myelodysplastic syndrome and Sezary syndrome. In one embodiment, the solid tumor is a non-lymphoma solid tumor. In some embodiments, the solid tumor may be multiple myeloma.

Exemplary antigens that may be targeted with an antibody used with the invention may include, but is not limited to, carbonic anhydrase IX, B7, CCCL19, CCCL21, CXCR4, CLL-1, CSAp, HER-2/neu, BrE3, CD1, CD1a, CD2, CD3, CD4, CD5, CD8, CD11A, CD14, CD15, CD16, CD18, CD19, CD20 (e.g., C2B8, hA20, 1F5 MAbs), CD21, CD22, CD23, CD25, CD29, CD30, CD32b, CD33, CD37, CD38, CD40, CD40L, CD44, CD45, CD46, CD52, CD54, CD55, CD59, CD64, CD67, CD70, CD74, CD79a, CD80, CD83, CD95, CD126, CD133, CD138, CD147, CD154, CEACAM5, CEACAM6, CTLA-4, alpha-fetoprotein (AFP), VEGF, ED-B fibronectin (e.g., L19), EGP-1 (TROP-2), EGP-2 (e.g., 17-1A), EGF receptor (ErbB1), ErbB2, ErbB3, Factor H, FHL-1, Flt-3, folate receptor, Ga 733, GRO-β, HMGB-1, hypoxia inducible factor (HIF), insulin-like growth factor (ILGF), IFN-γ, IFN-α, IFN-β, IFN-k, IL-2R, IL-4R, IL-6R, IL-13R, IL-15R, IL-17R, IL-18R, IL-2, IL-6, IL-8, IL-12, IL-15, IL-17, IL-18, IL-25, IP-10, IGF-1R, Ia, HM1.24, gangliosides, HCG, the HLA-DR antigen to which L243 binds, CD66 antigens, i.e., CD66a-d or a combination thereof, MAGE, mCRP, MCP-1, MIP-1A, MIP-1B, macrophage migration-inhibitory factor (MIF), MUC1, MUC2, MUC3, MUC4, MUC5ac, placental growth factor (PlGF), PSA (prostate-specific antigen), PSMA, PAM4 antigen, PD-L1 receptor, NCA-95, NCA-90, A3, A33, Ep-CAM, KS-1, Le(y), mesothelin, 5100, tenascin, TAC, Tn antigen, Thomas-Friedenreich antigens, tumor necrosis antigens, tumor angiogenesis antigens, TNF-α, TRAIL receptor (R1 and R2), TROP-2, VEGFR, RANTES, T101, as well as cancer stem cell antigens, complement factors C3, C3a, C3b, C5a, C5, and an oncogene product. These antigens also include the human, murine, porcine, or bovine homologs as applicable. Preferably, the antigen is HER2 or CLL-1. Methods of making antibodies to bind specific antigens are well known in the art, for example, as disclosed in Harlow and Lane, Antibodies: A Laboratory Manual, Cold Springs Harbor Laboratory Press, Cold Spring Harbor, N.Y. (1988); Sambrook et al., Molecular Cloning: A Laboratory Manual, 2nd Ed., Cold Spring Harbor Laboratory Press, Cold Spring Harbor, N.Y. (1989).

In other embodiments, the active agent may be a diagnostic agent useful for diagnosis of a certain condition or disease. Examples of detectable agents include various enzymes, prosthetic groups, fluorescent materials (e.g., fluorescein, rhodamine, Cy5), luminescent materials, bioluminescent materials, green fluorescence protein (GFP), a variant of GFP, a resonance energy transfer (RET) donor molecule, a RET acceptor molecule, radioactive nuclides, positron emitting metals (for use in positron emission tomography), and nonradioactive paramagnetic metal ions. See generally U.S. Pat. No. 4,741,900 for metal ions which can be conjugated to antibodies for use as diagnostics.

Suitable enzymes include horseradish peroxidase, alkaline phosphatase, beta-galactosidase, or acetylcholinesterase; suitable prosthetic groups include streptavidin, avidin and biotin; suitable fluorescent materials include umbelliferone, fluorescein, fluorescein isothiocyanate, rhodamine, dichlorotriazinylamine fluorescein, dansyl chloride and phycoerythrin; suitable luminescent materials include luminol; suitable bioluminescent materials include luciferase, luciferin, and aequorin; and suitable radioactive nuclides include $^{125}$I, $^{131}$I, $^{111}$In and $^{99}$Tc.

In some embodiments, the drug-to-antibody ratio (DAR) is about 1:1, 2:1, 3:1, 4:1, or 5:1. In preferred embodiments, the DAR is 2:1 or 4:1. In some embodiments, the antibody-drug conjugates can bind to and kill HER2 and CLL-1 expressing cancer cell by delivering a drug payload to the cancer cell.

In some embodiments of the antibody-drug conjugate, the ADP-ribosyl cyclase protein is covalently linked to an N-terminus or a C-terminus of one or both light chains of the antibody and/or to the N-terminus or a C-terminus of one or both heavy chains of the antibody. In another embodiment, the catalytic subunit of the ADP-ribosyl cyclase protein is covalently linked to both an N-terminus and a C-terminus of one or both light chains of the antibody and to both the N-terminus and a C-terminus of one or both heavy chains of the antibody. Preferably, a peptide linker sequence is present between the catalytic domain and the heavy and/or light chain of the antibody to which it is fused, and a payload is conjugated to each catalytic subunit of the ADP-ribosyl cyclase protein. Preferably, the payload is conjugated to glutamate 226 of catalytic domain of CD38. Preferably, the antibody binds to binds an epitope within the extracellular domain of the CLL-1 protein or a fragment thereof, or to the extracellular domain of the HER2 protein or fragments thereof.

In other embodiments of the antibody-drug conjugate, the catalytic subunit of the ADP-ribosyl cyclase protein is covalently linked to the C-terminus of one or more light chains of an antibody and to the C-terminus of one or more heavy chains of the antibody. Preferably, a peptide linker sequence is present between the catalytic domain and the heavy and/or light chain of the antibody to which it is fused, and a payload is conjugated to each catalytic subunit of the ADP-ribosyl cyclase protein. Preferably, the antibody binds to binds an epitope within the extracellular domain of the CLL-1 protein or a fragment thereof, or to the extracellular domain of the HER2 protein or fragments thereof. Preferably, the payload is conjugated to glutamate 226 of catalytic domain of CD38. In some embodiments, the CD38 comprises or consists of the SEQ ID NO: 2 or SEQ ID NO: 3 and the peptide linker comprises or consists of the sequence of SEQ ID NO: 21.

In some embodiments of the antibody-drug conjugate, the catalytic subunit of the ADP-ribosyl cyclase protein is covalently linked to the C-terminus of both the light chains of an antibody and to the C-terminus of both heavy chains of the antibody. Preferably, a peptide linker sequence is present between the catalytic domain and the heavy and/or light chain of the antibody to which it is fused, and a payload is conjugated to each catalytic subunit of the ADP-ribosyl cyclase protein. Preferably, the antibody binds to binds an epitope within the extracellular domain of the CLL-1 protein or a fragment thereof, or to the extracellular domain of the HER2 protein or fragments thereof. Preferably, the payload is conjugated to glutamate 226 of catalytic domain of CD38. In some embodiments, the CD38 comprises or consists of the SEQ ID NO: 2 or SEQ ID NO: 3 and the peptide linker comprises or consists of the sequence of SEQ ID NO: 21.

Certain embodiments provide an antibody-drug conjugate comprising a fusion protein including an anti-HER2 or anti-CLL-1 antibody covalently linked to an ADP-ribosyl cyclase protein via a peptide linker moiety at either an N-terminus or a C-terminus of the anti-HER2 antibody or anti-CLL-1 antibody, a 2'-X-araNAD$^+$-N3 moiety or a 2'-X-araNMN-P0$_4$ moiety wherein X is a fluorine atom, a chlorine atom, or a bromine atom, a payload wherein the 2'-X-araNAD$^+$-N3 moiety or a 2'-X-araNMN-P0$_4$ moiety is conjugated to both the payload and the ADP-ribosyl cyclase protein. Preferably, the payload is conjugated to glutamate 226 of catalytic domain of CD38. In some embodiments, the CD38 comprises or consists of the SEQ ID NO: 2 or SEQ ID NO: 3 and the peptide linker comprises or consists of the sequence of SEQ ID NO: 21.

In other embodiments, the antibody binds to the extracellular domain of CLL-1. In some embodiments, the antibody is the monoclonal antibody 1075.7 (Zhao et al., (2010), Haematologica 95, 71-78.). In some embodiments, the C-terminus of both heavy chains of the 1075.7 antibody are covalently linked to the catalytic subunit of the ADP-ribosyl cyclase protein (e.g., CD38). In another embodiment, the C-terminus of both heavy chains of the 1075.7 antibody are covalently linked to the catalytic subunit of the ADP-ribosyl cyclase protein and the C-terminus of both light chains of the 1075.7 antibody are covalently linked to the catalytic subunit of the ADP-ribosyl cyclase protein. In some embodiments, the CD38 comprises or consists of the SEQ ID NO: 2 or SEQ ID NO: 3 and the peptide linker comprises or consists of the sequence of SEQ ID NO: 21.

Certain embodiments provide an antibody-drug conjugate comprising a Herceptin antibody covalently linked to a catalytic subunit of CD38 via a peptide linker moiety, a 2'-X-araNAD$^+$-N3 moiety or a 2'-X-araNMN-P0$_4$ moiety wherein X is a fluorine atom, a chlorine atom, or a bromine atom, a payload comprising monomethyl auristatin F wherein the 2'-X-araNAD$^+$-N3 moiety or the 2'-X-araNMN-P0$_4$ moiety is conjugated to both the monomethyl auristatin F and the catalytic subunit of CD38 or BST1, and the 2'-X-araNAD$^+$-N3 moiety or the 2'-X-araNMN-P0$_4$ moiety bind to glutamate 226 of CD38. In some embodiments, the CD38 comprises or consists of the SEQ ID NO: 2 or SEQ ID NO: 3 and the peptide linker comprises or consists of the sequence of SEQ ID NO: 21.

One embodiment of the invention includes an antibody-drug conjugate comprising a fusion protein including an anti-HER2 antibody or an anti-CLL-1 antibody covalently linked to an ADP-ribosyl cyclase protein via a peptide linker moiety at one or more C-terminus of the anti-HER2 antibody or anti-CLl-1 antibody, a 2'-Cl-araNAD$^+$-N3 moiety, and a payload wherein the 2'-Cl-araNAD$^+$-N3 moiety is conjugated to both the payload and the ADP-ribosyl cyclase protein. Preferably, the payload is conjugated to glutamate 226 of catalytic domain of CD38. In some embodiments, the CD38 comprises or consists of the SEQ ID NO: 2 or SEQ ID NO: 3 and the peptide linker comprises or consists of the sequence of SEQ ID NO: 21.

One embodiment includes an antibody-drug conjugate comprising an anti-HER2 antibody or an anti-CLL-1 antibody covalently linked to a catalytic subunit of CD38 via a peptide linker moiety at each C-terminus of both of the heavy and light chains of the antibody, a 2'-Cl-araNAD$^+$-N3 moiety, a monomethyl auristatin F moiety wherein the 2'-Cl-araNAD$^+$-N3 moiety is conjugated to both the monomethyl auristatin F and the catalytic subunit of CD38, and 2'-Cl-araNAD$^+$-N3 moiety binds to glutamate 226 of CD38. In some embodiments, the CD38 comprises or consists of the SEQ ID NO: 2 or SEQ ID NO: 3 and the peptide linker comprises or consists of the sequence of SEQ ID NO: 21.

Certain embodiments provide an antibody-drug conjugate comprising monoclonal antibody 1075.7 covalently linked to a catalytic subunit of CD38 via a peptide linker moiety, a 2'-X-araNAD$^+$-N3 moiety or a 2'-X-araNMN-P0$_4$ moiety wherein X is a fluorine atom, a chlorine atom, or a bromine atom, a payload comprising monomethyl auristatin F wherein the 2'-X-araNAD$^+$-N3 moiety or the 2'-X-araNMN-P0$_4$ moiety is conjugated to both the monomethyl auristatin F and the catalytic subunit of the CD38, and the 2'-X-araNAD$^+$-N3 moiety or the 2'-X-araNMN-P0$_4$ moiety binds to glutamate 226 of CD38. In some embodiments, the CD38 comprises or consists of the SEQ ID NO: 2 OR SEQ ID NO: 3 and the peptide linker comprises or consist of the sequence of SEQ ID NO: 21.

Another embodiment includes an antibody-drug conjugate comprising the monoclonal antibody 1075.7 covalently linked to a catalytic subunit of CD38 via a peptide linker moiety at the C-terminus of each of the heavy and light chains of the antibody, a 2'-Cl-araNAD$^+$-N3 moiety, a monomethyl auristatin F moiety wherein the 2'-Cl-araNAD$^+$-N3 moiety is conjugated to both the monomethyl auristatin F and the catalytic subunit of CD38, and the 2'-Cl-araNAD$^+$-N3 moiety binds to glutamate 226 of CD38. In some embodiments, the CD38 comprises or consists of the SEQ ID NO: 2 or SEQ ID NO: 3 and the peptide linker comprises or consists of the sequence of SEQ ID NO: 21.

Certain embodiments include a method of treating cancer comprising administering to a subject having cancer a therapeutically effective amount of any one of the antibody-drug conjugates or compositions thereof disclosed herein to inhibit the growth of cancer cells or kill cancer cells.

Certain embodiments include a method of preparing an antibody-drug conjugate that includes the steps of providing an antibody-peptide linker-ADP-ribosyl cyclase fusion protein, combining a 2'-modified araNAD$^+$ analogue or a 2'-modified araNMN analogue and a payload moiety to form a 2'-modified araNAD$^+$ analogue-payload or a 2'-modified araNMN analogue-payload, and conjugating the antibody-peptide linker-ADP-ribosyl cyclase fusion protein to the a 2'-modified araNAD$^+$ analogue-payload or the 2'-modified araNMN analogue-payload to form an antibody-drug conjugate.

Certain embodiments comprise a method of preparing a pharmaceutical composition including the steps of providing an antibody-peptide linker-ADP-ribosyl cyclase fusion protein, combining a 2'-modified araNAD$^+$ analogue or a 2'-modified araNMN analogue and a payload moiety to form a 2'-modified araNAD$^+$ analogue-payload or a 2'-modified araNMN analogue-payload, and conjugating the antibody-peptide linker-ADP-ribosyl cyclase fusion protein to the a 2'-modified araNAD$^+$ analogue-payload or the 2'-modified araNMN analogue-payload to form an antibody-drug conjugate.

As noted above, preferably, the 2'-modified araNAD$^+$ analogue comprises 2'-X-araNAD-N$_3$ wherein X is a fluorine atom, a chlorine atom, or a bromine atom and the 2'-modified araNMN analogue comprises 2'-X-araNMN-P0$_4$ wherein X is a fluorine atom, a chlorine atom, or a bromine atom. In preferred embodiments, the 2'-modified araNAD$^+$ analogue is 2'-Cl-araNAD$^+$-N3 and the ADP-ribosyl cyclase protein is CD38 or BST1.

In some embodiments, the antibody-drug conjugate or composition comprising the same may be administered as a dose of 1 or 5 mg/kg every 72 hours for a total of 3 times through i.v. injections. In some embodiments, the dose is 5 mg/kg every 72 hours.

Discussion.

Applicants disclose herein the concept of transforming CD38 and its covalent inhibitors into a facile, single-step approach for generation of site-specific ADCs. It was achieved through coupling bifunctional antibody-CD38 fusion proteins with the designer covalent inhibitors with stably attached payloads. It may provide a general approach for production of homogeneous ADCs with defined DARs and can be extended to generate a variety of ADCs with distinct targeting antibodies and payloads. In addition, the success of ARC-ADC supports extension of CD38 fusion to other peptides and proteins for site-specific conjugations for biomedical applications, similar to other enzymatic conjugation strategies like Halo-tag and CLIP-tag.

Four distinct linker designs have been established for current ADCs with cytotoxic payloads, including disulfide bonds (reduction by thiol groups), hydrazones (cleavage at acidic pH), cathepsin B-cleavable dipeptides, and non-cleavable linkers. Optimal linkers are still limited for generating ADCs with non-cytotoxic payloads. The 2'-Cl-araNAD$^+$-N$_3$ linker displays considerable stability and efficiency for payload release, which provides a new linker design for the development of ADCs with potentially improved physicochemical and pharmacological properties through increasing solubility, tunability, and efficiency for the release of payloads. The 2'-Cl-araNAD$^+$-N$_3$ linker may add new and more effective strategies for the development of ADCs with non-cytotoxic payloads for non-oncological indications.

In addition, Applicants disclose a native human CD38 enzyme for generating site-specific ADCs. In silico prediction of immunogenic peptides of CD38 C-fusion IgG heavy chain was carried out by employing the NetMHCIIpan 3.2 server and selecting common subtypes of human major histocompatibility complex (MEW) class II among major populations. No peptides within the junction region of CD38 C-fusion IgG heavy chain were predicted to possess high binding affinity to the selected representative MHC class II molecules (Table 2). In addition to its excellent catalytic efficiency for rapid and single-step conjugation, the incorporation of catalytic domain of human CD38 may prevent immunogenicity possibly occurred for mutated, engineered, or non-human derived therapeutic proteins. This CD38-based site-specific ADCs may lay a foundation for the development of innovative ADCs with improved efficacy and safety.

As disclosed herein, genetically fused CD38 together with 2'-Cl-araNAD$^+$-N$_3$ covalent inhibitor enables facile production of site-specific ADCs. The resulting anti-HER2 ARC-ADC exhibits excellent stability and efficacy against HER2-positive breast cancer both in vitro and in vivo. This demonstrates a new approach for generation of site-specific ADCs, which may lead to the development of a novel class of ADCs with potentially enhanced properties for fighting various human diseases.

Table 1. In silico prediction of immunogenicity of CD38 C-fusion IgG heavy chain. (A) Lists of selected HLA genes and predicted immunogenic peptides. (B) A map of potentially immunogenic peptide fragments in CD38 C-fusion IgG heavy chain. Regions containing potentially immunogenic peptides are bolded. The junction region between Herceptin heavy chain and human CD38 catalytic domain is underlined. In silico prediction was performed by employing NetMHCIIpan 3.2 server.

TABLE 1A

| HLA Genes | Predicted High Binding Peptides | HLA Genes | Predicted High Binding Peptides |
|---|---|---|---|
| DRB1_0101 | SKNTAYLQMNSLRAE (SEQ ID NO: 48) | DRB1_1310 | VSVFWKTVSRRFAEA (SEQ ID NO: 49) |
| DRB1_0102 | SKNTAYLQMNSLRAE (SEQ ID NO: 48) | DRB1_1312 | VSVFWKTVSRRFAEA (SEQ ID NO: 49) |
| DRB1_0103 | SKNTAYLQMNSLRAE (SEQ ID NO: 48) | DRB1_1314 | VSVFWKTVSRRFAEA (SEQ ID NO: 49) |
| DRB1_0301 | DVVHVMLDGSRSKIF (SEQ ID NO: 50) | DRB1_1320 | VSVFWKTVSRRFAEA (SEQ ID NO: 49) |
| DRB1_0302 | None Detected | | NPVSVFWKTVSRRFA (SEQ ID NO: 51) |
| DRB1_0401 | SKNTAYLQMNSLRAE (SEQ ID NO: 48) RDMFTLEDTLLGYLA (SEQ ID NO: 52) | DRB1_1401 DRB1_1402 DRB1_1403 | None Detected None Detected None Detected |
| DRB1_0402 | SKNTAYLQMNSLRAE (SEQ ID NO: 48) SKNTAYLQMNSLRAE (SEQ ID NO: 48) | DRB1_1404 DRB1_1405 DRB1_1406 DRB1_1407 | None Detected None Detected None Detected None Detected |
| DRB1_0403 | GGSLRLSCAASGFNI (SEQ ID NO: 53) LYSLSSVVTVPSSSL (SEQ ID NO: 54) | DRB3_0101 DRB3_0201 DRB3_0202 | VKFNWYVDGVEVHNA (SEQ ID NO: 56) None Detected None Detected |
| DRB1_0404 | SKNTAYLQMNSLRAE (SEQ ID NO: 48) STYRVVSVLTVLHQD (SEQ ID NO: 55) | DRB3_0210 DRB3_0301 | None Detected KDTLMISRTPEVTCV (SEQ ID NO: 60) |
| DRB1_0405 | SKNTAYLQMNSLRAE (SEQ ID NO: 48) | DRB4_0101 DRB4_0104 DRB4_0103 | None Detected None Detected None Detected |
| DRB1_0406 | SKNTAYLQMNSLRAE (SEQ ID NO: 48) GGSLRLSCAASGFNI (SEQ ID NO: 53) LYSLSSVVTVPSSSL (SEQ ID NO: 54) | DRB1_1417 DRB1_1418 DRB1_1424 DRB1_1454 DRB1_1501 | None Detected VSVFWKTVSRRFAEA (SEQ ID NO: 49) None Detected None Detected None Detected |
| DRB1_0407 | SKNTAYLQMNSLRAE (SEQ ID NO: 48) | DRB1_1502 DRB1_1503 | None Detected None Detected |
| DRB1_0408 | SKNTAYLQMNSLRAE (SEQ ID NO: 48) GLYSLSSVVTVPSSS (SEQ ID NO: 57) | DRB1_1504 | VSVFWKTVSRRFAEA (SEQ ID NO: 49) NPVSVFWKTVSRRFA (SEQ ID NO: 51) CNKILLWSRIKDLAH (SEQ ID NO: 62) NKILLWSRIKDLAHQ (SEQ ID NO: 64) |
| DRB1_0409 | KNTAYLQMNSLRAED (SEQ ID NO: 58) RDMFTLEDTLLGYLA (SEQ ID NO: 52) GSFFLYSKLTVDKSR (SEQ ID NO: 59) | DRB1_1506 DRB1_1601 | None Detected VSVFWKTVSRRFAEA (SEQ ID NO: 49) NPVSVFWKTVSRRFA (SEQ ID NO: 51) SKNTAYLQMNSLRAE (SEQ ID NO: 48) |
| DRB1_0410 | SKNTAYLQMNSLRAE (SEQ ID NO: 48) | | |
| DRB1_0411 | SKNTAYLQMNSLRAE (SEQ ID NO: 48) | | |
| DRB1_0417 | SKNTAYLQMNSLRAE (SEQ ID NO: 48) RDMFTLEDTLLGYLA (SEQ ID NO: 52) | DRB1_1602 DRB1_1604 | SKNTAYLQMNSLRAE (SEQ ID NO: 48) VSVFWKTVSRRFAEA (SEQ ID NO: 49) NPVSVFWKTVSRRFA (SEQ ID NO: 51) |
| DRB1_0438 | SKNTAYLQMNSLRAE (SEQ ID NO: 48) RDMFTLEDTLLGYLA (SEQ ID NO: 52) | DRB1_1607 | SKNTAYLQMNSLRAE (SEQ ID NO: 48) |
| DRB1_0701 | NPVSVFWKTVSRRFA (SEQ ID NO: 51) | DRB5_0101 | VSVFWKTVSRRFAEA (SEQ ID NO: 49) |
| DRB1_0801 | VSVFWKTVSRRFAEA (SEQ ID NO: 49) NNPVSVFWKTVSRRF (SEQ ID NO: 61) | DRB5_0102 | VSVFWKTVSRRFAEA (SEQ ID NO: 49) VFWKTVSRRFAEAAC (SEQ ID NO: 66) |
| DRB1_0806 | VSVFWKTVSRRFAEA (SEQ ID NO: 49) CNKILLWSRIKDLAH (SEQ ID NO: 62) | DRB5_0103 | VSVFWKTVSRRFAEA (SEQ ID NO: 49) |
| DRB1_0807 | NSTYRVVSVLTVLHQ (SEQ ID NO: 63) VSVFWKTVSRRFAEA (SEQ ID NO: 49) | DRB5_0108N | VSVFWKTVSRRFAEA (SEQ ID NO: 49) VFWKTVSRRFAEAAC (SEQ ID NO: 66) |
| | | DRB5_0202 | None Detected |

TABLE 1A-continued

| HLA Genes | Predicted High Binding Peptides | HLA Genes | Predicted High Binding Peptides |
|---|---|---|---|
| DRB1_0810 | None Detected | DQA10501 | SKSTSGGTAALGCLV (SEQ ID NO: 67) |
| DRB1_0802 | VSVFWKTVSRRFAEA (SEQ ID NO: 49) | DQB10301 | LVESGGGLVQPGGSL (SEQ ID NO: 68) |
| DRB1_0803 | None Detected | | TVSWNSGALTSGVHT (SEQ ID NO: 69) |
| DRB1_0804 | VSVFWKTVSRRFAEA (SEQ ID NO: 49) | | SWNSGALTSGVHTFP (SEQ ID NO: 70) |
| DRB1_0811 | VSVFWKTVSRRFAEA (SEQ ID NO: 49) | | |
| DRB1_0901 | QSVWDAFKGAFISKH (SEQ ID NO: 65) | DQA10102 DQB10602 | GVHTFPAVLQSSGLY (SEQ ID NO: 71) |
| DRB1_1001 | SKNTAYLQMNSLRAE (SEQ ID NO: 48) NSTYRVVSVLTVLHQ (SEQ ID NO: 63) | DQA10301 DQB10302 | VKGFYPSDIAVEWES (SEQ ID NO: 72) LEDTLLGYLADDLTW (SEQ ID NO: 73) |
| DRB1_1101 | VSVFWKTVSRRFAEA (SEQ ID NO: 49) | DQA10401 DQB10402 | LEDTLLGYLADDLTW (SEQ ID NO: 73) |
| DRB1_1102 | NPVSVFWKTVSRRFA (SEQ ID NO: 51) | DQA10101 DQB10501 | LEDTLLGYLADDLTW (SEQ ID NO: 73) |
| DRB1_1103 | VSVFWKTVSRRFAEA (SEQ ID NO: 49) | | PEVKFNWYVDGVEVH (SEQ ID NO: 74) |
| DRB1_1104 | VSVFWKTVSRRFAEA (SEQ ID NO: 49) | DQA10501 DQB10201 | LEDTLLGYLADDLTW (SEQ ID NO: 73) |
| DRB1_1106 | VSVFWKTVSRRFAEA (SEQ ID NO: 49) | | PEVKFNWYVDGVEVH (SEQ ID NO: 74) |
| DRB1_1109 | VSVFWKTVSRRFAEA (SEQ ID NO: 49) | DPA10103 DPB10401 | None Detected |
| DRB1_1110 | VSVFWKTVSRRFAEA (SEQ ID NO: 49) | DPA10103 DPB10402 | None Detected |
| DRB1_1111 | VSVFWKTVSRRFAEA (SEQ ID NO: 49) NNPVSVFWKTVSRRF (SEQ ID NO: 61) | DPA10103 DPB10501 | VSVFWKTVSRRFAEA (SEQ ID NO: 49) SVFWKTVSRRFAEAA (SEQ ID NO: 75) |
| DRB1_1112 | VSVFWKTVSRRFAEA (SEQ ID NO: 49) | DPA10103 DPB10201 | None Detected |
| DRB1_1115 | VSVFWKTVSRRFAEA (SEQ ID NO: 49) | DPA10103 DPB10101 | None Detected |
| DRB1_1117 | None Detected | | |
| DRB1_1119 | None Detected | | |
| DRB1_1201 | None Detected | | |
| DRB1_1202 | VSVFWKTVSRRFAEA (SEQ ID NO: 49) | | |
| DRB1_1301 | NPVSVFWKTVSRRFA (SEQ ID NO: 51) | | |
| DRB1_1302 | None Detected | | |
| DRB1_1303 | VSVFWKTVSRRFAEA (SEQ ID NO: 49) | | |
| DRB1_1304 | VSVFWKTVSRRFAEA (SEQ ID NO: 49) PVSVFWKTVSRRFAE (SEQ ID NO: 76) | | |
| DRB1_1305 | CNKILLWSRIKDLAH (SEQ ID NO: 62) VSVFWKTVSRRFAEA (SEQ ID NO: 49) | | |
| DRB1_1307 | SVFWKTVSRRFAEAA (SEQ ID NO: 75) NNPVSVFWKTVSRRF (SEQ ID NO: 61) | | |

TABLE 1B

EVQLVESGGGLVQPGGSLRLSCAASGFNIKDTYIHWVRQAPGK
GLEWVARIYPTNGYTRYADSVKGRFTISADT**SKNTAYLQMNSL
RAED**TAVYYCSRWGDGFYAMDYWGQGTLVTVSSASTKGPSVF
PLAPSSKSTSGGTAALGCLVKDYFPEP**VTSWNSGALTSGVHT
FPAVLQSSGLYSLSSVVTVPSSSL**GTQTYICNVNHKPSNTKVD
KKVEPKSCDKTHTCPPCPAPELLGGPSVFLPPKPK**DTLMISR
TPEVTCVVVDVSHEDPEVKFNWYVDGVEVHNAKTKPREEQYNS
TYRVVSVLTVLHQ**DWLNGKEYKCKVSNKALPAPIEKTISKAKG
QPREPQVYTLPPSRDELTKNQVSLTCLVKGFYPSDIAVEWESN
GQPENNYKTTPPVLDSDGSFFLYSKLTVDKSRWQQGNVFSCSV
MHEALHNHYTQKSLSLSPGKGGGGSRWQQWSGPGTTKRFPET
VLARCVKYTEIHPEMRHVDCQSVWDAFKGAFISKHPCDITEED
YQPLMKLGTQTVPCNKILLWSRIKDLAHQFTQVQ**RDMFTLEDT
LLGYLADDLTWCGEFATSKINYQSCPDWRKDCSNNPVSVFWKT

TABLE 1B-continued

VSRRFAEAACDVVHVMLDGSRSKIFDKDSTFGSVEVHNLQPEK
VQTLEAWVIHGGREDSRDLCQDPTIKELESIISKRNIQFSCKN
IYRPDKFLQCVKNPEDSSCTSEI (SEQ ID NO: 18)

Pharmaceutical Formulations

The compounds described herein can be used to prepare therapeutic pharmaceutical compositions, for example, by combining the compounds with a pharmaceutically acceptable diluent, excipient, or carrier. The compounds may be added to a carrier in the form of a salt or solvate. For example, in cases where compounds are sufficiently basic or acidic to form stable nontoxic acid or base salts, administration of the compounds as salts may be appropriate.

Examples of pharmaceutically acceptable salts are organic acid addition salts formed with acids that form a physiologically acceptable anion, for example, tosylate, methanesulfonate, acetate, citrate, malonate, tartrate, succinate, benzoate, ascorbate, α-ketoglutarate, and β-glycerophosphate. Suitable inorganic salts may also be formed, including hydrochloride, halide, sulfate, nitrate, bicarbonate, and carbonate salts.

Pharmaceutically acceptable salts may be obtained using standard procedures well known in the art, for example by reacting a sufficiently basic compound such as an amine with a suitable acid to provide a physiologically acceptable ionic compound. Alkali metal (for example, sodium, potassium or lithium) or alkaline earth metal (for example, calcium) salts of carboxylic acids can also be prepared by analogous methods.

The compounds of the formulas described herein can be formulated as pharmaceutical compositions and administered to a mammalian host, such as a human patient, in a variety of forms. The forms can be specifically adapted to a chosen route of administration, e.g., oral or parenteral administration, by intravenous, intramuscular, topical or subcutaneous routes.

The compounds described herein may be systemically administered in combination with a pharmaceutically acceptable vehicle, such as an inert diluent or an assimilable edible carrier. For oral administration, compounds can be enclosed in hard- or soft-shell gelatin capsules, compressed into tablets, or incorporated directly into the food of a patient's diet. Compounds may also be combined with one or more excipients and used in the form of ingestible tablets, buccal tablets, troches, capsules, elixirs, suspensions, syrups, wafers, and the like. Such compositions and preparations typically contain at least 0.1% of active compound. The percentage of the compositions and preparations can vary and may conveniently be from about 0.5% to about 60%, about 1% to about 25%, or about 2% to about 10%, of the weight of a given unit dosage form. The amount of active compound in such therapeutically useful compositions can be such that an effective dosage level can be obtained.

The tablets, troches, pills, capsules, and the like may also contain one or more of the following: binders such as gum tragacanth, acacia, corn starch or gelatin; excipients such as dicalcium phosphate; a disintegrating agent such as corn starch, potato starch, alginic acid and the like; and a lubricant such as magnesium stearate. A sweetening agent such as sucrose, fructose, lactose, or aspartame; or a flavoring agent such as peppermint, oil of wintergreen, or cherry flavoring, may be added. When the unit dosage form is a capsule, it may contain, in addition to materials of the above type, a liquid carrier, such as a vegetable oil or a polyethylene glycol. Various other materials may be present as coatings or to otherwise modify the physical form of the solid unit dosage form. For instance, tablets, pills, or capsules may be coated with gelatin, wax, shellac or sugar and the like. A syrup or elixir may contain the active compound, sucrose or fructose as a sweetening agent, methyl and propyl parabens as preservatives, a dye and flavoring such as cherry or orange flavor. Any material used in preparing any unit dosage form should be pharmaceutically acceptable and substantially non-toxic in the amounts employed. In addition, the active compound may be incorporated into sustained-release preparations and devices.

The active compound may be administered intravenously or intraperitoneally by infusion or injection. Solutions of the active compound or its salts can be prepared in water, optionally mixed with a nontoxic surfactant. Dispersions can be prepared in glycerol, liquid polyethylene glycols, triacetin, or mixtures thereof, or in a pharmaceutically acceptable oil. Under ordinary conditions of storage and use, preparations may contain a preservative to prevent the growth of microorganisms.

Pharmaceutical dosage forms suitable for injection or infusion can include sterile aqueous solutions, dispersions, or sterile powders comprising the active ingredient adapted for the extemporaneous preparation of sterile injectable or infusible solutions or dispersions, optionally encapsulated in liposomes. The ultimate dosage form should be sterile, fluid and stable under the conditions of manufacture and storage. The liquid carrier or vehicle can be a solvent or liquid dispersion medium comprising, for example, water, ethanol, a polyol (for example, glycerol, propylene glycol, liquid polyethylene glycols, and the like), vegetable oils, nontoxic glyceryl esters, and suitable mixtures thereof. The proper fluidity can be maintained, for example, by the formation of liposomes, by the maintenance of the required particle size in the case of dispersions, or by the use of surfactants. The prevention of the action of microorganisms can be brought about by various antibacterial and/or antifungal agents, for example, parabens, chlorobutanol, phenol, sorbic acid, thimerosal, and the like. In many cases, it will be preferable to include isotonic agents, for example, sugars, buffers, or sodium chloride. Prolonged absorption of the injectable compositions can be brought about by agents delaying absorption, for example, aluminum monostearate and/or gelatin.

Sterile injectable solutions can be prepared by incorporating the active compound in the required amount in the appropriate solvent with various other ingredients enumerated above, as required, optionally followed by filter sterilization. In the case of sterile powders for the preparation of sterile injectable solutions, methods of preparation can include vacuum drying and freeze-drying techniques, which yield a powder of the active ingredient plus any additional desired ingredient present in the solution.

For topical administration, compounds may be applied in pure form, e.g., when they are liquids. However, it will generally be desirable to administer the active agent to the skin as a composition or formulation, for example, in combination with a dermatologically acceptable carrier, which may be a solid, a liquid, a gel, or the like.

Useful solid carriers include finely divided solids such as talc, clay, microcrystalline cellulose, silica, alumina, and the like. Useful liquid carriers include water, dimethyl sulfoxide (DMSO), alcohols, glycols, or water-alcohol/glycol blends, in which a compound can be dissolved or dispersed at effective levels, optionally with the aid of non-toxic surfactants. Adjuvants such as fragrances and additional antimicrobial agents can be added to optimize the properties for a given use. The resultant liquid compositions can be applied from absorbent pads, used to impregnate bandages and other dressings, or sprayed onto the affected area using a pump-type or aerosol sprayer.

Thickeners such as synthetic polymers, fatty acids, fatty acid salts and esters, fatty alcohols, modified celluloses, or modified mineral materials can also be employed with liquid carriers to form spreadable pastes, gels, ointments, soaps, and the like, for application directly to the skin of the user.

Examples of dermatological compositions for delivering active agents to the skin are known to the art; for example, see U.S. Pat. Nos. 4,992,478, 4,820,508, 4,608,392, and 4,559,157. Such dermatological compositions can be used in combinations with the compounds described herein where an ingredient of such compositions can optionally be replaced by a compound described herein, or a compound described herein can be added to the composition.

Useful dosages of the compositions described herein can be determined by comparing their in vitro activity, and in vivo activity in animal models. Methods for the extrapolation of effective dosages in mice, and other animals, to humans are known to the art; for example, see U.S. Pat. No. 4,938,949. The amount of a compound, or an active salt or derivative thereof, required for use in treatment will vary not only with the particular compound or salt selected but also with the route of administration, the nature of the condition being treated, and the age and condition of the patient, and will be ultimately at the discretion of an attendant physician or clinician.

In general, however, a suitable dose will be in the range of from about 0.5 to about 100 mg/kg, e.g., from about 10 to about 75 mg/kg of body weight per day, such as 3 to about 50 mg per kilogram body weight of the recipient per day, preferably in the range of 6 to 90 mg/kg/day, most preferably in the range of 15 to 60 mg/kg/day.

The compound is conveniently formulated in unit dosage form; for example, containing 5 to 1000 mg, conveniently 10 to 750 mg, most conveniently, 50 to 500 mg of active ingredient per unit dosage form. In one embodiment, the invention provides a composition comprising a compound of the invention formulated in such a unit dosage form.

The compound can be conveniently administered in a unit dosage form, for example, containing 5 to 1000 mg/m$^2$, conveniently 10 to 750 mg/m$^2$, most conveniently, 50 to 500 mg/m$^2$ of active ingredient per unit dosage form. The desired dose may conveniently be presented in a single dose or as divided doses administered at appropriate intervals, for example, as two, three, four or more sub-doses per day. The sub-dose itself may be further divided, e.g., into a number of discrete loosely spaced administrations.

The desired dose may conveniently be presented in a single dose or as divided doses administered at appropriate intervals, for example, as two, three, four or more sub-doses per day. The sub-dose itself may be further divided, e.g., into a number of discrete loosely spaced administrations; such as multiple inhalations from an insufflator or by application of a plurality of drops into the eye.

The compounds described herein can be effective anti-tumor agents and have higher potency and/or reduced toxicity as compared to known treatments for AML. Preferably, compounds of the invention are more potent and less toxic than known treatments, and/or avoid a potential site of catabolic metabolism encountered with known treatments, i.e., have a different metabolic profile than known treatments.

The invention provides therapeutic methods of treating cancer in a mammal, which involve administering to a mammal having cancer an effective amount of a compound or composition described herein. A mammal includes a primate, human, rodent, canine, feline, bovine, ovine, equine, swine, caprine, bovine and the like.

The ability of a compound of the invention to treat cancer may be determined by using assays well known to the art. For example, the design of treatment protocols, toxicity evaluation, data analysis, quantification of tumor cell-kill and the biological significance of the use of transplantable tumor screens are known. In addition, ability of a compound to treat cancer may be determined using the Tests as described below.

The following Examples are intended to illustrate the above invention and should not be construed as to narrow its scope. One skilled in the art will readily recognize that the Examples suggest many other ways in which the invention could be practiced. It should be understood that numerous variations and modifications may be made while remaining within the scope of the invention.

EXAMPLES

Example 1. Compound Synthesis and Characterization

A3

General Procedure for the Synthesis of A3:

To a solution of (2R,3R,4S,5R)-2-(6-chloro-9H-purin-9-yl)-5-(hydroxymethyl)tetrahydrofuran-3,4-diol (A1) (86 mg, 0.3 mmol) in EtOH (6.0 mL) were added 3-azidopropylamine (A2) (33 mg, 0.33 mmol, 1.1 eq) and DIPEA (158 µL, 0.9 mmol, 3 eq) at room temperature. Then the resulting mixture was heated to reflux until the reaction completed (monitored by TLC). Then the solvent was removed under reduced pressure and the residue was purified by a flash column chromatography to afford the desired product A3 (97 mg, 92%) as a colorless solid.

(2R,3R,4S,5R)-2-(6-((3-azidopropyl)amino)-9H-purin-9-yl)-5 (hydroxymethyl)tetrahydrofuran-3,4-diol (A3)

97 mg, 92% yield; $^1$H NMR (400 MHz, CD$_3$OD): δ 1.91-1.98 (m, 2H, CH$_2$), 3.45 (t, 2H, J=6.8 Hz, CH$_2$), 3.63-3.76 (m, 3H, CH$_2$+CH$_2$), 3.89 (dd, 1H, J=12.4, 2.4 Hz, CH$_2$), 4.17 (q, 1H, J=2.4 Hz, CH), 4.32 (dd, 1H, J=4.8, 2.4 Hz, CH), 4.74 (dd, 1H, J=6.4, 4.8 Hz, CH), 5.95 (d, 1H, J=6.4 Hz, CH), 8.23 (br, 1H, ArH), 8.25 (s, 1H, ArH); $^{13}$C NMR (100 MHz, CD$_3$OD): δ 29.8, 38.9, 50.1, 63.5, 72.7, 75.4, 88.2, 91.3, 141.6, 153.5, 156.4.

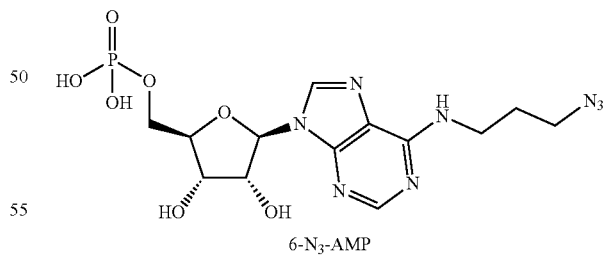

6-N$_3$-AMP

General Procedure for the Synthesis of 6-N$_3$-AMP:

To a stirred solution of compound A3 (70 mg, 0.2 mmol) in trimethylphosphate (3 mL) was added P(O)Cl$_3$ (56 µL, 0.6 mmol, 3 eq) at 0° C. and the resulting mixture was stirred at 0° C. for 6 hours. A few drops H$_2$O was then added to quench the reaction. The reaction was then concentrated in vacuo and the crude product was purified via preparative HPLC (semipreparative C18 Kinetex column (5 µm, 100 Å, 150×10.0 mm, Phenomenex Inc, Torrance, Calif.)) (mobile phase A: 0.1% formic acid (aq), mobile B: 0.1% formic acid in acetonitrile; flow rate=2.0 mL/min; 0-2 min: 0-4% B, 2-4 min: 4-10% B; 4-8 min: 10-20% B; 8-9 min: 20% B; 9-12 min: 20-50% B; 12-14 min: 50-0% B). Fractions containing the desired product were concentrated and lyophilized to yield the desired product 6-N3-AMP (60 mg, 70%) as a colorless solid.

((2R,3S,4R,5R)-5-(6-((3-azidopropyl)amino)-911-purin-9-yl)-3,4-dihydroxytetrahydrofuran-2-yl) methyl dihydrogen phosphate (6-N$_3$-AMP)

$^1$H NMR (400 MHz, D$_2$O): δ 1.94-2.01 (m, 2H, CH$_2$), 3.47 (t, 2H, J=6.8 Hz, CH$_2$), 3.69 (br, 2H, CH$_2$), 4.09-4.12 (m, 2H, CH$_2$), 4.35-4.38 (m, 1H, CH), 4.47 (dd, 1H, J=5.2, 4.0 Hz, CH$_2$), 4.73 (t, 1H, J=5.6 Hz, CH), 6.13 (d, 1H, J=5.6 Hz, CH), 8.27 (s, 1H, ArH), 8.45 (br, 1H, ArH); $^{13}$C NMR (100 MHz, D$_2$O): δ 26.7, 39.5, 48.1, 64.2 (d, J=4.8 Hz), 70.1, 74.6, 84.1 (d, J=8.1 Hz), 87.9, 118.8, 141.7, 144.6, 146.6, 148.7.

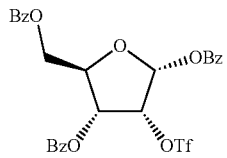

B2

General Procedure for the Synthesis of Compound B2:

The compound 1,3,5-tri-O-benzoyl-α-D-ribofuranose B1 (1.4 g, 3.0 mmol) was dissolved in DCM (20 mL) followed by the addition of pyridine (724 μL, 9.0 mmol, 3 eq) and Tf$_2$O (738 μL, 4.5 mmol, 1.5 eq) at 0° C. After stirring at the same temperature for 4 hours, the reaction mixture was diluted with EtOAc (120 mL) and quenched with water (2 mL), and the organic phase was washed with saturated aqueous CuSO$_4$ (3×20 mL) and brine (20 mL), dried over anhydrous Na$_2$SO$_4$, filtered and concentrated to give a residue. The residue was purified by a flash column chromatography on silica gel to afford the desired compound B2 (1.6 g, 91%) as a colorless oil.

(2R,3R,4R,5R)-5-((benzoyloxy)methyl) (((trifluoromethyl)sulfonyl)oxy)tetrahydrofuran-2,4-diyl dibenzoate (B2)

$^1$H NMR (400 MHz, CDCl$_3$): δ 4.62 (dd, 1H, J=12.4, 3.2 Hz, CH$_2$), 4.75 (dd, 1H, J=12.4, 3.2 Hz, CH$_2$), 4.86 (q, 1H, J=3.2 Hz, CH), 5.54 (dd, 1H, J=6.4, 4.4 Hz, CH), 5.78 (dd, 1H, J=6.4, 3.2 Hz, CH), 6.86 (d, 1H, J=4.4 Hz, CH), 7.38-7.43 (m, 2H, ArH), 7.45-7.51 (m, 4H, ArH), 7.58-7.68 (m, 3H, ArH), 8.01-8.04 (m, 2H, ArH), 8.09-8.15 (m, 4H, ArH); $^{13}$C NMR (100 MHz, CDCl$_3$): δ 63.4, 69.9, 79.4, 82.0, 93.1, 118.4 (q, J=317.8 Hz), 128.4, 128.54, 128.66, 128.67, 128.75, 129.1, 129.6, 130.02, 130.10, 133.6, 133.9, 134.1, 164.7, 165.5, 165.8.

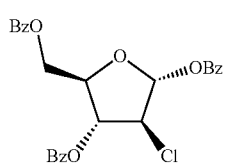

B3

General Procedure for the Synthesis of Compound B3:

To a stirred solution of B2 (892 mg, 1.5 mmol) in acetone (30 mL) was LiCl (634 mg, 15.0 mmol, 10.0 eq) at room temperature. Then the resulting mixture was stirred at the same temperature until the reaction completed (monitoring by TLC). Then the reaction was diluted with EtOAc (120 mL), and the organic phase was washed with saturated aqueous water (3×30 mL) and brine (20 mL), dried over anhydrous Na$_2$SO$_4$, filtered and concentrated to give a residue. The residue was purified by a flash column chromatography on silica gel to afford the desired compound B3 (650 mg, 90%) as a colorless oil.

(2R,3S,4R,5R)-5-((benzoyloxy)methyl)-3-chlorotetrahydrofuran-2,4-diyl dibenzoate (B3)

$^1$H NMR (400 MHz, CDCl$_3$): δ 4.62 (d, 1H, J=0.4 Hz, CH), 4.73 (dd, 1H, J=12.0, 5.6 Hz, CH$_2$), 4.78-4.87 (m, 2H, CH$_2$+CH), 5.61-5.63 (m, 1H, CH), 6.69 (s, 1H, CH), 7.38-7.45 (m, 6H, ArH), 7.54-7.64 (m, 3H, ArH), 8.03-8.06 (m, 4H, ArH), 8.10-8.13 (m, 2H, ArH); $^{13}$C NMR (100 MHz, CDCl$_3$): δ 61.8, 63.9, 80.0, 84.4, 102.4, 128.3, 128.48, 128.56, 128.64, 129.1, 129.5, 129.83, 129.88, 133.2, 133.7, 133.9, 164.6, 165.3, 166.2.

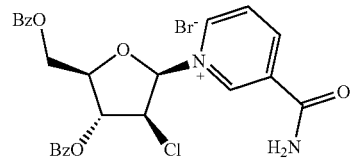

B4

General Procedure for the Synthesis of Compound B4:

Compound B3 (577 mg, 1.2 mmol) was dissolved in toluene (10 mL) and cooled to 0° C. HBr (33% (wt) in acetic acid) (311 μL, 1.8 mmol, 1.5 eq) was added dropwise and the reaction was stirred at 0° C. for 6 hours. After the starting material was consumed, the reaction was concentrated under reduced pressure to give a residue. The residue was azeotroped with toluene (3×20 mL) to remove remaining acetic acid and dried in vacuo. The crude product and nicotinamide (220 mg, 1.8 mmol, 1.5 eq) was dissolved in CH$_3$CN (20 mL). The reaction was stirred under Ar gas at room temperature for 24 hours. The reaction was concentrated in vacuo (the temperature was kept below 35° C.) and purified by a flash column chromatography on silica gel to afford the crude product which was then purified via preparative HPLC (C18-A column, 150×10.0 mm, 5 μm) (mobile phase A: 0.1% formic acid (aq), mobile B: 0.1% formic acid in acetonitrile; flow rate=2.0 mL/min; 0-2 min: 0-4% B, 2-4 min: 4-10% B, 4-6 min: 10-20% B, 6-12 min: 20-50% B, 12-17 min: 50-100% B, 17-20 min: 100-0% B) with detection of UV absorbance at 260 nm. Fractions containing the desired product were concentrated and lyophilized to yield the compound B4 (135 mg, 20%) as a colorless solid.

1-((2R,3S,4R,5R)-4-(benzoyloxy)-5-((benzoyloxy)methyl)-3-chlorotetrahydrofuran-2-yl)-3-carbamoylpyridin-1-ium (B4)

$^1$H NMR (400 MHz, CD$_3$OD): δ 4.89-4.93 (m, 1H, CH$_2$, overlap with the water residue peak), 5.01-5.04 (m, 1H, CH), 5.10 (dd, 1H, J=12.0, 6.4 Hz, CH$_2$), 5.42 (dd, 1H, J=4.0, 1.6 Hz, CH), 5.85 (dd, 1H, J=3.2, 1.6 Hz, CH), 7.10

(d, 1H, J=4.0 Hz, CH), 7.48-7.52 (m, 2H, ArH), 7.54-7.58 (m, 2H, ArH), 7.62-7.66 (m, 1H, ArH), 7.68-7.73 (m, 1H, ArH), 8.12-8.14 (m, 2H, ArH), 8.15-8.17 (m, 2H, ArH), 8.36 (dd, 1H, J=8.0, 6.4 Hz, ArH), 9.14 (d, 1H, J=8.0 Hz, ArH), 9.36 (d, 1H, J=6.4 Hz, ArH), 9.66 (s, 1H, ArH); $^{13}$C NMR (100 MHz, CD$_3$OD): δ 62.5, 64.5, 80.4, 85.2, 96.7, 129.2, 129.7, 129.9, 130.8, 130.9, 131.1, 134.7, 135.3, 135.7, 143.3, 144.6, 147.7, 164.7, 166.5, 167.9.

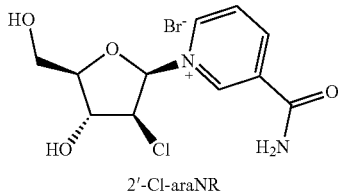

2'-Cl-araNR

General Procedure for the Synthesis of 2'-Cl-araNR

Compound B4 (225 mg, 0.40 mmol) was dissolved in ammonia (20 mL, 7 N in MeOH) and the reaction was stirred at 0° C. for 36 hours. The reaction was concentrated under reduced pressure and the crude product was dissolved in MeOH (0.5 mL). Addition of ethyl ether (10 mL) resulted in ppt of the desired product. The procedure was repeated five times to yield the corresponding desired product 2'-Cl-araNR (82 mg, 58%) as a colorless solid.

3-carbamoyl-1-((2R,3S,4R,5R)-3-chloro-4-hydroxy-5-(hydroxymethyl)tetrahydrofuran-2-yl)pyridin-1-ium bromide (2'-Cl-araNR)

$^1$H NMR (400 MHz, D$_2$O): δ 4.00 (dd, 1H, J=13.2, 2.8 Hz, CH$_2$), 4.14 (dd, 1H, J=13.2, 2.8 Hz, CH$_2$), 4.27 (dt, 1H, J=8.0, 2.8 Hz, CH), 4.52 (t, 1H, J=8.0 Hz, CH), 4.99 (dd, 1H, J=8.4, 6.4 Hz, CH), 6.78 (d, 1H, J=6.4 Hz, CH), 8.30 (dd, 1H, J=8.0, 6.4 Hz, ArH), 9.03 (dt, 1H, J=8.0, 1.6 Hz, ArH), 9.28 (d, 1H, J=6.4 Hz, ArH), 9.76 (s, 1H, ArH); $^{13}$C NMR (100 MHz, D$_2$O): δ 58.5, 61.8, 72.4, 84.5, 95.2, 127.8, 133.7, 141.3, 143.9, 146.1, 165.6.

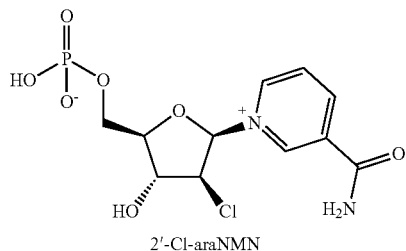

2'-Cl-araNMN

General Procedure for the Synthesis of Compound 2'-Cl-araNMN:

To a stirred solution of 2'-Cl-araNR (71 mg, 0.2 mmol) in trimethyl phosphate (2 mL) was added P(O)Cl$_3$ (130 μL, 1.4 mmol, 7 eq) at 0° C. and the resulting mixture was stirred at 0° C. for 6 hours. A few drops of H$_2$O were then added to quench the reaction. Trimethyl phosphate was removed by extraction with ethyl ether (3×20 mL). The remaining trimethyl phosphate was removed by a second extraction with THF (5 mL). The aqueous layer was concentrated in vacuo and the crude product was dissolved in MeOH (0.5 mL). Addition of ethyl ether (10 mL) resulted in ppt of the desired product. The procedure was repeated four times to yield the desired product 2'-Cl-araNMN (47 mg, 66%) as a colorless solid.

((2R,3R,4S,5R)-5-(3-carbamoylpyridin-1-ium-1-yl)-4-chloro-3-hydroxytetrahydrofuran-2-yl)methyl hydrogen phosphate (2'-Cl-araNMN)

$^1$H NMR (400 MHz, D$_2$O): δ 4.23-4.28 (m, 1H, CH$_2$), 4.34-4.42 (m, 2H, CH$_2$+CH), 4.57 (t, 1H, J=8.0 Hz, CH), 4.99 (dd, 1H, J=8.0, 6.0 Hz, CH), 6.78 (d, 1H, J=6.0 Hz, CH), 8.33 (dd, 1H, J=8.0, 6.4 Hz, ArH), 9.02 (dt, 1H, J=8.0 Hz, ArH), 9.41 (d, 1H, J=6.4 Hz, ArH), 9.44 (s, 1H, ArH); $^{13}$C NMR (100 MHz, D$_2$O): δ 61.6, 62.0 (d, J=4.4 Hz), 72.4, 83.2 (d, J=8.2 Hz), 95.2, 128.3, 133.3, 141.7, 143.2, 146.4, 165.5.

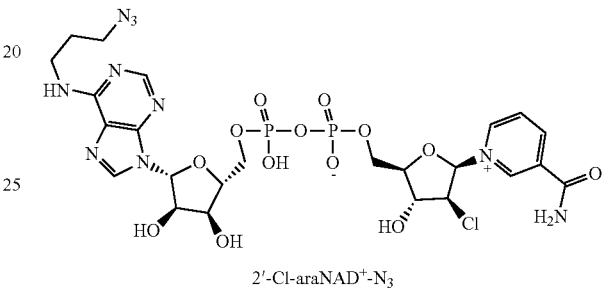

2'-Cl-araNAD$^+$-N$_3$

General Procedure for the Synthesis Compound 2'-Cl-araNAD$^+$-N$_3$:

To a stirred solution of 6-N$_3$-AMP (52 mg, 0.12 mmol, 1.2 eq) in dried DMF (2 mL) were added 1,1-carbonyldiimidazole (CDI) (63 mg, 0.50 mmol, 5 eq) and triethylamine (23 μL, 0.16 mmol. 1.6 eq). The reaction mixture was stirred at room temperature for 14 hours, and then quenched with 0.100 ml dried methanol. The solvent was removed under vacuum and the residue was co-evaporated 3 times each with 1.00 ml of dried DMF. The activated 6-N$_3$-AMP was dissolved in dried DMF (2 mL) and 2'-Cl-araNMN (35 mg, 0.10 mmol, 1.0 eq) was added. After stirring at room temperature for 4 days, H$_2$O (20 mL) was added to quench the reaction at 0° C. The resulting mixture was continued stirring at room temperature for 24 hours. The reaction was then concentrated in vacuo and the crude product was purified via preparative HPLC (C18-A column, 150×10.0 mm, 5 μm) (mobile phase A: 0.1% formic acid (aq), mobile B: 0.1% formic acid in methanol; flow rate=2.0 mL/min; 0-2 min: 0-4% B, 2-4 min: 4-10% B, 4-6 min: 10-20% B, 6-12 min: 20-50% B, 12-14 min: 50-0% B) with detection of UV absorbance at 260 nm. Fractions containing the desired product were concentrated and lyophilized to yield the compound 2'-Cl-araNAD$^+$-N$_3$ (30 mg, 39%) as a colorless solid.

1-((2R,3S,4R,5R)-5-(((((((2R,3S,4R,5R)-5-(6-((3-azidopropyl)amino)-9H-purin-9-yl)-3,4-dihydroxytetrahydrofuran-2-yl)methoxy)(hydroxy)phosphoryl)oxy)oxidophosphoryl)oxy)methyl)-3-chloro-4-hydroxytetrahydrofuran-2-yl)-3-carbamoylpyridin-1-ium (2'-Cl-araNAD$^+$-N$_3$)

$^1$H NMR (400 MHz, D$_2$O): δ 2.01-2.04 (m, 2H, CH$_2$), 3.50-3.53 (m, 2H, CH$_2$), 3.69 (br, 2H, CH$_2$), 4.20-4.28 (m, 2H, CH$_2$), 4.34-4.39 (m, 3H, CH$_2$+CH), 4.49-4.52 (m, 2H, 2CH), 4.55-4.59 (m, 1H, CH), 4.71-4.74 (m, 1H, CH), 4.97

(dd, 1H, J=8.0, 6.4 Hz, CH), 6.12 (d, 1H, J=5.2 Hz, CH), 6.74 (d, 1H, J=6.8 Hz, CH), 8.33 (dd, 1H, J=8.0, 6.4 Hz, ArH), 8.38 (s, 1H, ArH), 8.56 (s, 1H, ArH), 8.97 (d, 1H, J=8.0 Hz, ArH), 9.35 (d, 1H, J=6.4 Hz, ArH), 9.39 (s, 1H, ArH); $^{13}$C NMR (100 MHz, D$_2$O): δ 48.2, 61.4, 70.1, 72.2, 74.47, 74.49, 87.7, 95.2, 128.4, 133.2, 141.4, 141.5, 141.6, 142.1, 146.4, 189.2; HRMS (ESI) for $C_{24}H_{30}ClN_{10}O_{13}P_2Na_2^{+1}$ (M+2Na–H)$^+$: Calcd.: 809.0953 Da; Obs: 809.0970 Da.

General Procedure for the Synthesis of Alkynyl-MMAF:

To a stirred solution of MMAF (4.4 mg, 0.006 mmol), HATU (3.0 mg, 0.0078 mmol, 1.3 eq) and DMAP (0.2 mg, 0.0018 mmol, 0.3 eq) in DMF (0.5 mL) was added a solution of propargyl amine (3.3 mg, 0.06 mmol, 10 eq) and DIPEA (3 μL, 0.018 mmol, 3 eq) in DMF (0.5 mL) at 0° C. Then the reaction mixture was allowed to warm to room temperature and stirred at the same temperature until the reaction completed (monitoring by HPLC). The reaction was concentrated in vacuo and purified via preparative HPLC (C18-A column, 150×10.0 mm, 5 μm) (mobile phase A: 0.1% formic acid (aq), mobile B: 0.1% formic acid in acetonitrile; flow rate=2.0 mL/min; 0-2 min: 0-4% B, 2-4 min: 4-10% B, 4-6 min: 10-20% B, 6-12 min: 20-50% B, 12-17 min: 50-100% B, 17-20 min: 100-0% B) with detection of UV absorbance at 220 nm. Fractions containing the desired product were concentrated and lyophilized to yield the compound alkynyl-MMAF (2.5 mg, 54%) as a colorless solid. MS (ESI) for $C_{42}H_{69}N_6O_7^{+1}$ (M+H)$^+$ Obs: 769.5 Da.

General Procedure for the Synthesis of 2'-Cl-araNAD$^+$-MMAF:

To a stirred solution of 2'-Cl-araNAD$^+$-N$_3$ (7.7 mg, 0.01 mmol), CuSO$_4$·5H$_2$O (10.0 mg, 0.04 mmol, 4 eq) in H$_2$O (0.5 mL) were added a solution of alkynyl-MMAF (9.2 mg, 0.012 mmol, 1.2 eq) in DMSO (0.2 mL), THPTA (86.9 mg, 0.2 mmol, 20 eq) and sodium-L-ascorbate (63.4 mg, 0.32 mmol, 32 eq) at room temperature. Then the reaction mixture was stirred at the same temperature until the reaction completed (monitoring by HPLC). The reaction was purified via preparative HPLC (C18-A column, 150×10.0 mm, 5 μm) (mobile phase A: 0.1% formic acid (aq), mobile B: 0.1% formic acid in acetonitrile; flow rate=2.0 mL/min; 0-2 min: 0-4% B, 2-4 min: 4-10% B, 4-6 min: 10-20% B, 6-12 min: 20-50% B, 12-17 min: 50-100% B, 17-20 min: 100-0% B) with detection of UV absorbance at 260 nm. Fractions containing the desired product were concentrated and lyophilized to yield the compound 2'-Cl-araNAD$^+$-MMAF (8.4 mg, 55%) as a colorless solid. HRMS (ESI) for $C_{66}H_{97}ClN_{16}O_{20}P_2Na_2^{2+}$ (M+2Na-2H)$^{2+}$: Calcd.: 789.3085 m/z; Obs: 789.3092 m/z.

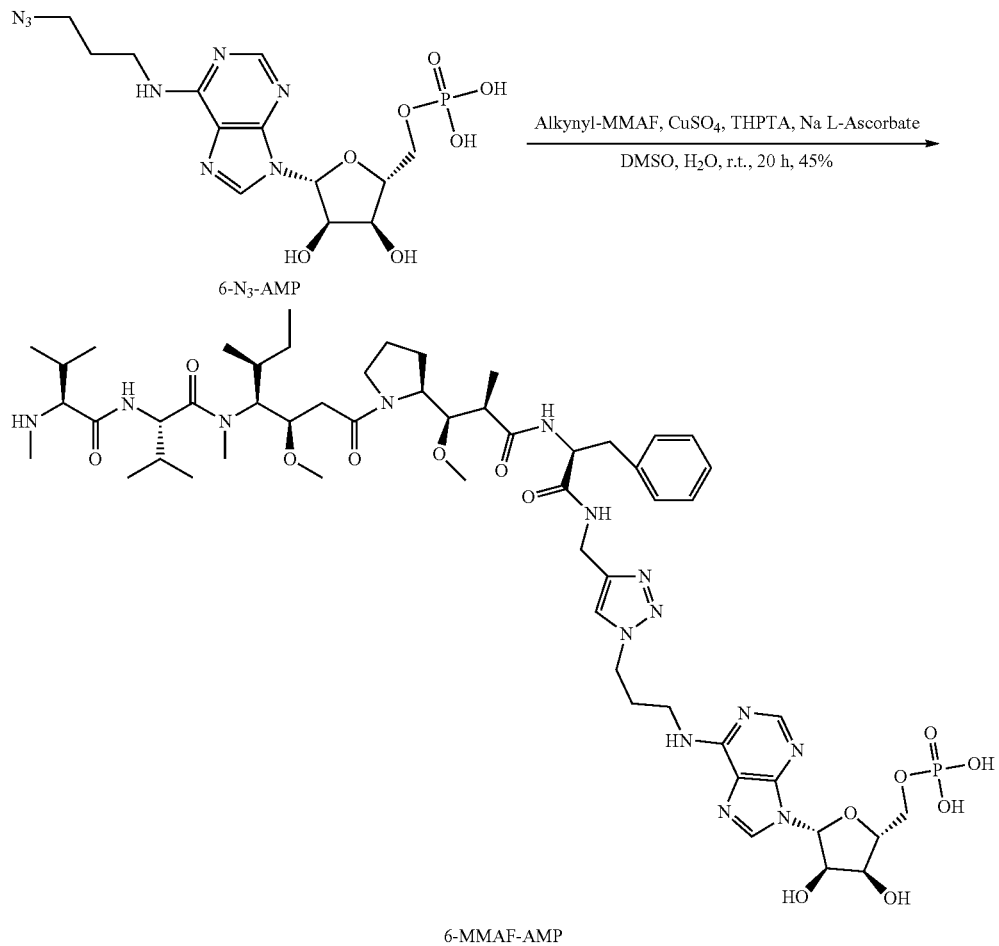

6-MMAF-AMP

General Procedure for the Synthesis of 6-MMAF-AMP:

To a solution of 6-N$_3$-AMP (0.24 mg, 0.56 μmol), CuSO$_4$·5H$_2$O (0.56 mg, 2.24 μmol, 4 eq) in H$_2$O (80 μL) were added a solution of alkynyl-MMAF (0.52 mg, 0.67 μmol, 1.2 eq) in DMSO (20 μL), THPTA (4.87 mg, 11.2

µmol, 20 eq) and sodium-L-ascorbate (3.55 mg, 17.92 µmol, 32 eq) at room temperature. Then the reaction mixture was stirred at the same temperature until the reaction completed (monitoring by HPLC). The reaction was purified via preparative HPLC (C18-A column, 150×4.6 mm, 5 µm) (mobile phase A: 0.1% formic acid (aq), mobile B: 0.1% formic acid in acetonitrile; flow rate=1.0 mL/min; 0-2 min: 0-4% B, 2-4 min: 4-10% B, 4-6 min: 10-20% B, 6-12 min: 20-50% B, 12-17 min: 50-100% B, 17-20 min: 100-0% B) with detection of UV absorbance at 260 nm. Fractions containing the desired product were concentrated and lyophilized to yield the compound 6-MMAF-AMP (0.3 mg, 45%) as a colorless solid. MS (ESI) for $C_{55}H_{88}N_{14}O_{14}P^+$ (M+H)$^+$: Calcd:1199.6 m/z; Obs: 1199.5 m/z.

General Procedure for the Synthesis of 6-MMAF-Adenosine:

To a solution of 6-N$_3$-Adenosine (A3) (0.20 mg, 0.56 µmol), CuSO$_4$.5H$_2$O (0.56 mg, 2.24 µmol, 4 eq) in H$_2$O (80 µL) were added a solution of alkynyl-MMAF (0.52 mg, 0.67 µmol, 1.2 eq) in DMSO (20 µL), THPTA (4.87 mg, 11.2 µmol, 20 eq) and sodium-L-ascorbate (3.55 mg, 17.92 µmol, 32 eq) at room temperature. Then the reaction mixture was stirred at the same temperature until the reaction completed (monitoring by HPLC). The reaction was purified via preparative HPLC (C18-A column, 150×4.6 mm, 5 µm) (mobile phase A: 0.1% formic acid (aq), mobile B: 0.1% formic acid in acetonitrile; flow rate=1.0 mL/min; 0-2 min: 0-4% B, 2-4 min: 4-10% B, 4-6 min: 10-20% B, 6-12 min: 20-50% B,

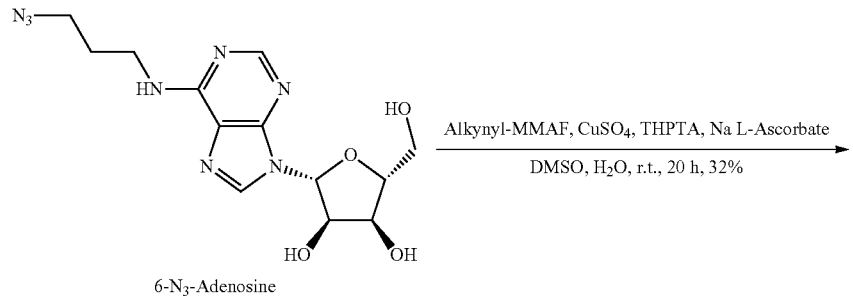

6-N$_3$-Adenosine

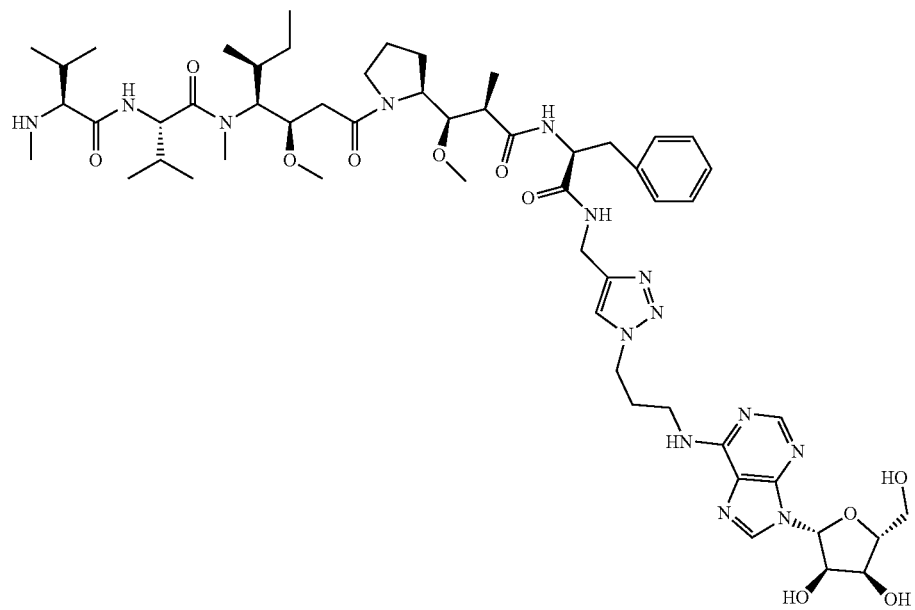

6-MMAF-Adenosine 12-17 min: 50-100% B, 17-20 min: 100-0% B) with detection of UV absorbance at 260 nm. Fractions containing the desired product were concentrated and lyophilized to yield the compound 6-MMAF-Adenosine (0.2 mg, 32%) as a colorless solid. MS (ESI) for $C_{55}H_{87}N_{14}O_{11}^+$ (M+H)$^+$: Calcd: 1119.7 m/z; Obs: 1119.7 m/z.

was purified via preparative HPLC (C18-A column, 150×4.6 mm, 5 μm) (mobile phase A: 0.1% formic acid (aq), mobile B: 0.1% formic acid in acetonitrile; flow rate=1.0 mL/min; 0-2 min: 0-4% B, 2-4 min: 4-10% B, 4-6 min: 10-20% B, 6-12 min: 20-50% B, 12-17 min: 50-100% B, 17-20 min: 100-0% B) with detection of UV absorbance at 260 nm.

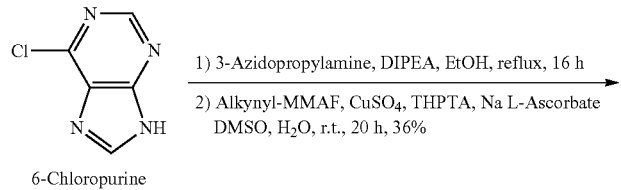

6-Chloropurine

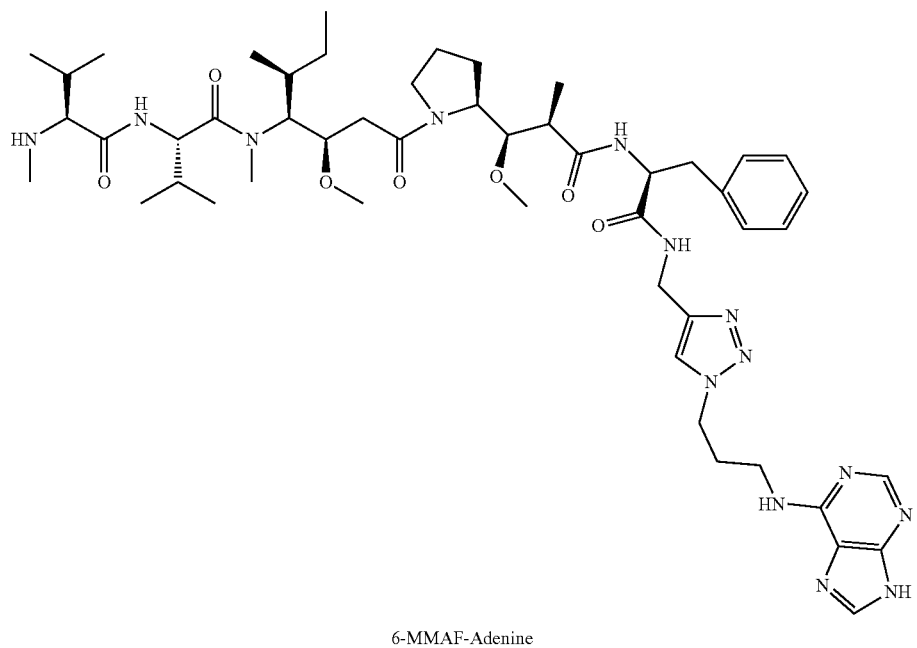

6-MMAF-Adenine

General Procedure for the Synthesis of 6-MMAF-Adenine:

To a solution of 6-chloropurine (8.7 mg, 56.0 μmol) in EtOH (1.0 mL) were added 3-azidopropylamine (A2) (6.2 mg, 61.6 μmol, 1.1 eq) and DIPEA (29.5 μL, 168.0 μmol, 3 eq) at room temperature. Then the resulting mixture was heated to reflux until the reaction completed (monitoring by HPLC). Then the solvent was removed under reduced pressure to give a residue. The residue was dissolved in DMSO (1.0 mL) to form a solution of 6-N$_3$-Adenine. To a solution of alkynyl-MMAF (0.52 mg, 0.67 μmol, 1.2 eq) in DMSO (20 μL) was added above prepared solution of 6-N$_3$-Adenine (10 μL), CuSO$_4$·5H$_2$O (0.56 mg, 2.24 μmol, 4 eq), THPTA (4.87 mg, 11.2 μmol, 20 eq) and sodium-L-ascorbate (3.55 mg, 17.92 μmol, 32 eq) at room temperature. Then the reaction mixture was stirred at the same temperature until the reaction completed (monitoring by HPLC). The reaction Fractions containing the desired product were concentrated and lyophilized to yield the compound 6-MMAF-Adenine (0.2 mg, 36%) as a colorless solid. MS (ESI) for $C_{50}H_{79}N_{14}O_7^+$ (M+H)$^+$: Calcd: 987.6 m/z; Obs: 987.7 m/z.

Example 2. Site-Specific Antibody-Drug Conjugates with ADP-Ribosyl Cyclases

Figure 4:
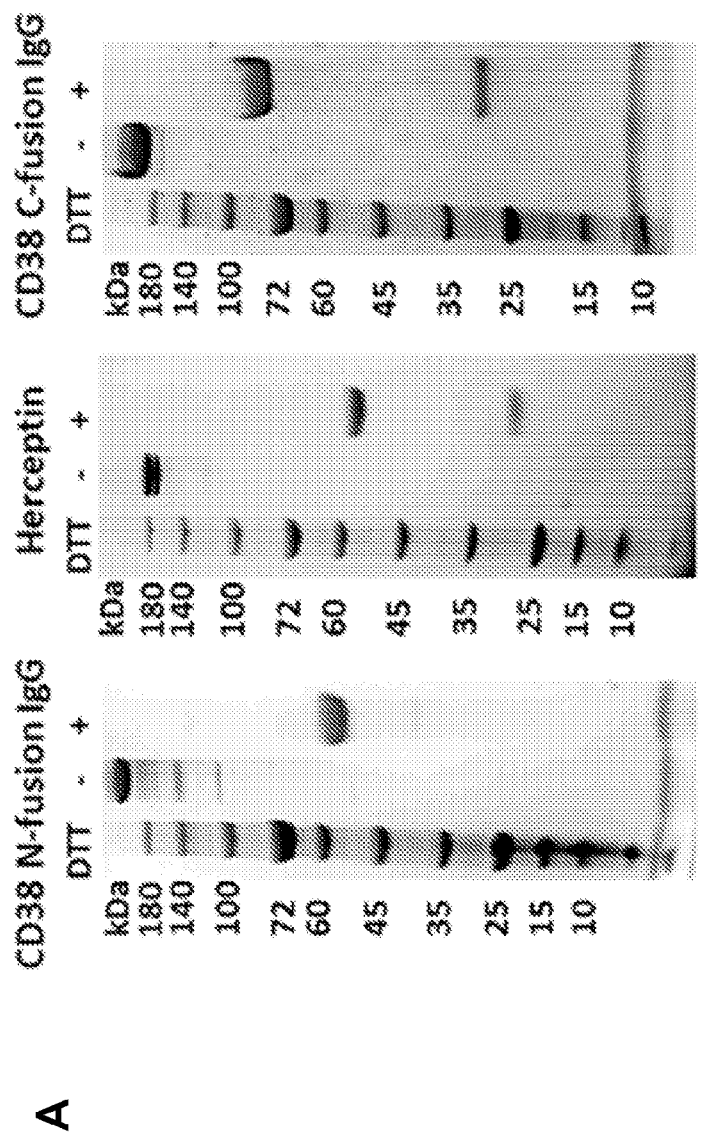
FIG. 4 illustrates purified antibody and antibody fusions and chemical synthesis of 6-azido-2'-Cl-araNAD$^+$ (2'-Cl-araNAD$^+$-$N_3$). (A) SDS-PAGE gels of purified antibody and antibody fusions stained by Coomassie blue. (B) g-COSY spectra of B4 (solvent: $CD_3OD$). (C) NOESY spectra of B4 (solvent: $CD_3OD$)
Figure 4:
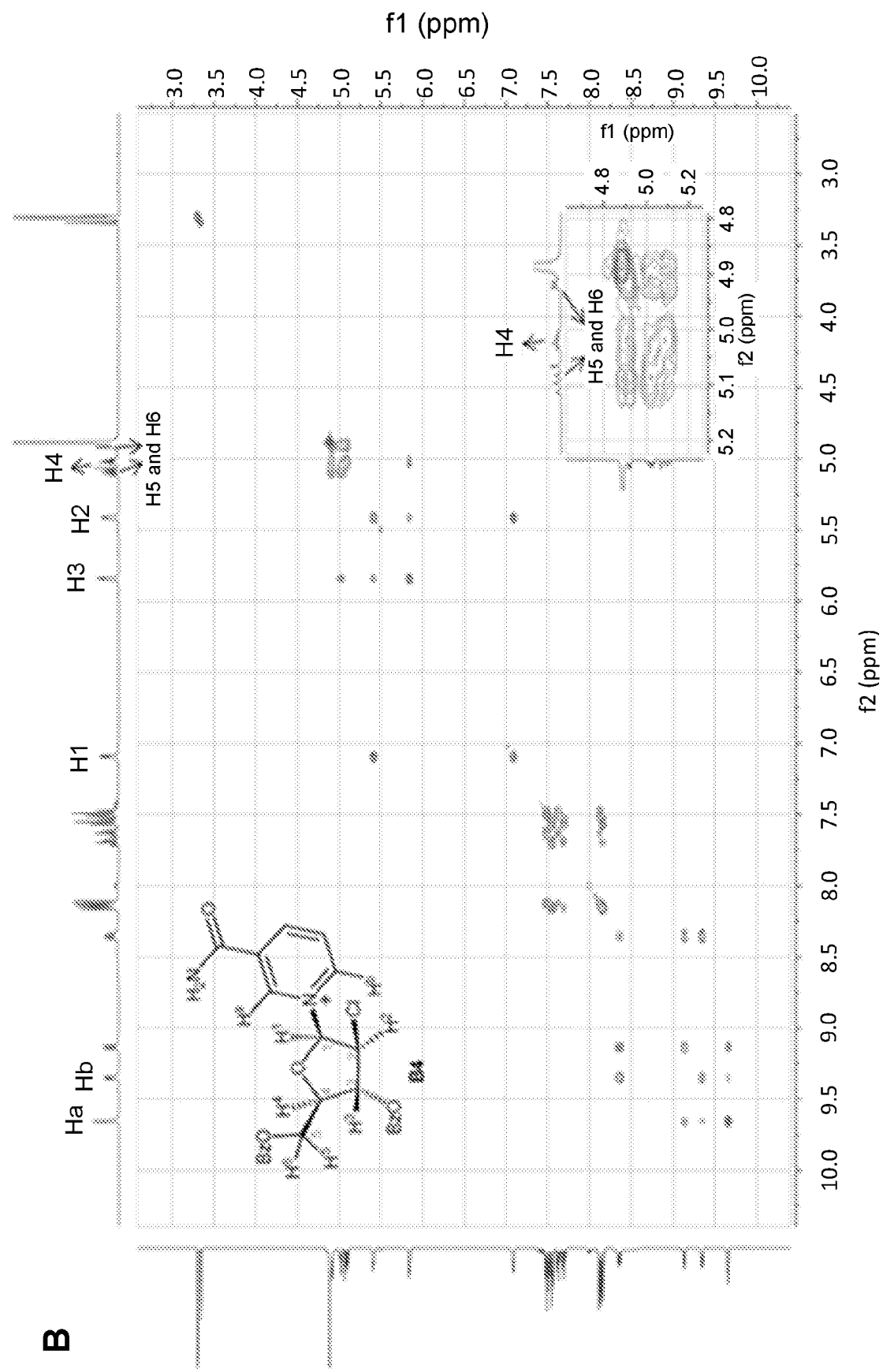
Figure 4:
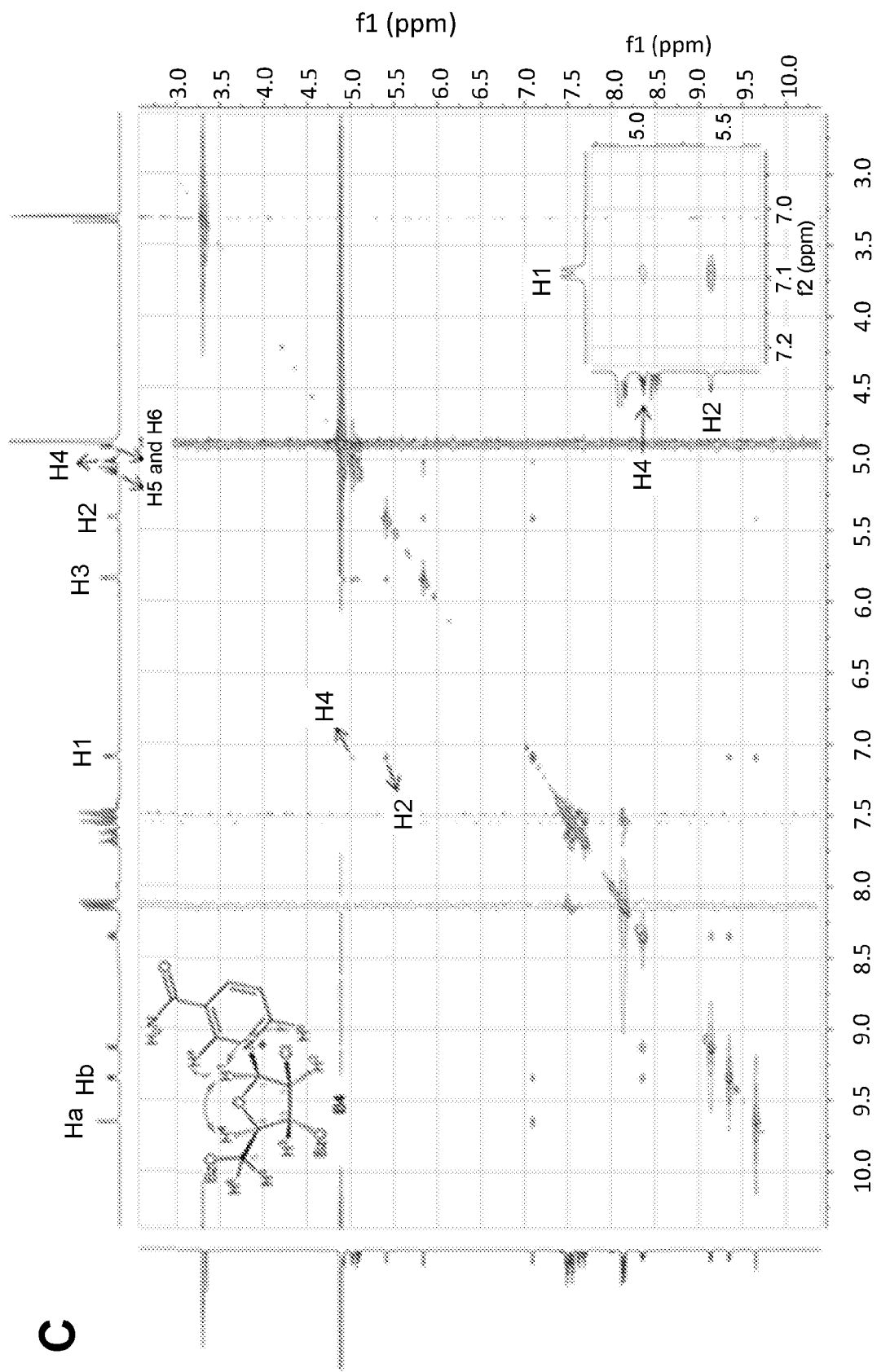

To create ARC-ADCs, full-length anti-human HER2 antibody Herceptin was used as a model antibody. Based on x-ray structures of Herceptin fragment antigen-binding (Fab), IgG fragment crystallizable (Fc) region, and CD38 extracellular domain, we reasoned that genetic fusion of CD38 catalytic domain to the light chain N-terminus or heavy chain C-terminus of Herceptin may result in bifunctional fusion proteins with retained HER2-binding affinity and CD38 enzymatic activity. To this end, a flexible GGS peptide linker was genetically inserted between CD38 catalytic domain and Herceptin light/heavy chain. The designed CD38 fusion proteins designated as CD38 N-fusion IgG and CD38 C-fusion IgG (FIG. 1A) together with Herceptin IgG were expressed in mammalian cells and purified to homogeneity (FIG. 4A). The yields are ~12 mg/L for CD38 N-fusion IgG and 9.5 mg/L for CD38 C-fusion IgG, slightly lower than that of Herceptin (15 mg/L). Their binding affinity to HER2 receptor was then examined by ESLIA. Compared with CD38 N-fusion IgG with an $EC_{50}$ of 8.32±0.99 nM for recombinant HER2, CD38 C-fusion IgG displays higher binding affinity ($EC_{50}$ of 1.02±0.47 nM), comparable to that of Herceptin ($EC_{50}$=0.80±0.10 nM) (FIG. 1B). Thus, CD 38 C-fusion IgG was chosen for analysis of its CD38 enzymatic activity. Fluorescence-based activity assays revealed that in contrast to CD38 catalytic domain, CD38 C-fusion IgG exhibits significantly higher activity for nicotinamide guanine dinucleotide ($NGD^+$) (FIG. 1C). These results indicate that genetic fusion of CD38 catalytic domain to Herceptin has little effects on antibody binding and its enzymatic activity.

To create functionalized CD38 covalent inhibitors as drug linkers for ARC-ADCs, we envisioned that relative to 2'-F-araNAD$^+$-derived analogues, 2'-Cl-substituted NAD$^+$ analogues may act as CD38 covalent inhibitors with improved stability for the arabinosyl-ester bonds formed with CD38 E226 residue. Moreover, structural analysis of CD38 indicated that the adenine moiety of NAD$^+$ is largely solvent exposed and has limited interactions with surrounding residues. Additionally, the pyrophosphate diester bond within NAD$^+$ revealed excellent plasma stability and rapid release of payloads upon cellular internalization for ADCs. We thus designed and synthesized a novel 2'-Cl-araNAD$^+$ analogue with an azido group at N6 of adenine (2'-Cl-araNAD$^+$-N$_3$) (FIGS. 1D and Schemes 4A and 4B).

Scheme 4A:

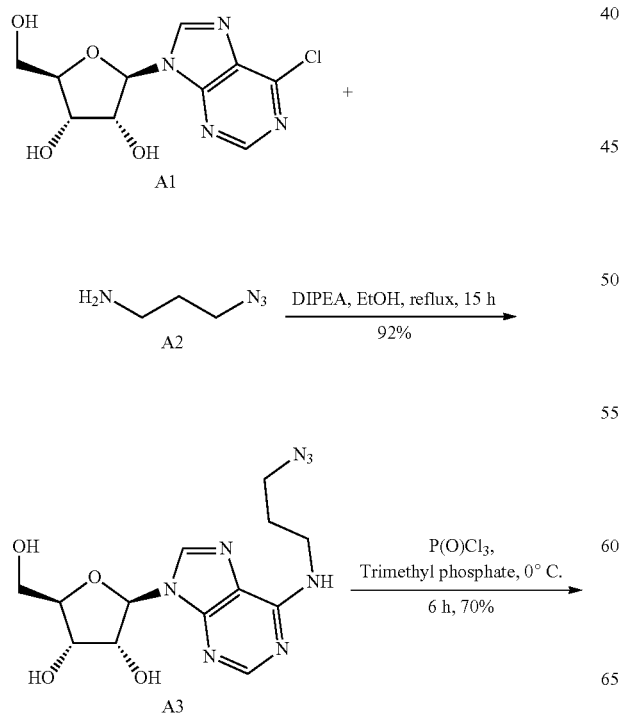

Scheme 4B:

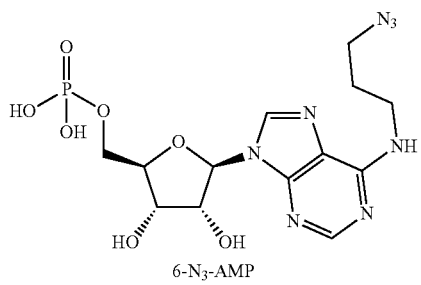

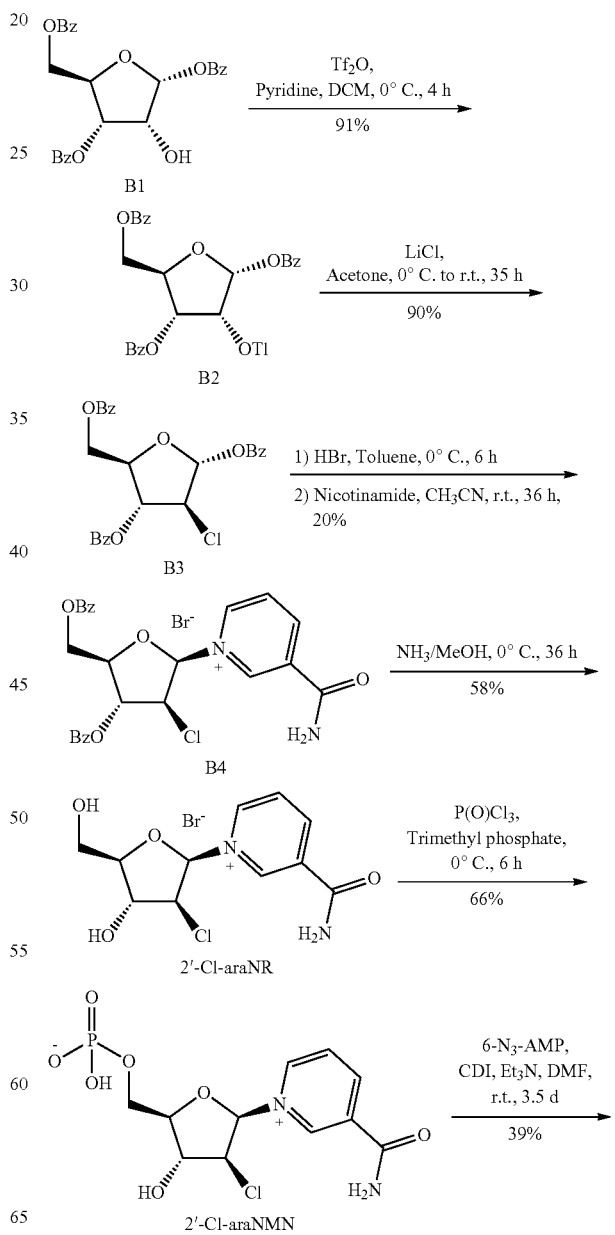

-continued

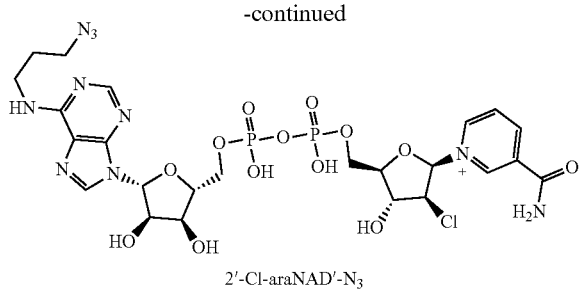

2'-Cl-araNAD'-N₃

The stereochemistry of the intermediate O-benzoyl protected 2'-Cl-arabinose nicotinamide riboside (2'-Cl-araNR) (Scheme 4C) was determined as β-isomer based on ¹H-¹H COSY and subsequent NOESY experiments (FIGS. 4B-C). Scheme 4C:

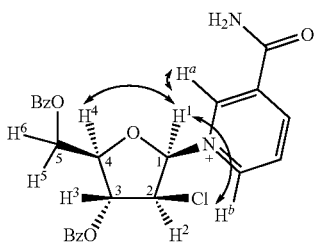

Figure 5:
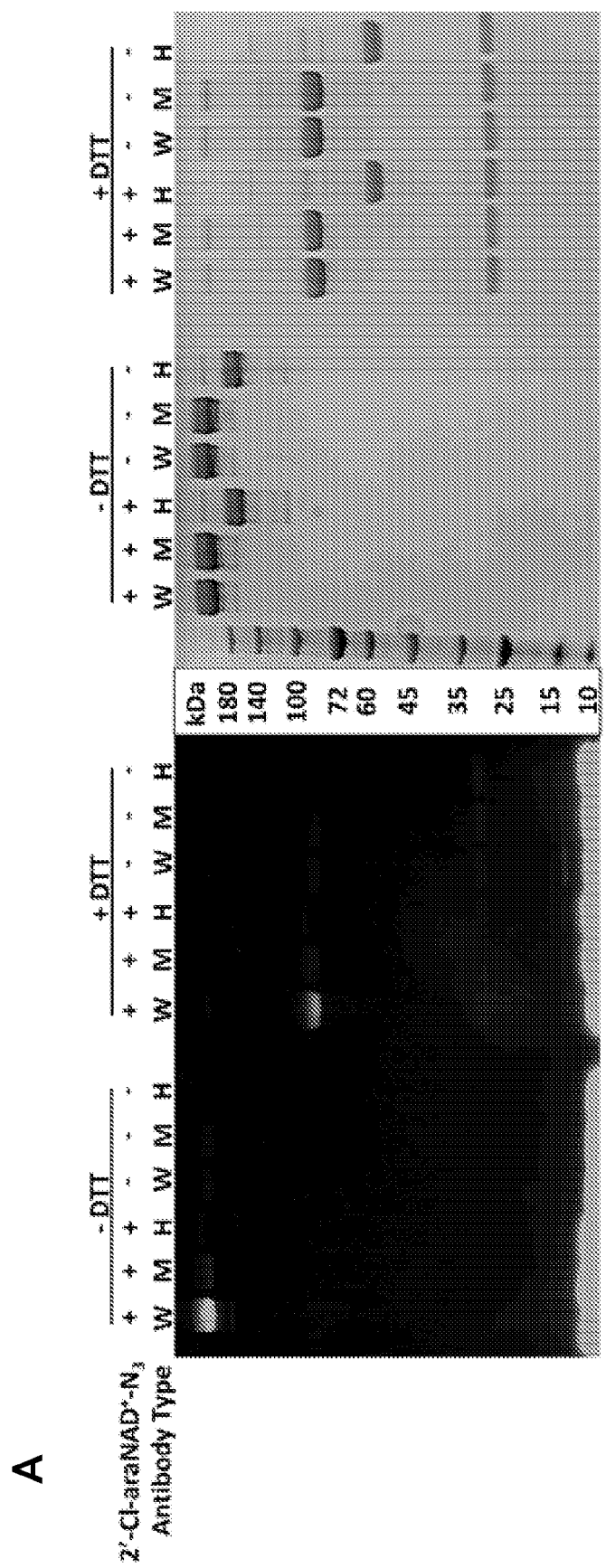
FIG. 5 illustrates Alexa Fluor 488 conjugation and cellular uptake of CD38 C-fusion IgG. (A) Conjugation of CD38 C-fusion IgG with Alexa Fluor 488. CD38 C-fusion IgG wild-type, CD38 C-fusion IgG E226Q mutant, and Herceptin, which are shown as 'W', 'M', and 'H' in the figures, respectively, were incubated without and with 2'-Cl-araNAD$^+$-$N_3$ on ice for 2 hours, followed by incubation with Alexa Fluor 488-DBCO for 30-min on ice, SDS-PAGE analysis without and with DTT, and in-gel fluorescence imaging (left) and Coomassie staining (right). (B) Confocal microscopy of selective cellular uptake of Alexa Fluor 488-conjugated CD38 C-fusion IgG. HCC1954 (HER2++) and MDA-MB-468 (HER2-) cells were incubated with conjugates for 2 hours at 4° C. or 37° C. with 5% $CO_2$, followed by washing with DPBS, fixation, permeabilization for DAPI staining, and confocal imaging.
Figure 5:
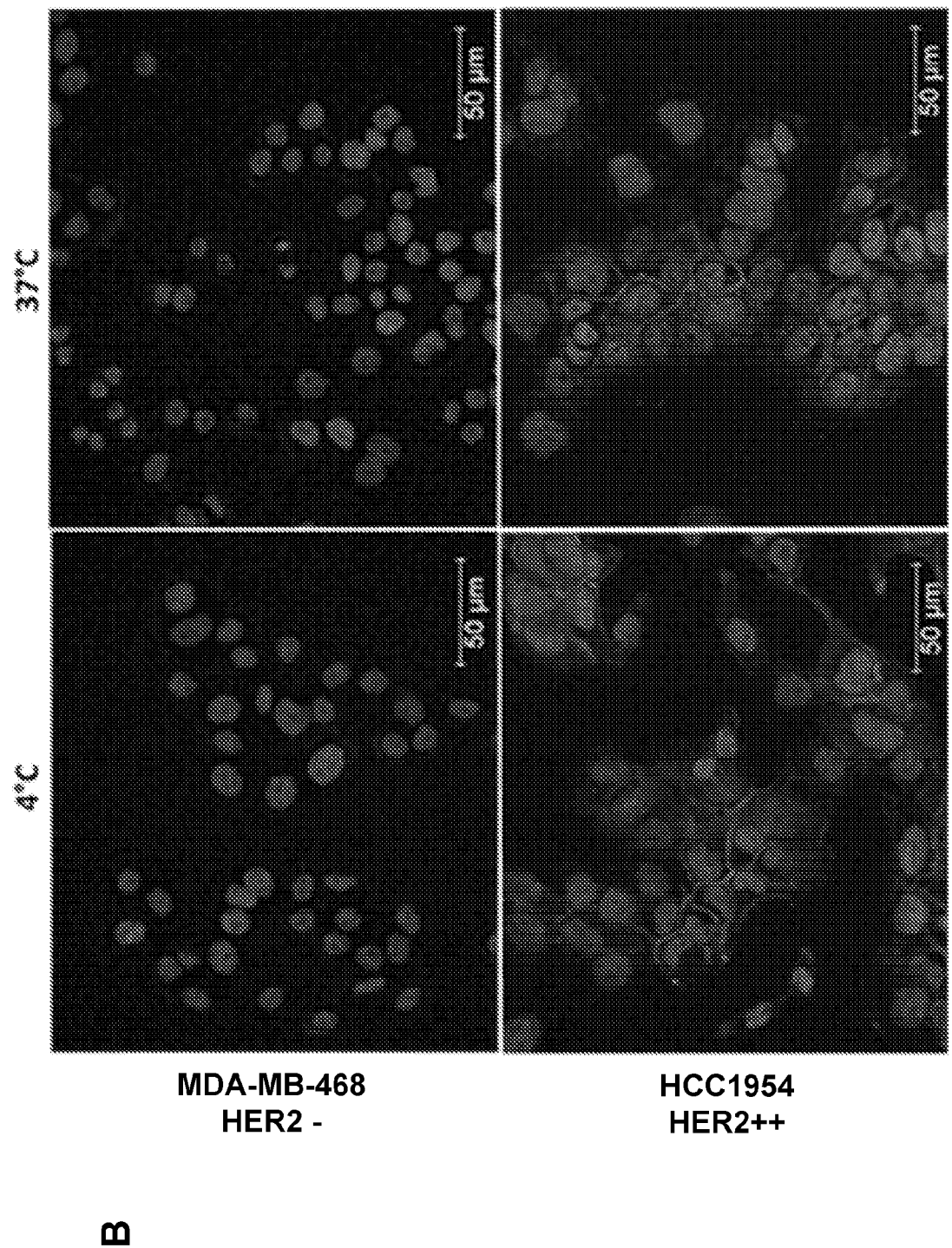

Fluorescence-based activity assays indicated that 2'-Cl-araNAD⁺-N₃ could inactivate CD38 C-fusion IgG with a $k_{inact}$ of 0.0039±0.0007 s⁻¹ (FIG. 1E). To confirm CD38 C-fusion IgG is covalently labeled at E226 by 2'-Cl-araNAD⁺-N₃, the E226 residue was mutated to glutamine, which was shown to abolish catalytic activity of CD38. CD38 C-fusion IgG, its mutant (E226), and Herceptin were then incubated without and with 2'-Cl-araNAD⁺-N₃, followed by conjugation with Alex Fluor 488-DBCO via click chemistry. In-gel fluorescence imaging and Coomassie stained SDS-PAGE gels revealed that only the heavy chain of wild-type CD38 C-fusion IgG was labeled with fluorescent dyes (FIG. 5A). These results suggest that E226 of CD38 C-fusion IgG is the conjugation site.

Figure 6:
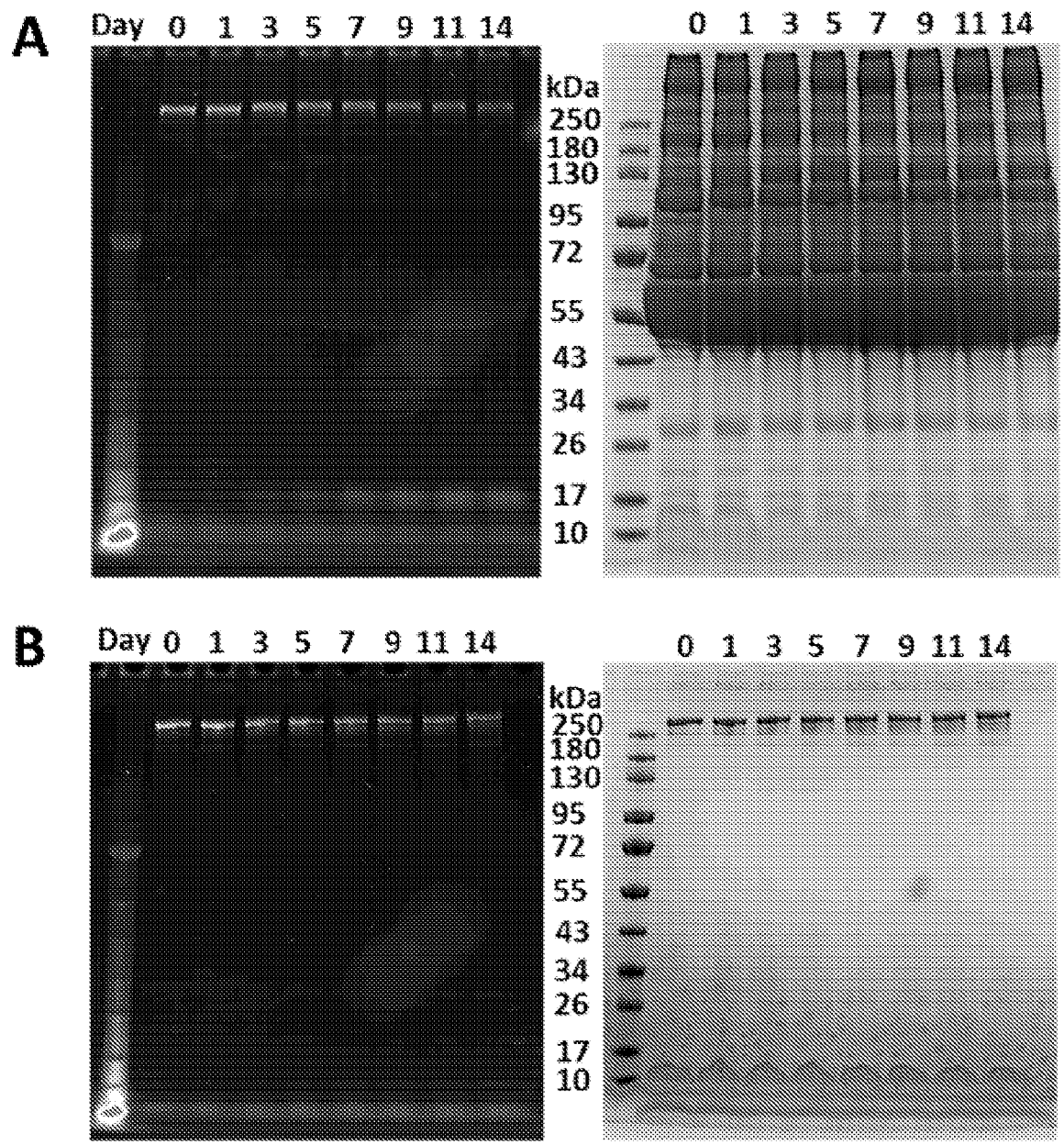
FIG. 6 illustrates stability of Alexa Fluor 488-conjguated CD38 C-fusion IgG and fluorescein-labeled exendin-4 in mouse plasma and PBS. (A) and (B) Stability of Alexa Fluor 488-conjugated CD38 C-fusion IgG in mouse plasma and PBS. Alexa Fluor 488-conjugated CD38 C-fusion IgG was incubated in (A) mouse plasma or (B) PBS at 37° C. for up to 14 days, followed by (left) in-gel fluorescence imaging and (right) Coomassie staining. (C) and (D) Stability of fluorescein-labeled exendin-4 in mouse plasma and PBS. Fluorescein-labeled exendin-4 was incubated in (C) mouse plasma or (D) PBS at 37° C. for up to 11 days, followed by (left) in-gel fluorescence imaging and (right) Coomassie staining. (E)-(H) Quantification of fluorescence intensities for intact Alexa Fluor 488-conjugated CD38 C-fusion IgG in (E) mouse plasma and (F) PBS and fluorescein-labeled exendin-4 in (G) mouse plasma and (H) PBS.
Figure 6:
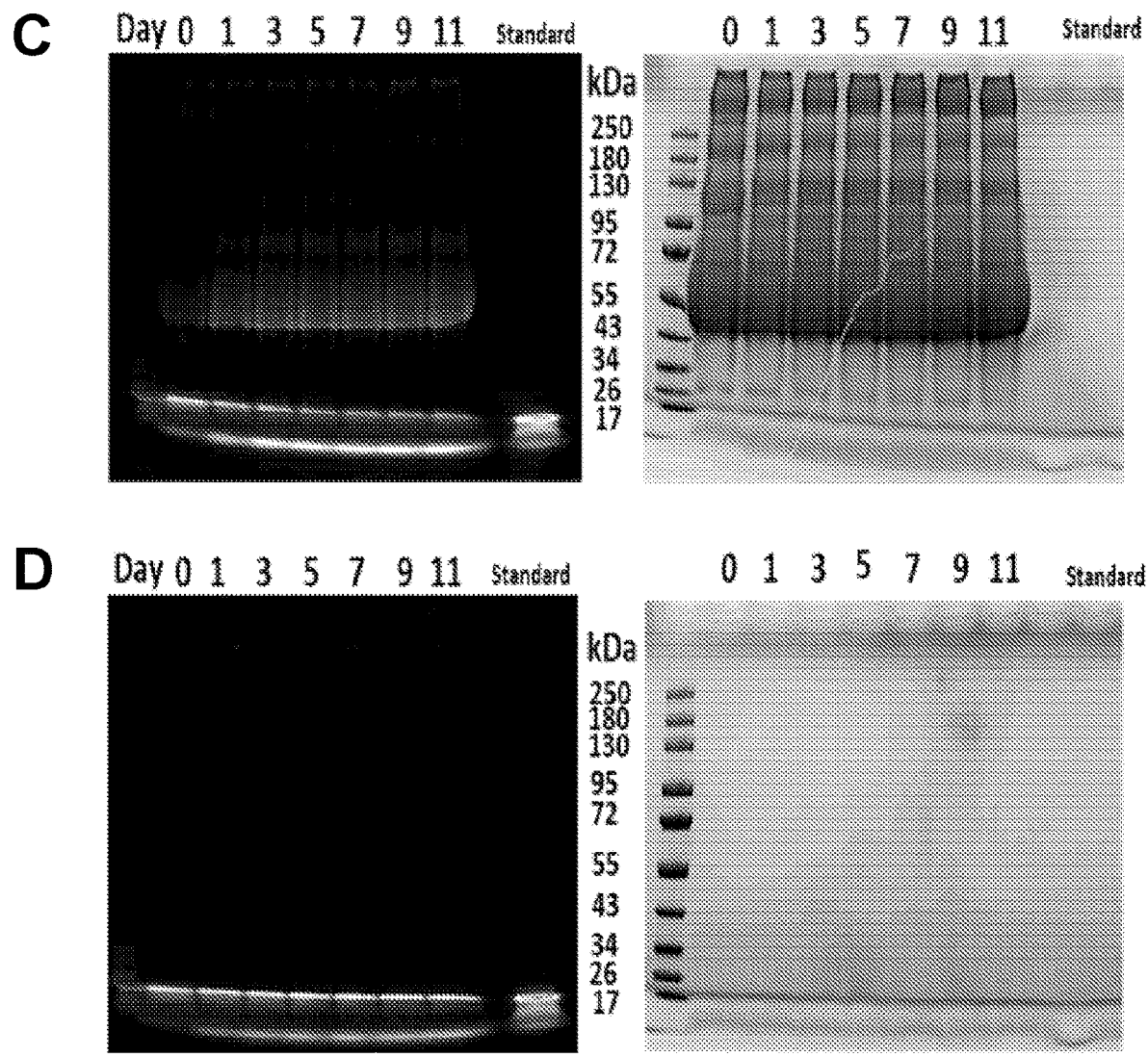
Figure 6:
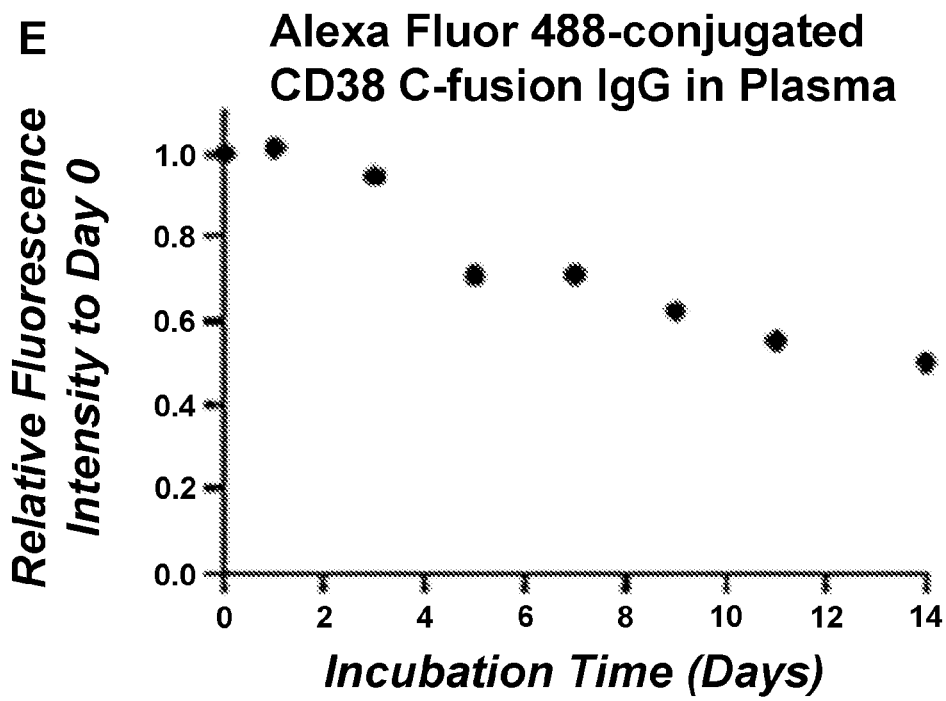
Figure 6:
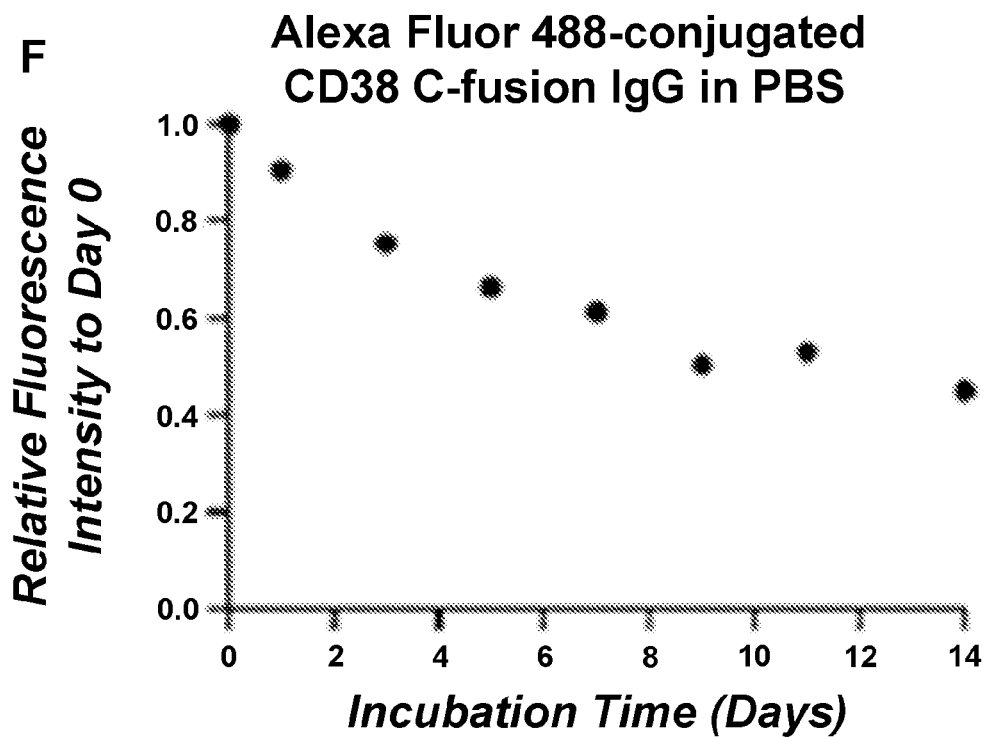
Figure 6:
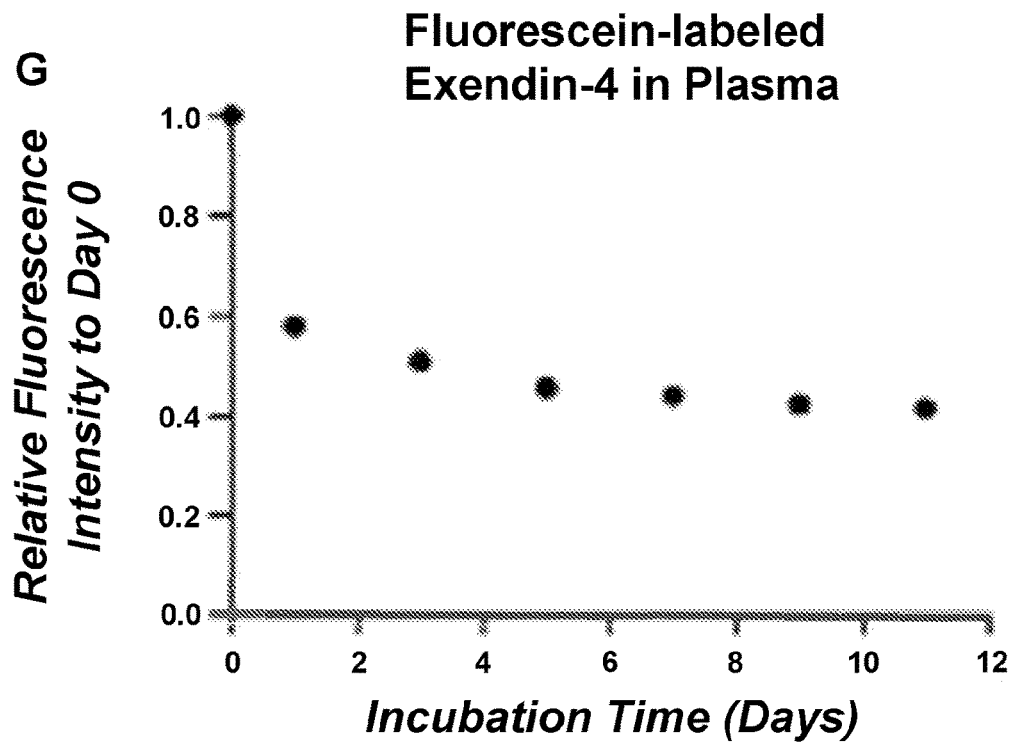
Figure 6:
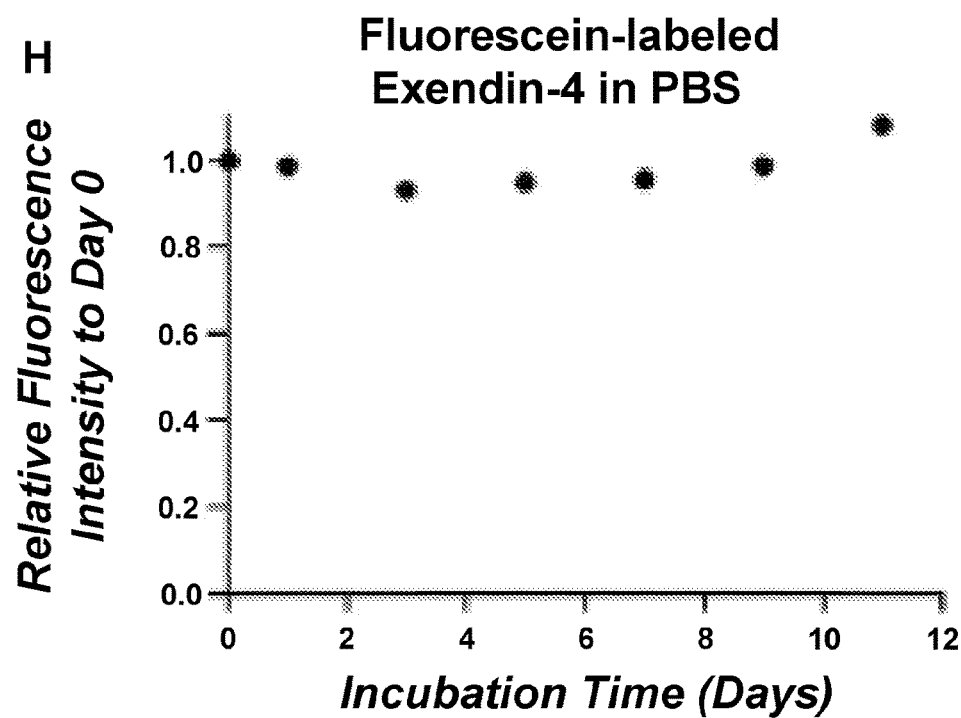

Using Alexa Fluor 488-conjugated CD38 C-fusion IgG, cellular uptake assays were performed. Confocal microscopy indicated that fluorescently labeled CD38 C-fusion IgG could be selectively internalized into HER2-positive HCC1954 cells, whereas HER2-negative MDA-MB-468 cells showed no detectable uptake (FIG. 5B). Notably, in-gel fluorescence imaging revealed that a substantial portion of Alexa Fluor 488-conjugated CD38 C-fusion IgG remained intact after 14-day incubation in mouse plasma at 37° C. (FIGS. 1F and 6), supporting excellent stability for the 2'-Cl-araNAD⁺-N₃-based linker.

Figure 2:
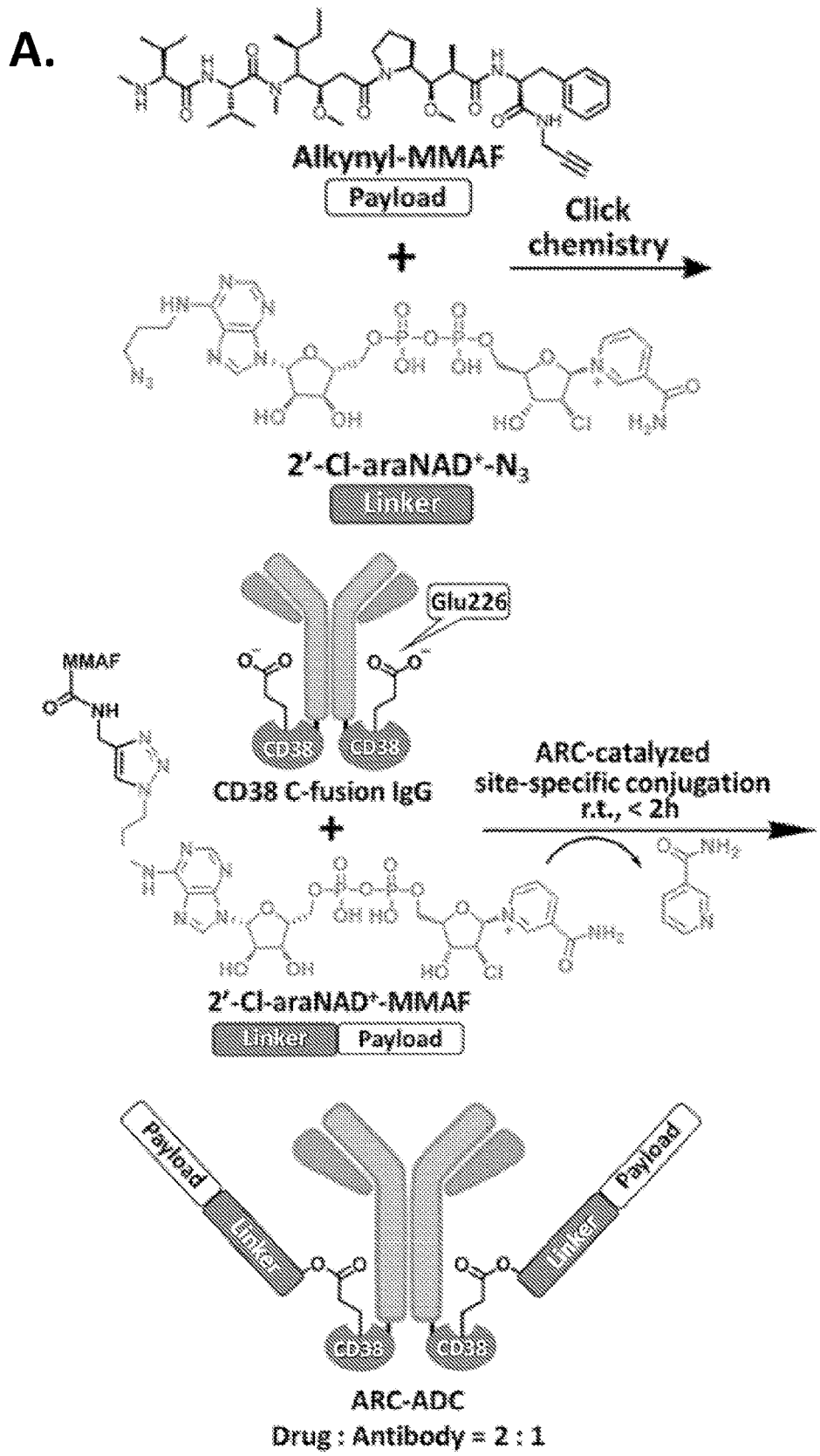
FIG. 2 illustrates the generation and in vitro evaluation of anti-HER2 ARC-ADC. (A) Scheme for generating anti-HER2 ARC-ADC. (B) Conjugation kinetics of drug-linker to CD38 C-fusion IgG. 2'-Cl-araNAD$^+$-MMAF (1 mM) was incubated with CD38 C-fusion IgG (10 µM) in 50 mM Tris buffer (pH 8.5) for various amounts of time on ice. The residual enzymatic activity determined by fluorescence-based activity assays was plotted as a function of incubation time. (C) and (D) Mass spectra of light chains (C) and heavy chains (D) for CD38 C-fusion IgG and anti-HER2 ARC-ADC. (E) X-ray structure of human CD38 catalytic domain with 2'-Cl-araNAD$^+$ covalently attached to Glu226 residue. (F) Flow cytometric analysis of HER2 expression for four breast cancer cell lines. (G)-(J) In vitro cytotoxicity of anti-HER2 ARC-ADC. HCC1954 (G), MCF7 (H), MDA-MB-231 (I), and MDA-MB-468 (J) cells with varied levels of HER2 expression were incubated for 72 hours at 37° C. with 5% $CO_2$ in the presence of various concentrations of ARC-ADC, 2'-Cl-araNAD+-MMAF, Herceptin, and CD38 C-fusion IgG. Cell viability was measured by MTT assays. Cells treated with culture media and 5 µM paclitaxel were included as 100% viability and 0% viability controls, respectively.
Figure 2:
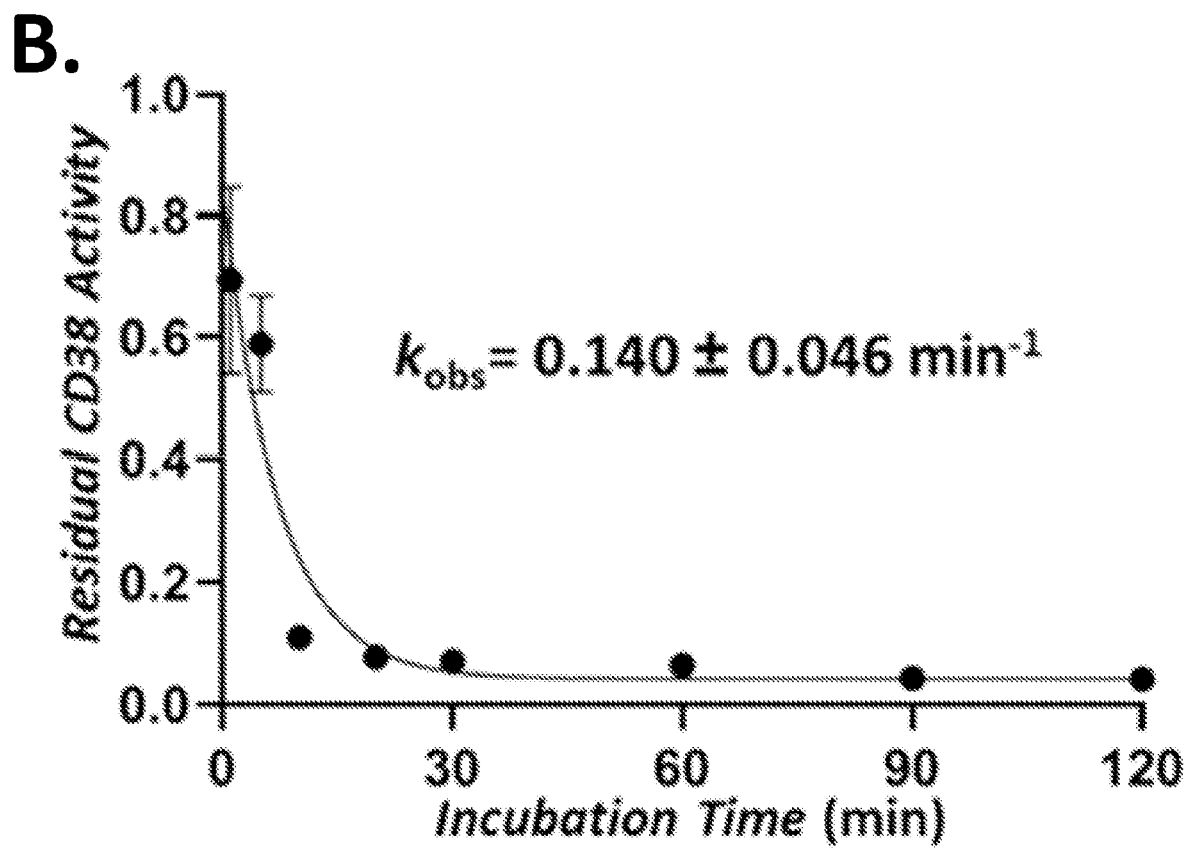
Figure 2:
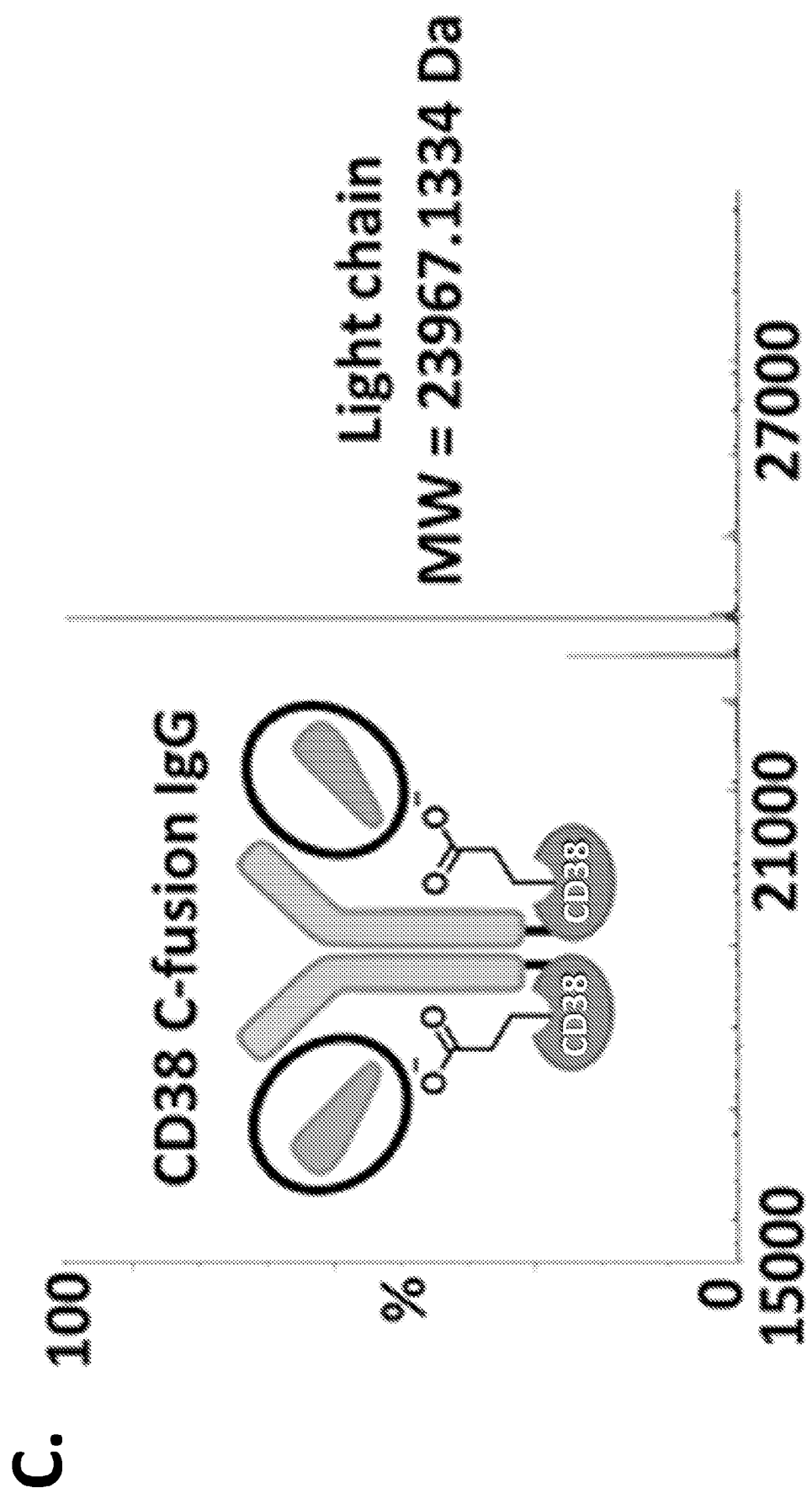
Figure 2:
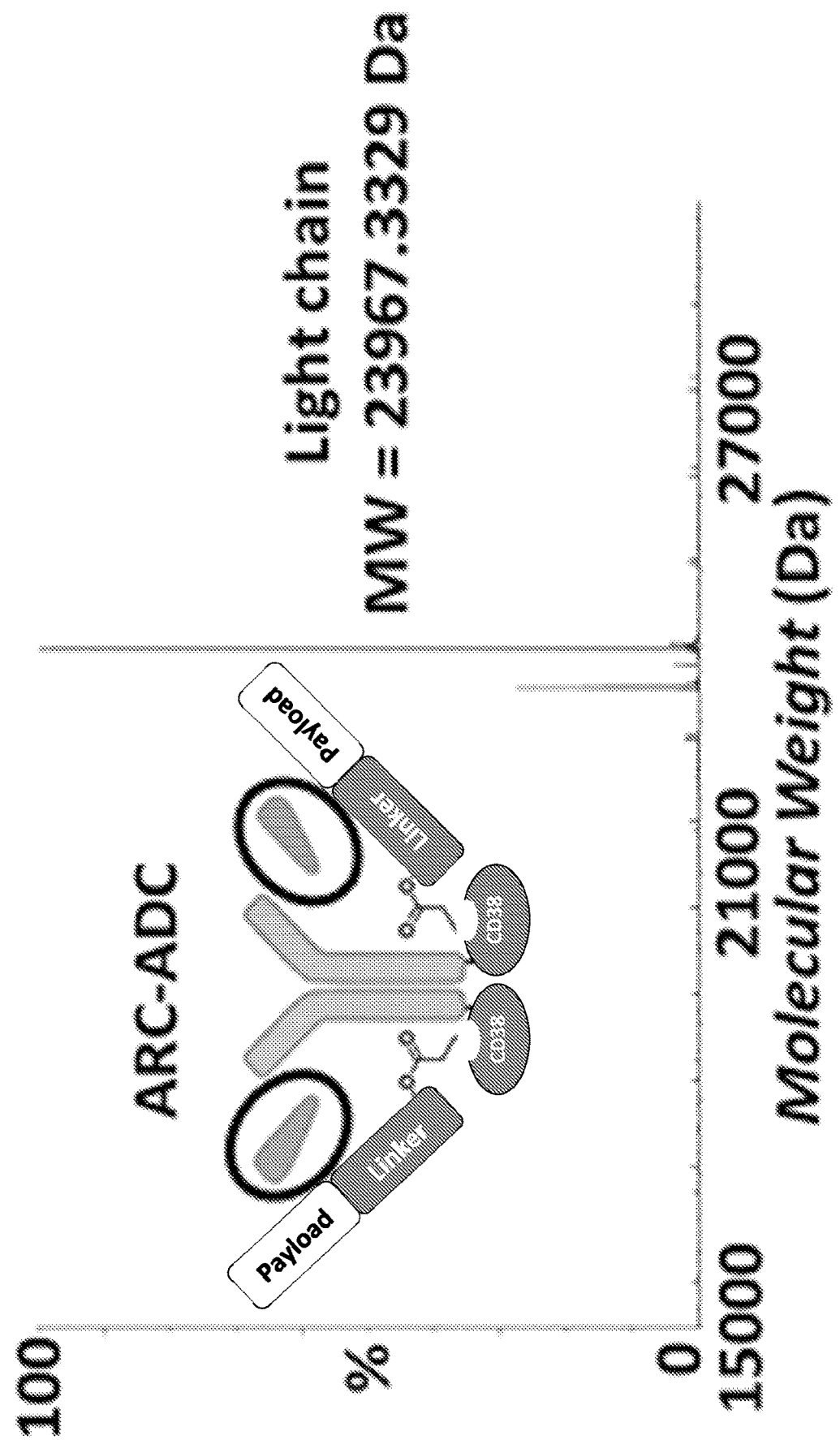
Figure 2:
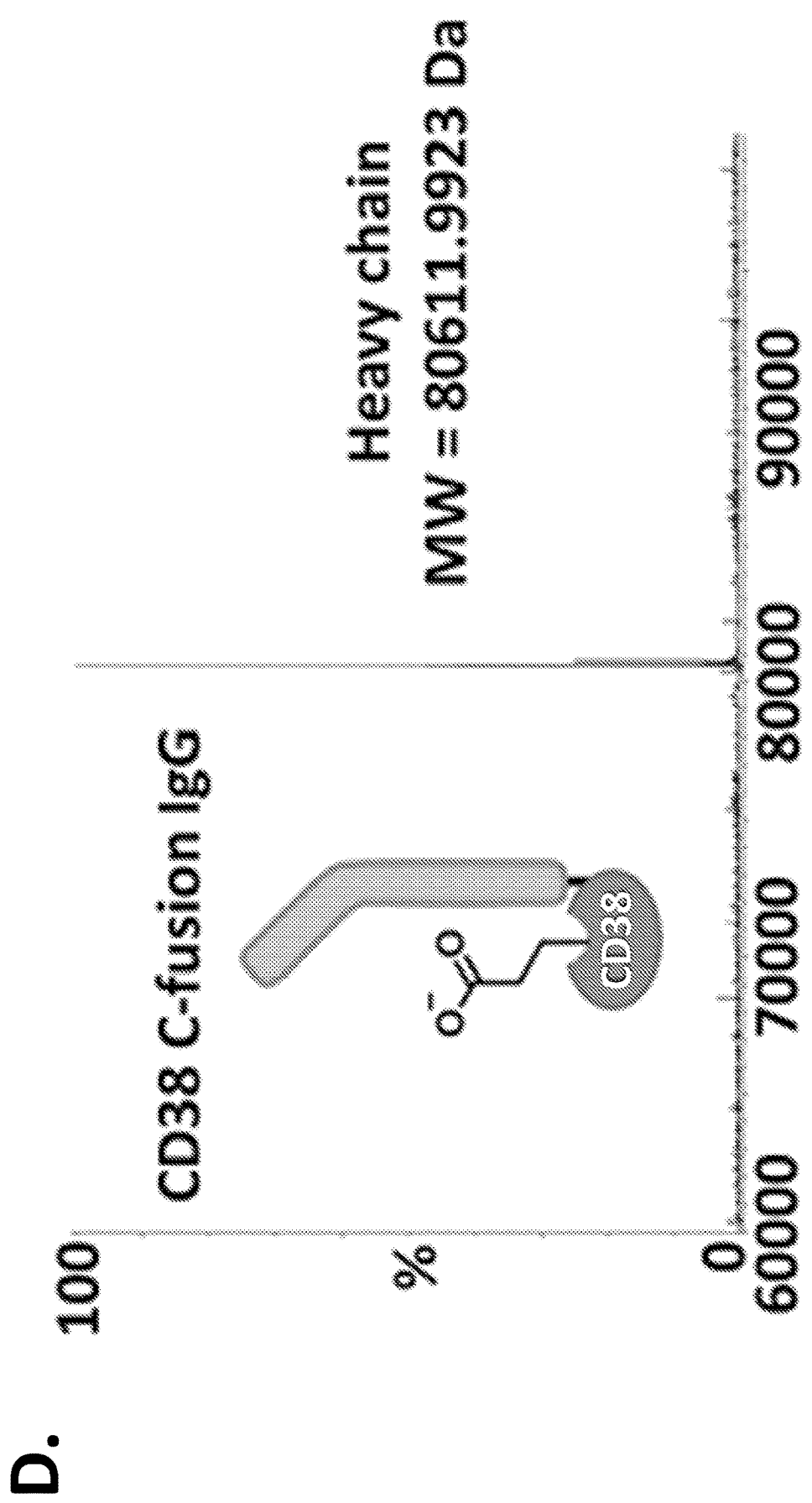
Figure 2:
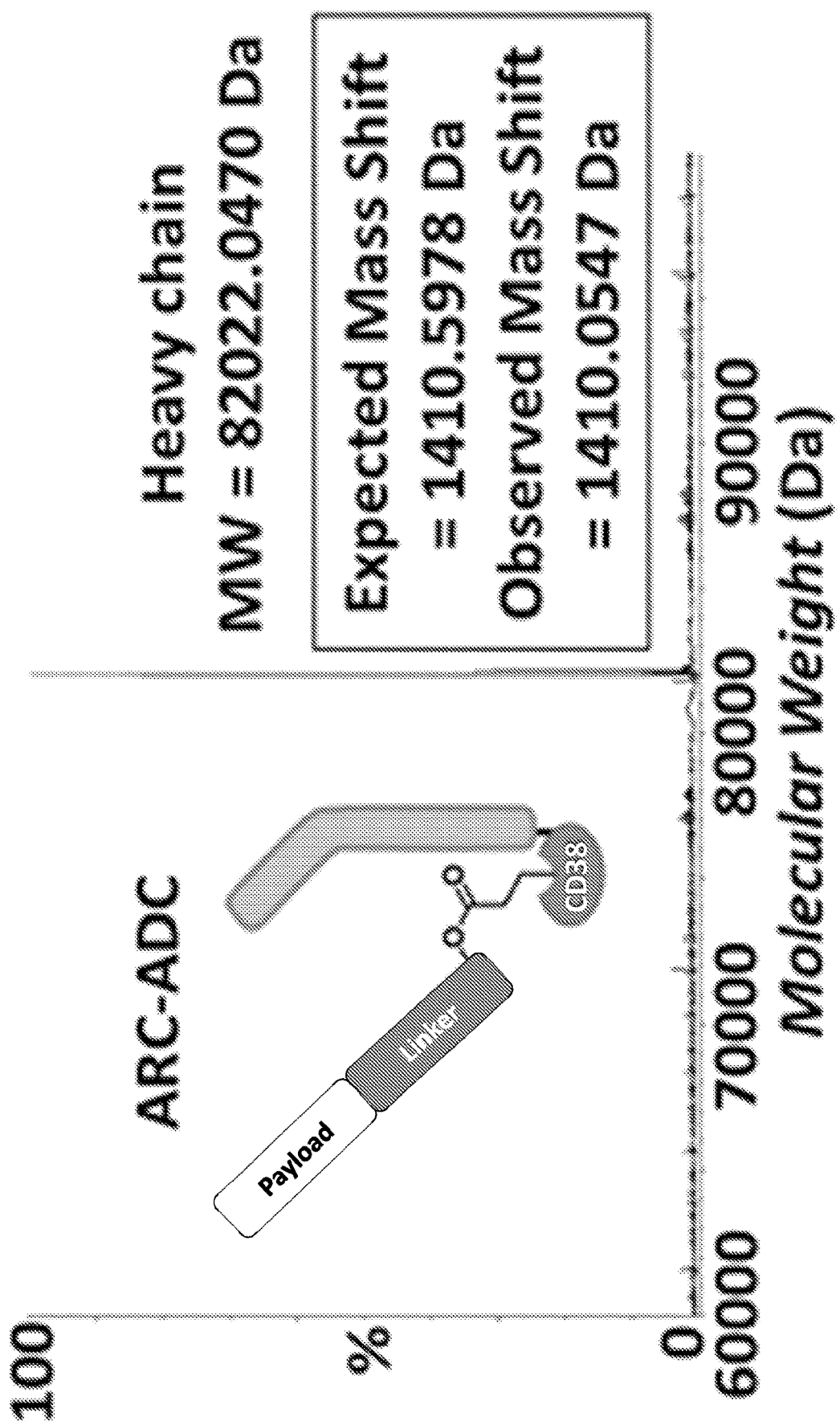
Figure 2:
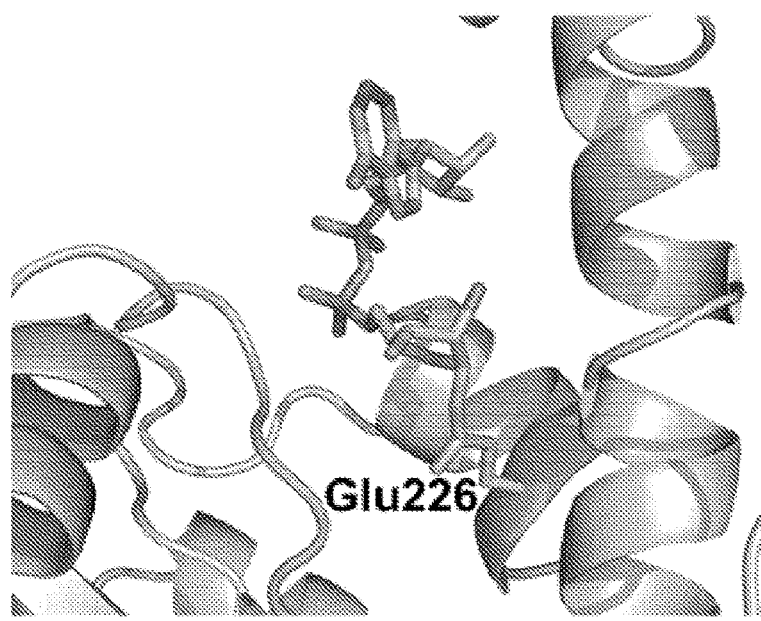
Figure 2:
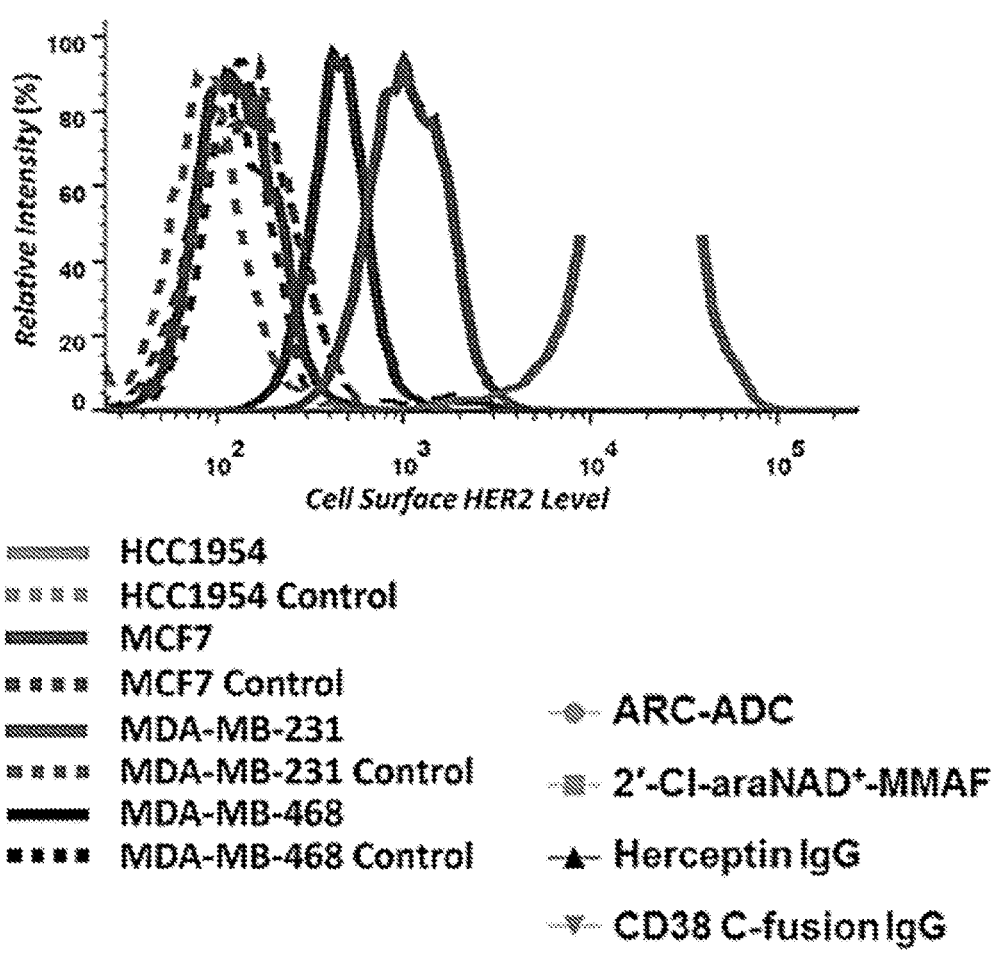
Figure 2:
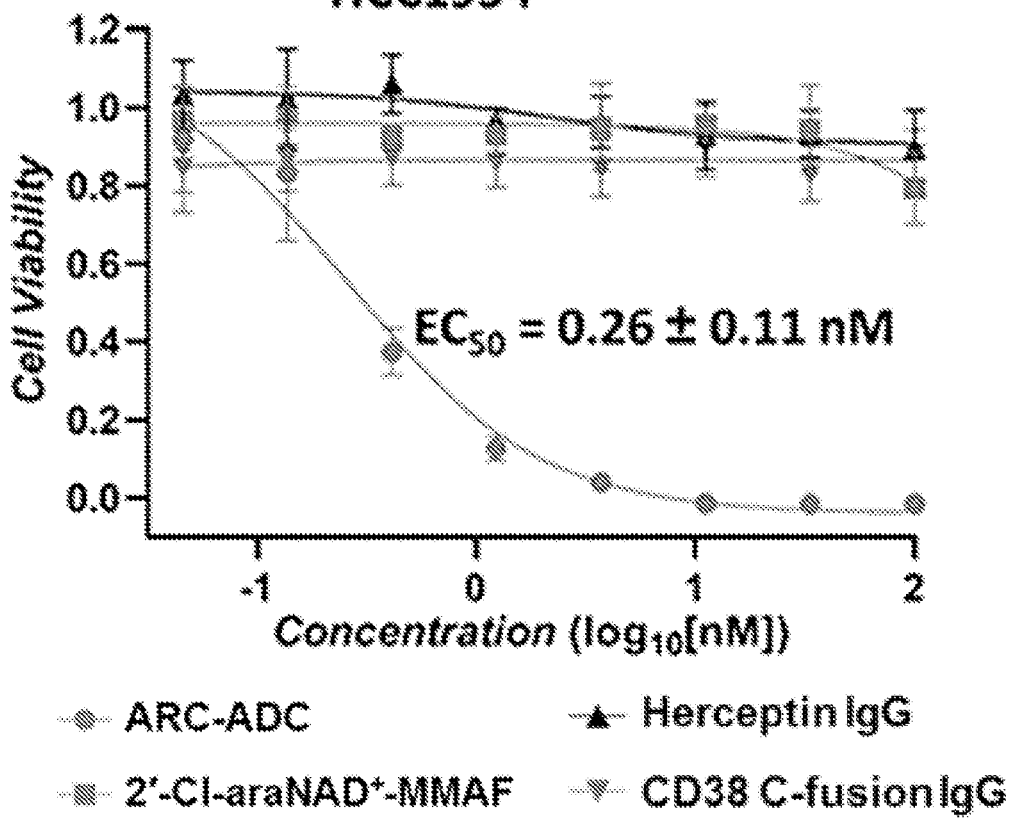
Figure 2:
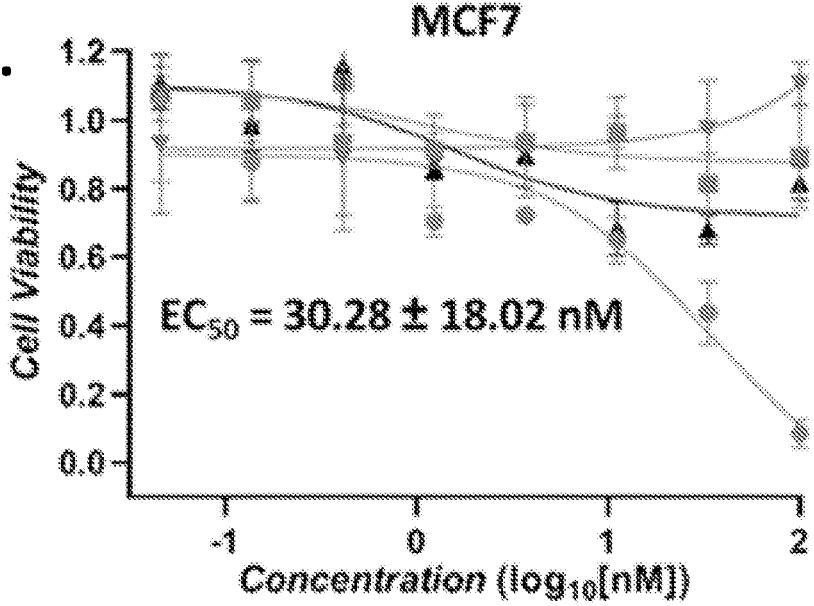
Figure 2:
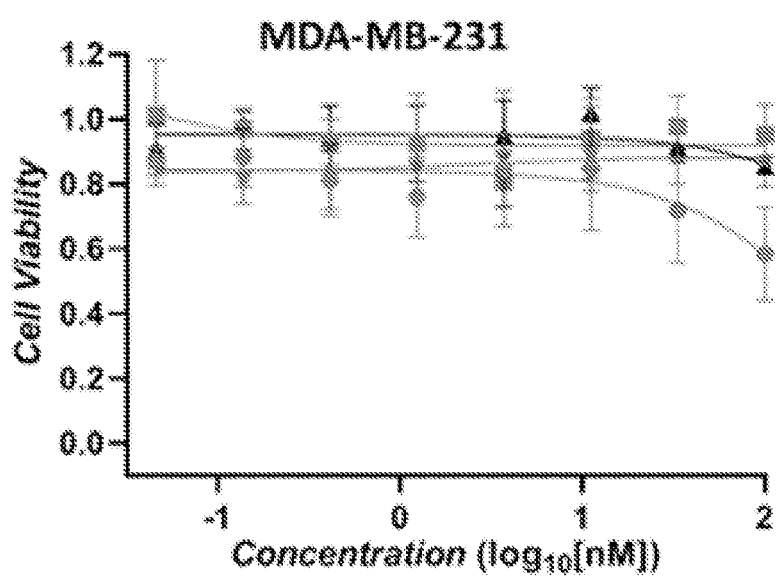
Figure 2:
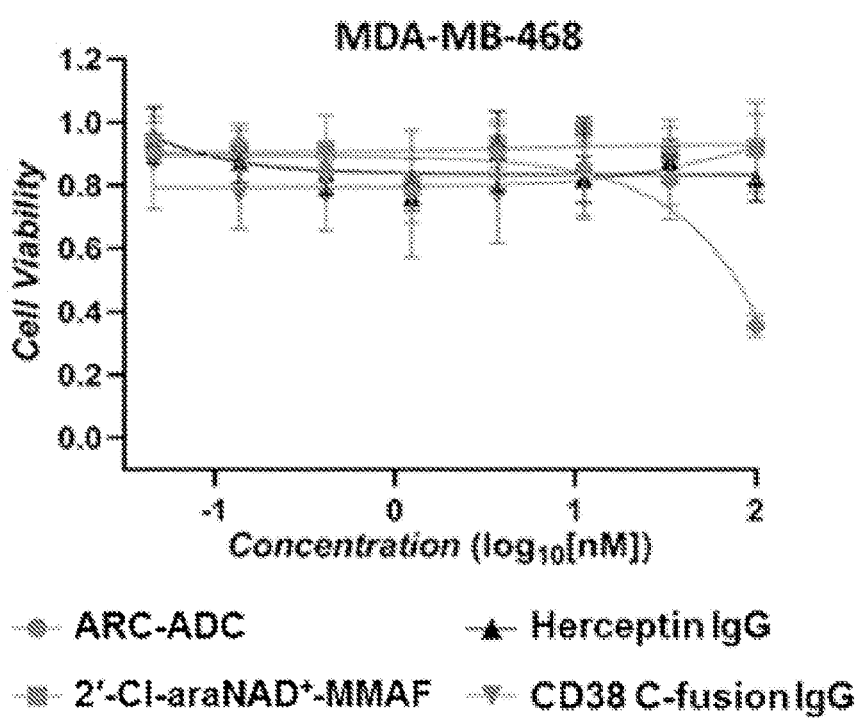
Figure 7:
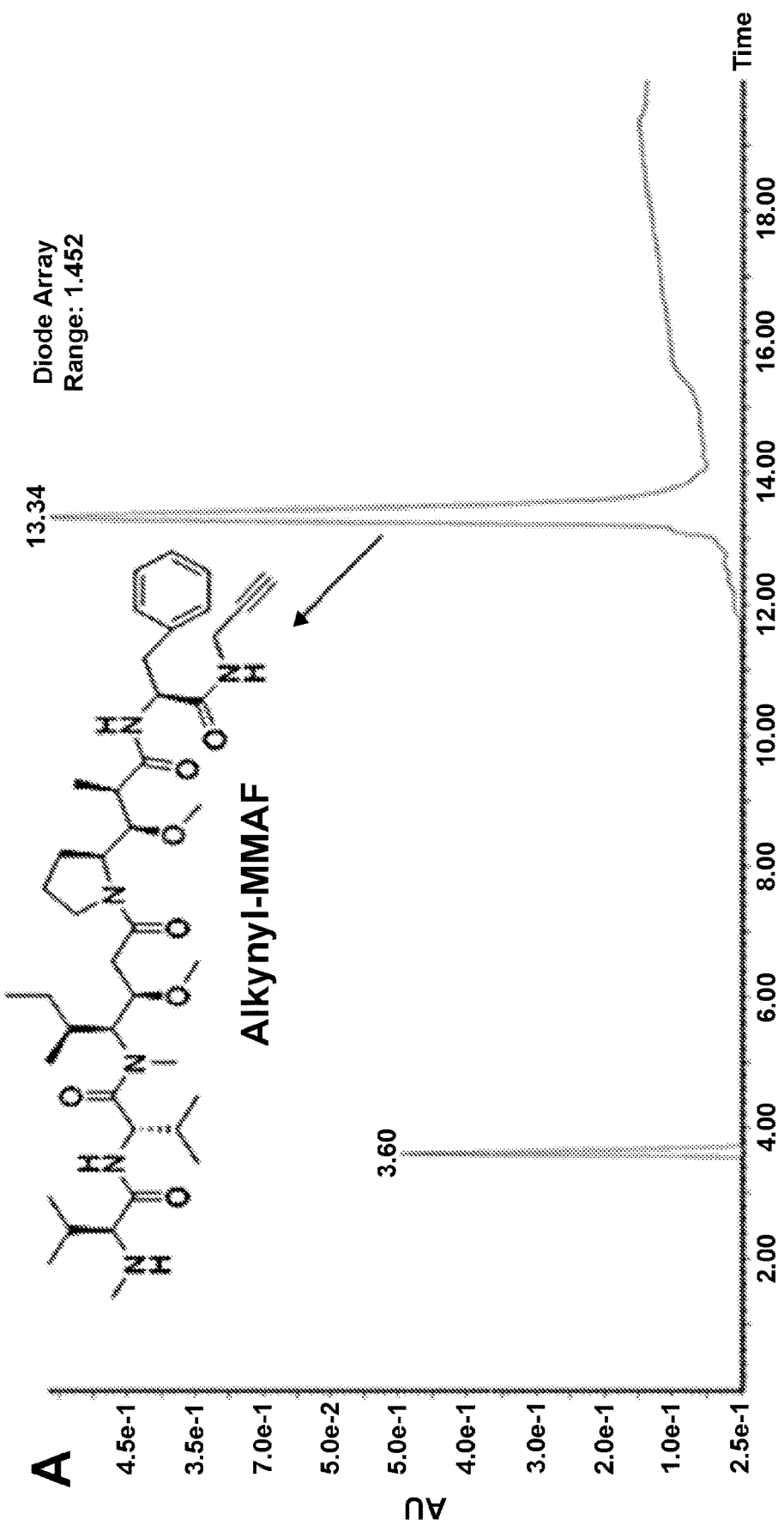
FIG. 7 illustrates HPLC and mass spectrometric analysis. (A) HPLC profile of the reaction mixture containing alkynyl-MMAF. (B) HPLC profile of the click chemistry reaction mixture containing 2'-Cl-araNAD$^+$-MMAF (payload-linker). (C) Mass spectrum of heavy chain of CD38 C-fusion IgG E226Q mutant. (D) Mass spectrum of heavy chain of CD38 C-fusion IgG E226Q mutant following conjugation with 2'-Cl-araNAD$^+$-MMAF at a molar ratio of 100 for overnight on ice. (E) Mass spectrum of light chain of CD38 C-fusion IgG E226Q mutant. (F) Mass spectrum of light chain of CD38 C-fusion IgG E226Q mutant following conjugation with 2'-Cl-araNAD$^+$-MMAF at a molar ratio of 100 for overnight on ice. (G) Mass spectra of peptides of CD38 C-fusion IgG and anti-HER2 ARC-ADC derived from trypsin digestion. Unconjugated CD38 C-fusion IgG and anti-HER2 ARC-ADC were overnight digested by trypsin and subjected to LC-MS analysis. In contrast to the mass spectrum for CD38 C-fusion IgG (upper), the mass spectrum for anti-HER2 ARC-ADC revealed a unique peptide with m/z of 800.6759 (bottom), which matches the peptide DSTFGSVE$_{226}$VHNLQPEK (SEQ ID NO: 81) attached with 2'-Cl-arabinose-ADP-MMAF.
Figure 7:
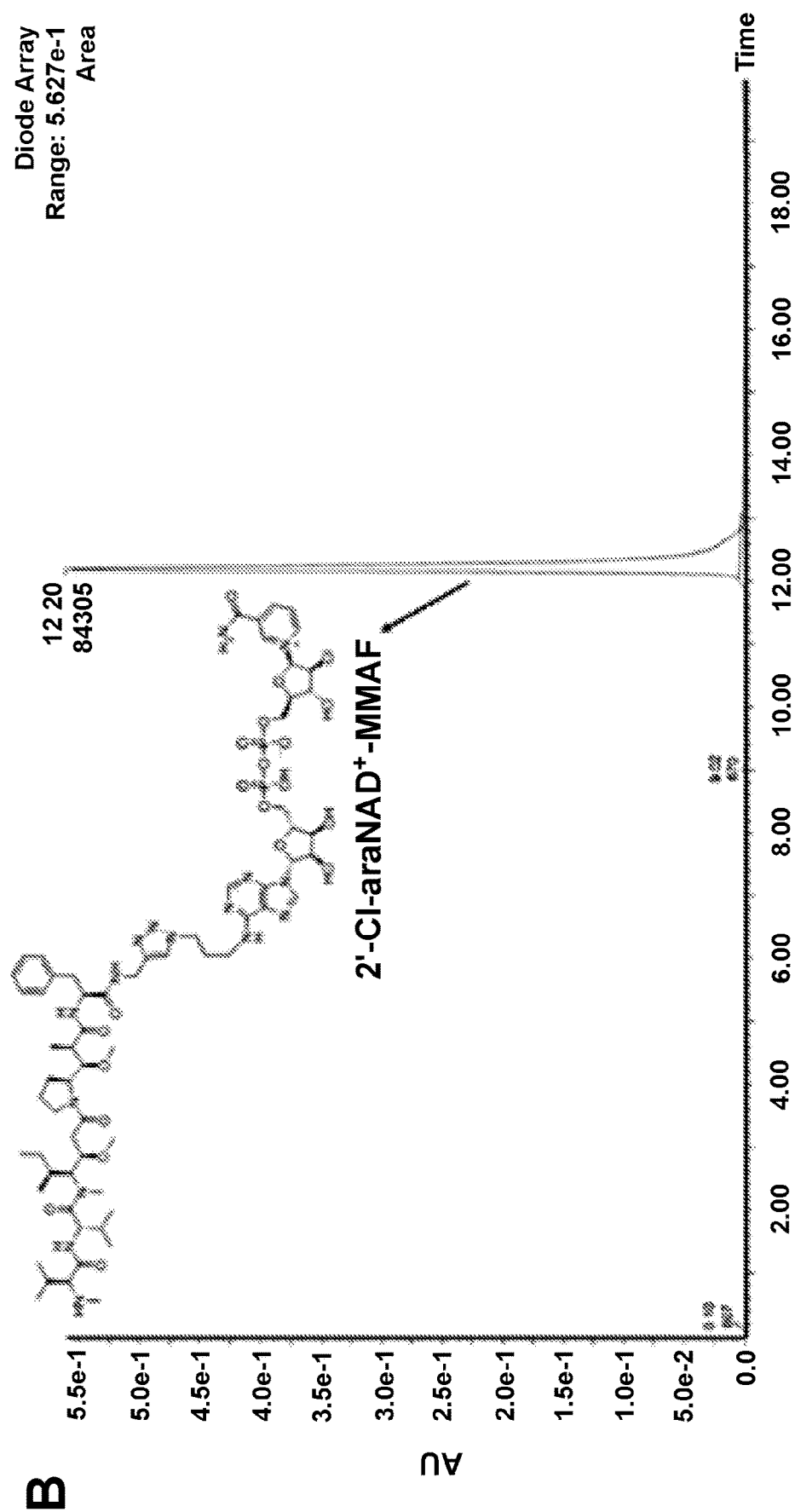
Figure 7:
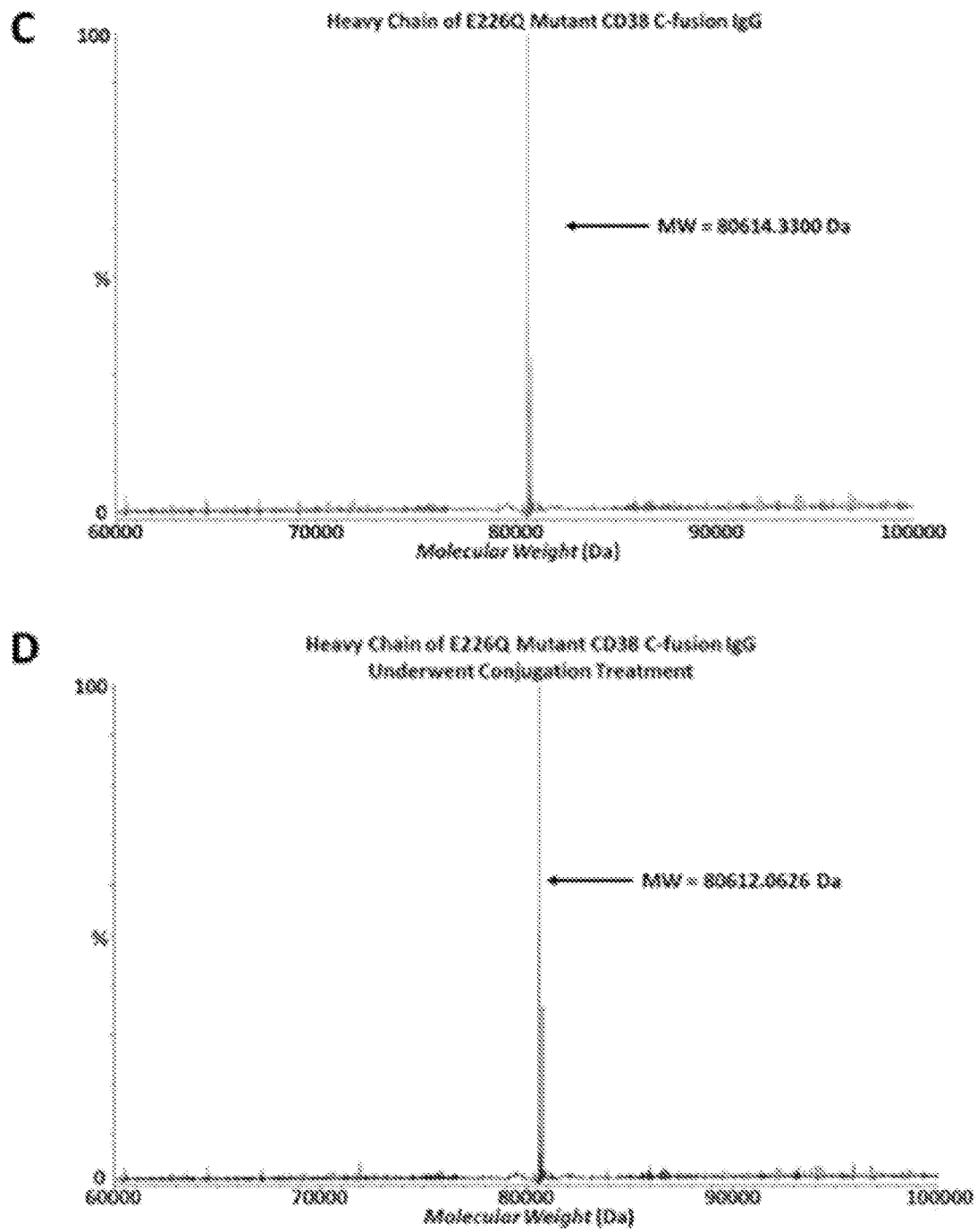
Figure 7:
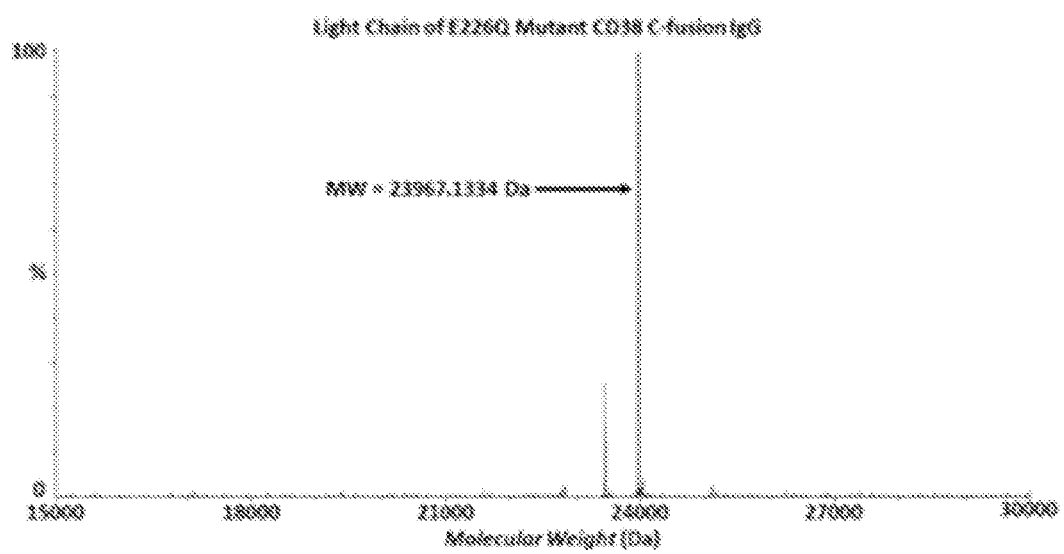
Figure 7:
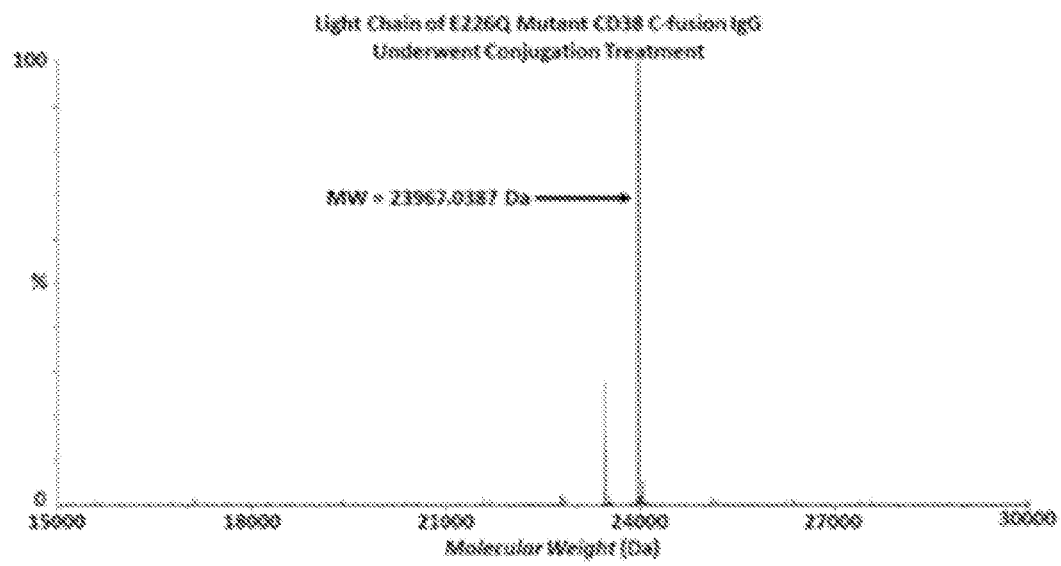
Figure 7:
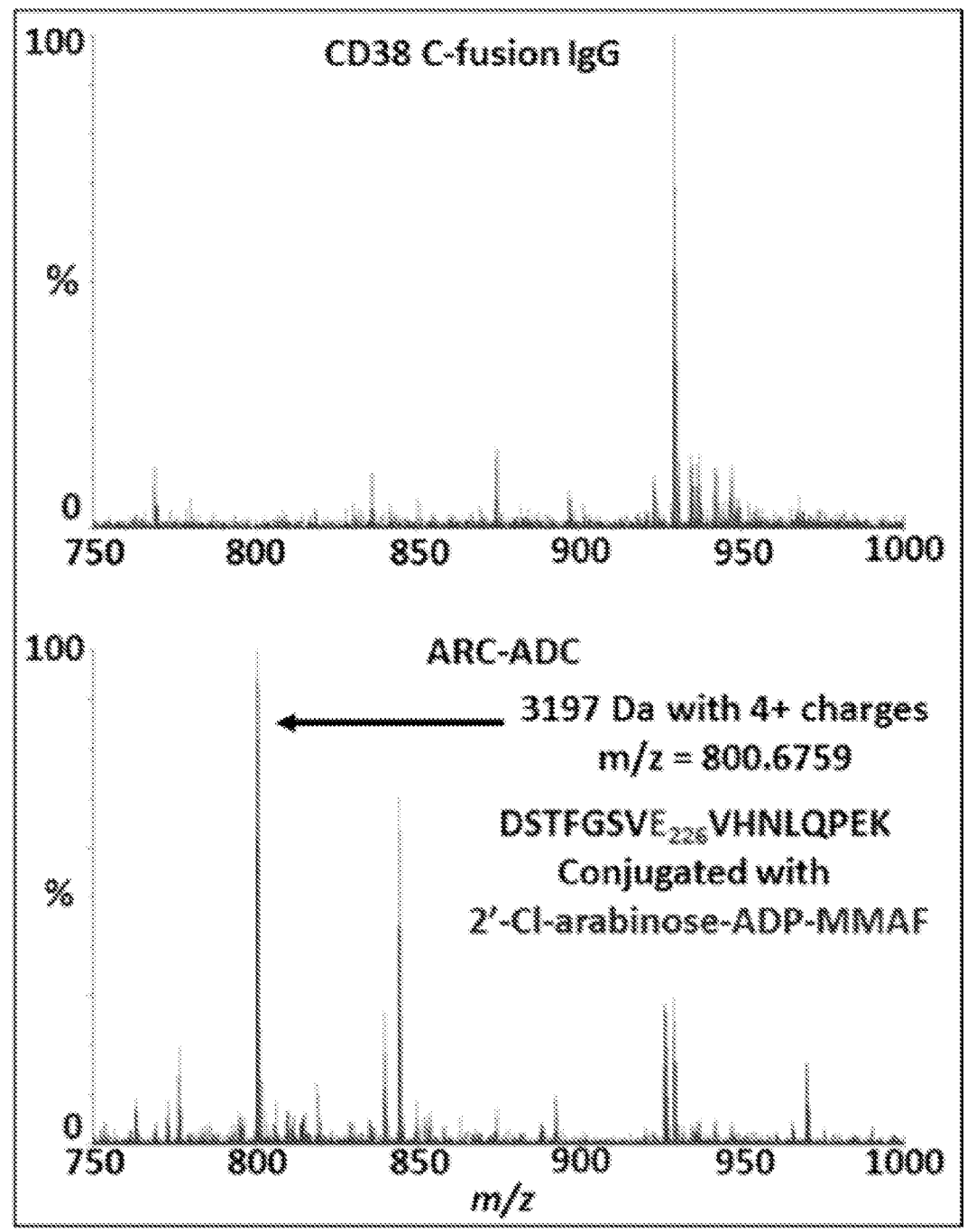

Next, the 2'-Cl-araNAD⁺-N₃ linker was attached with a model payload, tubulin inhibitor monomethyl auristatin F (MMAF), through click chemistry (FIGS. 2A and 7A-B). The resulting 2'-Cl-araNAD⁺-MMAF conjugate was incubated with CD38 C-fusion IgG at a molar ratio of 100 for various amounts of time. Based on residual enzymatic activity, 2'-Cl-araNAD⁺-MMAF could rapidly inactivate CD38 C-fusion IgG with a $k_{obs}$ of 0.140±0.046 min⁻¹ (FIG. 2B). Nearly more than 90% of initial CD38 activity was lost after 20-minute incubation. The anti-HER2 ARC-ADC was then prepared by incubating CD38 C-fusion IgG with the 2'-Cl-araNAD⁺-MMAF (molar ratio 1:100) for overnight on ice, followed by removal of the free drug-linker conjugate. Mass spectrometry analysis of CD38 C-fusion IgG and ARC-ADC indicated no mass shifts for the light chain of ARC-ADC but an increase of 1410 Da for the heavy chain of ARC-ADC, matching the calculated addition for a 2'-Cl-arabinose-ADP-MMAF moiety (FIGS. 2C-D). And no unmodified heavy chain was observed for the ARC-ADC, consistent with its undetectable CD38 enzymatic activity. These results demonstrate the facile production of ARC-ADC with a defined DAR of 2. Furthermore, the CD38 C-fusion IgG E226Q mutant was incubated with 2'-Cl-araNAD⁺-MMAF (molar ratio 1:100) for overnight on ice. Mass spectrometry indicated no mass shifts for both light and heavy chains of the CD38 C-fusion IgG E226Q mutant underwent conjugation treatment (FIGS. 7C-F). Importantly, liquid chromatography-mass spectrometry (LC-MS) analysis of CD38 C-fusion IgG and anti-HER2 ARC-ADC treated by trypsin revealed a unique peptide for ARC-ADC which matches an E226-containing peptide attached with 2'-Cl-arabinose-ADP-MMAF (FIG. 7G). Moreover, we crystallized human CD38 catalytic domain with covalently attached 2'-Cl-araNAD⁺. The solved high-resolution (1.5 Å) x-ray structure revealed that 2'-Cl-arabinose-ADP forms an arabinosyl-ester bond with E226 residue at the active site of CD38 (FIG. 2E and Table 2). Together with the fluorescent dye conjugation analysis (FIG. 5A), these results support catalytic E226 residue as the conjugation site for ARC-ADC.

TABLE 2

Crystallographic statistics of x-ray structure of CD38 with 2'-Cl-araNAD⁺.

| Data collection[a] | |
|---|---|
| Wavelength (Å) | 1.033149 |
| Space group | P 4₁ 2 2 |
| Unit cell dimensions [a, b, c (Å)] | a = 114.76 |
| | b = 114.76 |
| | c = 97.15 |
| Resolution range (Å) | 29.07-1.5 |
| Highest resolution shell (Å) | 1.58-1.50 |
| No. of observed reflections | 2052773 |
| No. of unique reflections | 103758 |
| Multiplicity | 19.8 (18.1) |
| Completeness (%) | 100.0 (100.0) |
| <I/σI> | 16.2 (1.5) |
| Rmerge (%) | 8.8 (175.0) |
| Rpim (%) | 2.0 (42.0) |
| CC1/2 (%) | 99.9 (74.8) |
| Wilson B-factor | 19.1 |
| Refinement | |
| Rwork (%) | 16.64 |
| Rfree (%) | 19.02 |
| No. atoms | |
| Macromolecules | A: 2251 |
| | B: 2130 |
| Water | C: 512 |
| Ions/PEG | D: 81 |
| B-factor (Å2) | |
| Macromolecules | A: 28.15 |
| | B: 36.38 |
| Solvent | C: 41.90 |
| Ions/PEG | D: 57.16 |
| R.m.s. deviations | |
| Bond lengths (Å) | 0.015 |
| Bond angles (deg) | 1.84 |

TABLE 2-continued

Crystallographic statistics of x-ray structure of CD38 with 2'-Cl-araNAD+.

| Ramachandran statistics (%) | |
| --- | --- |
| Favored | 96.51 |
| Outliers | 0.37 |
| Molprobity score | 1.66 |
| PDB ID | 6VUA |

[a]Values in parentheses are for the highest-resolution shell.

Figure 8:
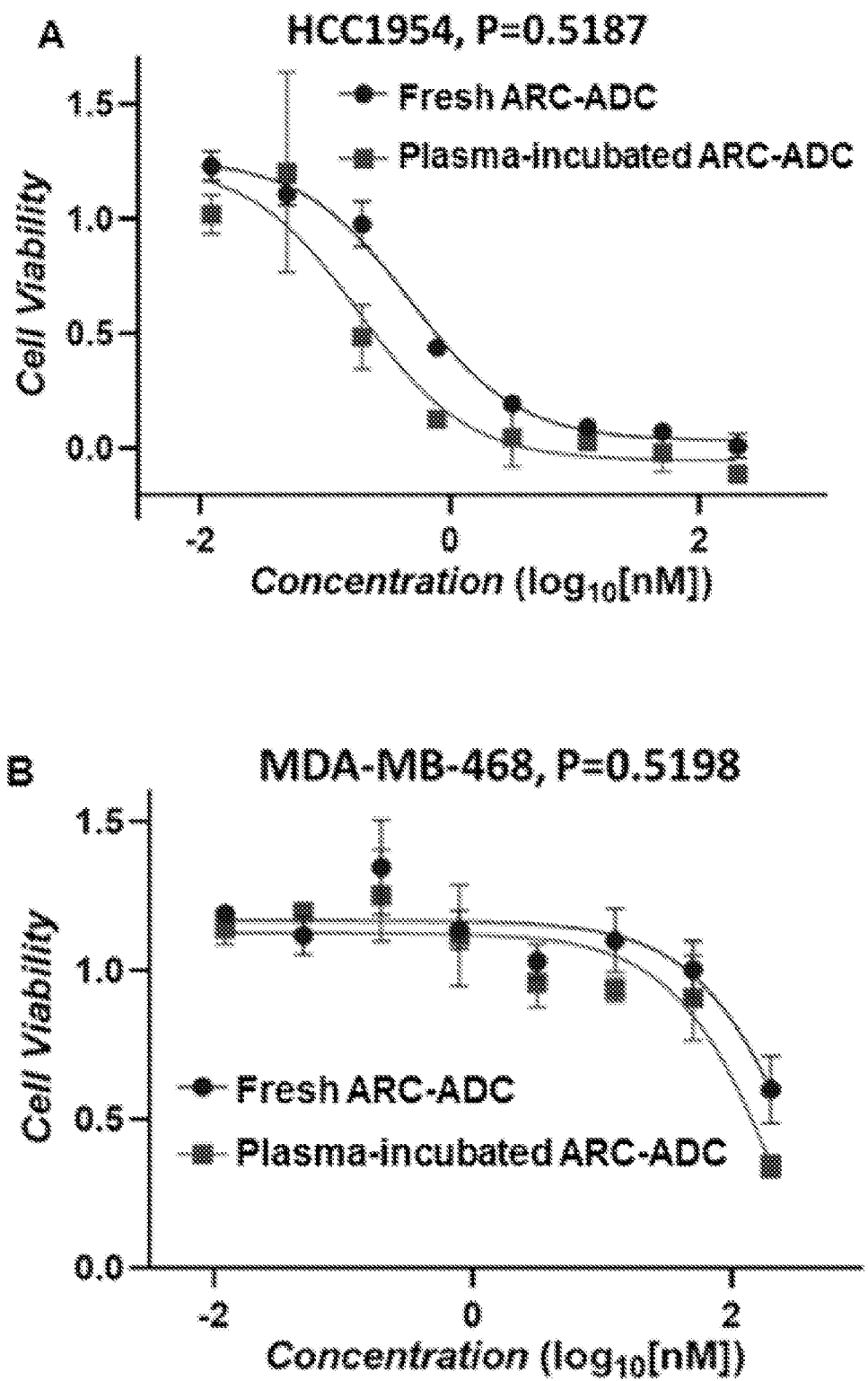
FIG. 8 illustrates stability of anti-HER2 ARC-ADC in plasma. Anti-HER2 ARC-ADC was first incubated in mouse plasma at 37° C. for 72 hours. (A) HCC1954 (HER2++) or (B) MDA-MB-468 (HER2−) cells were then incubated for 72 hours at 37° C. with 5% $CO_2$ in the presence of various concentrations of fresh ARC-ADC or plasma-incubated ARC-ADC. Cell viability was measured by MTT assays. Cells treated with culture media and 5 μM paclitaxel were included as 100% and 0% viability controls, respectively. Non-parametrical t tests indicated no significant difference (P=0.5187 for HCC1954 cells; P=0.5198 for MDA-MB-468 cells) in cytotoxicity for fresh ARC-ADC and plasma-incubated ARC-ADC.

In vitro cytotoxicity was then evaluated for the anti-HER2 ARC-ADC using four breast cancer cell lines with various levels of HER2 expression (FIG. 2F). The ARC-ADC could potently suppress proliferation of HCC1954 cells with an $EC_{50}$ of 0.26±0.11 nM. Its cytotoxicity positively correlates with levels of HER2 expression (FIGS. 2G-J). In contrast, 2'-Cl-araNAD+-MMAF, CD38 C-fusion IgG, and Herceptin displayed no cytotoxicity for these cell lines under the same conditions. These results indicate excellent in vitro potency and specificity for the anti-HER2 ARC-ADC. In addition, anti-HER2 ARC-ADC was incubated with mouse plasma for 3 days at 37° C. There was no significant difference (P=0.5187 for HCC1954 cells; P=0.5198 for MDA-MB-468 cells) in cytotoxicity for fresh and plasma-incubated ARC-ADCs (FIG. 8). These results are consistent with plasma stability of Alexa Fluor 488-conjugated CD38 C-fusion IgG (FIG. 1F) and support high stability of 2'-Cl-araNAD+-$N_3$ linker and its mediated covalent attachments to CD38 C-fusion IgG.

Figure 9:
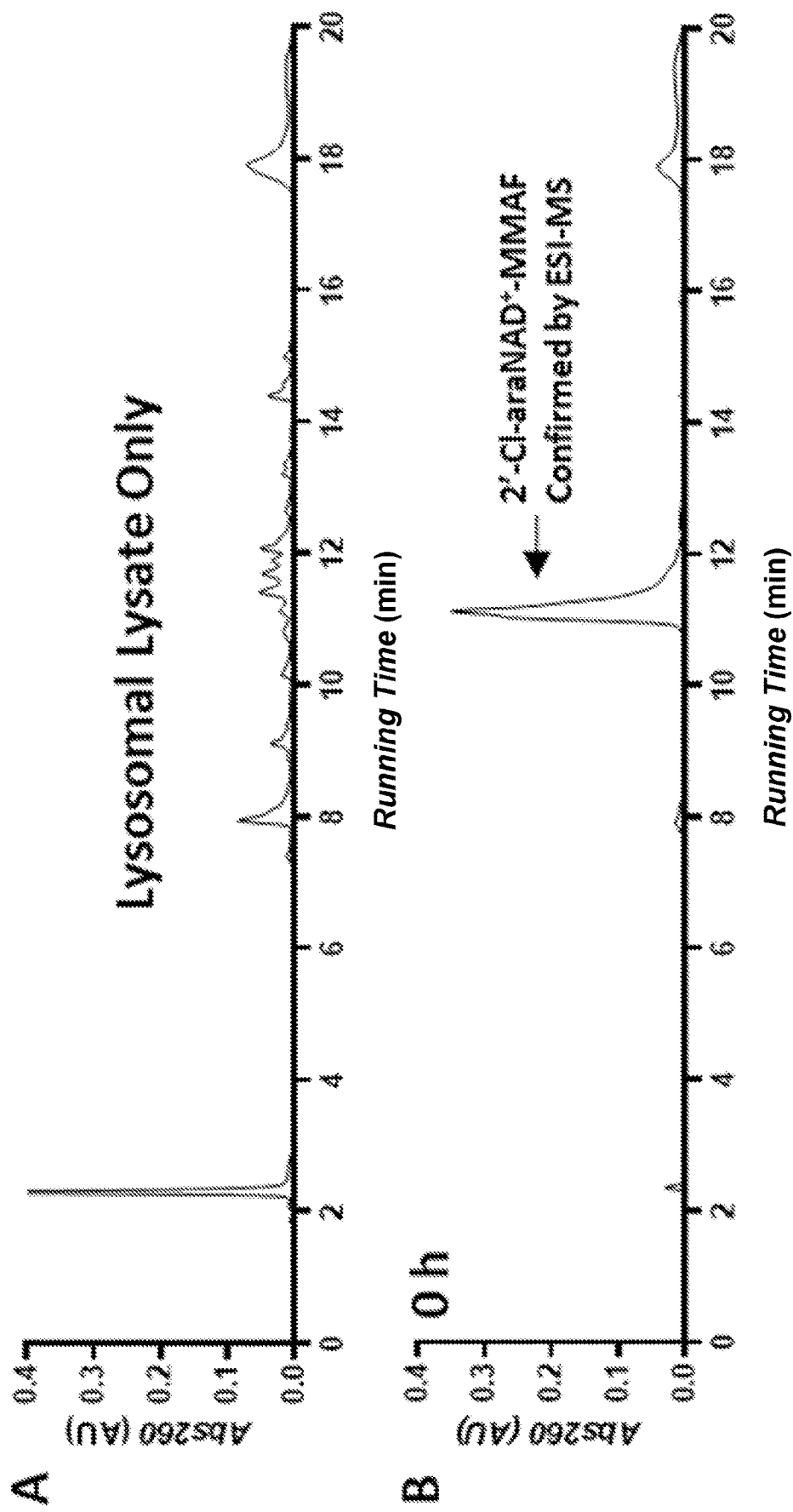
FIG. 9 illustrates HPLC analysis of degradation of 2'-Cl-araNAD$^+$-MMAF in rat liver lysosomal lysates. 2'-Cl-araNAD$^+$-MMAF was incubated with rat liver lysosomal lysates at 37° C. and the mixture was sampled at different time points for HPLC analysis. (A) Rat liver lysosomal lysates alone. (B) 2'-Cl-araNAD$^+$-MMAF combined with boiled (inactivated) rat liver lysosomal lysates at the beginning of incubation. (C)-(F) 2'-Cl-araNAD$^+$-MMAF incubated with rat liver lysosomal lysates for 0.5-22 h. (G)-(I) 2'-Cl-araNAD$^+$-MMAF, 6-AMP-MMAF, and 6-Adenosine-MMAF standards.
Figure 9:
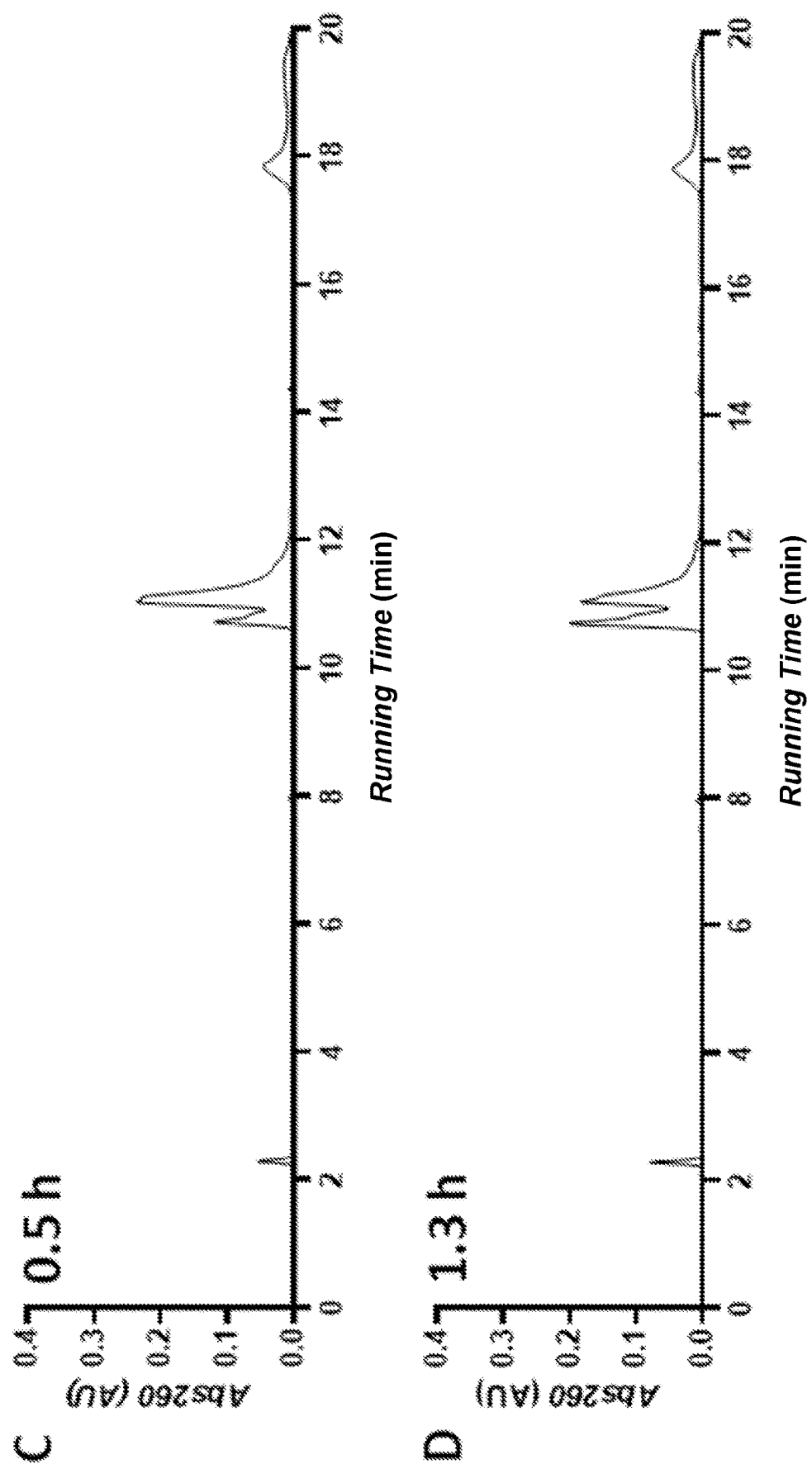
Figure 9:
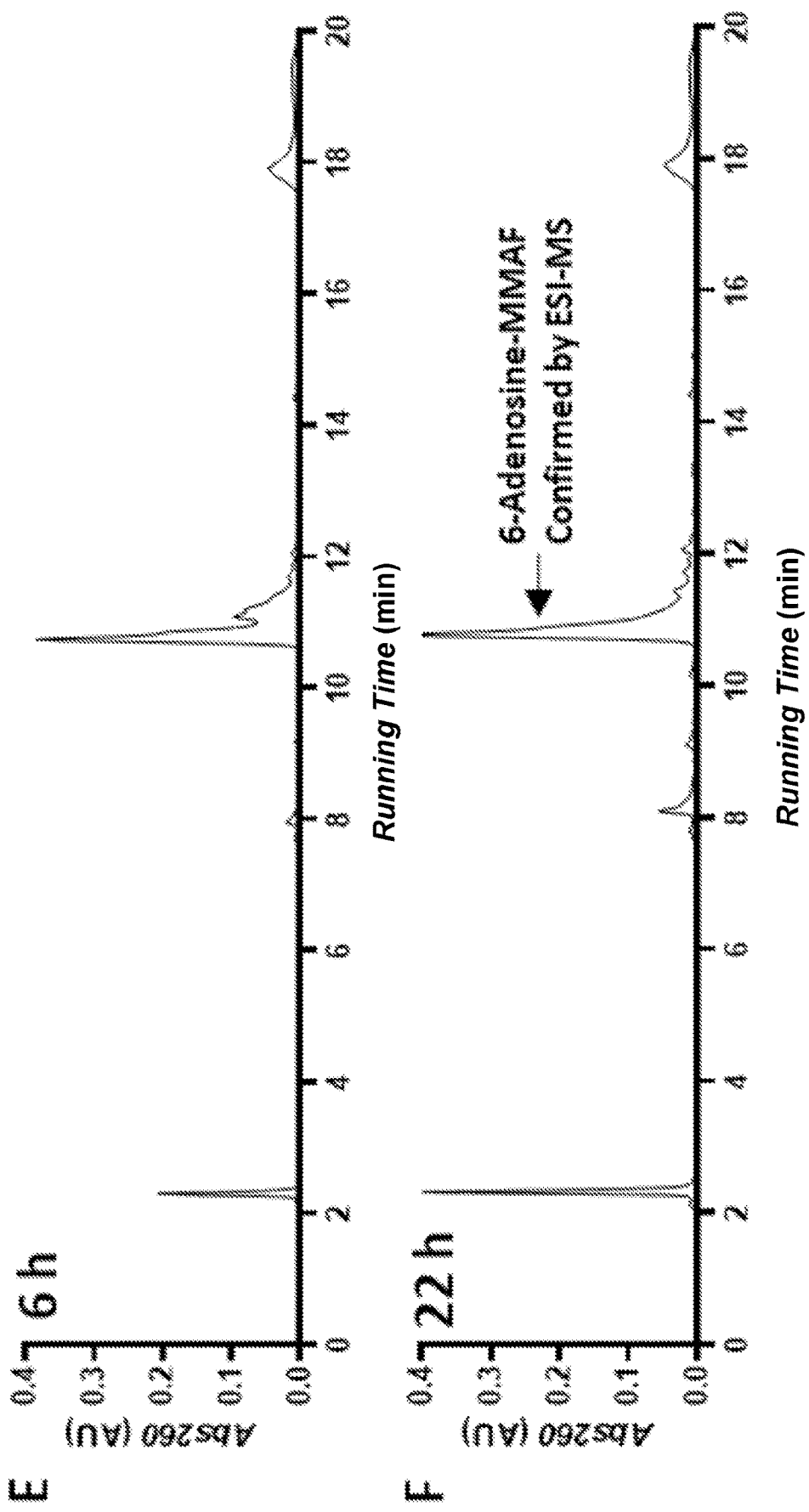
Figure 9:
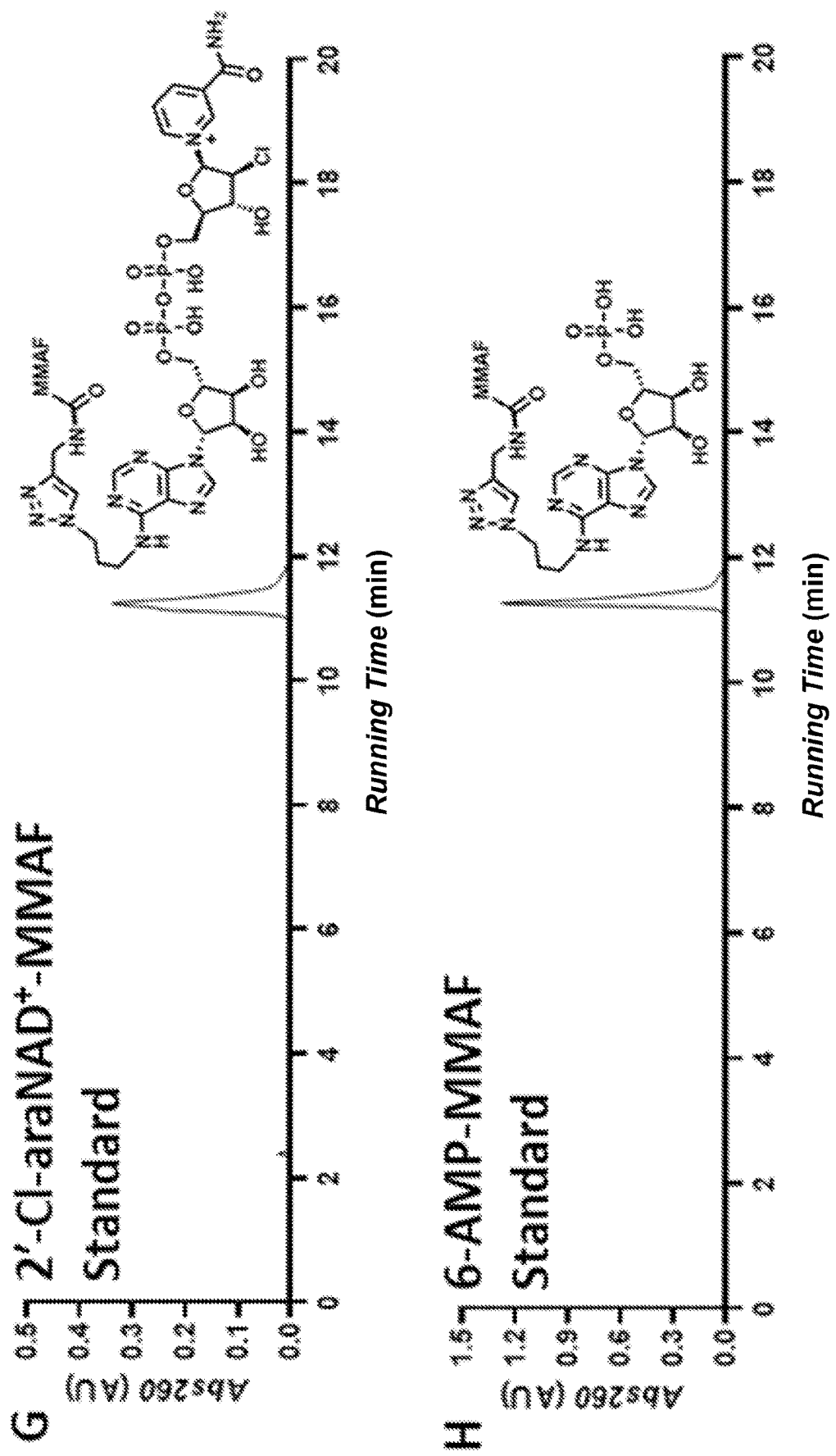
Figure 9:
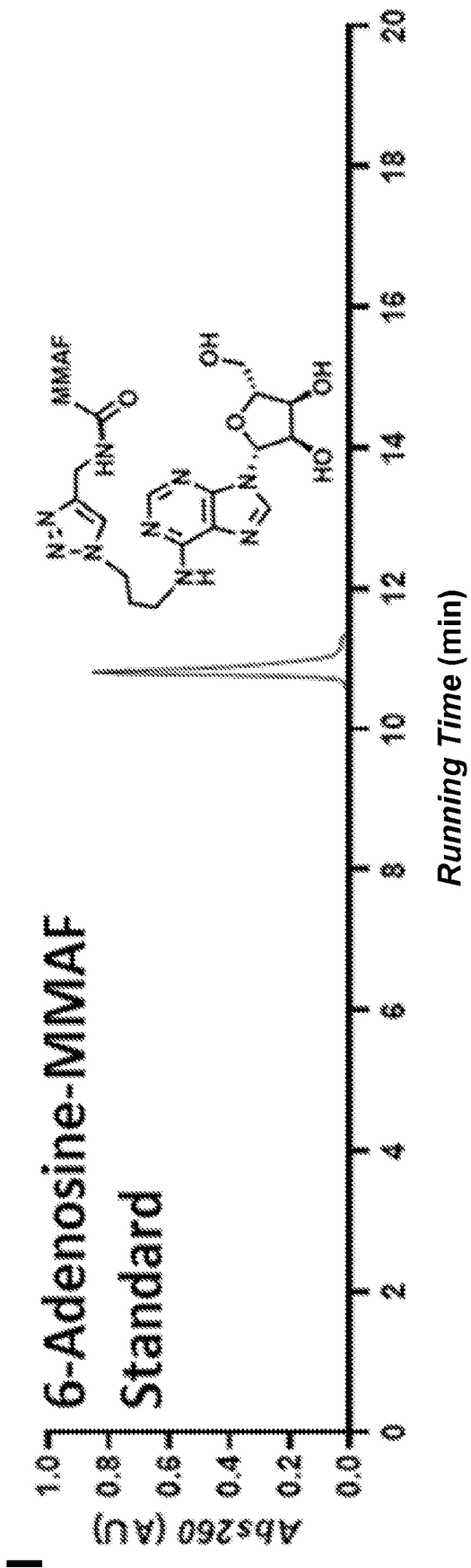
Figure 10:
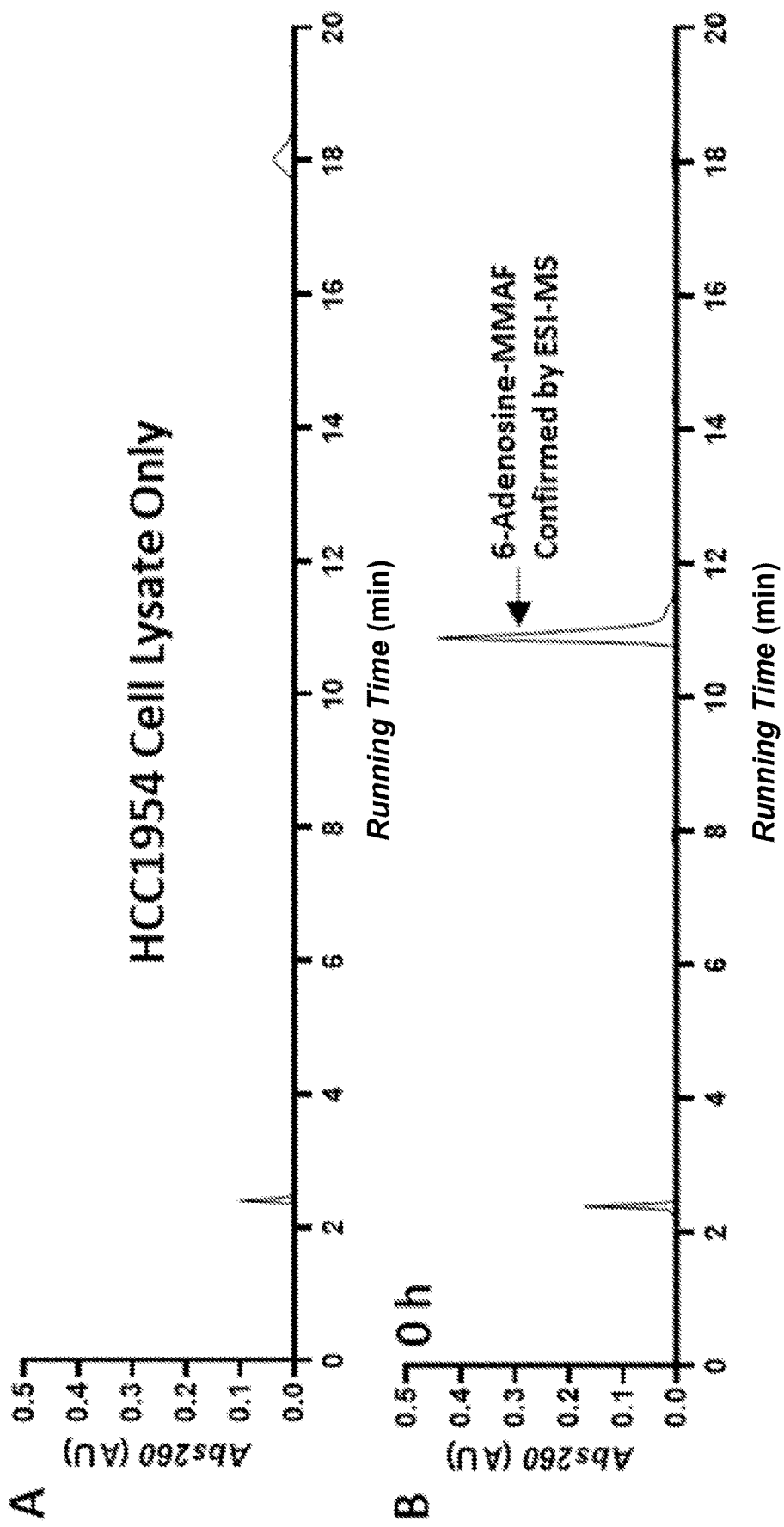
FIG. 10 illustrates HPLC analysis of degradation of rat liver lysosomal lysate-treated 2'-Cl-araNAD$^+$-MMAF in cell lysates. 2'-Cl-araNAD$^+$-MMAF was first incubated with rat liver lysosomal lysates at 37° C. for overnight, followed by treatment with HCC1954 cell lysates. The mixture was sampled at different time points for HPLC analysis. (A) HCC1954 cell lysates alone. (B) Overnight rat liver lysosomal lysate-treated 2'-Cl-araNAD$^+$-MMAF combined with boiled (inactivated) HCC1954 cell lysates at the beginning of incubation. (C)-(G) Overnight rat liver lysosomal lysate-treated 2'-Cl-araNAD$^+$-MMAF incubated with HCC1954 cell lysates for 1-22 h. (H)-(I) 6-Adenine-MMAF and 6-Adenosine-MMAF standards.
Figure 10:
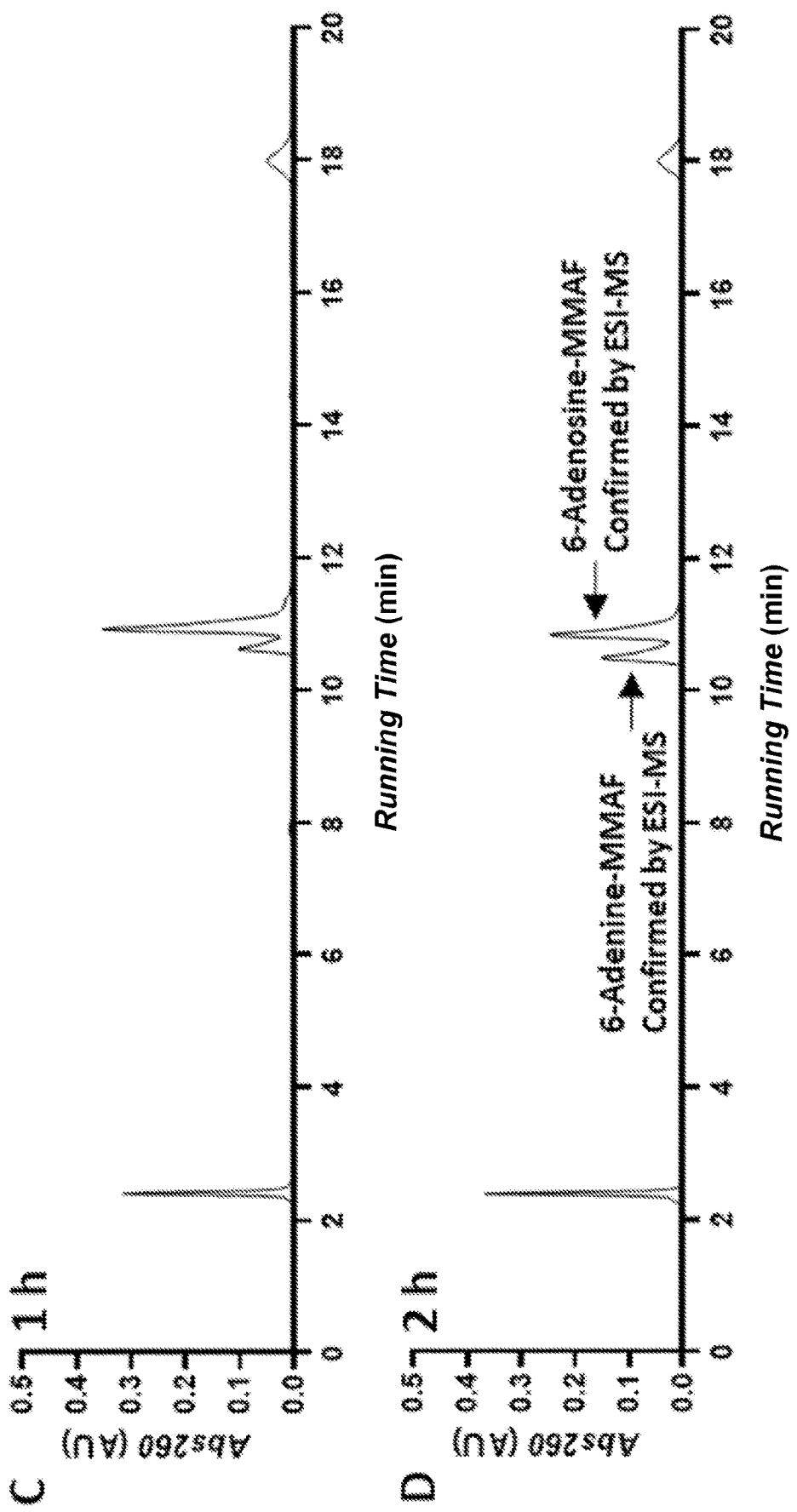
Figure 10:
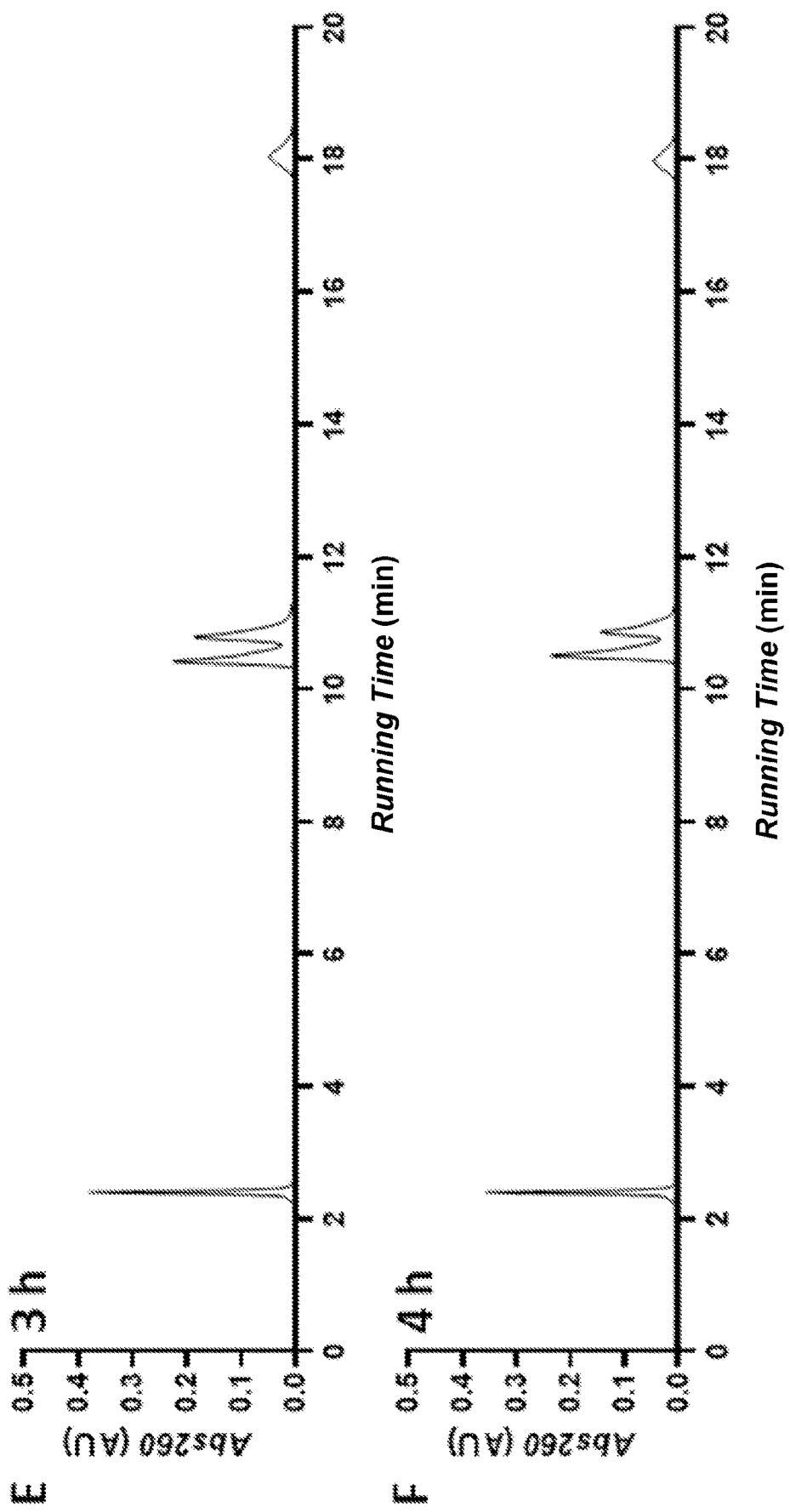
Figure 10:
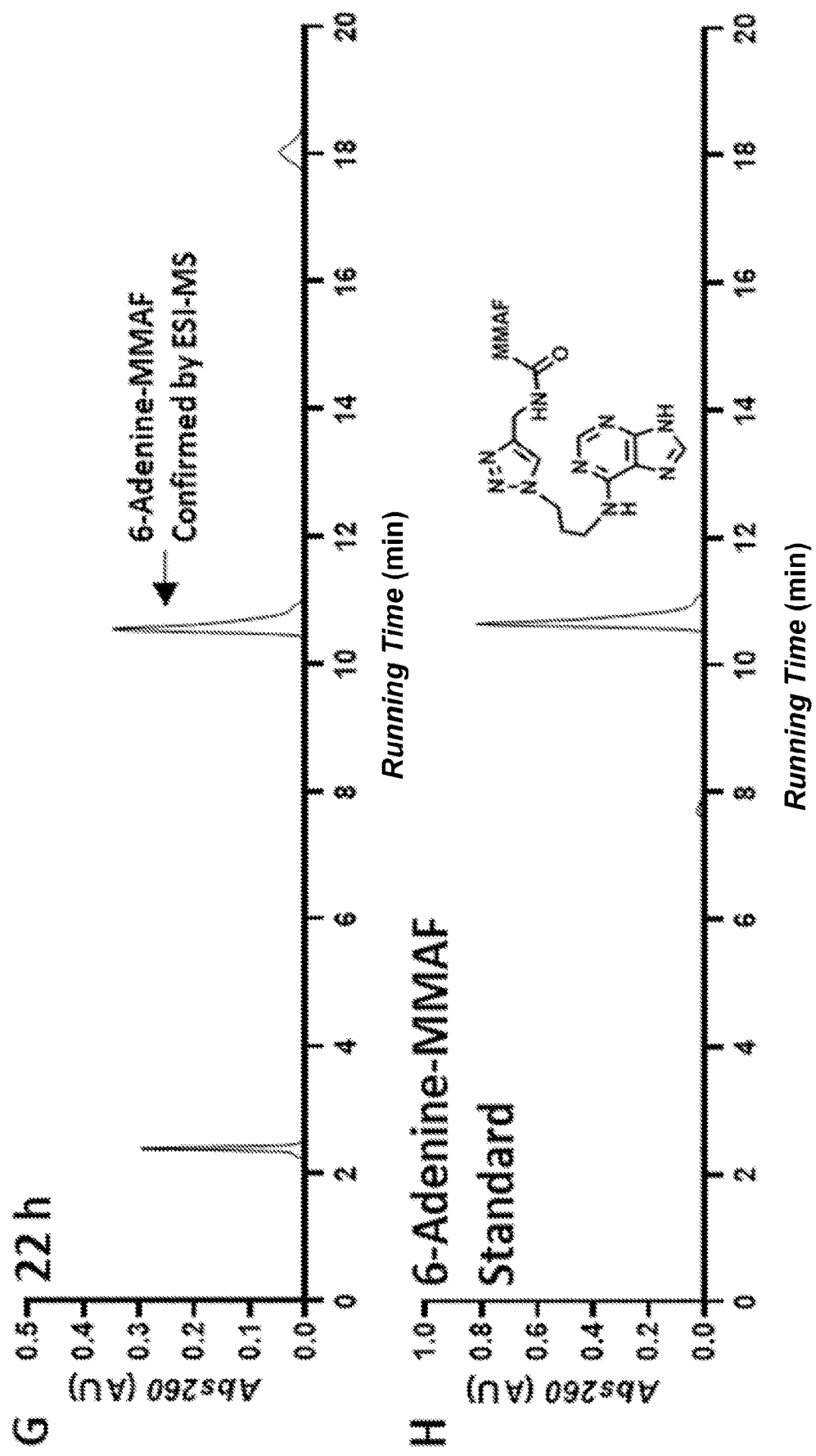
Figure 10:
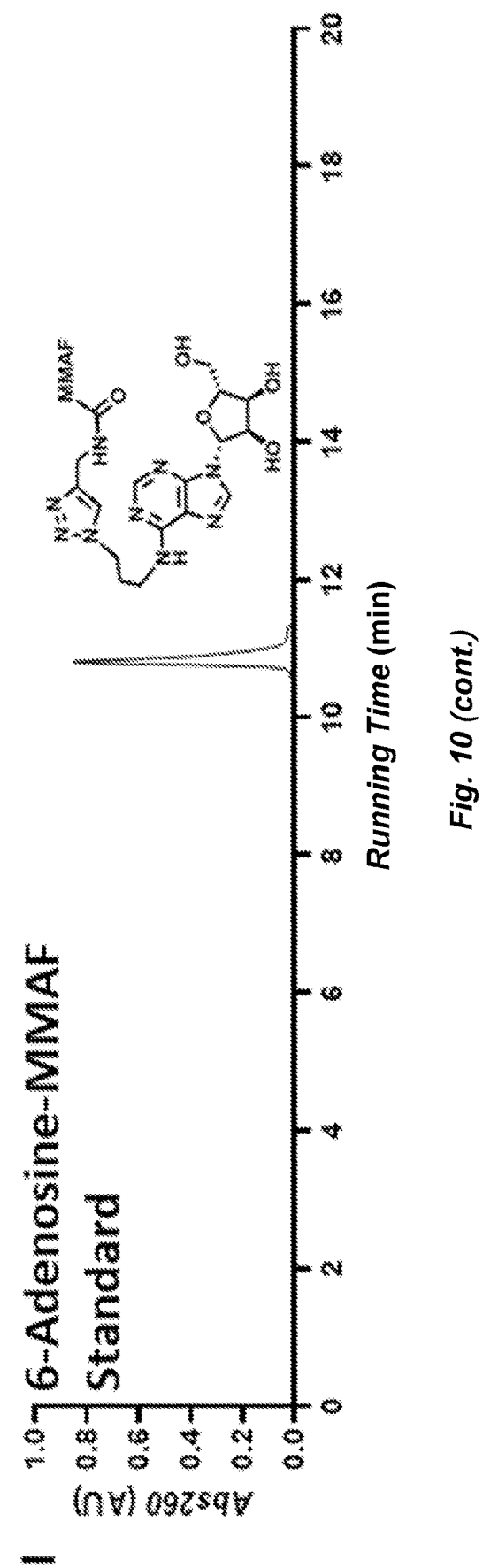

To investigate payload release of the ARC-ADC upon cellular internalization, 2'-Cl-araNAD+-MMAF was first incubated with rat liver lysosomal lysates at 37° C. for various amounts of time. Based on HPLC retention times with reference to synthesized standards and MS analysis (FIG. 9), 2'-Cl-araNAD+-MMAF could be rapidly degraded into 6-adenosine-MMAF in the lysosomal environment. Subsequent treatment of the lysosomal reaction mixture by HCC1954 cell lysates led to full conversion into 6-adenine-MMAF as revealed by HPLC and MS analysis (FIG. 10). These results suggest that 6-adenine-MMAF may be the major form of MMAF released from anti-HER2 ARC-ADC inside target cells.

Figure 3:
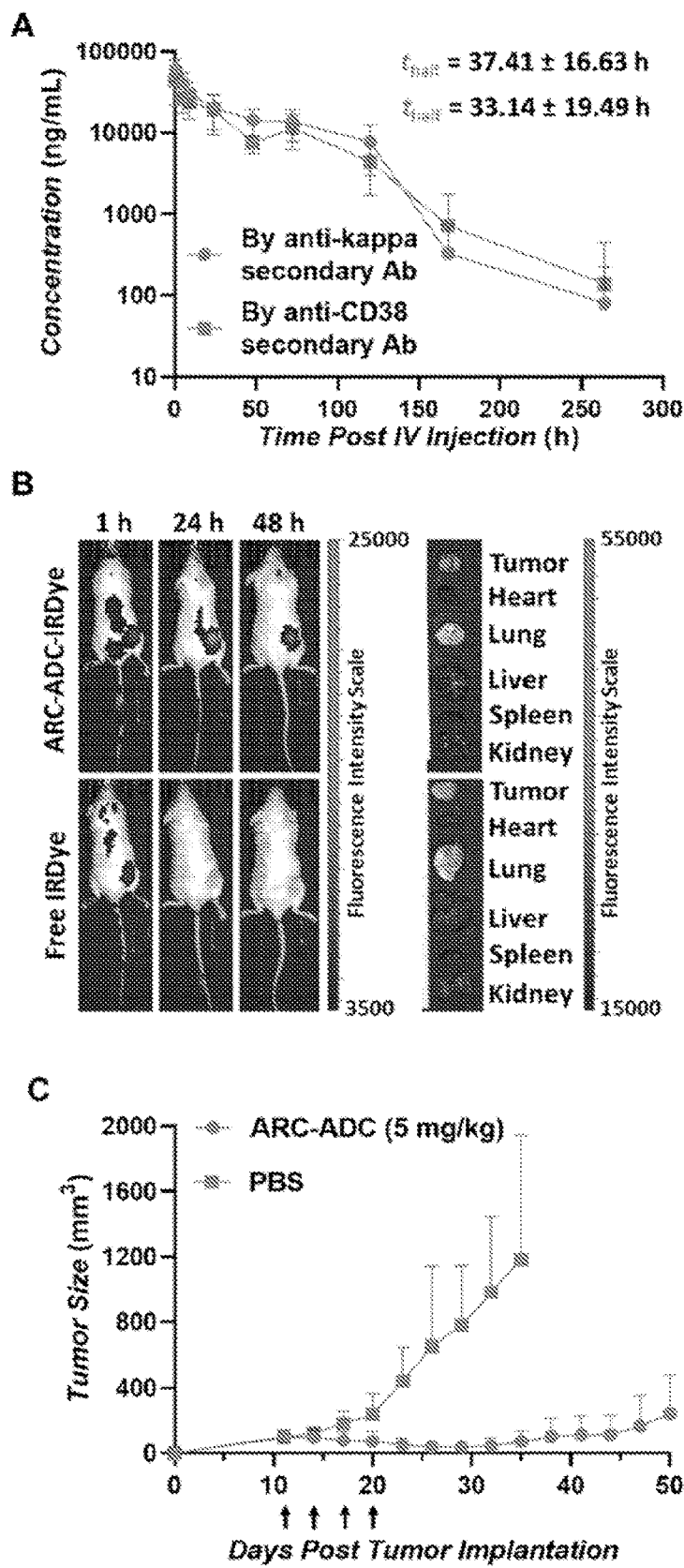
FIG. 3 illustrates the pharmacokinetics and pharmacodynamics in mice. (A) Pharmacokinetics of CD38 C-fusion IgG in mice. A single dose (3 mg/kg) of CD38 C-fusion IgG was administered by i.v. injection into CD-1 mice (n=5). Plasma concentrations of CD38 C-fusion IgG were determined by two sandwich ELISAs using the same capture antibody (anti-human IgG (H+L)) but different detection antibodies (anti-kappa light chain or anti-CD38). (B) Biodistribution of anti-HER2 ARC-ADC in mice. HCC1954 cells were s.c. implanted into the flank of female NSG mice. IRDye-labeled anti-HER2 ARC-ADC (5 mg/kg) or free IRDye at the same molar concentration was administered i.v. through tail vein one-week post tumor implantation. Mice were then imaged at 1, 24, and 48 hours post injection, followed by euthanasia and imaging of harvested tumors and major organs. (C) In vivo efficacy of anti-HER2 ARC-ADC. HCC1954 cells were s.c. implanted into the flank of female NSG mice. Once the tumor sizes reached 100 mm$^3$, mice (n=6) were treated with PBS or ARC-ADC (5 mg/kg) by i.v. injection (black arrows) every three days for a total of four times. (D) Body weights of mice during the in vivo efficacy study. (E) Ratios of major organ weight to body weight of mice at the end of in vivo efficacy study. (F) Kaplan-Meier survival curve for PBS- and ARC-ADC-treated groups.
Figure 3:
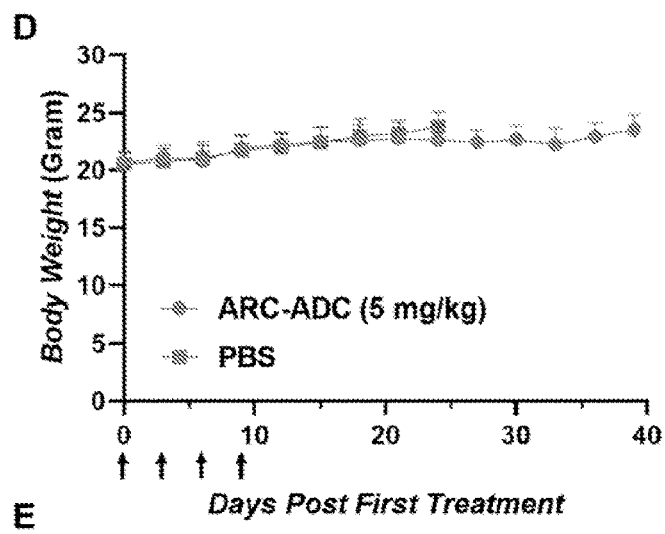
Figure 3:
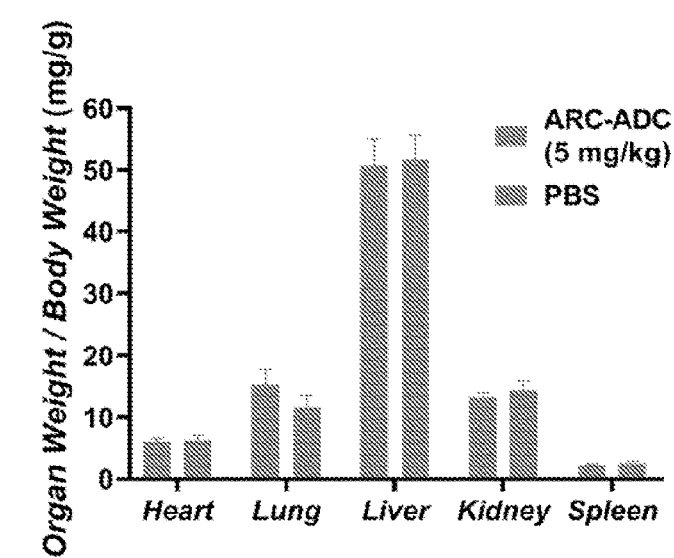
Figure 3:
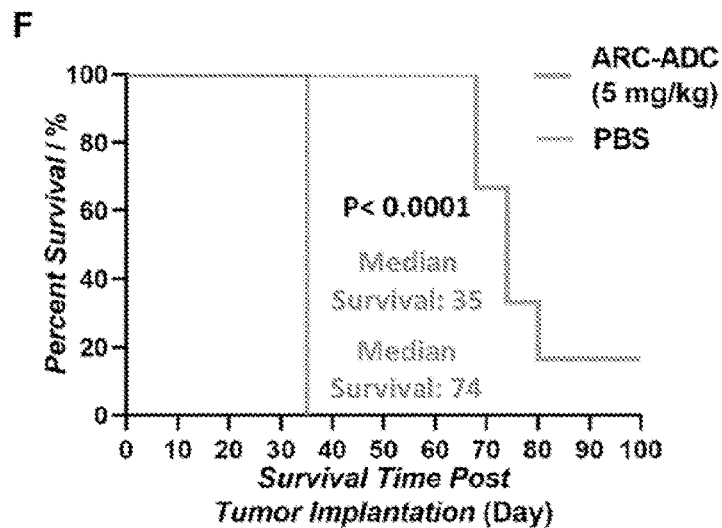
Figure 11:
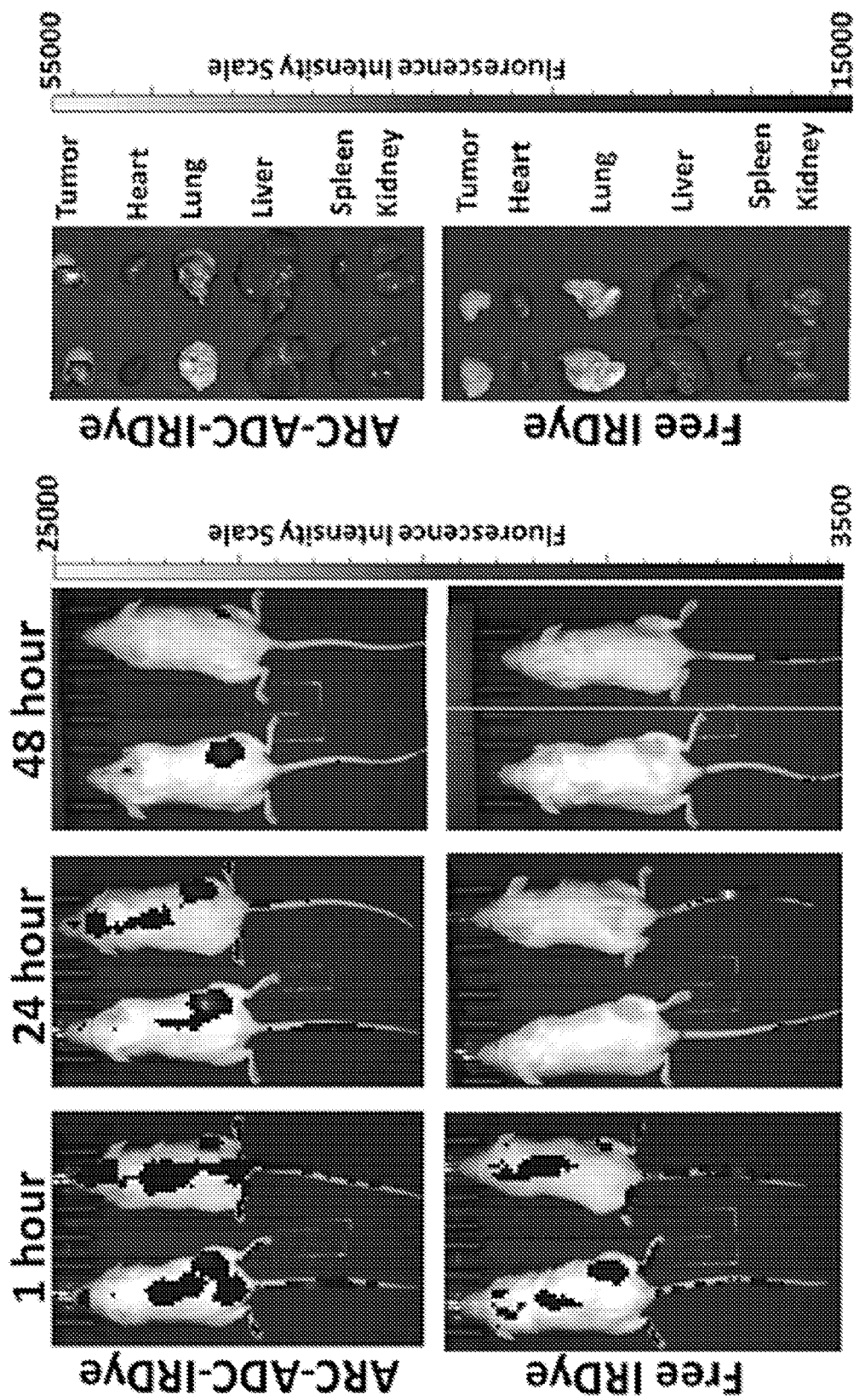
FIG. 11 illustrates biodistribution of anti-HER2 ARC-ADC in mice. (A) and (B) In vivo imaging of mice bearing human tumors and harvested tumors and organs post injection of IRDye-labeled anti-HER2 ARC-ADC and free IRDye in two independent experiments. HCC1954 cells were s.c. implanted into the flank of female NSG mice (n=2 for (A) and n=1 for (B)). IRDye-labeled anti-HER2 ARC-ADC (5 mg/kg) or free IRDye at the same molar concentration was injected i.v. through tail vein one-week post tumor implantation. Mice were then imaged at 1, 24, and 48 hours post injection, followed by euthanasia and imaging of harvested tumors and major organs.
Figure 11:
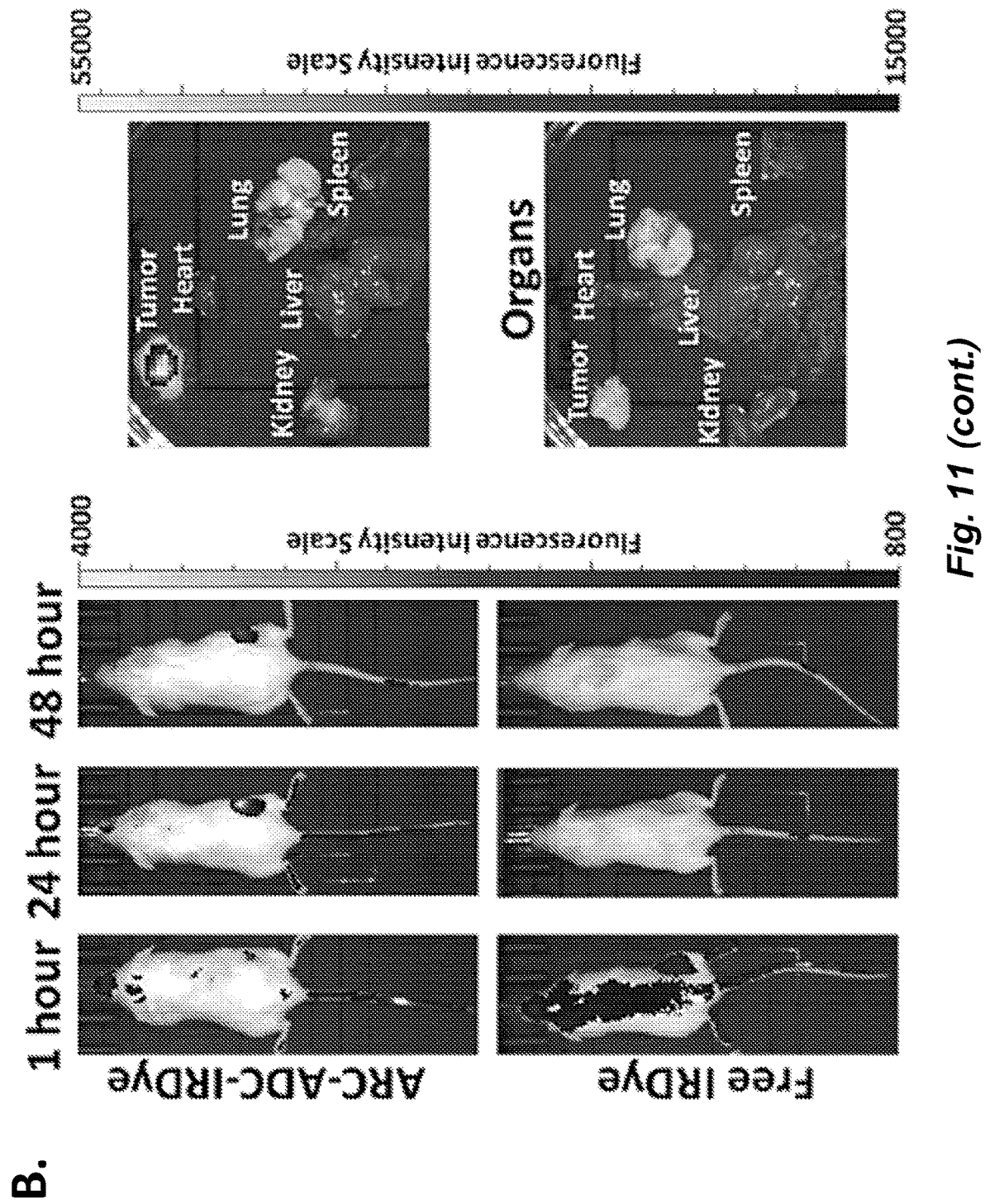

Pharmacokinetics of CD38 C-fusion IgG was then examined in mice. Two sandwich ELISAs using different detection antibodies revealed comparable half-lives (37.41±16.63 hours by anti-kappa light chain; 33.14±19.49 hours by anti-CD38) for intravenously administered CD38 C-fusion IgG in mice (FIG. 3A). Next, in vivo biodistribution and efficacy were evaluated for the anti-HER2 ARC-ADC using NSG mice bearing tumors derived from HER2-expressing HCC1954 cells. Near-infrared fluorescence-based imaging revealed the implanted human tumors as major locations for IRDye-labeled anti-HER2 ARC-ADC post intravenous injections (FIGS. 3B and 11). In contrast to the PBS-treated group with rapidly growing tumors, mice treated with anti-HER2 ARC-ADC showed tumor shrinkage upon treatment initiation and significant inhibition of tumor growth (FIG. 3C). These results demonstrate excellent in vivo efficacy of the anti-HER2 ARC-ADC for established tumors in mice. No loss of body weight or major organ weights or overt toxicity was observed for both groups during the study (FIGS. 3D-E). Importantly, in comparison to the median survival of PBS-treated group (35 days), the median survival of ARC-ADC-treated group (74 days) was increased by more than 110% (FIG. 3F).

Materials and Methods

Materials.

Synthetic gBlocks DNA fragments and oligonucleotides were purchased from Integrated DNA Technologies (IA, USA). AccuPrime Pfx DNA Polymerase kit (12344024), electroporation cuvettes plus (FB101), Expi293F cells (A14527), Opti-MEM I reduced serum medium (31985070), Ni-NTA resin (88221), goat anti-human kappa light chain secondary antibody with HRP (18853), anti-CD38 monoclonal antibody (clone: HIT2) with biotin (13-0389-82), QuantaBlu fluorogenic peroxidase substrate kit (15169), fetal bovine serum (26140079), 0.25% trypsin-EDTA with phenol red (25200056), and MTT reagent (M6494) were purchased from Thermo Fisher Scientific (MA, USA). Anti-human IgG (H+L) antibody (50-668-06) and 4% paraformaldehydesolution in PBS (AAJ19943K2) were purchased from Fisher Scientific (NH, USA). EcoRI DNA restriction enzyme (R3101S), NheI DNA restriction enzyme (R3131S), and T4 DNA ligase (M0202S) were purchased from New England Biolabs (MA, USA). Zymoclean gel DNA recovery kit (D4001) was purchased from Zymo Research (CA, USA). Zeocin solution (ant-zn-05) was purchased from Invivogen (CA, USA). Protein G resin (L00209) and exendin-4 were purchased from Genscript (NJ, USA). Rat liver tritosomes were purchased from Xenotech (KS, USA). PEI MAX-transfection grade linear polyethylenimine hydrochloride (24765-1) was purchased from PolySciences Inc. (PA, USA). BalanCD HEK293 medium (91165) was purchased from Irvine Scientific (CA, USA). Nicotinamide guanine dinucleotide (NGD+) (sc-215563) was purchased from Santa Cruz Biotechnology (TX, USA).

Alex-Fluor dye 488 DBCO conjugation reagent (1278-1) was purchased from Click Chemistry Tools (AZ, USA). IRDye 800CW was purchased from LI-COR Biosciences (NE, USA). Tissue culture treated vented flasks (250 mL) (25-209) were purchased from Genesee Scientific (CA, USA). Multivette 600 LH-Gel (15.1675) for plasma preparation was purchased from Sarstedt Group (Nümbrecht, Germany). Care touch twist top lancets (30 Gauge) for blood sample collection (160104T) was purchased from CareTouch (NY, USA). QuikChange II site-directed mutagenesis kit (200521) was purchased from Agilent Technologies (CA, USA). Black 96-well microplates (655209) and black 96-well microplates with high-binding base (655077) were purchased from Greiner Bio-One (Kremsmünster, Austria). Recombinant human ErbB2/Her2-Fc chimera protein (1129-ER-050) and streptavidin-HRP (DY998) were purchased from R&D Systems (MN, USA). Amicon ultra-15 centrifugal filter units with 10 kDa protein size cut-off (UFC901024) and 30 kDa protein size cut-off (UFC903024) and bovine serum albumin (1265925GM) were purchased from MilliporeSigma (MA, USA). Dulbecco's Modified Eagle's Medium (10-017-CV), Roswell Park Memorial Institute 1640 medium (10-040-CV), Dulbecco's Phosphate-Buffered Saline (21-031-CM), and Corning matrigel matrix (354248) were purchased from Corning Inc. (NY, USA). Erlenmeyer flasks (500 mL) (89095-278), fluoromount mounting reagent (99990-086), round cover slips (89167-106), U-100 BD micro-fine IV insulin syringes (BD-329424), TC-treated 96-well plates (10062-900) and TC-treated 24-well plates (10062-896) were purchased from VWR International (PA, USA).

Cell Lines.

Breast cancer cell lines: HCC1954, MCF7, MDA-MB-231, and MDA-MB-468 were purchased from American Type Culture Collection (VA, USA).

Chemical Synthesis and Characterization.

The experimental details and results for chemical synthesis of 2'-Cl-araNAD$^+$-N$_3$, alkynyl-MMAF, 2'-Cl-araNAD$^+$-MMAF, 6-MMAF-AMP, 6-MMAF-Adenosine, and 6-MMAF-Adenine are provided in the Supplementary Information.

Molecular cloning. Synthetic DNA encoding human CD38 extracellular domain (R45-I300) with 4 mutated asparagine residues (N100D, N164A, N129D and N209D) (SEQ ID NO: 3). for the removal of N-glycosylation was purchased from IDT (Integrated Device Technology, CA).

The overlap extension polymerase chain reaction (PCR) was adopted to generate DNA fragments encoding (1) the light chain of CD38 N-fusion IgG (the extracellular domain of CD38 fused to the N-terminus of Herceptin light chain with a GGS linker between two domains) and (2) the heavy chain of CD38 C-fusion IgG (the extracellular domain of CD38 fused to the C-terminus of Herceptin heavy chain with a GGS linker between two domains). Primers for amplifying DNA fragments and conducting the overlap extension PCRs are listed below.

Primers for amplifying CD38 DNA for constructing CD38 N-fusion IgG light chain: (1) Forward: 5'-TCACGAATTCGAGATG-GAGGCAACAATGGTCAGG-3' (SEQ ID NO: 22); (2) Reverse: 5/-CGCCACCCCCGATCTCACTAGTACAT-GAACTATCCTCTGGG-3' (SEQ ID NO: 23). Primers for amplifying Herceptin light chain DNA for constructing CD38 N-fusion IgG light chain: (1) Forward: 5'-TGAGATCGGGGGTGGCGGAAGCGAC-ATCCA-GATGACCCAGTCTCC-3' (SEQ ID NO: 24); (2) Reverse: 5'-CAGCTAGCACTTATCAACACTCTCCC-3'(SEQ ID NO: 25). Primers for amplifying CD38 DNA for constructing CD38 C-fusion IgG heavy chain: (1) Forward: 5'-GGGGGTGGCGGAAGCAGATG-GAGGCAACAATGGTCAGG-3' (SEQ ID NO: 26); (2) Reverse: 5'-CCAGCTAGCACTTATCAGATCT-CACTAGTACATGAACTATCCTCTGGGTT-3' (SEQ ID NO: 27). Primers for amplifying Herceptin heavy chain DNA for constructing CD38 C-fusion IgG heavy chain: (1) Forward: 5'-CACGAATTCGGAGGTGCAGCTG-3' (SEQ ID NO: 28); (2) Reverse: 5'-GCTTCCGCCACCCCCTT-TACCCGGAGACAGGGAGAGG-3' (SEQ ID NO: 29).

Bands of the generated DNA fragments for each fusion protein were excised from agarose gels and purified by DNA extraction kits (Zymo Research, CA). Cleaned DNA fragments were processed by DNA restriction enzymes, NheI and EcoRI (New England Biolabs, MA), followed by ligation into empty pFUSE vector backbone by DNA T4 ligase (New England Biolabs, MA). Finally, ligation products were used to transform DH10B Escherichia coli electrocompetent cells and positive colonies selected from zeocin resistance were picked for DNA sequencing to confirm the designed fusion proteins in the pFUSE expression vectors.

Molecular Cloning of CD38 C-Fusion IgG E226Q Mutant.

The generated pFUSE expression vector for CD38 C-fusion IgG heavy chain was used as a template for constructing the pFUSE expression vector for CD38 C-fusion IgG heavy chain E226Q mutant. Site-directed mutagenesis was performed with QuikChange II site-directed mutagenesis kit (Agilent Technologies, CA) per manufacturer's instructions using primers listed below: (1) Forward: 5'-TTCG-GAAGTGTTCAGGTACATAACCTC-CAACCCGAAAAAGTGC-3' (SEQ ID NO: 30); (2) Reverse: 5'-GGAGGTTATGTACCT-GAACACTTCCGAAGGTGGAATCTTTATCGA-3' (SEQ ID NO: 31). Upon electroporation with DH10B electrocompetent cells, zeocin-based selection (InvivoGen, CA) was carried out and the identified positive colonies were picked for DNA sequencing to confirm the designed CD38 C-fusion IgG heavy chain E226Q mutant in the pFUSE expression vectors.

Mammalian Cell Expression and Purification of Antibodies and Antibody Fusions.

Herceptin IgG, CD38 N-fusion IgG, CD38 C-fusion IgG, and CD38 C-fusion IgG E226Q mutant were expressed and purified by procedures described below. pFUSE expression vectors for antibody light chain (120 µg) and heavy chain (240 µg) in 12 mL of Opti-MEM medium (ThermoFisher Scientific, MA) were mixed with 960 µL of transfection grade linear polyethylenimine hydrochloride (1 mg/mL) (Polyscience, PA) for the transfection of 240 mL of Expi293 cells (ThermoFisher Scientific, MA) cultured at the density of 2.5 million mL$^{-1}$ per manufacturer's instructions. After 6-day incubation on an orbital shaker (125 rpm) in a 37° C. incubator with 5% CO$_2$, secreted antibodies or fusion antibodies in the culture media were collected and purified by protein G affinity chromatography (GenScript, NJ) per manufacturer's instructions. Eluted proteins by 100 mM glycine (pH 2.7) were dialyzed against PBS buffer (pH 7.4) and concentrated with 30 kDa filters (MilliporeSigma, MA). The purified proteins were examined by SDS-PAGE stained with Coomassie blue. Protein concentrations were determined using a NanoDrop 2000C spectrophotometer (ThermoFisher Scientific, MA) with their respective calculated molar extinction coefficients.

The pFUSE expression vector for recombinant CD38 extracellular domain with the C-terminal 6-histidine tag (SEQ ID NO: 77) was constructed as previously described. Briefly, cell culture media with recombinant CD38 was first dialyzed against storage buffer (25 mM HEPES, 250 mM NaCl, pH 7.5) prior to purification by Ni-NTA resins (ThermoFisher Scientific, MA). Dialyzed media were gradually passed through the Ni-NTA resins in a gravity flow column twice, followed by washing with 15 column volumes of wash buffer (20 mM Tris-HCl, pH 8.0, 200 mM NaCl, 30 mM imidazole). Recombinant CD38-His6 were then eluted in 15 column volumes of elution buffer (20 mM Tris-HCl, pH 8.0, 200 mM NaCl, 400 mM imidazole) and were dialyzed into PBS buffer (pH=7.4) for overnight at 4° C. and then in the same fresh buffer for another 8 hours under the same conditions. Finally, recombinant CD38-His6 was concentrated by 10 kDa cut-off filters (MilliporeSigma, MA). The purified proteins were examined by SDS-PAGE stained with Coomassie blue. Protein concentrations were determined using a NanoDrop 2000C spectrophotometer (ThermoFisher Scientific, MA) with the calculated molar extinction coefficient.

Binding to Recombinant HER2-Fc Fusion by ELISA.

Recombinant HER2-Fc fusion protein (R&D System, MN) (50 µg mL$^{-1}$) was coated overnight on 96-well ELISA plates at room temperature (Greiner Bio-One, NC) in 80 µL of PBS buffer (pH 7.4). After the coated wells were blocked with 3% bovine serum albumin (BSA) (MilliporeSigma, MA) in PBS buffer (pH 7.4) for 2 hours at room temperature followed by three times wash with 200 µL of 0.1% PBST solution, CD38 N-fusion IgG, CD38 C-fusion IgG, and Herceptin in PBS buffer (pH 7.4) were applied to the wells at various final concentrations (0.0005, 0.005, 0.05, 0.5, 5, 50, 500, and 1000 nM) and incubated at room temperature for 1 hour. After three times wash by PBST, 80 µL anti-human IgG kappa antibody horseradish peroxidase (HRP) conjugates (ThermoFisher Scientific, MA) were applied and incubated at room temperature for 1 hour prior to the three times wash by PBST and subsequent additions of 80 µL QuantaBlu fluorogenic substrates (ThermoFisher Scientific, MA). The fluorescence intensities (excitation at 325 nm; emission at 420 nm) were recorded by a Synergy H1 plate reader (Biotek, VT) after 5-minute incubation at room temperature. The Sigmoidal dose-response function in GraphPad Prism (GraphPad, CA) was adopted to calculate the $EC_{50}$ (half maximal binding concentration) for different constructs against the recombinant HER2 extracellular domain.

Enzymatic Activities of CD38 and CD38 IgG Fusions.

$NGD^+$ (Sigma-Aldrich, MO) was used as a substrate to determine ADP-ribosyl cyclase activity of purified CD38 and CD38 C-fusion IgG. Cyclic GDP-ribose (cGDPR) form from CD38 cyclase activity is characterized by fluorescence emission at 410 nm (excitation at 300 nm). Reactions were initiated by additions of purified CD38 (20 nM), CD38 C-fusion IgG (10 nM), or Herceptin IgG (10 nM) into assay wells with 100 µM $NGD^+$ in PBS buffer (pH 7.4), followed by monitoring the reactions through fluorescence at 410 nm (excitation at 300 nm) for 5 minutes using a Synergy $H_1$ plate reader (BioTek, VT).

Inhibition Activities of 2'-Cl-araNAD$^+$-$N_3$ for CD38 C-Fusion IgG.

Various concentrations of 2'-Cl-araNAD$^+$-$N_3$ were incubated with 2 nM of CD38 C-fusion IgG and 100 µM of $NGD^+$ for 20 minutes in 50 mM Tris buffer (pH 8.5). The formation of cyclic GDP-ribose was monitored by a Synergy $H_1$ plate reader (Biotek, VT) under the kinetic mode with excitation wavelength set at 300 nm and emission wavelength at 410 nm. The initial velocities ($v_{initial}$) of cyclic GDP-ribose generation in the presence of different concentrations of 2'-Cl-araNAD$^+$-$N_3$ were used to determine covalent inactivation constant ($k_{inact}$) by a 2-step regression model as follows, $[P]=v_{initial}(1-\exp(k_{obst}))/k_{obs}$ and $k_{obs}=k_{inact}[I]/([I]+K_I)$, where [P] is the concentration of product formed at given time points; $v_{initial}$ is the initial reaction rate; $k_{obs}$ is the rate constant; $k_{inact}$ is the inactivation rate constant for the covalent inhibitor; [I] is the concentration of covalent inhibitor; and $K_I$ is the concentration of covalent inhibitor giving rise to an inactivation rate equal to half of $k_{inact}$.

Fluorescent Dyes Conjugation for CD38 C-Fusion IgGs and In-Gel Fluorescence Analysis.

2 µM of CD38 C-fusion IgG, CD38 C-fusion IgG E226Q mutant, and Herceptin IgG were first incubated in the absence or presence of 40 µM of 2'-Cl-araNAD+-$N_3$ in 50 mM Tris buffer (pH 8.5) for 2 hours on ice. The reaction mixtures were then added with Alexa Fluor 488 DBCO (Click Chemistry Tools, AZ) at final concentrations of 200 µM and kept on ice for 0.5 hour prior to SDS-PAGE analysis. The SDS-PAGE gels were first imaged by a ChemiDoc Touch (BioRad, CA) imager for the fluorescence of Alexa Fluor 488 and then stained with Coomassie blue for white-light imaging.

Plasma Stability of Alexa Fluor 488-Conjugated CD38 C-Fusion IgG and Fluorescein-Labeled Exendin-4.

To prepare CD38 C-fusion IgG conjugated with Alexa Fluor 488, 5 µM of CD38 C-fusion IgG was incubated with 500 µM 2'-Cl-araNAD+-$N_3$ in 50 mM Tris buffer (pH 8.5) on ice for 2 hours, followed by buffer exchange with 30 kDa size cut-off filters to remove free 2'-Cl-araNAD$^+$-$N_3$. The resulting CD38 C-fusion IgG labelled with 2'-Cl-arabinose-ADP-$N_3$ was then mixed with Alexa Fluor 488 DBCO (Click Chemistry Tools, AZ) at a molar ratio of 1:50 and incubated on ice for 30 minutes prior to buffer exchange for removing free Alexa Fluor 488 DBCO. To prepare exendin-4 labeled by NHS-fluorescein (Thermo-Fisher Scientific, MA), 3 mg/mL exendin-4 was incubated with 1 mM of NHS-fluorescein in PBS buffer on ice for 2 hours, followed by passing through Zeba spin desalting columns (7K MWCO, Thermo-Fisher Scientific, MA) per manufacturer's instruction.

The generated CD38 C-fusion IgG conjugated with 2'-Cl-arabinose-ADP-Alexa 488 and fluorescein-labeled exendin-4 were mixed with fresh CD-1 mouse plasma or PBS at a final concentration of 3 µM for Alexa Fluor 488-conjugated CD38 C-fusion IgG and 0.75 mg/mL for fluorescein-labeled exendin-4 in the presence of 100 µg/mL penicillin and streptomycin and placed at 37° C. in an incubator with 5% $CO_2$ for up to 14 days with fixed amounts of mixtures sampled and frozen at various time points for SDS-PAGE gel analysis at the end of study. SDS-PAGE gels were first imaged using a ChemiDoc Touch (Biorad, CA) imager for the Alexa Fluor 488 or fluorescein signals and then stained with Coomassie blue for white-light imaging. The fluorescence intensities of the protein bands representing intact CD38 C-fusion IgG-2'-Cl-arabinose-ADP-Alexa 488 or fluorescein-labeled exendin-4 were quantified by ImageLab (Biorad, CA).

Cellular uptake assays for Alexa-Fluor 488-conjugated CD38 C-fusion IgG. The CD38 C-fusion IgG-2'-Cl-arabinose-ADP-Alexa 488 was prepared as described above in the plasma stability section. HCC1954 cells were cultured in RPMI1640 medium (Corning, N.Y.) supplemented with 10% FBS and MDA-MB-468 cells were cultured in DMEM medium (Corning, N.Y.) supplemented with 10% FBS. Both cell lines were kept in a 37° C. incubator with 5% CO2. First, 1 104 HCC1954 or MDA-MB-468 cells at passage 3 were seeded onto 12 mm round cover slides (VWR, PA) in 24-well plates (VWR, PA) for overnight in the incubator. Culture media were removed next day, followed by three times wash with DPBS (Corning, N.Y.). 200 µL of DPBS containing 200 nM of CD38 C-fusion IgG-2'-Cl-arabinose-ADP-Alexa 488 was then added for incubation with cells for 2 hours in a 37° C. incubator with 5% CO2 or on ice. As negative controls, both cell lines in DPBS only were also incubated under 2 conditions mentioned above.

Following the incubation, DPBS with CD38 C-fusion IgG-2'-Cl-arabinose-ADP-Alexa 488 were decanted, washed three times with ice-cold DPBS, and fixed by ice-cold 4% paraformaldehyde for 20 minutes on ice. After the fixation and three times washing with DPBS, the cells were incubated with 0.1% Triton X-100 (MilliporeSigma, MA) for 10 minutes at room temperature for permeabilization. Finally, permeabilized cells washed by DPBS were stained for nuclei with 300 nM DAPI water solution (ThermoFisher Scientific, MA) for 20 minutes at room temperature and then sealed into slides for confocal imaging using a Leica SP8 confocal laser scanning microscope (Leica, Germany) equipped with a 40×/1.3 oil immersion objective lens (HC PL APO 40×/1.30 Oil CS2). DAPI and Alexa 488 were excited at 405 nm and 488 nm, respectively. Images were processed by Leica Application Suite X (LAS X) software (Leica, Germany).

Conjugation of 2'-Cl-araNAD+-MMAF to CD38 C-Fusion IgG.

To determine the conjugation kinetics, 1 mM 2'-Cl-araNAD+-MMAF was incubated with 10 µM CD38 C-fusion IgG in 50 mM Tris buffer (pH 8.5) for different amounts of periods (1, 5, 10, 20, 30, 60, 90, and 120 minutes) on ice. Then, 1 µL of the mixtures was transferred into 100 µL of PBS buffer (pH 7.4) containing 100 µM NGD+ on 96-well plates. The initial rates of formation of cyclic GDP-ribose based on fluorescence intensity measured at 410 nm by a Synergy H1 plate reader (Biotek, VT) under kinetic mode were used to define the residual CD38 catalytic activities. The 100% CD38 enzymatic activities were determined using 1 µL of 10 µM CD38 C-fusion IgG in 50 mM Tris buffer (pH 8.5) incubated for 120 minutes on ice. Data points were fit to the first-order decay function $A(t)=A0e(-kobst)$, where A0 is 100% activity, A(t) is activity measured at a given time t, and kobs is the rate constant.

One-Step Preparation of ARC-ADC.

5 µM of CD38 C-fusion IgG and 500 µM 2'-Cl-araNAD+-MMAF were incubated in 50 mM Tris buffer (pH 8.5) for overnight on ice, followed by buffer exchange using 30 kDa size cut-off filters (MilliporeSigma, MA) to remove free 2'-Cl-araNAD+-MMAF.

Mass Spectroscopy Study for Conjugation of CD38 C-Fusion IgG by 2'-Cl-araNAD+-MMAF.

All protein samples were diluted to 0.2 mg/mL in 50 mM ammonium bicarbonate (pH 8.0). Glycans were removed using 1:100 w/w PNGaseF (New England Biolabs, MA) at 37° C. overnight. They intermolecular disulfide bonds were cleaved using 0.1 M dithiothreitol (DTT) for 5 minutes at room temperature. 4 uL of samples were injected onto the Xevo using the method below.

Intact protein samples were analyzed by LC-MS (ACQUITY UPLC H-class system, Xevo G2-XS QTOF, Waters corporation). Proteins were separated away from reaction buffer salts using a phenyl guard column (ACQUITY UPLC BEH Phenyl VanGuard Pre-column, 130 Å, 1.7 µm, 2.1 mm×5 mm, Waters corporation). The 5-min method used a 0.2 mL/min flow rate of a gradient of buffer A consisting of 0.1% formic acid in water (water LC-MS #9831-02, J. T. Baker; formic acid LC-MS #85178, Thermo Scientific) and buffer B, acetonitrile (acetonitrile UHPLC/MS #A956, Thermo Scientific). The gradient running program (flow rate set at 0.2 mL/min, curve set as 6) is: maintaining 100% buffer A from 0 s to 30 s, adjusting to 10% buffer A and 90% buffer B from 30 s to 120 s as gradient, maintaining 10% buffer A and 90% buffer B from 120 s to 150 s, reaching to 100% buffer A from 150 s to 240 s as a gradient and maintaining 100% buffer A from 240 s to 300 s.

The Xevo Z-spray source was operated in positive MS resolution mode with a capillary voltage of 3000 V and a cone voltage of 40 V (NaCsI calibration, Leu-enkephalin lock-mass). Nitrogen was used as the desolvation gas and a total flow of 800 L h-1. Total average mass spectra were reconstructed from the charge state ion series using the MaxEnt1 algorithm from Waters MassLynx software V4.1 SCN949 according to the manufacturer's instructions. To obtain the ion series described, the major peaks of the chromatogram were selected for integration before further analysis.

Mass Spectroscopy Study for Conjugation Site of 2'-Cl-araNAD+-MMAF with CD38 C-Fusion IgG.

The CD38 C-fusion IgG and anti-HER2 ARC-ADC were subjected to overnight solution digestion with trypsin gold (Promega) at 37° C. and pH 8.5. All LC-MS/MS experiments were performed using the same Waters Xevo Q-TOF set up and buffer system as the intact protein analysis described above. Separation of peptides was performed by reverse-phase chromatography using a reverse-phase C4 column (ACQUITY UPLC Protein BEH C4 Column, 300 Å, 1.7 µm, 2.1 mm×50 mm, Waters corporation). The gradient running program (flow rate set at 0.3 mL/min, curve set as 6) is: maintaining 97% buffer A and 3% buffer B from 0 s to 30 s, reaching to 40% buffer A and 60% buffer B from 30 s to 120 s as a gradient, maintaining 40% buffer A and 60% buffer B from 120 s to 150 s, reaching to 10% buffer A and 90% buffer B from 150 s to 180 s as a gradient, maintaining 10% buffer A and 90% buffer B from 180 s to 210 s, reaching to 97% buffer A and 3% buffer B from 210 s to 240 s as a gradient and maintain 97% buffer A and 3% buffer B from 240 s to 300 s.

Peptide data were acquired after a 0.5 min waste divert to remove buffer salts. The Xevo Z-spray source was operated with a capillary voltage of 3000 V and a cone voltage of 40 V (NaCsI calibration, Leu-enkephalin lock-mass). Nitrogen was used as the desolvation gas and a total flow of 800 L h-1. Data were acquired across the 100-2000 da range in MSe continuum mode with alternating 0.5 sec scans at alternating collision energy, low energy, 0 V, and a high collision energy ramp (15-45 V). The high energy data correspond to the MS2 secondary fragmentation of the low energy scans of a similar time. The data were processed for exact mass peptide matching and b&y ion fragmentation confirmation using Biopharmalynx software (Version 1.3.5 Water corp). The software generates in-silico peptide digestion data including all potential modifications and maps the real data at 30 ppm error to the theoretically calculated masses.

X-Ray Crystallography of 2'-Cl-araNAD+-Human CD38 Complex.

Recombinant human CD38 catalytic domain was prepared and then incubated with 2'-Cl-araNAD+ at a molar ratio of 1:100 on ice for overnight. The covalent protein complex was purified by gel filtration column and kept in 15 mM HEPES, pH 7.5, 50 mM NaCl at a concentration of 160 uM. Crystallization was performed at 22° C. using vapor diffusion method in a hanging-drop manner with a 1:1 ratio of 1 µL of the reservoir solution and 1 µL of the protein solution. Initial crystals grew under similar condition. The optimized condition for the crystal growth resulting in well diffracting crystals showed to be 100 mM HEPES pH 7.0, 100 mM potassium phosphate dibasic and 38-42% morpheus precipitant mix 1 (MD2-250-84) from Molecular Dimension (Newmarket, Suffolk, England), where PEG 3350 was the essential component. Single crystals appeared after 3 days and grew to their maximum size within 10-15 days. Crystals were flash-frozen by liquid nitrogen directly before they were mounted for data collection. The best data was collected at Advance Photon Source (APS), beamline 23-ID-B at Argonne National Laboratory, equipped with an Eiger 16M detector.

The collected data were indexed and integrated with XDS4 and scaled using Scala, a part of the CCP4 suite. Initial phase information was obtained by molecular replacement using PHASER with the previously solved structure of human CD38 catalytic domain (PDB ID: 6EDR) as the search model. Waters were added using ArpWarp during the initial round of the refinement and the ligand was built using Ligand Builder in Coot. The structure was improved by iterative rounds of model building and refinement using the programs Coot and Refmac5. The crystals belong to space group P 41 2 2 and it contains two molecules per asymmetric unit with Mathew coefficient of 2.73. Crystallographic details and statistics are listed in Table 2.

Flow Cytometric Analysis.

HCC1954 cells were cultured in RPMI1640 medium (Corning, N.Y.) supplemented with 10% FBS (ThermoFisher Scientific, MA) in 37° C. incubator with 5% CO2. MCF7, MDA-MB-231, and MDA-MB-468 cells were cultured under the same conditions but with DMEM medium (Corning, N.Y.) supplemented with 10% FBS. All cells used for the flow cytometry were at passage 3 with 80% confluency. Cells were detached from 125-mL tissue culture flasks (Genesee Scientific, CA) with 0.5 mL 0.25% trypsin-EDTA (ThermoFisher Scientific, MA) for 5 minutes in a 37° C. incubator with 5% CO2, followed by neutralization by the additions of 5 mL of culture media with 10% FBS. After centrifugation at 100×g for 5 minutes and subsequent removals of culture media, cell pellets were washed once by resuspending in 5 mL of DPBS followed with centrifugation at 100×g for 5 minutes. Cells were then resuspended in 1 mL ice-cold DPBS containing 200 nM Herceptin IgG and incubated at 4° C. for 30 minutes followed with 3 wash cycles with DPBS. Then, cells were resuspended in 1 mL ice-cold DPBS with 200 nM goat anti-human IgG (H+L) cross-adsorbed secondary antibody with Alexa Fluor 488 (ThermoFisher Scientific, MA) and incubated at 4° C. for 30 minutes, followed with 3 wash cycles using 5 mL DPBS. Finally, cells were resuspended in 1 mL DPBS for flow cytometry analysis by a BD Fortessa X20 Cell Analyzer (BDbiosciences, CA) for cellular Alex Fluor 488 intensities. Cells treated only with 200 nM goat anti-human IgG (H+L) cross-absorbed secondary antibody with Alex Fluor 488 were used as controls.

In Vitro Cytotoxicity Assays.

All cells used for in vitro cytotoxicity assays were at passage 3. Cells were first seeded into 96-well cell culture plates (VWR, PA) in 90 µL culture media and incubated at 37° C. in an incubator with 5% CO2 for overnight with penicillin-streptomycin (ThermoFisher Scientific, MA) at following densities: 3,000 cells per well for HCC1954, 8,000 cells per well for MCF7, 5,000 cells per well for MDA-MB-231, and 10,000 cells per well for MDA-MB-468. Then, the anti-HER2 ARC-ADC, CD38 C-fusion IgG, Herceptin IgG, and 2'-Cl-araNAD$^+$-MMAF in culture media at various concentrations were added in triplicates. Plates were placed at 37° C. in the incubator with 5% CO2 for 72 hours prior to adding the MTT reagents (ThermoFisher Scientific, MA) per manufacturer's instructions, followed by cell lysis with 100 µL lysis buffer (20% SDS in 50% dimethylformamide). After 1-hour incubation at 37° C. with 5% CO2, UV absorbance at 580 nm were measured by a Synergy H1 plate reader (Biotek, VT). Cells treated with culture media and 5 µM paclitaxel (MilliporeSigma, MA) were included as 100% and 0% viability controls, respectively. The data were fitted by the Sigmoidal function in GraphPad Prism (GraphPad, CA) to determine EC50 values.

Plasma Stability of ARC-ADC Based on In Vitro Cytotoxicity.

HCC1954 cells and MDA-MB-468 cells at passage 3 were seeded into 96-well cell culture plates (VWR, PA) with 90 µL culture media the night before the experiments (3,000 cells per well for HCC1954 and 10,000 cells per well for MDA-MB-468). Plasma-incubated ARC-ADC was prepared by mixing ARC-ADC with CD-1 mice plasma at a final concentration of 10 µM and then placed at 37° C. in an incubator with 5% CO2 for 72 hours. Freshly prepared and plasma-incubated ARC-ADC were serially diluted into culture media at various concentrations and added into cultured cells on 96-well plates. After 3-day incubation at 37° C. with 5% CO2, 10 µL of MTT reagents (ThermoFisher Scientific, MA) were added, followed by 2-hour incubation at 37° C. in an incubator with 5% CO2. Cells were then lysed with the additions of 100 µL lysis buffer (20% SDS in 50% dimethylformamide) and incubated for 1 hour at 37° C. UV absorbance at 580 nm were measured by a plate reader (Biotek, VT). Cells treated with culture media and 5 µM paclitaxel (MilliporeSigma, MA) were included as 100% and 0% viability controls, respectively. The data were fitted by the Sigmoidal function in GraphPad Prism (GraphPad, CA) to determine EC50 values.

In Vitro Drug Release of 2'-Cl-araNAD+-MMAF.

To examine the degradation of 2'-Cl-araNAD+-MMAF in lysosomes, 2'-Cl-araNAD+-MMAF at a final concentration of 0.5 mM in 50 mM sodium acetate buffer (pH 5) with 10% (v/v) rat liver lysosomal lysates was incubated at 37° C. for up to 22 hours with fixed volumes sampled at different time points. Equal volumes of acetonitrile were then added for extraction, followed by HPLC analysis with a C18-A column (Agilent Technologies, CA) through measurements of UV absorbance at 260 nm. The inlet method for the HPLC analysis is as follows: mobile phase A: 0.1% formic acid (aq), mobile B: 0.1% formic acid in acetonitrile, flow rate=2.0 mL/min, 0-2 min: 0-4% B, 2-4 min: 4-10% B, 4-6 min: 10-20% B, 6-12 min: 20-50% B, 12-17 min: 50-100% B, 17-20 min: 100-0% B. The final degradation product was identified based on retention times of synthesized standards and mass spectrometry analysis.

To further examine the degradation of rat liver lysosomal lysate-treated 2'-Cl-araNAD+-MMAF in cytosol, 2'-Cl-araNAD+-MMAF at a final concentration of 2 mM in 50 mM sodium acetate buffer (pH 5) with 40% (v/v) rat liver lysosomal lysates was first incubated at 37° C. for overnight. Then, the overnight reaction mixtures were diluted by PBS buffer at 1:3 volume ratio containing 10% (v/v) HCC1954 cell lysates and incubated at 37° C. for up to 22 hours with fixed volumes sampled at different time points. Equal volumes of acetonitrile were then added for extraction, followed by HPLC analysis with a C18-A column through measurements of UV absorbance at 260 nm. Same HPLC method as mentioned above was used for analysis. The final degradation product was identified based on retention times of synthesized standards and mass spectrometry analysis.

Pharmacokinetic Studies of CD38 C-Fusion IgG in Mice.

Five female CD-1 mice (6 weeks) were given CD38 C-fusion IgG in DPBS by tail vein intravenous (IV) injection at 3 mg/kg. Tail venipuncture was then performed for blood collection at different time points (0.5, 5, 9, 24, 48, 72, 120, 168 and 264 hours). Plasma concentrations of CD38 C-fusion IgG were determined using two different sandwich ELISAs. Standards used for the ELISA-based quantification were prepared through serial dilutions of 100 µg mL-1 antibody fusion in mouse plasma.

For the first sandwich ELISA, anti-human IgG (H+L) antibody (8 µg mL-1) (Seracare, MA) was coated on ELISA plates overnight at room temperature, followed by blocking with 3% BSA in PBS (pH 7.4) for 2 hours at room temperature. After 3-cycle wash with 200 µL 0.1% PBST, 80 µL of 100-fold diluted plasma samples were added in triplicates. Following 2-hour incubation at room temperature and 3-cycle wash with 200 µL 0.05% PBST, 80 µL of 2000-fold diluted anti-human IgG kappa antibody HRP conjugate (ThermoFisher Scientific, MA) was applied and incubated at room temperature for 1 hour. Finally, after three times wash with 0.1% PBST, 80 µL of QuantaBlu fluorogenic substrates (ThermoFisher Scientific, MA) were added and allowed for 5-minute incubation prior to measurements of the fluorescence at 425 nm by the Synergy H1 plate reader (BioTek, VT).

For the second sandwich ELISA, the same capture antibody, anti-human IgG (H+L) antibody, was used to capture the fusion antibody in plasma samples. Following blocking with 3% BSA and incubation with 100-fold diluted plasma samples, biotinylated anti-human CD38 antibody (ThermoFisher Scientific, MA) was used as the detection antibody and incubated for 1 hour at room temperature. After three times wash with 0.1% PBST, 80 μL of streptavidin-HRP conjugate (R&D System, MN) was added and incubated for 1 hour. Following three times wash with 0.1% PBST, 80 μL of the fluorogenic substrates were added and followed by measurements of fluorescence intensities by the plate reader. Based on the measured fluorescence intensities, plasma concentrations of the CD38 C-fusion IgG were calculated by fitting into the standard curves generated from the standards prepared on the same plates. Pharmacokinetic parameters including half-life (thalf) were determined by fitting data into a non-compartmental analysis model in SimBiology of MATLAB software package (Mathworks, MA).

Biodistribution of Anti-HER2 ARC-ADC in Mice.

HCC1954 cells (2 million cells per mouse, passage 3) in 50% matrigel were subcutaneously implanted into the flank of female NOD.Cg-Prkdcscid Il2rgtm1Wjl/SzJ (NSG) mice (6 weeks). One week post tumor implantation, mice were administered intravenously though tail vein with IRDye 800CW-labeled anti-HER2 ARC-ADC (5 mg/kg) which was prepared per the manufacturer's instruction or free IRDye 800CW at the same molar concentration which was neutralized by diluting in 50 mM Tris buffer (pH 7.4). Mice were then imaged at 1, 24, and 48 hours post intravenous injection using IVIS in vivo imaging system (PerkinElmer, MA), followed by euthanasia and imaging of harvested tumors and major organs (heart, lung, liver, spleen, and kidney).

In Vivo Efficacy Studies of Anti-HER2 ARC-ADC in Mice.

HCC1954 cells (1.5 million cells per mouse, at passage 3) in 50% matrigel (Corning, N.Y.) were subcutaneously implanted into the flank of female NSG mice (6 weeks). When tumor sizes reached 100 mm3, mice (n=6) were administered intravenously through tail vein with PBS or ARC-ADC (5 mg kg-1) every three days for a total of four times. Body weights and tumor sizes were measured every three days. The volume of tumor was calculated as mm3=0.5×(length)×(width)2. Mice were euthanized once the tumor sizes exceeded 1,000 mm3. Weights of harvested major organs (heart, lung, liver, spleen, and kidney) and body weights were measured. A Kaplan-Meier survival analysis was conducted in GraphPad Prism (GrapPad, CA). All procedures were approved by Institutional Animal Care and Use Committee of the University of Southern California.

In Silico Prediction for Immunogenicity of CD38 C-Fusion IgG.

The amino acid sequence of CD38 C-fusion IgG heavy chain was uploaded into the NetMHCIIpan 3.2 server for predicting immunogenic peptides which possess high binding affinity to selected representative human MHC class II molecules. Peptide sequences predicted with strong binding potentials to selected MHC class II molecules were recorded.

Among all MHC class II genes in human, the subtypes selected for prediction included all common HLA-DR alleles listed in the catalogue of common and well-documented HLA alleles, 5 common HLA-DP haplotypes, and 6 common HLA-DQ haplotypes. For HLA-DP and HLA-DQ, only haplotypes present in more than 15% of all major populations globally were chosen for prediction. HLA-DPA0103 was the only allele selected to pair with 5 HLA-DPB alleles, as common HLA-DPA subtypes that account for over 90% of all populations in total are significantly less polymorphic and their polymorphic regions make minimal contribution to binding of immunogenic peptides.

Statistical Analysis.

Two-tailed unpaired t tests were performed for comparison between two groups. Tumor growth curves of the control and treatment groups were analyzed using two-tailed unpaired t tests. A P<0.05 was defined as statistically significant. Data are shown as mean±SD. Kaplan-Meier method was adopted to compare the survival time between two groups of mice. All statistical analyses were performed using GraphPad Prism (GraphPad, CA).

Example 3. Generating Homogeneous Antibody-Drug Conjugates with Variable Drug-to-Antibody-Ratios by ADP-Ribosyl Cyclases Antibody-drug conjugates (ADCs) can deliver small-molecule drugs covalently linked to the immunoglobulin scaffold to specific types of cells with surface-expressed target antigens. Due to limitations on conjugation strategies, all currently approved ADCs are heterogeneous with varying locations and numbers of payloads. Each ADC used in clinic contains multiple populations with different drug-to-antibody ratios (DARs) that perform distinctively in vivo, raising efficacy and safety concerns.

Figure 12:
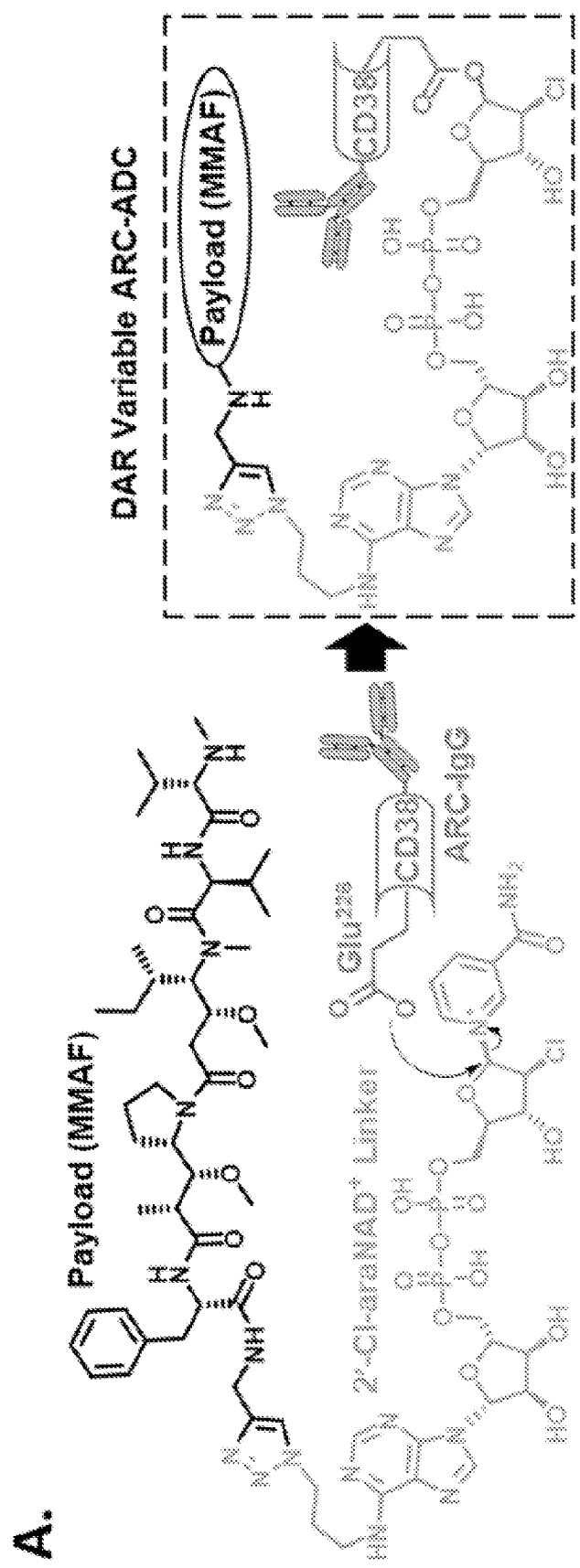
FIG. 12 illustrates homogeneous ARC-ADCs with variable DARs. (A) Schematic of 2'-Cl-araNAD$^+$ linker-mediated site-specific antibody-drug conjugation. (B) Generation of anti-hCLL-1 IgG, anti-hCLL-1-CD38 C-fusions, and anti-hCLL-1 ARC-ADCs with DARs of 2 and 4. Lower panel: Coomassie-stained SDS-PAGE gels for purified anti-hCLL-1 IgG (native antibody), anti-hCLL-1-CD38 C-fusions (DAR2-ARC-IgG and DAR4-ARC-IgG), and anti-hCLL-1 ARC-ADCs.
Figure 12:
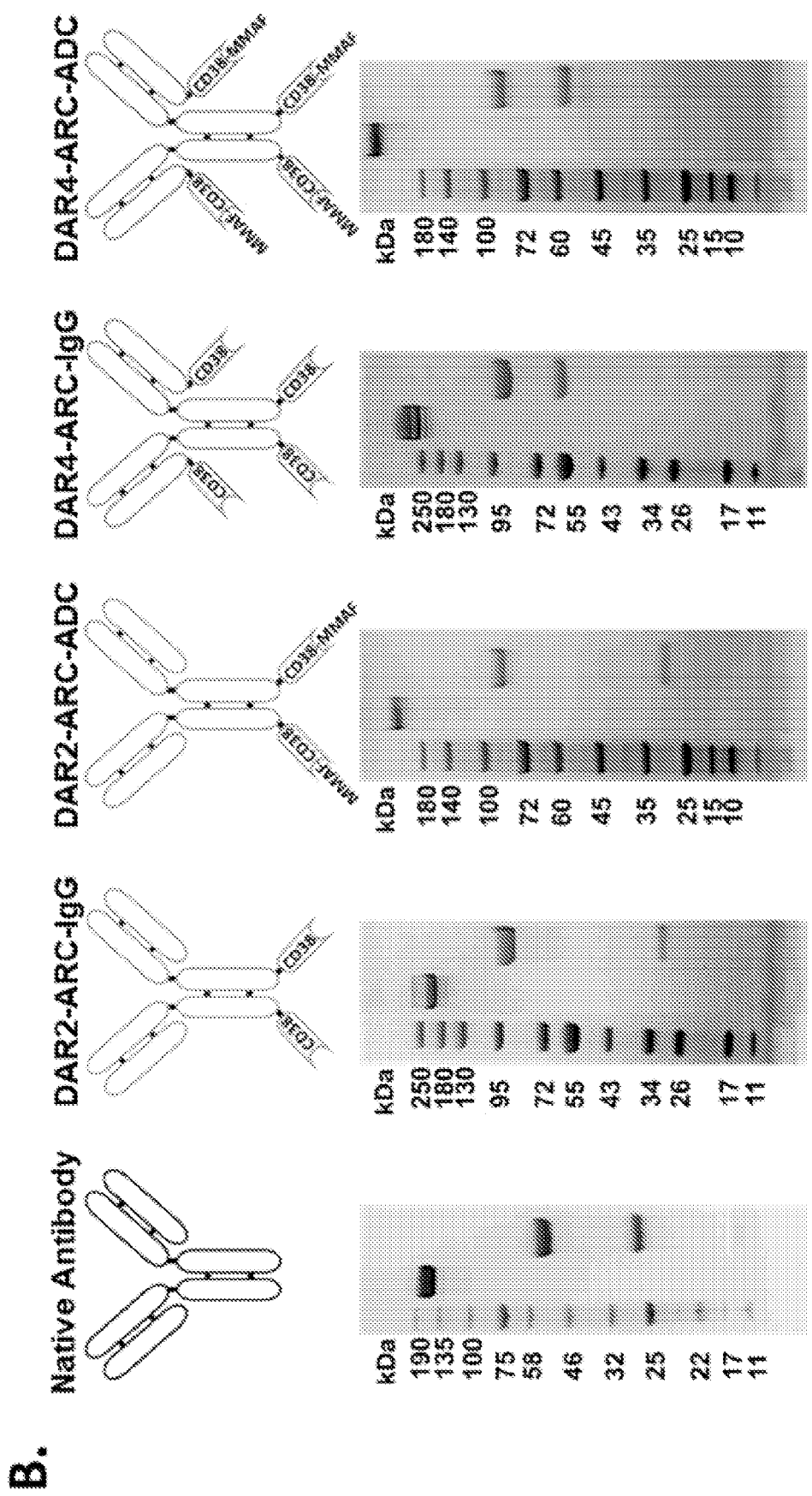

Different technologies have been established to develop homogeneous ADCs such as utilizing engineered amino acids and carbohydrates, incorporating unnatural amino acids, grafting peptides, and fusing protein domains for creating handles for conjugation. By exploiting the enzymatic activity of human CD38, a member of ADP-ribosyl cyclase family, we recently developed a new approach for single-step generation of site-specific ADCs, named ADP-ribosyl cyclase-enabled ADCs (ARC-ADCs). Through a 2'-Cl-arabinose nicotinamide adenine dinucleotide (2'-Cl-araNAD$^+$)-based covalent inhibitor of CD38, cytotoxic monomethyl auristatin F (MMAF) could be covalently attached to antibodies genetically fused with CD38 via its catalytic glutamate 226 (Glu226) residue (FIG. 12A). The resulting ARC-ADC with a DAR of 2 shows excellent stability and efficacy in treating breast cancer in preclinical models.

Given the CD38-enabling nature for site-specific conjugation, we envisioned that ARC-ADCs may provide unique opportunities for facile production of homogeneous ADCs with customizable DARs. To test this notion, we designed and generated two forms of ARC-ADCs with DARs of 2 and 4, designated as DAR2-ARC-ADC and DAR4-ARC-ADC, respectively, which exhibit remarkable in vitro and in vivo efficacy against human acute myeloid leukemia (AML) cells through specifically targeting human C-type lectin-like molecule-1 (hCLL-1). AML is the most common type of acute leukemia in adults with 5-year survival rate below 30%. CLL-1 is frequently overexpressed in blasts and leukemia stem cells (LSCs) of AML patients, but absent on normal hematopoietic stem cells (HSCs) in bone marrow, representing a promising target for AML treatment. Our anti-hCLL-1 ARC-ADCs not only provide new therapeutic candidates for AML but also demonstrate ARC-ADC as a general approach for making homogeneous ADCs with tailored DARs.

Results

Since the DAR of an ARC-ADC is associated with the number of fused CD38 catalytic domain, fusing additional CD38 extracellular domains to the immunoglobulin scaffold may thus increase numbers of payloads, likely resulting in site-specific ADCs with enhanced potency (FIG. 12A). To this end, we genetically fused human CD38 enzymatic domain to C-termini of light chain (LC) and heavy chain (HC) of an anti-hCLL-1 monoclonal antibody 1075.7 (SEQ ID NO: 6 and SEQ ID NO:8). The resulting HC-CD38 C-fusion construct was paired with LC or LC-CD38 C-fusion expression vector for transient transfection in mammalian cells for production of an anti-hCLL-1 IgG HC-CD38 C-fusion (denoted as DAR2-ARC-IgG) and an anti-hCLL-1 IgG HC-CD38 & LC-CD38 C-fusion (denoted as DAR4-ARC-IgG). Together with expressed native anti-hCLL-1 antibody, DAR2-ARC-IgG and DAR4-ARC-IgG were analyzed by Coomassie-stained SDS-PAGE gels (FIG. 12B). The observed sizes of light and heavy chains for each construct are consistent with molecular designs. The yields are about 10 mg $L^{-1}$ and 7 mg $L^{-1}$ for DAR2-ARC-IgG and DAR4-ARC-IgG, respectively, lower than that of anti-hCLL-1 antibody (14 mg $L^{-1}$).

Figure 13:
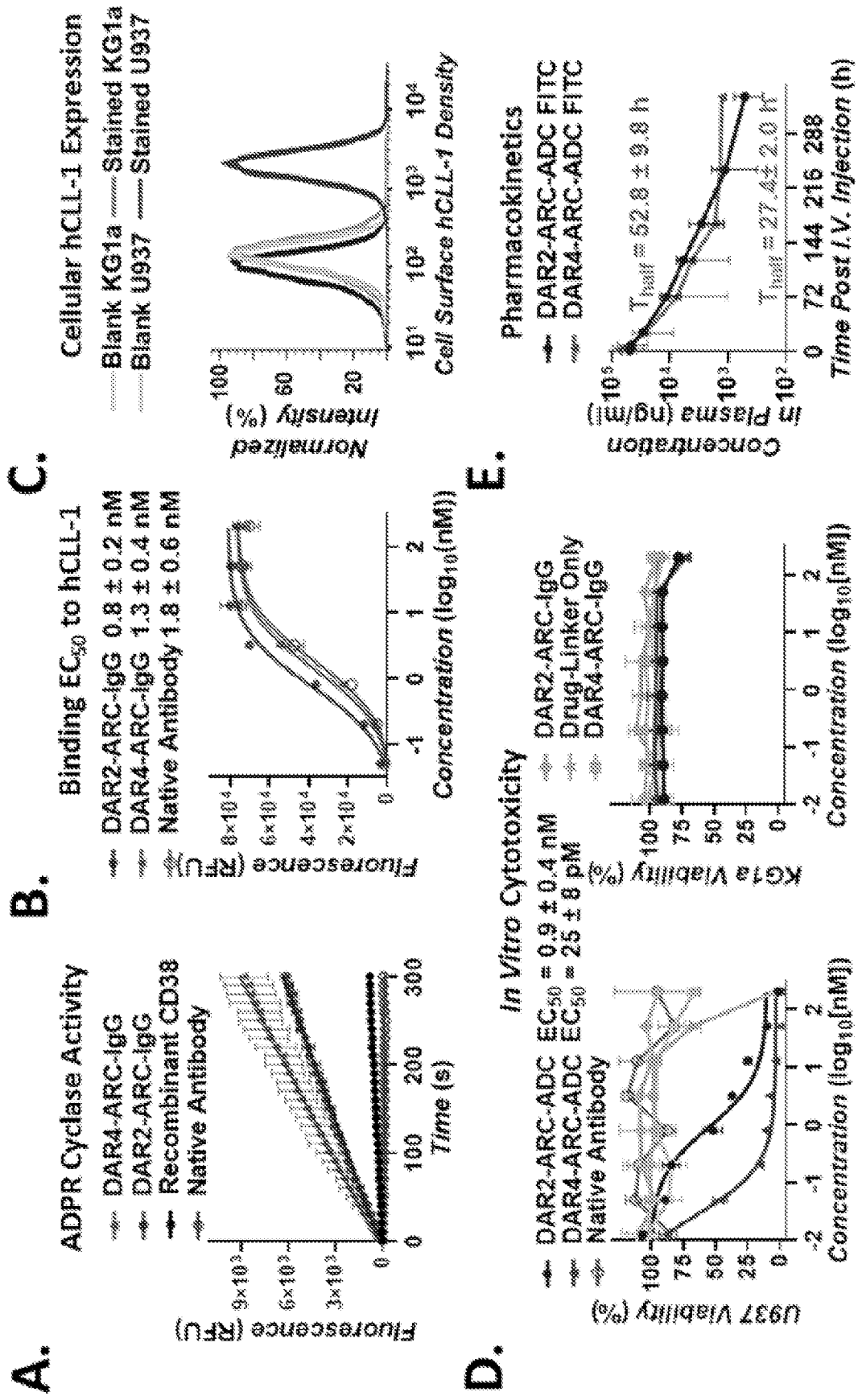
FIG. 13 illustrates the characterization of anti-hCLL-1-CD38 C-fusions and anti-hCLL-1 ARC-ADCs. (A) Analysis of ADP-ribosyl cyclase activity. Purified CD38 (20 nM), anti-hCLL-1 antibody (10 nM), DAR2-ARC-IgG (10 nM), or DAR4-ARC-IgG (10 nM) was incubated with 100 μM NGD$^+$ in PBS to monitor ADPR cyclase activity based on the formation of fluorescent cyclic GDP-ribose at 410 nm. (B) ELISA analysis of binding to recombinant hCLL-1 extracellular domain. (C) Flow cytometric analysis of hCLL-1 expression on human U937 and KG1a cells. (D) In vitro cytotoxicity of DAR2-ARC-ADC and DAR4-ARC-ADC. U937 or KG1a cells were incubated for 72 hours at 37° C. with 5% $CO_2$ with various concentrations of ARC-ADCs, drug-linker conjugate, native anti-hCLL-1 antibody, and ARC-IgGs. Cell viability was determined by MTT assays with data for cells incubated with culture medium or 5 μM paclitaxel as 100% viable or 0% viable references, respectively. (E) Pharmacokinetics in mice for surrogate DAR2-ARC-ADC and DAR4-ARC-ADC with FITC as the payloads. Noncompartmental analysis was conducted based on the plasma concentrations of surrogate ARC-ADCs determined through a sandwich ELISA by utilizing an anti-FITC polyclonal antibody as capture antibody and an anti-human kappa light chain monoclonal antibody conjugated with HRP as detection antibody.

Next, CD38 enzymatic activity and hCLL-1 binding affinity were examined for DAR2-ARC-IgG and DAR4-ARC-IgG. Fluorescence-based activity assays indicated that both fusion IgGs possess significantly higher catalytic activities than that of recombinant human CD38 extracellular domain, possibly due to improved stability (FIG. 13A). Reactions catalyzed by DAR4-ARC-IgG show approximate 50% rate increase relative to those by DAR2-ARC-IgG, owing to two extra CD38 domains. As a control, native anti-hCLL-1 antibody gives no enzymatic activity. Enzyme linked immunosorbent assay (ELISA) analysis revealed tight binding to recombinant hCLL-1 for both DAR2-ARC-IgG and DAR4-ARC-IgG, comparable to that of native anti-hCLL-1 antibody (FIG. 13B). These results support successful generation of anti-hCLL-1-CD38 fusions with robust CD38 enzymatic activity and high affinity to hCLL-1 antigen, allowing rapid generation of anti-hCLL-1 ARC-ADCs with distinct DARs.

Figure 16:
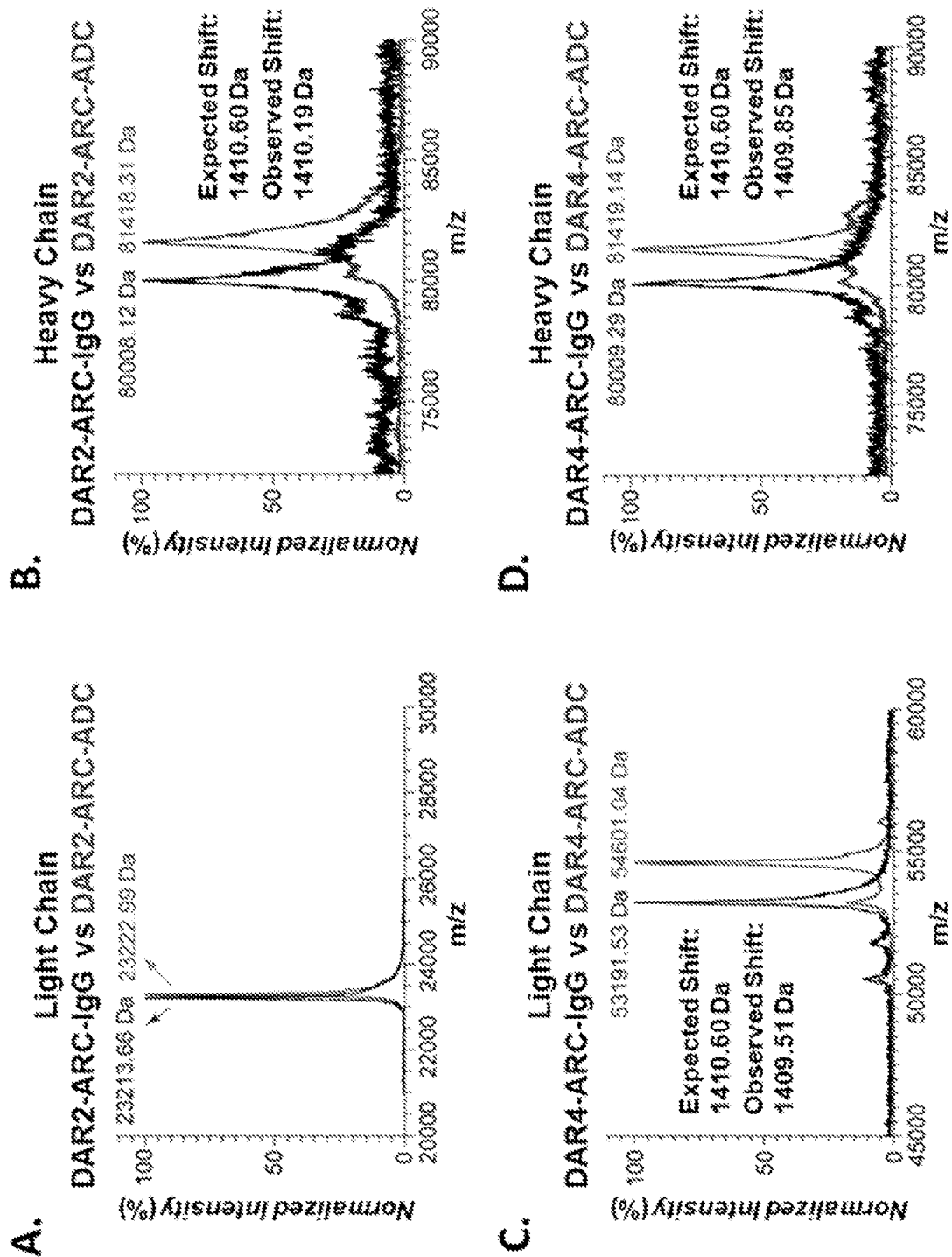
FIG. 16 illustrates MALDI-TOF mass spectra of light chain and heavy chain of (A) DAR2-ARC-IgG, (B) DAR2-ARC-ADC, (C) DAR4-ARC-IgG, and (D) DAR4-ARC-ADC.

Anti-hCLL-1 ARC-ADCs were then generated by incubating DAR2-ARC-IgG or DAR4-ARC-IgG with synthesized drug-linker conjugate (2'-Cl-araNAD$^+$-MMAF) on ice for 1 hour, resulting in DAR2-ARC-ADC and DAR4-ARC-ADC (FIG. 12B). As a tubulin inhibitor, MMAF is a potent cytotoxic payload. Mass spectrometry confirmed the generation of anti-hCLL-1 ARC-ADCs with DARs of 2 and 4 (FIG. 16). In vitro cytotoxicity of the anti-hCLL-1 ARC-ADCs was then evaluated using human AML cell lines U937 (CLL-1$^+$) and KG1a (CLL-1$^-$) (FIG. 13C-D). DAR4-ARC-ADC exhibits highly potent cytotoxicity ($EC_{50}$=25±8 pM) against U937 cells and DAR2-ARC-ADC displays relatively lower potency with an $EC_{50}$ of 0.9±0.4 nM (FIG. 13D). The drug-linker and ARC-IgGs have much weaker or little cytotoxicity for U937 cells. In comparison, none of these agents reveals significant toxicity for KG1a cells. These results demonstrate outstanding potency and specificity of anti-hCLL-1 ARC-ADCs and markedly enhanced efficacy for DAR4-ARC-AD.

Figure 17:
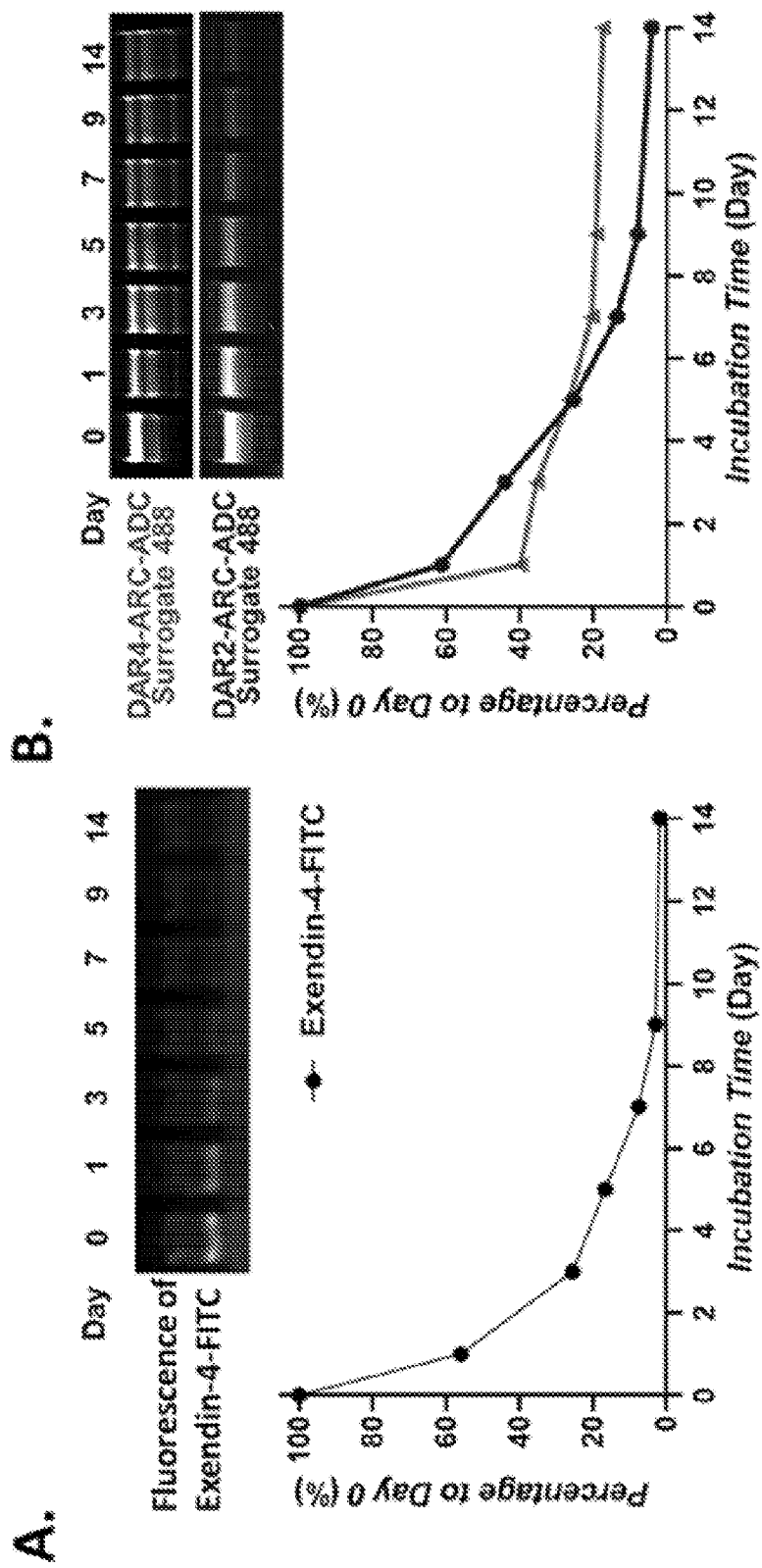
FIG. 17 illustrates stability in mouse plasma for surrogate DAR2-ARC-ADC and DAR4-ARC-ADC with Alexa Fluor 488 as the payloads. (A) Stability of fluorescein-labeled exendin-4 in mouse plasma. Upper panel: in-gel fluorescence imaging; lower panel: quantification of fluorescence intensities for intact fluorescein-labeled exendin-4 in mouse plasma. (B) Stability of surrogate DAR2-ARC-ADC and DAR4-ARC-ADC with Alexa Fluor 488. Upper panel: in-gel fluorescence imaging; lower panel: quantification of fluorescence intensities for intact surrogate ARC-ADCs in mouse plasma. (C) A Coomassie blue-stained SDS-PAGE gel for fluorescein-labeled exendin-4 in mouse plasma. (D) Coomassie blue-stained SDS-PAGE gels for surrogate ARC-ADCs.
Figure 17:
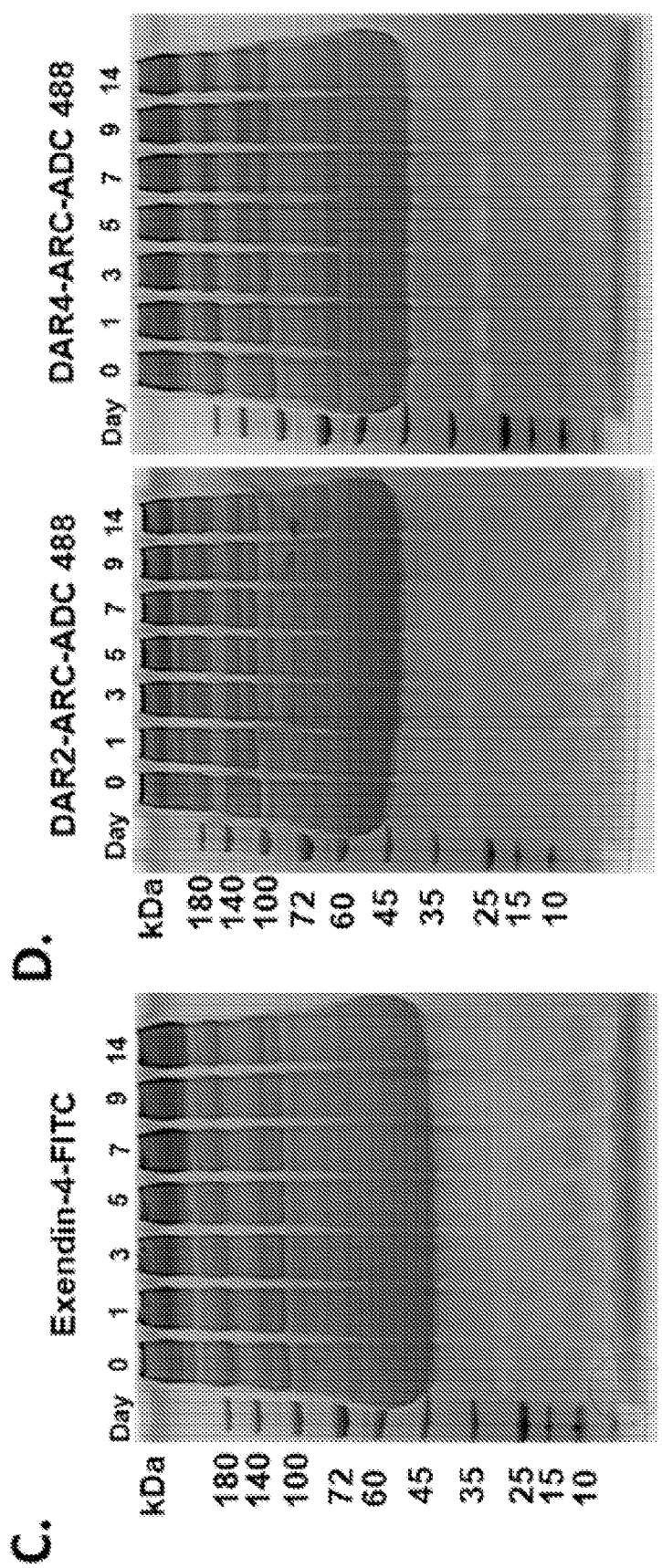

To examine stability, surrogate ARC-ADCs were generated using Alexa Fluor 488 or fluorescein isothiocyanate (FITC) as the payloads. In-gel fluorescence-based imaging revealed considerable stability for both surrogate DAR2-ARC-ADC and DAR4-ARC-ADC incubated in fresh mouse plasma (FIG. 17). Pharmacokinetic studies were then performed in mice. Following single-dose intravenous (i.v.) injections of FITC-conjugated surrogate ARC-ADCs, sandwich ELISA assays were conducted for collected plasma samples by using anti-FITC and anti-human kappa light chains antibodies as capture and detection reagents. The measured plasma concentrations indicated a half-life of 52.8±9.8 hours for DAR2-ARC-ADC FITC and 27.4±2.0 hours for DAR4-ARC-ADC FITC (FIG. 13E), suggesting reduced stability for ARC-ADC with increased payloads.

Figure 14:
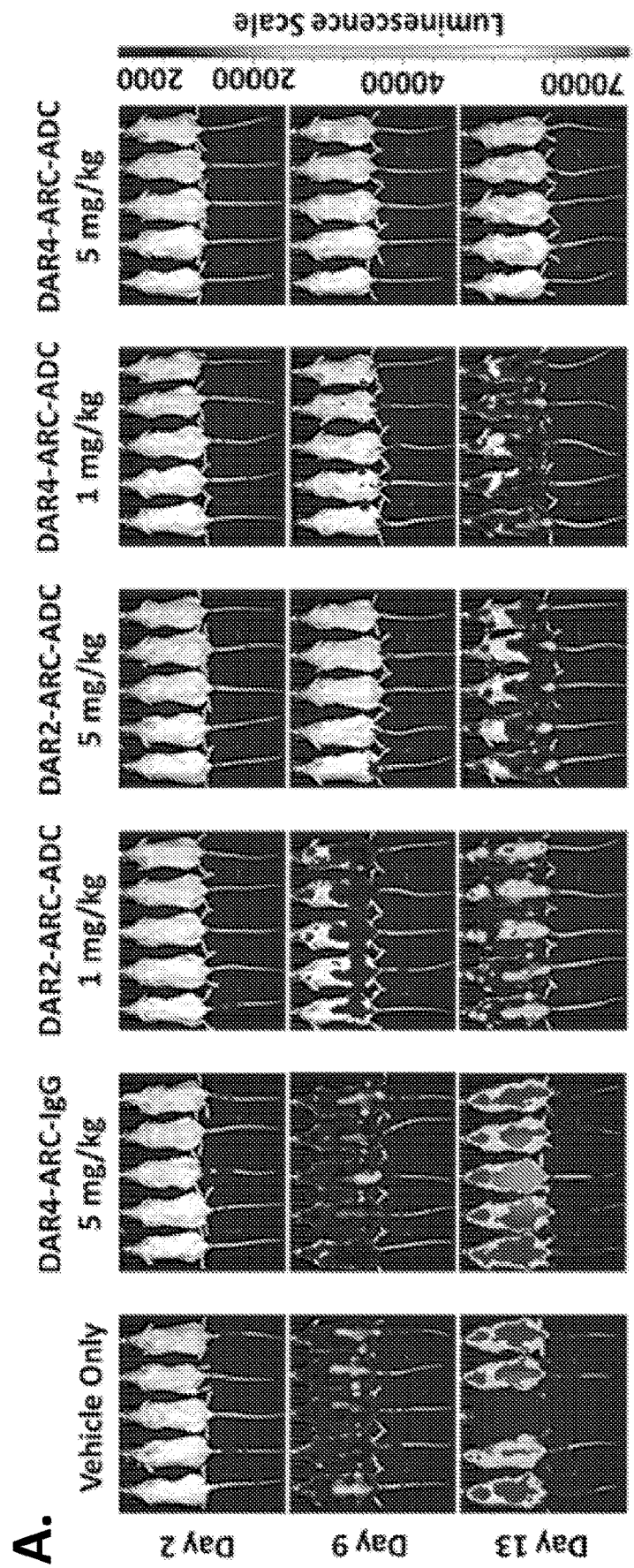
FIG. 14 illustrates the in vivo efficacy and toxicity of DAR2-ARC-ADC and DAR4-ARC-ADC. (A) IVIS images of mice in different groups post inoculation of luciferase-expressing U937 cells. (B) Luminescence intensities for mice in different treatment groups after injecting luciferase-expressing U937 cells. Black arrows indicate treatments by i.v. injections. (C) Kaplan-Meier survival curves and medians of survival for different treatment groups. (D) Average body weight of mice in different groups throughout the in vivo study. (E)-(G) Plasma ALT activities (E) and creatinine concentrations (F) and percentages of mCD34$^+$ mCD45$^+$ cell population in total living cells of bone marrows (G) on day 13 after U937 implantation.
Figure 14:
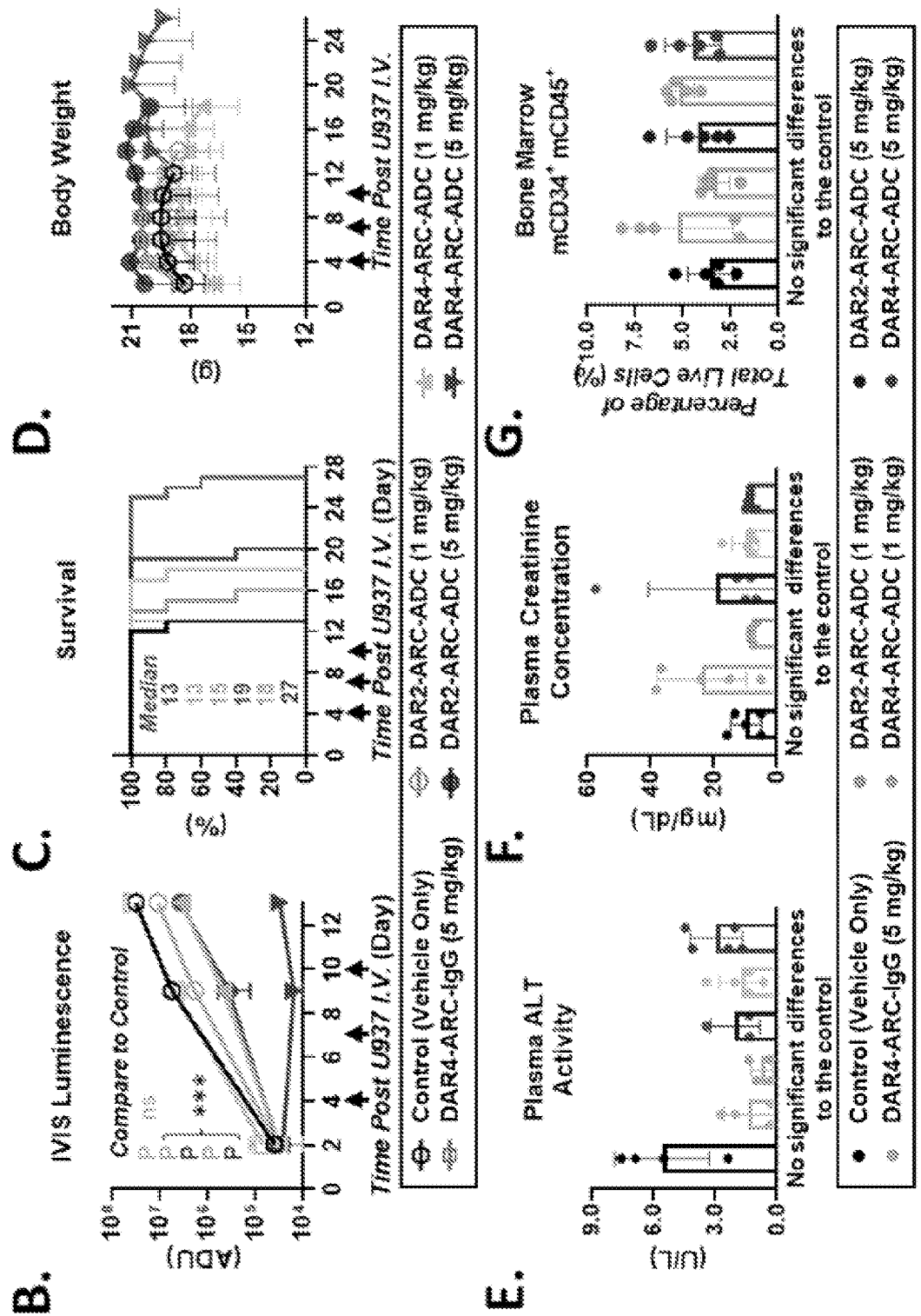
Figure 18:
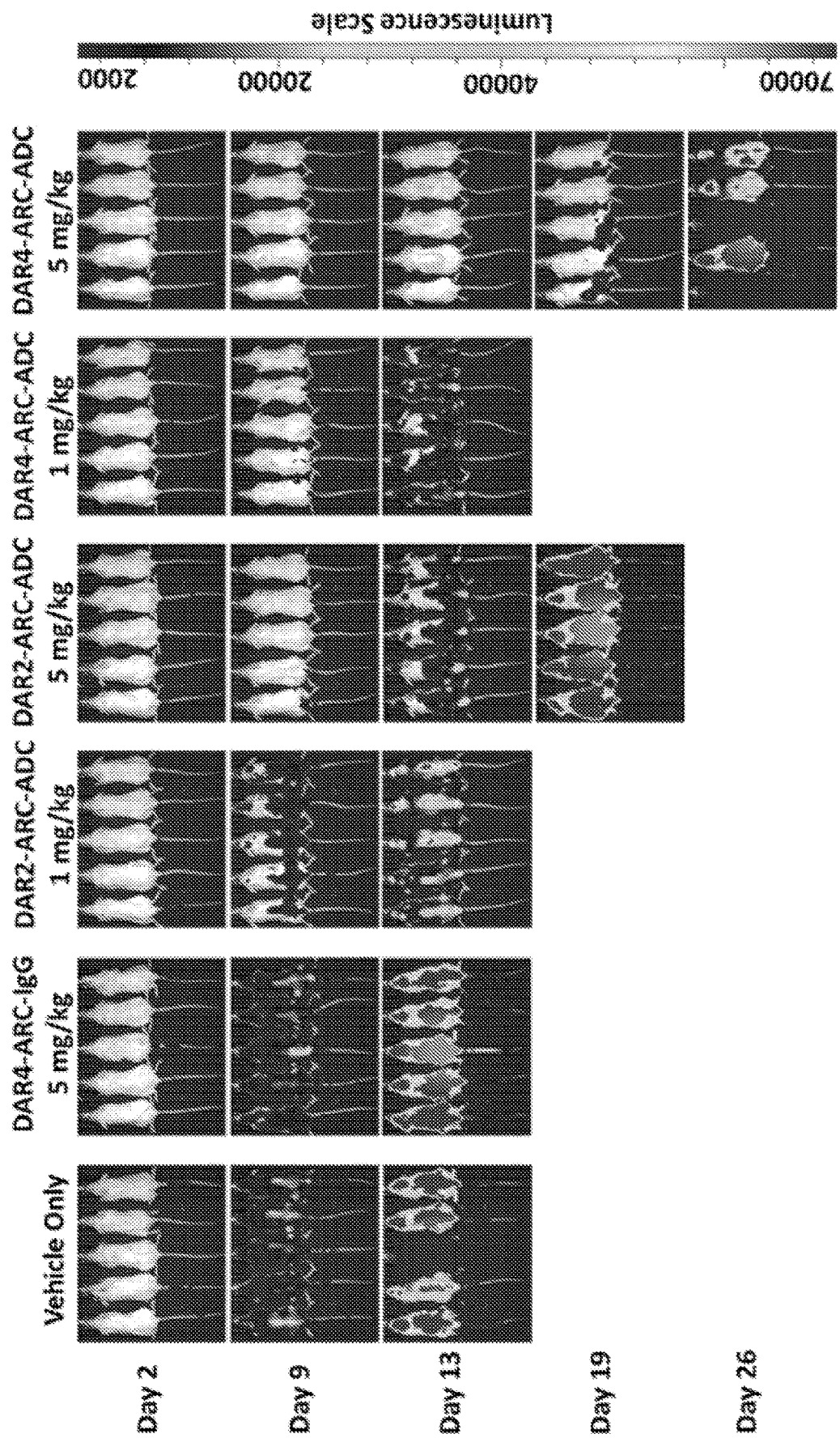
FIG. 18 illustrates IVIS images for mice from all treatment groups of the in vivo efficacy study. IVIS imaging was started on day 2 post i.v. inoculation of luciferase-expressing U937 cells and continued on a weekly basis.
Figure 19:
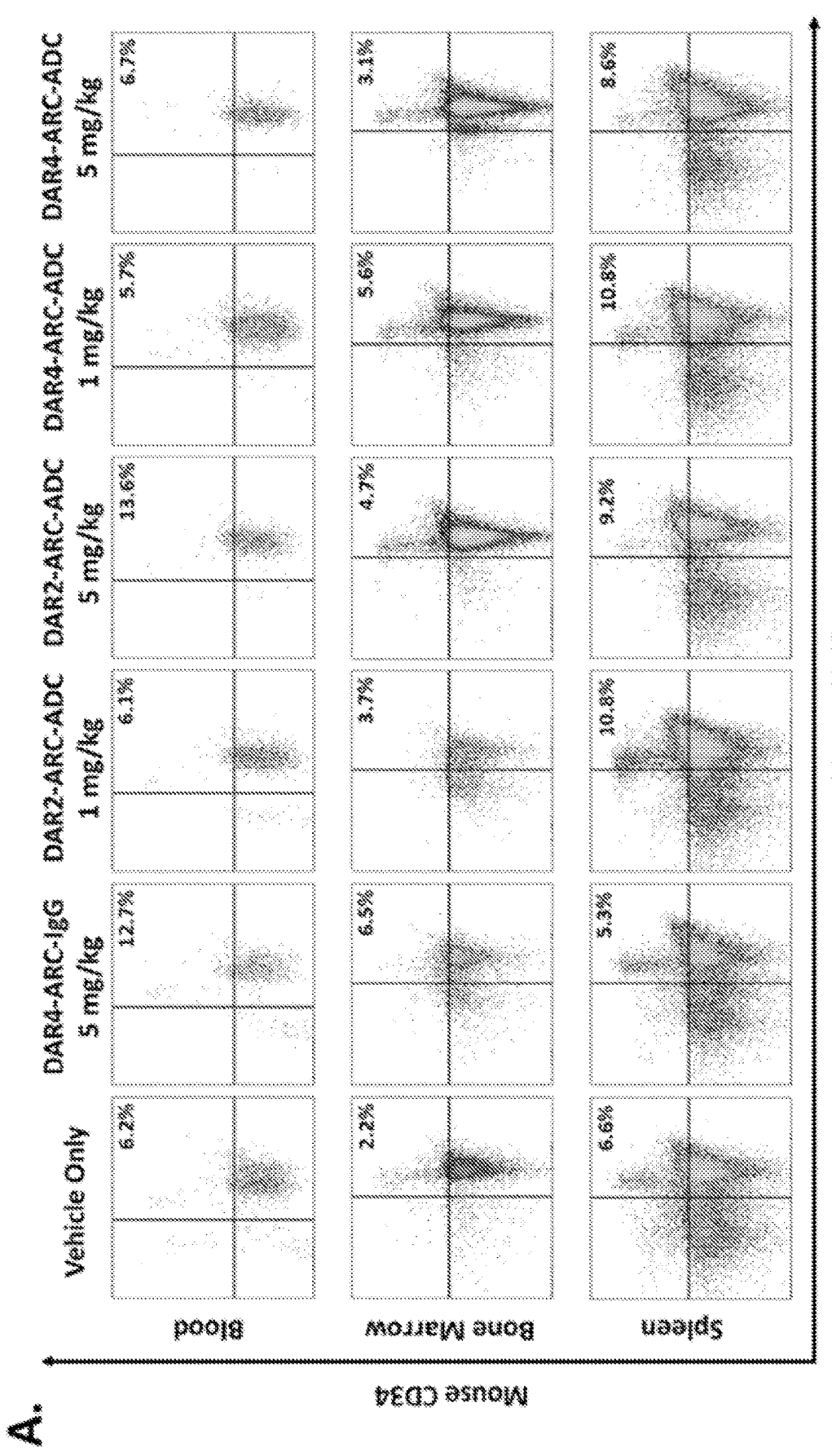
FIG. 19 illustrates flow cytometric analysis of tissue samples collected on day 13 post U937 implantation. (A) Representative flow cytometry data for percentages of mCD34+ mCD45+ cell population in total living cells in blood, bone marrow, and spleen among different treatment groups. (B-D) Percentages of mCD34+ mCD45+ cells in total living cells in blood (B), bone marrow (C), and spleen (D) among different treatment groups.
Figure 19:
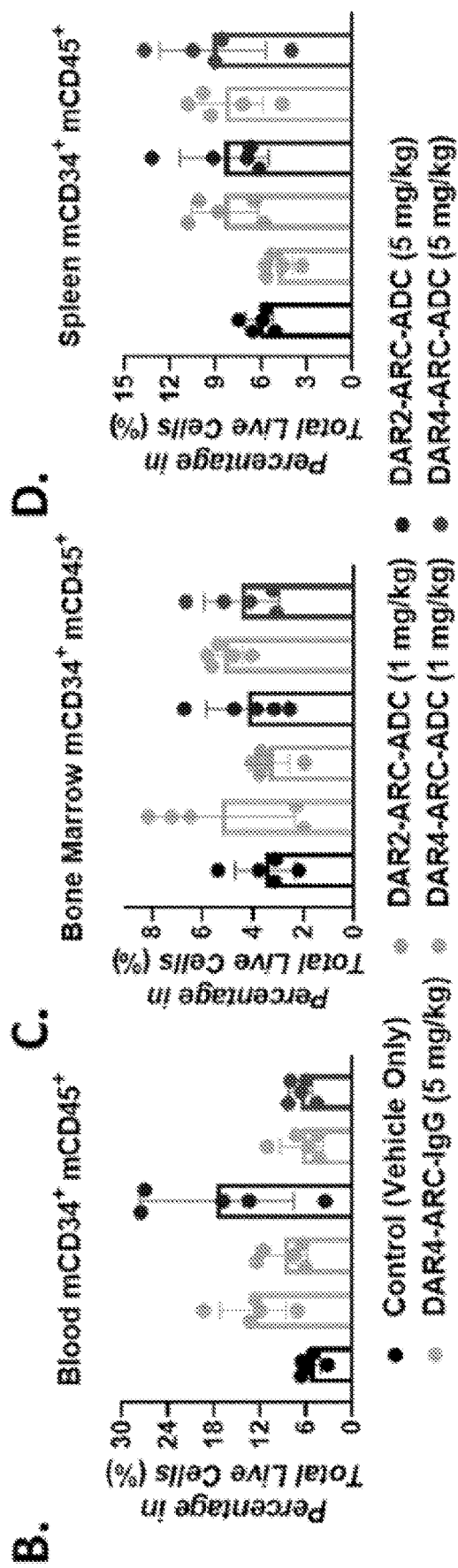
Figure 20:
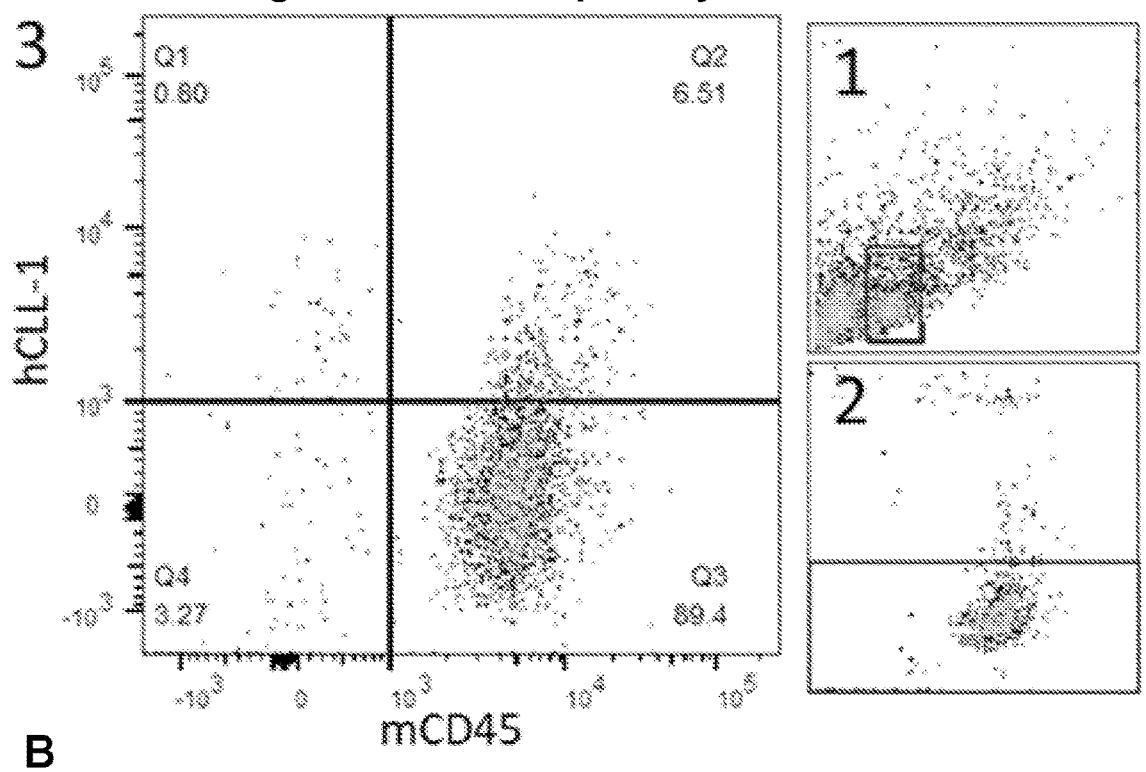
FIG. 20 illustrates gating strategies for blood samples analyzed by flow cytometry. (A) Gating of blood samples by mCD45 and hCLL-1. Step 1: SSC-FSC-based gating for peripheral blood cells. Step 2: mCD45-propidium iodide (PI)-based gating for live cells (PI negative cells) from a population selected in step 1. Step 3: arrange live peripheral blood cells selected in step 2 by mCD45 and hCLL-1 surface density for cell population analysis (B) Gating of blood samples by mCD45 and mCD34. Step 1: SSC-FSC-based gating for peripheral blood cells. Step 2: mCD45-propidium iodide (PI)-based gating for live cells (PI negative cells) from a population selected from step 1. Step 3: arrange live peripheral blood cells selected in step 2 by mCD45 and mCD34 surface density for cell population analysis.
Figure 20:
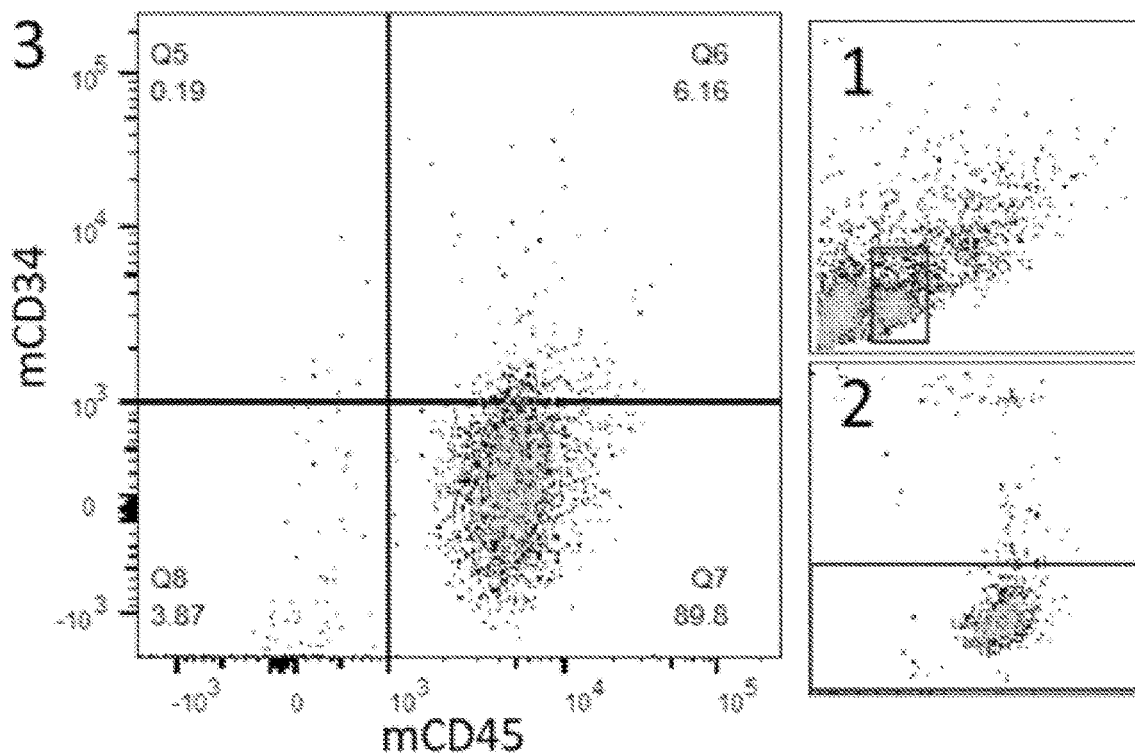
Figure 21:
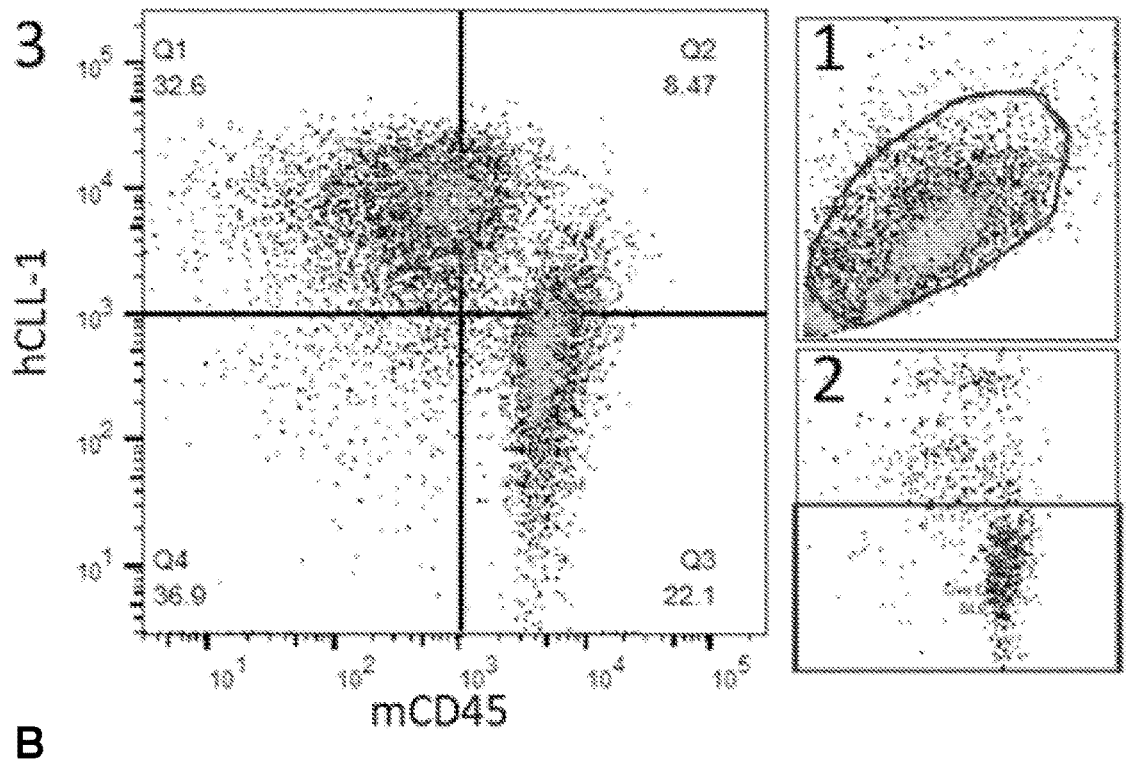
FIG. 21 illustrates gating strategies for bone marrow samples analyzed by flow cytometry. (A) Gating of bone marrow samples by mCD45 and hCLL-1. Step 1: SSC-FSC-based gating to remove debris. Step 2: mCD45-propidium iodide (PI)-based gating for live cells (PI negative cells) from a population selected in step 1. Step 3: arrange live bone marrow cells selected in step 2 by mCD45 and hCLL-1 surface density for cell population analysis. (B) Gating of bone marrow sample by mCD45 and mCD34. Step 1: SSC-FSC-based gating to remove debris. Step 2: mCD45-propidium iodide (PI)-based gating for live cells (PI negative cells) from a population selected in step 1. Step 3: arrange live bone marrow cells selected in step 2 by mCD45 and mCD34 surface density for cell population analysis.
Figure 21:
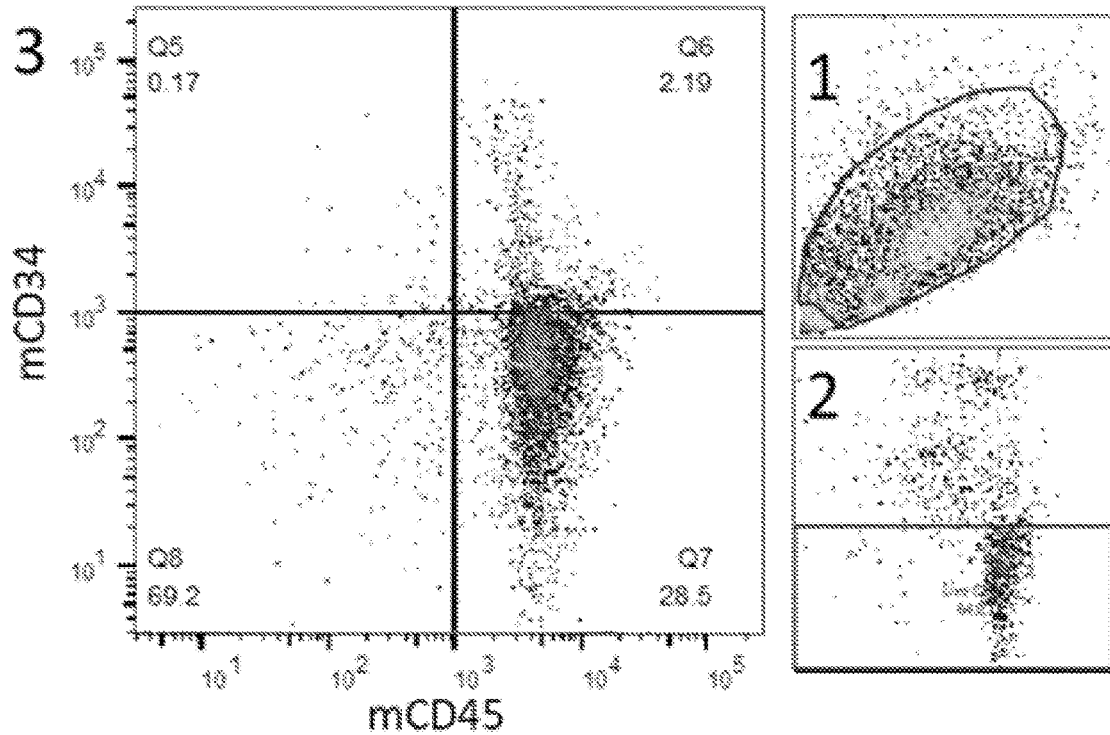
Figure 22:
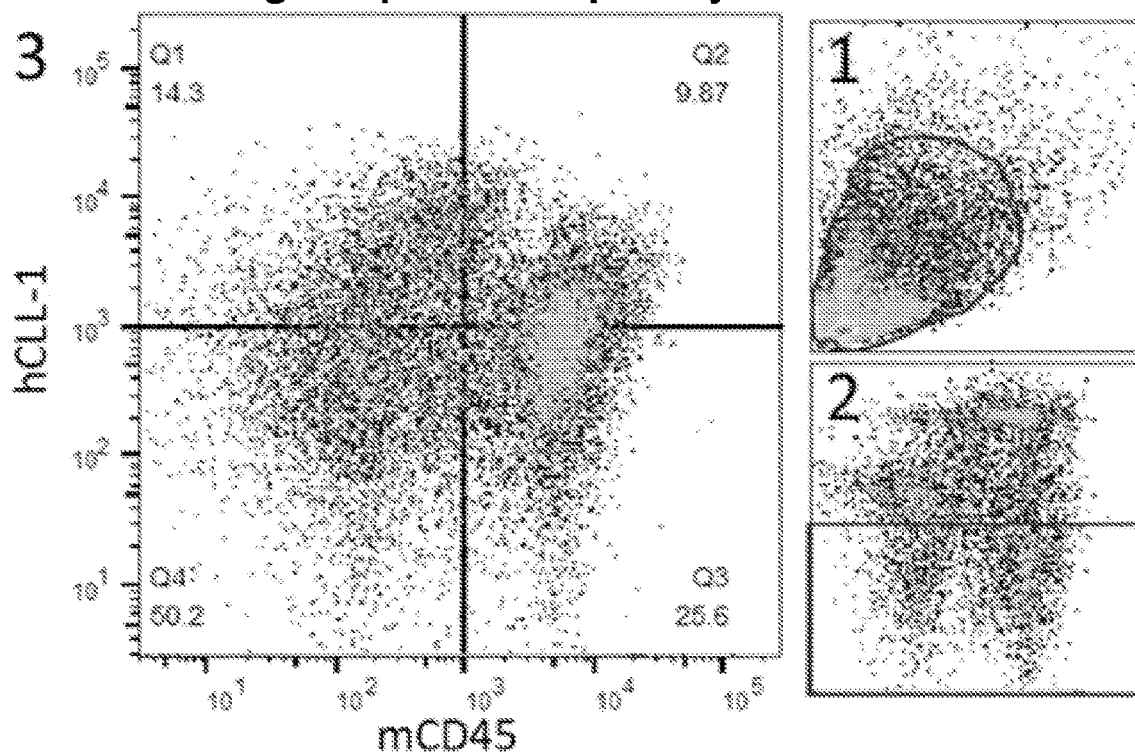
FIG. 22 illustrates gating strategies for spleen samples analyzed by flow cytometry. (A) Gating of spleen samples by mCD45 and hCLL-1. Step 1: SSC-FSC-based gating to remove debris. Step 2: mCD45-propidium iodide (PI)-based gating for live cells (PI negative cells) from a population selected in step 1. Step 3: arrange live bone marrow cells selected in step 2 by mCD45 and hCLL-1 surface density for cell population analysis. (B) Gating of bone marrow sample by mCD45 and mCD34. Step 1: SSC-FSC-based gating to remove debris. Step 2: mCD45-propidium iodide (PI)-based gating for live cells (PI negative cells) from a population selected in step 1. Step 3: arrange live bone marrow cells selected in step 2 by mCD45 and mCD34 surface density for cell population analysis.
Figure 22:
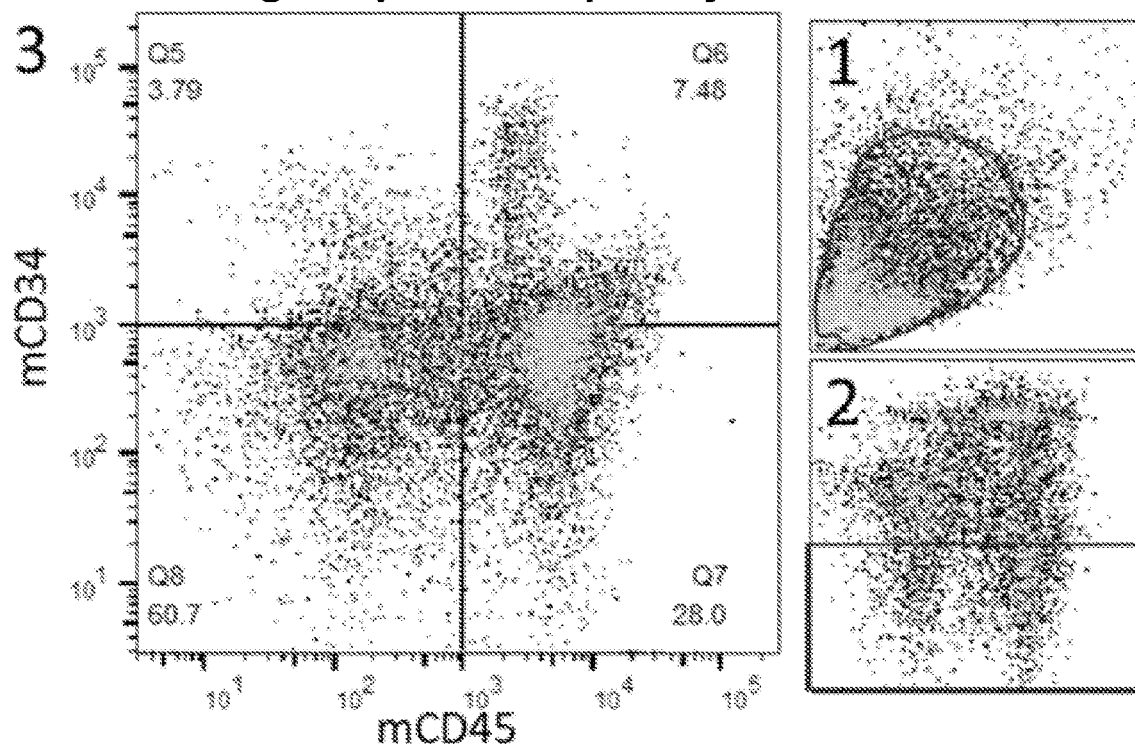

Next, in vivo therapeutic efficacy of DAR2-ARC-ADC and DAR4-ARC-ADC were evaluated using AML, mouse xenograft models. Immunodeficient mice were intravenously injected with firefly luciferase labeled U937 cells via tail vein. Beginning on day 4 post U937 cell implantation, mice were treated with ARC-ADCs at a dose of 1 or 5 mg/kg every 72 hours for a total of 3 times through i.v. injections. PBS vehicle and DAR4-ARC-IgG (5 mg/kg) were included as controls. From day 2 post i.v. implantation of luciferase expressing U937 cells, whole-body luminescence imaging was taken for each group of mice and continued on a weekly basis. IVIS imaging and quantified luminescence indicated rapid proliferation of U937 cells for mice treated by PBS vehicle and DAR4-ARC-IgG. By contrast, administered ARC-ADCs show significant anti-leukemia activity in dose- and DAR-dependent manners (FIGS. 14A-B and 18). Notably, DAR4-ARC-ADC at the dose of 5 mg/kg displays highly potent inhibition against the proliferation of engrafted U937 cells. In comparison to PBS- and DAR4-ARC-IgG-treated groups with median survivals of 13 days, DAR4-ARC-ADC-treated group at 5 mg/kg shows more than 100% increase of median survival (27 days) (FIG. 14C). Consistent with IVIS imaging analysis, the median survivals for mice treated by DAR2-ARC-ADC and DAR4-ARC-ADC are dependent on dose and DAR. Same as the in vitro cytotoxicity studies, in vivo results support excellent anti-leukemia activities for anti-hCLL-1 ARC-ADCs and significantly improved efficacy for DAR4-ARC-ADC.

Toxicities of the administered anti-hCLL-1 ARC-ADCs on mice were also assessed. During the efficacy study, treatments with ARC-ADCs cause no negative impact on mice body weights in comparison to control groups (FIG. 14D). On day 13 after U937 implantation, plasma alanine aminotransferase (ALT) activity and creatinine concentration and percentages of mouse CD34$^+$CD45$^+$ cells in blood, bone marrow, and spleen samples were determined. No significant differences were observed among all groups (FIGS. 14E-G and 19). Taken together, these results show no apparent toxicity for anti-hCLL-1 ARC-ADCs.

Figure 15:
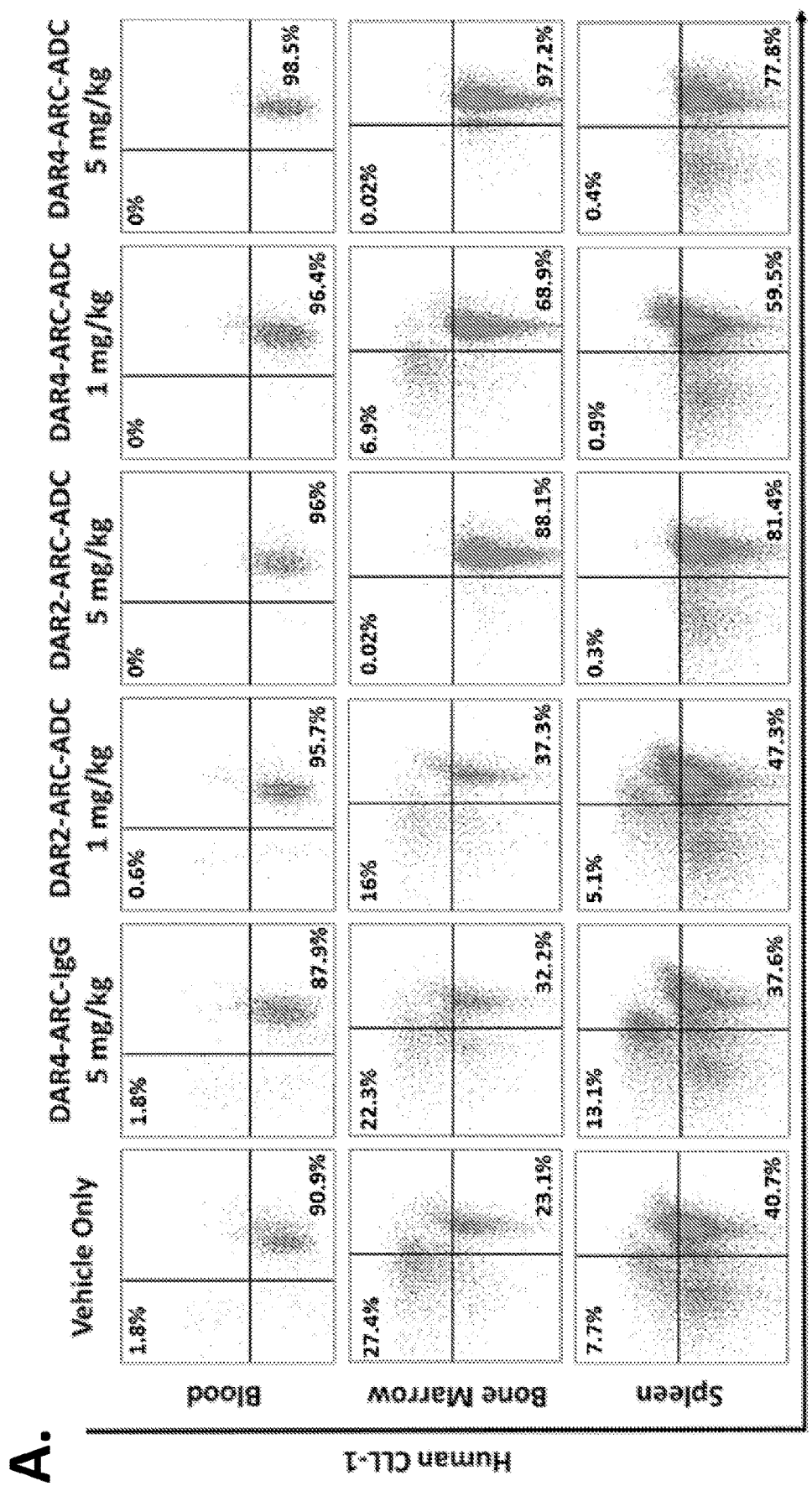
FIG. 15 illustrates flow cytometric analysis of tissue samples collected on day 13 post U937 implantation. (A) Representative flow cytometry data for hCLL-1 and mCD45 expression in blood, bone marrow, and spleen cells among different groups. Percentages were shown for hCLL-1$^+$ mCD45$^−$ and mCD45$^+$ hCLL-1$^−$ cells in total living cells. (B-D) Percentages of hCLL-1$^+$ mCD45$^−$ cells in total living cells in blood (B), bone marrow (C), and spleen (D) samples among different groups. (E-G) Percentages of mCD45$^+$ hCLL-1$^−$ cells in total living cell in blood (E), bone marrow (F), and spleen (G) among different groups.
Figure 15:
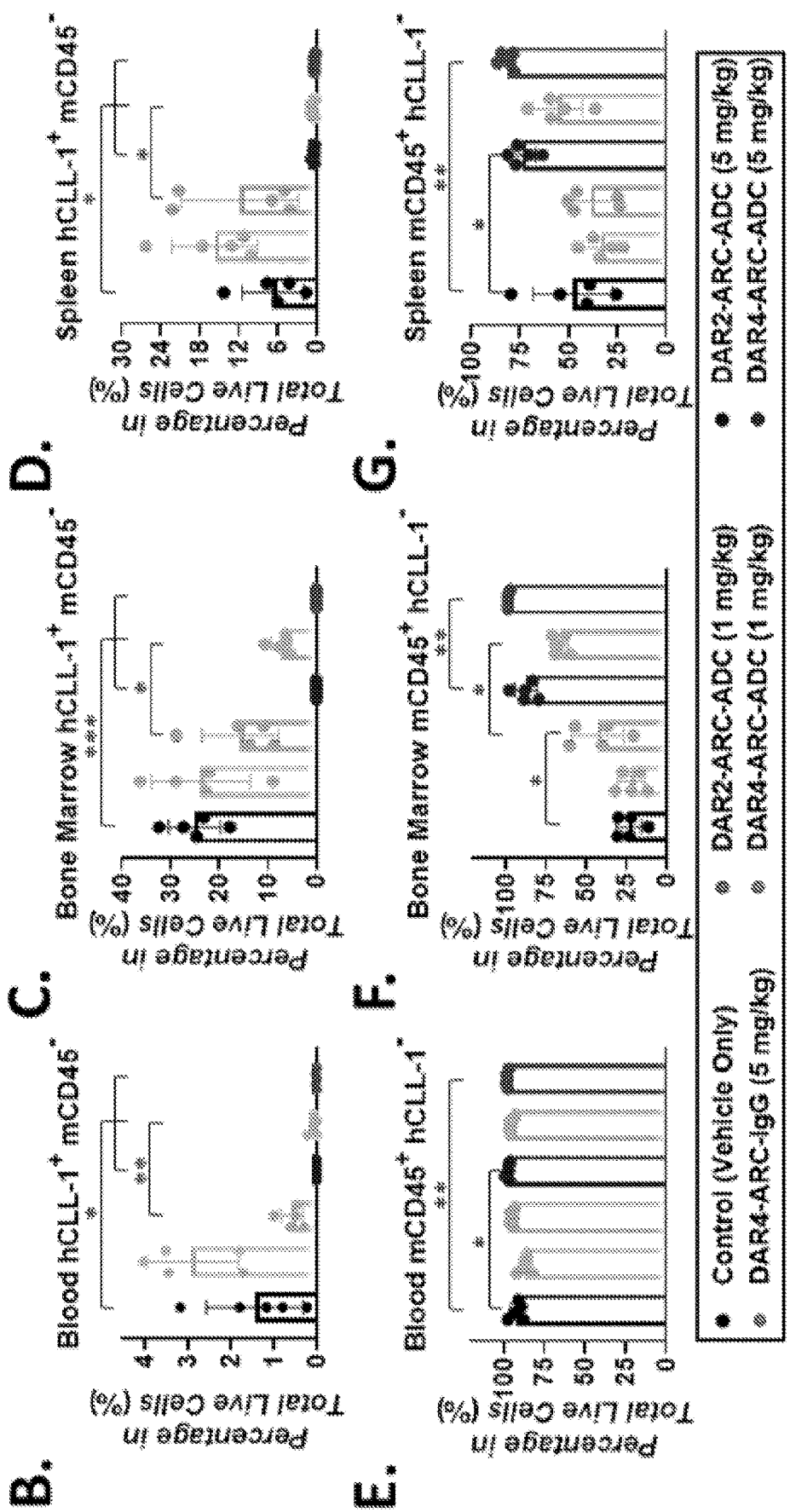

In addition to IVIS imaging analysis, blood, bone marrow, and spleen were collected for all groups on day 13 post U937 implantation for flow cytometry. Consistent with the luminescence-based whole-body imaging, flow cytometric analysis indicate higher levels of engrafted U937 cells and lower percentages of mouse CD45$^+$ (mCD45$^+$) cells in bone marrow, spleen, and blood for mice treated by PBS and DAR4-ARC-IgG (FIG. 15A-G). Less than 0.5% of hCLL-1$^+$ cells were observed across 3 different types of tissues for mice treated by DAR2-ARC-ADC and DAR4-ARC-ADC at 5 mg/kg (FIG. 15B-D), indicating their potent activities in suppressing U937 cells expansion. Relative to control groups, significantly higher percentages of mCD45$^+$ were observed for mice treated by ARC-ADCs at both 1 and 5 mg/kg in bone marrow and at 5 mg/kg in spleen and blood (FIG. 15F-G). Similar to the quantified luminescence intensities, the measured percentages of hCLL-1$^+$ among different tissues for mice treated by ARC-ADCs inversely correlate with dose and DAR. In comparison to mice receiving DAR2-ARC-ADC at 1 mg/kg, DAR4-ARC-ADC-treated mice at 1 mg/kg revealed significantly lower percentages of hCLL-1$^+$ cells in blood, bone marrow, and spleen (FIG. 15B-D). Moreover, mice given with DAR4-ARC-ADC have higher levels of mCD45$^+$ in bone marrow compared with DAR2-ARC-ADC-treated ones at both 1 and 5 mg/kg doses (FIG. 15F). These results support remarkable efficacy for anti-hCLL-1 ARC-ADCs and considerably increased potency for DAR4-ARC-ADC.

Discussion

Anti-hCLL-1 ARC-ADCs were successfully generated with DARs of 2 and 4 by utilizing antibody-CD38 fusions coupled with an NAD$^+$ analogue-derived drug linker. By specifically binding to hCLL-1 antigen, ARC-ADCs allow targeted delivery of tubulin inhibitor MMAF to human AML cells, resulting in potent in vitro and in vivo anti-leukemia activities. Despite reduced plasma half-life, DAR4-ARC-ADC exhibits notably enhanced therapeutic efficacy in both cellular and animal AML models, suggesting potential benefits for developing homogeneous ADCs with increased DARs.

Genetic fusions of CD38 catalytic domains to an antibody enable facile production of site-specific ADCs through single-step enzymatic reactions. In addition to rapidly mediating drug conjugation at Glu226 of CD38, the 2'-Cl-araNAD$^+$-based dinucleotide linker can stably carry payloads to target cells for rapid release upon internalization. The DARs of ARC-ADCs can be adjusted by fusing additional CD38 domains. Meanwhile, attachments of CD38 to an immunoglobulin can potentially affect the overall stability of fusion proteins, binding affinity to target antigens, and tissue penetration.

DAR4-ARC-ADC was generated by fusing CD38 to C-termini of light and heavy chains of the anti-hCLL-1 antibody. Different formats of ARC-ADC with a DAR of 4 could be developed by placing CD38 at different positions. While having the same DAR, these ARC-ADC may possess distinguished physicochemical properties and biological activities, which requires further examination. By changing the fusion location or peptide linkers used between the antibody and CD38 domain, stability and efficacy for ARC-ADCs could be further optimized. Importantly, ARC-ADCs with additionally increased DARs can potentially be synthesized and evaluated for pharmacological activities.

To understand how varied number of payloads affect cytotoxicity of ADCs, cellular uptake and drug release need to be quantitatively analyzed for ARC-ADCs with different DARs. The ARC-ADCs can also be extended to other types of payloads and antibodies specific for disease-associated antigens.

In summary, anti-hCLL-1 ARC-ADCs with DARs of 2 and 4 were generated through harnessing genetically fused CD38 catalytic activity. DAR4-ARC-ADC is highly potent in killing CLL-1-positive AML, cells both in vitro and in vivo, providing a new candidate for AML, targeted therapy. This study demonstrates ARC-ADC as a general and versatile approach for developing homogeneous ADCs with defined DARs.

Materials and Methods

Molecular Cloning.

Synthetic gBLOCK DNA fragment for recombinant human CLL-1 extracellular domain natural variant (Uniprot ID: Q5QGZ9, VAR_037669, amino acid I70-A265) with a 6*His tag (SEQ ID NO: 77) fused at C terminus was purchased from Integrated DNA Technologies (IA, USA). The synthetic DNA fragment above was amplified by polymerase chain reaction (PCR) with primers incorporating DNA restriction enzyme cleavage sites for EcoRI and NheI at the 5' and 3' end, respectively. Primers used for amplification include CLL-1-Forward: 5'-CACGAATTC-GATCGAGATGAAGAAGATGAACAAAC-3' (SEQ ID NO: 32); CLL-1-Reverse: 5'-CCAGCTAGCACT-CACTAATGATGATGGTG-3'; SEQ ID NO: 33).

Synthetic gBLOCK DNA fragments for anti-human CLL-1 IgG light chain (LC) and heavy chain (HC) fragment of antigen binding (Fab) (clone 1075.7) were purchased from Integrated DNA Technologies (IA, USA). The anti-human CLL-1 IgG LC DNA fragment was amplified by PCR with primers incorporating DNA restriction enzyme cleavage sites for EcoRI and NheI at the 5' and 3' end, respectively. The full-length anti-human CLL-1 IgG HC was generated through overlap extension PCR using the anti-human CLL-1 Fab HC and human IgG1 Fc fragments using primers containing DNA restriction enzyme cleavage sites for EcoRI and NheI at the 5' and 3' end, respectively. Primers mentioned above include Anti-CLL-1 IgG LC F: 5'-CACGAATTCGGAGAACGTGCTCACCCAATCCCC-3' (SEQ ID NO: 34); Anti-CLL-1 IgG LC R: 5'-CCAGCTAGCACTTATCAACACTCTCCCCTGTT-GAAGCTCTTTGTG-3' (SEQ ID NO: 35); Anti-CLL-1 IgG HC F1: 5'-CACGAATTCGGACATCCAGCTGCAG-GAGAGCG-3 (SEQ ID NO: 36)'; Anti-CLL-1 IgG HC R1: 5'-CGCAAGATTTGGGTTCCACTTTCTTGTC-CACCTTGGTGTTGCTG-3' (SEQ ID NO: 37; Anti-CLL-1 IgG HC F2: 5'-GGTGGACAAGAAAGTGGAACC-CAAATCTTGCGACAAAACTCACACATG-3' (SEQ ID NO: 38); Anti-CLL-1 IgG HC R2: 5'-CCAGCTAGCACT-TATCATTTACCCGGAGACAGGGAGAGGC-3' (SEQ ID NO: 39).

Acquired PCR products were then analyzed by DNA gel electrophoresis with the bands at target sizes excised and purified by DNA gel extraction kits (Zymo Research, CA, USA) to yield the target DNA fragment inserts. Purified DNA fragment inserts were first treated with DNA restriction enzyme EcoRI and NheI (New England Biolabs, MA, USA) per the manufacturer's instructions and then cleaned by DNA cleaning & concentrating kits (Zymo Research, CA, USA). The treated and cleaned DNA fragments were then spliced in-frame to pFUSE expression vector backbone by T4 DNA ligase (New England Biolabs, MA, USA). Ligation products were utilized to transform DH10B Escherichia coli (E. coli) electro-competent cells, followed with positive selection for Zeocin-resistant colonies and DNA sequencing of the extracted plasmids.

The sequence-confirmed pFUSE expression vectors for anti-human CLL-1 IgG LC and anti-human CLL-1 IgG HC were utilized as DNA templates for constructing anti-CLL-1 IgG LC CD38 C-fusion and anti-CLL-1 IgG HC CD38 C-fusion pFUSE expression vectors, respectively. Synthetic gBLOCK DNA fragment of the extracellular domain of human CD38 (Uniprot ID: P28907, R45-I300) with four mutated asparagine residues (N100D, N164 Å, N129D, and N209D) and a flexible GGGGS peptide linker (SEQ ID NO: 21) at N-terminus was purchased from Integrated DNA Technologies (IA, USA). Overlap extension PCR reactions were performed to generate LC-CD38 C-fusion and HC-CD38 C-fusion fragments. Primers utilized for cloning include Anti-CLL-1 LC CD38 F1: 5'-GTCACGAATTCG-GAGAACGTGCTC-3' (SEQ ID NO: 40); Anti-CLL-1 LC CD38 R1: 5'-CGCCACCCCACACTCTCCCCTGTT-GAAGCTCTTTG-3' (SEQ ID NO: 41); Anti-CLL-1 LC CD38 F2: 5'-GGAGAGTGTGGGGGTGGCGGAAGC-3' (SEQ ID NO: 42); Anti-CLL-1 LC CD38 R2: 5'-CTGGCCAGCTAGCACTTATCAGATCTC-3' (SEQ ID NO: 43); Anti-CLL-1 HC CD38 F1: 5'-CACGAATTCGGA-CATCCAGCTGCAGGAGAGCG-3' (SEQ ID NO: 44); Anti-CLL-1 HC CD38 R1: 5'-CGCAAGATTTGGGTTC-CACTTTCTTGTCCACCTTGGTGTTGCTG-3' (SEQ ID NO: 45); Anti-CLL-1 HC CD38 F2: 5'-GGTGGACAAGAAAGTGGAACC-CAAATCTTGCGACAAAACTCACACATG-3' (SEQ ID NO: 46); Anti-CLL-1 HC CD38 R2: 5'-CTGGCCAGCTAGCACTTATCAGATCTC-3' (SEQ ID NO: 47).

Acquired PCR products were then analyzed by DNA gel electrophoresis with the bands at target sizes excised and purified by DNA gel extraction kits (Zymo Research, CA, USA) to yield the target DNA fragment inserts. Purified DNA fragment inserts were first treated with DNA restriction enzyme EcoRI and NheI (New England Biolabs, MA, USA) per the manufacturer's instructions and then cleaned by DNA cleaning & concentrating kits (Zymo Research, CA, USA). The treated and cleaned DNA fragments were then spliced in-frame to pFUSE expression vector backbone by T4 DNA ligase (New England Biolabs, MA, USA). Ligation products were utilized to transform DH10B E. coli electro-competent cells, followed with positive selection for Zeocin-resistant colonies and DNA sequencing of the extracted plasmids.

Protein Expression and Purification.

Recombinant human CD38 extracellular domain, human CLL-1 extracellular domain, anti-hCLL-1 IgG, anti-hCLL-1 IgG HC-CD38 C-fusion (DAR2-ARC-IgG), and anti-hCLL-1 IgG HC-CD38 & LC-CD38 C-fusion (DAR4-ARC-IgG) were all expressed in Expi293F cells (Thermo Fisher Scientific, MA, USA). Sequence-confirmed pFUSE expression vector for human CD38 (240 µg), CLL-1 (240 µg), or antibody light chain (120 µg) combined with heavy chain (120 µg) in 12 mL of Opti-MEM medium (Thermo Fisher Scientific, MA, USA) was added with 960 µL of transfection-grade linear polyethylenimine hydrochloride at 1 mg mL$^{-1}$ (Polysciences, PA, USA) for transfecting 240 mL of Expi293F cells cultured at a density of 2.5 million cells per mL per manufacturers' instructions. Cells were then incubated with shaking (125 rpm) in a 37° C. incubator with 5% CO$_2$. On day 5 post transfection, media containing target proteins were collected. Cells were removed by a 2-step serial centrifugation with centrifugal force at 100×g for 10 minutes first, followed by 4,000×g for 30 minutes.

The recombinant human CD38 and CLL-1 extracellular domains were purified by the same protocol as previously reported. In brief, media with target proteins were first dialyzed against storage buffer for overnight (25 mM HEPES, 250 mM NaCl, pH 7.5) before applying to the Ni-NTA resin-based affinity chromatography. Dialyzed media were gradually loaded onto a gravity-flow column with 1 mL of Ni-NTA resin and let passing through the resin twice, followed by washing with 15 column volumes of wash buffer (20 mM Tris-HCl, 200 mM NaCl, 30 mM imidazole, pH 8). Recombinant proteins were eluted in 15 column volumes of elution buffer (20 mM Tris-HCl, 200 mM NaCl, 400 mM imidazole, pH 8) and dialyzed into PBS buffer (pH 7.4) for overnight at 4° C. and then in the same freshly prepared buffer for another 8 hours under the same condition. Finally, recombinant proteins were concentrated with 10 kDa-cutoff concentrators (MilliporeSigma, MA, USA). The purified proteins were examined by Coomassie blue stained SDS-PAGE gels. Protein concentrations were determined by UV absorbance at 280 nm with a NanoDrop 2000C spectrophotometer (Thermo Fisher Scientific, MA, USA) corrected by calculated molar extinction coefficients.

All antibodies were purified by protein G affinity chromatography resins (GenScript, NJ, USA) per the manufacturer's protocol. Antibodies were eluted by 15 column volumes of 100 mM glycine (pH 2.7) and then dialyzed against PBS buffer (pH 7.4). After being concentrated by 30 kDa-cut-off concentrators (MilliporeSigma, MA, USA), the purified antibodies were examined by Coomassie blue stained SDS-PAGE gels. Protein concentrations were determined based on UV absorbance at 280 nm (corrected by calculated molar extinction coefficients) by a NanoDrop 2000C spectrophotometer.

Preparation of Drug-Linker Conjugate (2'-Cl-araNAD$^+$-MMAF).

2'-Cl-araNAD$^+$-MMAF was synthesized as reported previously. To a stirred solution of 2'-Cl-NAD$^+$-N$_3$ (7.7 mg, 0.01 mmol), CuSO$_4$.5H$_2$O (10.0 mg, 0.04 mmol, 4 eq) in H$_2$O (0.5 mL) were added a solution of alkynyl-MMAF (9.2 mg, 0.012 mmol, 1.2 eq) in DMSO (0.2 mL), THPTA (86.9 mg, 0.2 mmol, 20 eq) and sodium-L-ascorbate (63.4 mg, 0.32 mmol, 32 eq) at room temperature. Then the reaction mixture was stirred at the same temperature until the reaction completed (monitored by HPLC). The product was purified via preparative HPLC (C18-A column, 150×10.0 mm, 5 µm) (mobile phase A: 0.1% formic acid (aq), mobile B: 0.1% formic acid in acetonitrile; flow rate=2.0 mL/min; 0-2 min: 0-4% B, 2-4 min: 4-10% B, 4-6 min: 10-20% B, 6-12 min: 20-50% B, 12-17 min: 50-100% B, 17-20 min: 100-0% B) with detection of UV absorbance at 260 nm. Fractions containing the desired product were concentrated and lyophilized to yield the compound 2'-Cl-NAD$^+$-MMAF (8.4 mg, 55%) as a colorless solid. FIRMS (ESI) for $C_{66}H_{97}ClN_{16}O_{20}P_2Na_2^{2+}$ (M+2Na-2H)$^{2+}$: Calcd.: 789.3085 Da; Obs: 789.3092 Da.

Preparation of ADCs and ADC Surrogates.

DAR2-ARC-IgG and DAR4-ARC-IgG at above 10 µM stock concentrations were combined with the drug-linker conjugate (2'-Cl-araNAD$^+$-MMAF) in Tris buffer (50 mM Tris, pH 8.5) at a final molar concentration ratio of 1:200 (antibody: drug-linker conjugate) on ice for 1 hour. Then, buffer exchange was performed using PBS and filters with 30 kDa cut-off (MilliporeSigma, MA, USA) to remove free drug-linker conjugate.

To generate ADC surrogates with Alexa Fluor 488 or FITC as the payload, the linker 2'-Cl-araNAD$^+$-N$_3$ was first conjugated to DAR2-ARC-IgG or DAR4-ARC-IgG with the same method described above. Then, acquired fusion antibody-linkers were incubated with Alexa Fluor 488 DBCO (Click Chemistry Tools, AZ, USA) or DBCO-PEG3-FITC (CONJU-PROBE, CA, USA) in PBS buffer (pH 7.4) at a molar ratio of 1:50 (antibody-linker: fluorescent dye) for 30 minutes on ice. Finally, buffer exchange was performed using PBS (pH 7.4) and filters with 30 kDa cut-off to remove free surrogate payloads. The concentrations of generated ADCs and ADCs surrogates were determined by Bradford assay kits (Thermo Fisher Scientific, MA, USA).

In Vitro Plasma Stability of Alexa Fluor 488-Conjugated Surrogate ADCs.

Exendin-4 (GenScript, NJ, USA) at a concentration of 3 mg mL$^{-1}$ was labeled with 1 mM N-hydroxysuccinimide (NHS)—fluorescein (Thermo Fisher Scientific, MA, USA) on ice for 2 hours in PBS buffer (pH 7.4). Then, the reaction mixture was passed through Zeba spin desalting columns (Thermo Fisher Scientific, MA) with molecular weight cut-off at 7 kDa for removing free NHS-fluorescein.

Acquired fluorescein-labeled exendin-4 (0.75 mg mL$^{-1}$) and Alexa Fluor 488-conjugated surrogate DAR2-ARC-ADC (3 µM) and DAR4-ARC-ADC (3 µM) were incubated in fresh CD-1 mouse plasma containing 100 µg mL$^{-1}$ of penicillin-streptomycin (Thermo Fisher Scientific, MA) in a 37° C. incubator with 5% CO2 for 14 days. During the incubation, 1 µL of mixture was periodically extracted and frozen at −20° C. until the final SDS-PAGE gel analysis. Prior to Coomassie staining, SDS-PAGE gels were imaged by a ChemiDoc Touch Imager (Bio-Rad, CA, USA) for the presence of intact conjugated surrogate ADCs or fluorescein-labeled exendin-4 under the fluorescence mode. The intensity of fluorescent bands on SDS-PAGE gels were quantified by Image Lab (Bio-Rad, CA, USA).

Matrix-Assisted Laser Desorption Ionization Time-of-Flight Mass Spectrometry (MALDI-TOF MS) for IgG Modification Analysis.

DAR2-ARC-IgG, DAR2-ARC-ADC, DAR4-ARC-IgG, and DAR4-ARC-ADC (~2 mg/mL) were deglycosylated with PNGase F (450 U mL$^{-1}$) in the presence of 10 mM DTT and mixed with 2,6 dihydroxyacetophenone (DHAP) solution (20 mg mL$^{-1}$ in 50% acetonitrile:0.1% formic acid) at a ratio of 1:5 (by volume). Half microliter of each solution was spotted on a 384-Big Anchor MALDI target and let dry at room temperature. Crystalized samples were then analyzed using Bruker Rapiflex MALDI-TOF MS equipped with a Smartbeam 3D, 10 kHz, 355 nm Nd:YAG laser. The laser parameters were optimized as follows: scan range=26 μm; number of shots per sample=1000; laser frequency=5000 Hz. The mass spectrometer was calibrated for high-mass range using protein A and trypsinogen standards under a linear mode. Data were analyzed using FlexAnalysis software and plotted using GraphPad Prism (CA, USA).

ADP-Ribosyl Cyclase Activities.

Acquired recombinant human CD38 extracellular domain, DAR2-ARC-IgG, DAR4-ARC-IgG, and the anti-hCLL-1 antibody were all diluted to the final concentration of 20 nM for CD38 or 10 nM for antibody or ARC-IgGs in 100 μL of PBS buffer (pH 7.4) with 100 μM of nicotinamide guanine dinucleotide (NGD$^+$). The rate of cyclic guanine dinucleotide phosphate-ribose (cGDPR) generation was monitored by a Synergy H1 plate reader (BioTek, VT, USA) for its signature fluorescence (excitation at 300 nm; emission at 410 nm) for 5 minutes.

Binding to Recombinant Human CLL-1.

Purified recombinant human CLL-1 extracellular domain was coated overnight on 96-well ELISA plates at room temperature (Greiner Bio-One, NC) in 80 μL of PBS buffer (pH 7.4) at a final concentration of 50 μg mL$^{-1}$. Then, coated wells were blocked with PBS (pH 7.4) containing 3% bovine serum albumin (BSA) (MilliporeSigma, MA, USA) for 2 hours at room temperature followed by a three-time-wash with 200 μL of 0.05% Tween-20-containing PBS (pH 7.4) buffer (PBST). Next, anti-CLL-1 antibody, DAR2-ARC-IgG, and DAR-4-ARC-IgG in PBS buffer (pH 7.4) were added into wells at a gradient of concentrations and let incubated at room temperature for 1 hour. After a three-time-wash by 0.05% PBST buffer (pH 7.4), 80 μL of 1000-fold diluted anti-human kappa light chain antibody with conjugated horse reddish peroxidase (HRP) (Thermo Fisher Scientific, MA, USA) in PBS buffer (pH 7.4) were added and let incubated at room temperature for 1 hour followed by a three-time-wash by 0.05% PBST buffer (pH 7.4). Finally, 80 μL of QuantaBlu fluorogenic substrate (Thermo Fisher Scientific, MA, USA) was added into wells. Fluorescence intensities (excitation at 325 nm; emission at 420 nm) were recorded by a Synergy H1 Plate Reader after a 5-minute incubation at room temperature. The results were analyzed by GraphPad Prism software for calculating the $EC_{50}$ for different antibody constructs binding to the recombinant human CLL-1 extracellular domain.

In Vitro Cytotoxicity of ADCs.

U937 or KG1a cells in RPMI1640 medium (Corning, N.Y., USA) supplemented with 10% FBS (Thermo Fisher Scientific, MA, USA) and 100 μg mL$^{-1}$ penicillin-streptomycin (Thermo Fisher Scientific, MA, USA) at passage 3 were placed into 96-well plates (5,000 cells per well) (Corning, N.Y., USA) in a total volume of 100 μL per well. For the positive control wells, paclitaxel (MilliporeSigma, MA) was added to the final concentration of 5 μM. For the treatment group wells, DAR2-ARC-ADC and DAR4-ARC-ADC were added in a gradient of concentrations. For other control groups wells, anti-CLL-1 antibody, DAR2-ARC-IgG, DAR4-ARC-IgG, or 2'-Cl-araNAD$^+$-MMAF were added in a gradient of concentrations. After a 72-hour incubation in a 37° C. incubator with 5% $CO_2$, 10 μL MTT reagent (Thermo Fisher Scientific, MA) was added into each well and let incubated for 2 hours in a 37° C. incubator with 5% $CO_2$. Then, 100 μL of lysis buffer (20% SDS and 50% dimethylformamide dissolved in water, pH 4.7) was added and let incubated for 1 hour at 37° C. Finally, absorbance at 580 nm was measured with a Synergy H1 plate reader (BioTek, VT, USA). The average readings from the positive control wells were designated as 0% viability, while the average readings from wells containing only cells with culture medium and antibiotics were designated as 100% viability. The data were fitted by the sigmoidal function in GraphPad Prism to calculate $EC_{50}$ values.

Generation of Luciferase-Expressing U937 Cell Line.

HEK293T cells were maintained to achieve 70-95% confluence in DMEM medium (Corning, N.Y., USA) with 10% FBS. The pCDH-FFluc-GFP plasmid was used to transfect HEK293T cells together with packaging plasmids (pRRE, pVSVG, and pREV) with the calcium-phosphate transfection method. The lentivirus was collected and concentrated using filters with the molecular weight cut-off at 100 kDa (Thermo Fisher Scientific, MA, USA). U937 cells (approximately 5×10$^5$ cells) were then loaded on a 24-well plate together with the concentrated lentivirus for centrifugation at 2,200 rpm for 90 minutes. The cells were washed twice into fresh RPMI1640 medium on the next day. After the transduced U937 cells cultured in RPMI1640 medium supplemented with 10% FBS reached a total number of 3 million, cells were harvested by centrifugation at 100×g for 5 minutes and resuspended in DPBS (Corning, N.Y., USA) containing 10% FBS for sorting based on intracellular green fluorescence protein (GFP) intensity on a BD FACSAria Fusion Cell Sorter (CA, USA). Data were analyzed by FACSDiva (CA, USA) and top 5% of U937 cells with the strongest GFP fluorescence intensity were selected for the in vivo study.

Pharmacokinetics of Surrogate ADCs with FITC as the Payload.

Female CD-1 mice (Jackson Laboratory, ME, USA) at age of 6 weeks were randomly grouped into 5 mice per group. Surrogate ADCs with FITC as the payload at a dose of 5 mg kg$^{-1}$ were administered by tail vein intravenous (IV.) injection. Blood samples were collected at various time points throughout the 14-day-long study by tail venipuncture and processed for plasma samples by Multivette 600 μL lithium heparin gel collection tubes (Sarstedt Inc., Germany) per manufacturer's protocol. To detect the presence of intact surrogate ADCs by ELISA, anti-FITC polyclonal antibody (Thermo Fisher Scientific, MA, USA) at 8 mg mL$^{-1}$ in PBS buffer (pH 7.4) was first coated on high-binding ELISA plates (Greiner Bio-One, Austria) at 80 μL per well for overnight at room temperature. After a 3-time-wash by 0.05% PBST buffer (pH 7.4), 100-fold diluted plasma samples in PBS buffer (pH 7.4) were applied into wells and let incubated at room temperature for 2 hours followed by a 3-time-wash by 0.05% PBST buffer (pH 7.4). Next, 80 μL of 1000-fold diluted goat anti-human kappa light chain antibody with HRP (Thermo Fisher Scientific, MA, USA) in PBS buffer (pH 7.4) was added and let incubated for 1 hour at room temperature followed by a 3-time-wash by 0.05% PBST buffer (pH 7.4). Finally, 80 µL of QuantaBlu fluorogenic substrate (Thermo Fisher Scientific, MA) was added. Fluorescence intensity of each well (excitation at 325 nm; emission at 420 nm) was recorded by a Synergy H1 plate reader (BioTek, VT, USA). Standards for different concentrations of surrogate ADCs were prepared by diluting surrogate ADCs into fresh CD-1 mice plasma, and fluorescence signals corresponding to each standard concentration were acquired by the same method mentioned above. Concentrations of surrogate ADCs in plasma samples were calculated based on a standard curve of fluorescence-concentration extrapolated from the standards. Noncompartmental analysis in MatLab SimBiology (MathWorks, MA, USA) was employed to analyze pharmacokinetic parameters of surrogate ADCs.

In Vivo Efficacy Study.

Female NOD. Cg-Prkdc$^{scid}$ Il2rg$^{tm1Wjl}$/SzJ (NSG) mice at age of 6 weeks were purchased from the Jackson Laboratory (ME, USA). Each mouse was inoculated with 1 million luciferase expressing U937 cells in 200 µL DPBS by tail vein I.V. injection. On day 2 post U937 cells implantation, mice were randomized into 5 per group and given 150 mg kg$^{-1}$ of D-luciferin (Syd Labs, MA, USA), followed by imaging using an IVIS Lumina III Imaging System (PerkinElmer, MA, USA) for luminescence generated by luciferase-expressing U937 cells. On days 4, 7, and 10 post U937 cells inoculation, different groups of mice were given one of the following treatment options: (1) 200 µL of DPBS (vehicle only); (2) DAR4-ARC-IgG at 5 mg kg$^{-1}$; (3) DAR2-ARC-ADC at 1 mg kg$^{-1}$; (4) DAR2-ARC-ADC at 5 mg kg$^{-1}$; (5) DAR4-ARC-ADC at 1 mg kg$^{-1}$; (6) DAR4-ARC-ADC at 5 mg kg'. In order to conduct both the interim efficacy analysis (when conditions of control group mice reach the endpoint per IACUC protocol) based on tissue sample analysis by flow cytometry as well as study for survival difference between groups, 2 groups of mice were given treatment option (3), (4), (5) or (6) with one group for interim efficacy analysis while the other group for survival analysis. Since the completion of first IVIS imaging, all live mice were continued to be imaged by IVIS weekly.

When mice in the control group (treatment option (1)) reached the humane endpoint, they were euthanized together with other groups of mice given the treatment option (2)-(6). Blood, spleen, and bone marrow samples were collected from each group, and samples were prepared into single cell suspension with red blood cells lysed by red blood cell lysis buffer (Biolegend, CA, USA) in DPBS containing 2% FBS. Prepared tissue samples were stained with anti-mouse CD34 PE antibody (119308, Biolegend, CA, USA), anti-mouse CD45 Pacific Blue antibody (MCD4528, Thermo Fisher Scientific, MA), anti-human CLL-1 APC antibody (353606, Biolegend, CA, USA), and propidium iodide (Thermo Fisher Scientific, MA). All samples were acquired by a BD LSRFortessa X-20 Cell Analyzer (CA, USA) and analyzed by FACSDiva and FlowJo software. Data for blood samples were first gated based on morphology (FSC-A/SSC-A) for peripheral blood myeloid cell population and then all live cells (propidium iodide-staining negative) populations were analyzed on fluorescence intensities of different antibodies used for staining. Data for spleen and bone marrow samples were first gated based on morphology (FSC-A/SSC-A) to remove non-cell debris, and then all live cells (propidium iodide-staining negative) populations were analyzed on fluorescence intensities of different antibodies used for staining. Gating strategies for all samples were shown in FIGS. 20-23.

For toxicology study, part of the blood samples collected during the interim efficacy analysis study were processed for plasma samples by Multivette 600 µL lithium heparin gel collection tubes (Sarstedt Inc., Germany) per manufacturer's protocol and frozen at −80° C. To measure the concentration of creatine in plasma, thawed plasma samples were first deproteinized by mixing with equal volume of 1.2 M trichloroacetic acid (Oakwood Chemicals, SC, USA) and the supernatants after centrifugation at 10,000×g for 5 minutes were then mixed with twice the volume of working solution, containing 38 mM picric acid premixed with equal volume of 1.2 M NaOH. After incubation at room temperature for 20 minutes, absorbance at 510 nm were recorded by a Synergy H1 plate reader (BioTek, VT, USA). Creatine powder (MilliporeSigma, MA, USA) was prepared into a series of concentrations of standards and utilized in the assay mentioned above for extrapolating a standard curve.

To measure alanine aminotransferase (ALT) activity in plasma, 5 µL of thawed plasma samples were first mixed with 25 µL of substrate solution (0.2 M alanine and 2 mM 2-oxoglutarate in 0.1 M disodium phosphate, pH 7.4) for 1 hour at 37° C. Then, the mixture was added with 25 µL of 1 mM 2,4-dinitrophenylhydrazine in 1 M HCl for 20 minutes at room temperature, followed by addition of 250 µL of 0.5 M NaOH. Absorbance at 510 nm was then measured by a Synergy H1 plate reader (BioTek, VT, USA). Pyruvate powder (MilliporeSigma, MA, USA) was prepared into a series of concentrations of standards and used to replace plasma samples in the above protocol for extrapolating a standard curve.

Statistical Analysis.

Two-tailed unpaired t tests were performed for comparison between two groups. Tumor growth curves of the control and treatment groups were analyzed using two-tailed unpaired t tests. $P<0.05$ was defined as statistically significant. Data are shown as mean±SD. Kaplan-Meier method was adopted to compare survival time between two groups of mice. All statistical analyses were performed using GraphPad Prism.

Example 4. Exemplary Amino Acid and DNA Sequences

CD38 Amino Acid Sequence (SEQ ID NO: 1):

```
MANCEFSPVSGDKPCCRLSRRAQLCLGVSILVLILVVVLAVVV

PRWRQQWSGPGTTKRFPETVLARCVKYTEIHPEMRHVDCQSVW

DAFKGAFISKHPCNITEEDYQPLMKLGTQTVPCNKILLWSRIK

DLAHQFTQVQRDMFTLEDTLLGYLADDLTWCGEFNTSKINYQS

CPDWRKDCSNNPVSVFWKTVSRRFAEAACDVVHVMLNGSRSKI

FDKNSTFGSVEVHNLQPEKVQTLEAWVIHGGREDSRDLCQDPT

IKELESIISKRNIQFSCKNIYRPDKFLQCVKNPEDSSCTSEI.
```
(Glutamate 226 is underlined)

Extracellular Domain of CD38 amino acid sequence (SEQ ID NO: 2):

```
RWRQQWSGPGTTKRFPETVLARCVKYTEIHPEMRHVDCQSVWD

AFKGAFISKHPCNITEEDYQPLMKLGTQTVPCNKILLWSRIKD

LAHQFTQVQRDMFTLEDTLLGYLADDLTWCGEFNTSKINYQSC
```

PDWRKDCSNNPVSVFWKTVSRRFAEAACDVVHVMLNGSRSKIF

DKNSTFGSVEVHNLQPEKVQTLEAWVIHGGREDSRDLCQDPTI

KELESIISKRNIQFSCKNIYRPDKFLQCVKNPEDSSCTSEI (Glutamate 226 is underlined)

Extracellular Domain of CD38 amino acid sequence (with N100D, N164A, N129D and N209D mutations) (SEQ ID NO: 3):

RWRQQWSGPGTTKRFPETVLARCVKYTEIHPEMRHVDCQSVWD

AFKGAFISKHPCDITEEDYQPLMKLGTQTVPCNKILLWSRIKD

LAHQFTQVQRDMFTLEDTLLGYLADDLTWCGEFATSKINYQSC

PDWRKDCSNNPVSVFWKTVSRRFAEAACDVVHVMLDGSRSKIF

DKDSTFGSVEVHNLQPEKVQTLEAWVIHGGREDSRDLCQDPTI

KELESIISKRNIQFSCKNIYRPDKFLQCVKNPEDSSCTSEI hBST1 amino acid sequence (SEQ ID NO: 4):

MAAQGCAASRLLQLLLQLLLLLLLLAAGGARARWRGEGTSAHLRDIFLG

RCAEYRALLSPEQRNKNCTAIWEAFKVALDKDPCSVLPSDYDLFINLSR

HSIPRDKSLFWENSHLLVNSFADNTRRFMPLSDVLYGRVADFLSWCRQK

NDSGLDYQSCPTSEDCENNPVDSFWKRASIQYSKDSSGVIHVMLNGSEP

TGAYPIKGFFADYEIPNLQKEKITRIEIWVMHEIGGPNVESCGEGSMKV

LEKRLKDMGFQYSCINDYRPVKLLQCVDHSTHPDCALKSAAAATQRKAP

SLYTEQRAGLIIPLFLVLASRTQL hCLL-1 amino acid sequence (SEQ ID NO: 5):

MSEEVTYADQFQNSSEMEKIPEIGKFGEKAPPAPSHVWRPAALFLTLLC

LLLLIGLGVLASMFHVTLKIEMKKMNKLQNISEELQRNISLQLMSNMNI

SNKIRNLSTTQTIATKLCRELYSKEQEHKCKPCPRRWIWHKDSCYFLSD

DVQTWQESKMACAAQNASLLKINNKNALEFIKSQSRSYDYWLGLSPEED

STRGMRVDNIINSSAWVIRNAPDLNNMYCGYINRLYVQYYHCTYKKRMI

CEKMANPVQLGSTYFREA anti-hCLL1 antibody light chain amino acid sequence (SEQ ID NO: 6):

ENVLTQSPAIMSASPGEKVTMTCRASSNVISSYVHWYQQRSGASPKLWI

YSTSNLASGVPARFSGSGSGTSYSLTISSVEAEDAATYYCQQYSGYPLT

FGAGTKLELKRAAAAPSVFIFPPSDEQLKSGTASVVCLLNNFYPREAKV

QWKVDNALQSGNSQESVTEQDSKDSTYSLSSTLTLSKADYEKHKVYACE

VTHQGLSSPVTKSFNRGEC anti-hCLL1 antibody light chain DNA sequence (SEQ ID NO: 7):

5'-gagaacgtgctcacccaatcccccgccattatgtccgcctcccag gcgaaaaggtgacaatgacctgcagggccagctccaacgtgatcagctc ttacgtgcactggtaccagcaacggtccggcgcctcccctaagctgtgg atctatagcacaagcaacctggcttccggcgtgcctgcacggttcagcg gaagcggaagcggaacaagttactccctcaccatttctagcgttgaagc cgaggatgccgctacatactattgtcaacagtacagcggatacccctg accttcggagccggcacaaaactggagctcaagagagcagctgcagctc ccagcgtgttcattttcctccctccgacgaacaactgaaaagcggaac agcctctgtcgtttgcctgttgaacaatttctaccctagggaggccaag gtccagtggaaagtggataacgctctgcaaagcggaaattctcaggaaa gcgttaccgaacaggattctaaggactctacatactctctgtctagcac actcacgctgagcaaagcagactacgagaaacacaaagtctacgcctgc gaagtcacccatcagggcctgtcctcgcccgtcacaaagagcttcaaca ggggagagtgt-3' anti-hCLL1 antibody heavy chain sequence (SEQ ID NO: 8):

DIQLQESGPGLVKPSQSLSLTCSVTGYSITSAYYWNWIRQFPGNKLEWM

GYISYDGRNNYNPSLKNRISITRDTSKNQFFLKLNSVTTEDTATYYCAK

EGDYDVGNYYAMDYWGQGTSVTVSSARTKGPSVFPLAPSSKSTSGGTAA

LGCLVKDYFPEPVTVSWNSGALTSGVHTFPAVLQSSGLYSLSSVVTVPS

SSLGTQTYICNVNHKPSNTKVDKKVEPKSCDKTHTCPPCPAPELLGGPS

VFLFPPKPKDTLMISRTPEVTCVVVDVSHEDPEVKFNWYVDGVEVHNAK

TKPREEQYNSTYRVVSVLTVLHQDWLNGKEYKCKVSNKALPAPIEKTIS

KAKGQPREPQVYTLPPSRDELTKNQVSLTCLVKGFYPSDIAVEWESNGQ

PENNYKTTPPVLDSDGSFFLYSKLTVDKSRWQQGNVFSCSVMHEALHNH

YTQKSLSLSPGK anti-hCLL1 antibody heavy chain sequence (SEQ ID NO: 9):

5'-gacatccagctgcaggagagcggccccggcctggtgaagcccagcc agagcctgagcctgacctgcagcgtgaccggctacagcatcaccagcgc ctattactggaactggatccggcagttccccggcaacaagctggagtgg atgggctacatcagctacgacggccggaacaactacaacccaagcctga agaaccggatcagcatcacccgggacaccagcaagaaccagttttttcct gaagctgaacagcgtgaccacagaggacaccgccacctattactgcgcc aaggagggagactacgacgtgggcaactactacgccatggactactggg gccagggcaccagcgtgaccgtgtctagcgcccggaccaagggcccag cgtgttcccctggccccagctctaagagcaccagcggcggaaccgcc gctctgggctgcctggtgaaggactacttccccgagcccgtgaccgtga gctggaacagcggcgccctgaccagcggcgtgcacaccttccccgccgt gctgcagagctctggcctgtacagcctgagcagcgtggttaccgtgccc agttcttccctgggcacccagacctacatctgcaacgtgaaccacaagc

```
ccagcaacaccaaggtggacaagaaagtggaacccaaatcttgcgacaa aactcacacatgcccaccgtgcccagcacctgaactcctgggggaccg tcagtcttcctcttccccccaaaacccaaggacaccctcatgatctcc ggaccctgaggtcacatgcgtggtggtggacgtgagccacgaagaccc tgaggtcaagttcaactggtacgtggacggcgtggaggtgcataatgcc aagacaaagccgcgggaggagcagtacaacagcacgtaccgtgtggtca gcgtcctcaccgtcctgcaccaggactggctgaatggcaaggagtacaa gtgcaaggtctccaacaaagccctcccagcccccatcgagaaaaccatc tccaaagccaaagggcagccccgagaaccacaggtgtacaccctgcccc catcccgggatgagctgaccaagaaccaggtcagcctgacctgcctggt caaaggcttctatcccagcgacatcgccgtggagtgggagagcaatggg cagccggagaacaactacaagaccacgcctcccgtgctggactccgacg gctccttcttcctctacagcaagctcaccgtggacaagagcaggtggca gcaggggaacgtcttctcatgctccgtgatgcatgaggctctgcacaac cactacacgcagaagagcctctccctgtctccgggtaaa-3'
```

Anti-human CLL1 antibody light chain with CD38 fused at C-terminal amino acid sequence (SEQ ID NO: 10):

```
ENVLTQSPAIMSASPGEKVTMTCRASSNVISSYVHWYQQRSGASPKLWI

YSTSNLASGVPARFSGSGSGTSYSLTISSVEAEDAATYYCQQYSGYPLT

FGAGTKLELKRAAAAPSVFIFPPSDEQLKSGTASVVCLLNNFYPREAKV

QWKVDNALQSGNSQESVTEQDSKDSTYSLSSTLTLSKADYEKHKVYACE

VTHQGLSSPVTKSFNRGECGGGGSRWRQQWSGPGTTKRFPETVLARCVK

YTEIHPEMRHVDCQSVWDAFKGAFISKHPCDITEEDYQPLMKLGTQTVP

CNKILLWSRIKDLAHQFTQVQRDMFTLEDTLLGYLADDLTWCGEFATSK

INYQSCPDWRKDCSNNPVSVFWKTVSRRFAEAACDVVHVMLDGSRSKIF

DKDSTFGSVEVHNLQPEKVQTLEAWVIHGGREDSRDLCQDPTIKELESI

ISKRNIQFSCKNIYRPDKFLQCVKNPEDSSCTSEI
```

Anti-human CLL1 antibody light chain with CD38 fused at C-terminal DNA sequence (SEQ ID NO: 11):

```
5'-gagaacgtgctcacccaatccccgccattatgtccgcctcccag gcgaaaggtgacaatgacctgcagggccagctccaacgtgatcagctc ttacgtgcactggtaccagcaacggtccggcgcctcccctaagctgtgg atctatagcacaagcaacctggcttccggcgtgcctgcacggttcagcg gaagcggaagcggaacaagttactccctcaccatttctagcgttgaagc cgaggatgccgctacatactattgtcaacagtacagcggataccccctg accttcggagccggcacaaaactggagctcaagagagcagctgcagctc ccagcgtgttcattttcctccctccgacgaacaactgaaaagcggaac agcctctgtcgtttgcctgttgaacaatttctaccctagggaggccaag gtccagtggaaagtggataacgctctgcaaagcggaaattctcaggaaa
```

```
gcgttaccgaacaggattctaaggactctacatactctctgtctagcac actcacgctgagcaaagcagactacgagaaacacaaagtctacgcctgc gaagtcacccatcagggcctgtcctcgcccgtcacaaagagcttcaaca ggggagagtgtgggggtggcggaagcagatggaggcaacaatggtcagg ccccggaacaacaaaacgatttccagaaacggtcctggcacggtgtgtg aaatatacagaaatacatcccgaaatgcgccatgttgattgccaatctg tatgggatgctttcaaaggcgcattcattagcaagcacccatgcgatat aaccgaggaagactaccagcccctgatgaaacttggcacacaaactgtc ccgtgcaataaaatcctgctgtggtcacggatcaaagaccttgcccatc agtttactcaggttcagcgagatatgttcacacttgaggatacgttgtt ggggtacctcgcagatgatctgacctggtgtggggagttcgccacgtca aagataaattaccaaagttgtcctgattggagaaaagactgcagtaata accctgtctctgttttctggaaaactgtaagccgcaggttcgctgaagc agcctgcgatgtggttcacgttatgctggatggatctcggagcaagatt ttcgataaagattccaccttcggaagtgttgaagtacataacctccaac ccgaaaaagtgcagacacttgaggcatgggttattcatggaggccgaga ggacagccgggacctgtgccaggaccctaccataaaggaacttgagtct attatctcaaagcgaaatattcagttttcctgcaagaatatttatcggc cagataaatttcttcaatgcgtcaaaaacccagaggatagttcatgtac tagtgagatc-3'
```

Anti-human CLL1 antibody heavy chain with CD38 fused at C-terminal amino acid sequence (SEQ ID NO: 12):

```
DIQLQESGPGLVKPSQSLSLTCSVTGYSITSAYYWNWIRQFPGNKLEWM

GYISYDGRNNYNPSLKNRISITRDTSKNQFFLKLNSVTTEDTATYYCAK

EGDYDVGNYYAMDYWGQGTSVTVSSARTKGPSVFPLAPSSKSTSGGTAA

LGCLVKDYFPEPVTVSWNSGALTSGVHTFPAVLQSSGLYSLSSVVTVPS

SSLGTQTYICNVNHKPSNTKVDKKVEPKSCDKTHTCPPCPAPELLGGPS

VFLFPPKPKDTLMISRTPEVTCVVVDVSHEDPEVKFNWYVDGVEVHNAK

TKPREEQYNSTYRVVSVLTVLHQDWLNGKEYKCKVSNKALPAPIEKTIS

KAKGQPREPQVYTLPPSRDELTKNQVSLTCLVKGFYPSDIAVEWESNGQ

PENNYKTTPPVLDSDGSFFLYSKLTVDKSRWQQGNVFSCSVMHEALHNH

YTQKSLSLSPGKGGGGSRWRQQWSGPGTTKRFPETVLARCVKYTEIHPE

MRHVDCQSVWDAFKGAFISKHPCDITEEDYQPLMKLGTQTVPCNKILLW

SRIKDLAHQFTQVQRDMFTLEDTLLGYLADDLTWCGEFATSKINYQSCP

DWRKDCSNNPVSVFWKTVSRRFAEAACDVVHVMLDGSRSKIFDKDSTFG

SVEVHNLQPEKVQTLEAWVIHGGREDSRDLCQDPTIKELESIISKRNIQ

FSCKNIYRPDKFLQCVKNPEDSSCTSEI
```

Anti-human CLL1 antibody heavy chain with CD38 fused at C-terminal DNA sequence (SEQ ID NO: 13):

5'-gacatccagctgcaggagagcggccccggcctggtgaagcccagcc
agagcctgagcctgacctgcagcgtgaccggctacagcatcaccagcgc
ctattactggaactggatccggcagttccccggcaacaagctggagtgg
atgggctacatcagctacgacggccggaacaactacaacccaagcctga
agaaccggatcagcatcacccgggacaccagcaagaaccagttttcct
gaagctgaacagcgtgaccacagaggacaccgccacctattactgcgcc
aaggagggagactacgacgtgggcaactactacgccatggactactggg
gccagggcaccagcgtgaccgtgtctagcgcccgaccaagggcccag
cgtgttccccctggccccagctctaagagcaccagcggcggaaccgcc
gctctgggctgcctggtgaaggactacttccccgagcccgtgaccgtga
gctggaacagcggcgccctgaccagcggcgtgcacaccttcccgccgt
gctgcagagctctggcctgtacagcctgagcagcgtggttaccgtgccc
agttcttccctgggcacccagacctacatctgcaacgtgaaccacaagc
ccagcaacaccaaggtggacaagaaagtggaacccaaatcttgcgacaa
aactcacacatgcccaccgtgcccagcacctgaactcctgggggaccg
tcagtcttcctcttccccccaaaacccaaggacaccctcatgatctccc
ggacccctgaggtcacatgcgtggtggtggacgtgagccacgaagaccc
tgaggtcaagttcaactggtacgtggacggcgtggaggtgcataatgcc
aagacaaagccgcgggaggagcagtacaacagcacgtaccgtgtggtca
gcgtcctcaccgtcctgcaccaggactggctgaatggcaaggagtacaa
gtgcaaggtctccaacaaagccctcccagccccatcgagaaaaccatc
tccaaagccaaagggcagccccgagaaccacaggtgtacaccctgcccc
catcccgggatgagctgaccaagaaccaggtcagcctgacctgcctggt
caaaggcttctatcccagcgacatcgccgtggagtgggagagcaatggg
cagccggagaacaactacaagaccacgcctcccgtgctggactccgacg
gctccttcttcctctacagcaagctcaccgtggacaagagcaggtggca
gcaggggaacgtcttctcatgctccgtgatgcatgaggctctgcacaac
cactacacgcagaagagcctctccctgtctccgggtaaaggggtggcg
gaagcagatggaggcaacaatggtcaggccccggaacaacaaaacgatt
tccagaaacggtcctggcacggtgtgtgaaatatacagaaatacatccc
gaaatgcgccatgttgattgccaatctgtatgggatgctttcaaaggcg
cattcattagcaagcacccatgcgatataaccgaggaagactaccagcc
cctgatgaaacttggcacacaaactgtcccgtgcaataaaatcctgctg
tggtcacggatcaaagaccttgcccatcagtttactcaggttcagcgag
atatgttcacacttgaggatacgttgttggggtacctcgcagatgatct
gacctggtgtggggagttcgccacgtcaaagataaattaccaaagttgt
cctgattggagaaaagactgcagtaataaccctgtctctgttttctgga
aaactgtaagccgcaggttcgctgaagcagcctgcgatggttcacgt
tatgctggatggatctcggagcaagattttcgataaagattccaccttc ggaagtgttgaagtacataacctccaacccgaaaaagtgcagacacttg
aggcatgggttattcatggaggccgagaggacagccgggacctgtgcca
ggaccctaccataaaggaacttgagtctattatctcaaagcgaaatatt
cagttttcctgcaagaatatttatcggccagataaatttcttcaatgcg
tcaaaaacccagaggatagttcatgtactagtgagatc-3'

Herceptin heavy chain amino acid sequence (SEQ ID NO: 14):

EVQLVESGGGLVQPGGSLRLSCAASGFNIKDTYIHWVRQAPGKGLEWVA
RIYPTNGYTRYADSVKGRFTISADTSKNTAYLQMNSLRAEDTAVYYCSR
WGGDGFYAMDYWGQGTLVTVSSASTKGPSVFPLAPSSKSTSGGTAALGC
LVKDYFPEPVTVSWNSGALTSGVHTFPAVLQSSGLYSLSSVVTVPSSSL
GTQTYICNVNHKPSNTKVDKKVEPKSCDKTHTCPPCPAPELLGGPSVFL
FPPKPKDTLMISRTPEVTCVVVDVSHEDPEVKFNWYVDGVEVHNAKTKP
REEQYNSTYRVVSVLTVLHQDWLNGKEYKCKVSNKALPAPIEKTISKAK
GQPREPQVYTLPPSREEMTKNQVSLTCLVKGFYPSDIAVEWESNGQPEN
NYKTTPPVLDSDGSFFLYSKLTVDKSRWQQGNVFSCSVMHEALHNHYTQ
KSLSLSPGK.

Herceptin Light chain amino acid sequence (SEQ ID NO: 15):

DIQMTQSPSSLSASVGDRVTITCRASQDVNTAVAWYQQKPGKAPKLLIY
SASFLYSGVPSRFSGSRSGTDFTLTISSLQPEDFATYYCQQHYTTPPTF
GQGTKVEIKRTVAAPSVFIFPPSDEQLKSGTASVVCLLNNFYPREAKVQ
WKVDNALQSGNSQESVTEQDSKDSTYSLSSTLTLSKADYEKHKVYACEV
THQGLSSPVTKSFNRGEC

N-terminal CD38-Herceptin light chain fusion protein amino acid sequence (SEQ ID NO: 16):

RWRQQWSGPGTTKRFPETVLARCVKYTEIHPEMRHVDCQSVWDAFKGAF
ISKHPCDITEEDYQPLMKLGTQTVPCNKILLWSRIKDLAHQFTQVQRDM
FTLEDTLLGYLADDLTWCGEFATSKINYQSCPDWRKDCSNNPVSVFWKT
VSRRFAEAACDVVHVMLDGSRSKIFDKDSTFGSVEVHNLQPEKVQTLEA
WVIHGGREDSRDLCQDPTIKELESIISKRNIQFSCKNIYRPDKFLQCVK
NPEDSSCTSEIGGGGSDIQMTQSPSSLSASVGDRVTITCRASQDVNTAV
AWYQQKPGKAPKLLIYSASFLYSGVPSRFSGSRSGTDFTLTISSLQPED
FATYYCQQHYTTPPTFGQGTKVEIKRTVAAPSVFIFPPSDEQLKSGTAS
VVCLLNNFYPREAKVQWKVDNALQSGNSQESVTEQDSKDSTYSLSSTLT
LSKADYEKHKVYACEVTHQGLSSPVTKSFNRGEC

C-terminal CD38-Herceptin light chain fusion protein amino acid sequence (SEQ ID NO: 17):

DIQMTQSPSSLSASVGDRVTITCRASQDVNTAVAWYQQKPGKAPKLLIY

SASFLYSGVPSRFSGSRSGTDFTLTISSLQPEDFATYYCQQHYTTPPTF

GQGTKVEIKRTVAAPSVFIFPPSDEQLKSGTASVVCLLNNFYPREAKVQ

WKVDNALQSGNSQESVTEQDSKDSTYSLSSTLTLSKADYEKHKVYACEV

THQGLSSPVTKSFNRGECGGGGSRWRQQWSGPGTTKRFPETVLARCVKY

TEIHPEMRHVDCQSVWDAFKGAFISKHPCDITEEDYQPLMKLGTQTVPC

NKILLWSRIKDLAHQFTQVQRDMFTLEDTLLGYLADDLTWCGEFATSKI

NYQSCPDWRKDCSNNPVSVFWKTVSRRFAEAACDVVHVMLDGSRSKIFD

KDSTFGSVEVHNLQPEKVQTLEAWVIHGGREDSRDLCQDPTIKELESII

SKRNIQFSCKNIYRPDKFLQCVKNPEDSSCTSEI

C-terminal CD38-Herceptin heavy chain fusion protein amino acid sequence (SEQ ID NO: 18):

EVQLVESGGGLVQPGGSLRLSCAASGFNIKDTYIHWVRQAPGKGLEWVA

RIYPTNGYTRYADSVKGRFTISADTSKNTAYLQMNSLRAEDTAVYYCSR

WGGDGFYAMDYWGQGTLVTVSSASTKGPSVFPLAPSSKSTSGGTAALGC

LVKDYFPEPVTVSWNSGALTSGVHTFPAVLQSSGLYSLSSVVTVPSSSL

GTQTYICNVNHKPSNTKVDKKVEPKSCDKTHTCPPCPAPELLGGPSVFL

FPPKPKDTLMISRTPEVTCVVVDVSHEDPEVKFNWYVDGVEVHNAKTKP

REEQYNSTYRVVSVLTVLHQDWLNGKEYKCKVSNKALPAPIEKTISKAK

GQPREPQVYTLPPSRDELTKNQVSLTCLVKGFYPSDIAVEWESNGQPEN

NYKTTPPVLDSDGSFFLYSKLTVDKSRWQQGNVFSCSVMHEALHNHYTQ

KSLSLSPGKGGGGSRWRQQWSGPGTTKRFPETVLARCVKYTEIHPEMRH

VDCQSVWDAFKGAFISKHPCDITEEDYQPLMKLGTQTVPCNKILLWSRI

KDLAHQFTQVQRDMFTLEDTLLGYLADDLTWCGEFATSKINYQSCPDWR

KDCSNNPVSVFWKTVSRRFAEAACDVVHVMLDGSRSKIFDKDSTFGSVE

VHNLQPEKVQTLEAWVIHGGREDSRDLCQDPTIKELESIISKRNIQFSC

KNIYRPDKFLQCVKNPEDSSCTSEI

Example 5. Pharmaceutical Dosage Forms

The following formulations illustrate representative pharmaceutical dosage forms that may be used for the therapeutic or prophylactic administration of a compound or composition generically or specifically described herein (hereinafter referred to as 'Composition X'):

| (i) Tablet 1 | mg/tablet |
|---|---|
| 'Composition X' | 100.0 |
| Lactose | 77.5 |
| Povidone | 15.0 |
| Croscarmellose sodium | 12.0 |
| Microcrystalline cellulose | 92.5 |
| Magnesium stearate | 3.0 |
| | 300.0 |

| (ii) Tablet 2 | mg/tablet |
|---|---|
| 'Composition X' | 20.0 |
| Microcrystalline cellulose | 410.0 |
| Starch | 50.0 |
| Sodium starch glycolate | 15.0 |
| Magnesium stearate | 5.0 |
| | 500.0 |

| (iii) Capsule | mg/capsule |
|---|---|
| 'Composition X' | 10.0 |
| Colloidal silicon dioxide | 1.5 |
| Lactose | 465.5 |
| Pregelatinized starch | 120.0 |
| Magnesium stearate | 3.0 |
| | 600.0 |

| (iv) Injection 1 (1 mg/mL) | mg/mL |
|---|---|
| 'Composition X' (free acid form) | 1.0 |
| Dibasic sodium phosphate | 12.0 |
| Monobasic sodium phosphate | 0.7 |
| Sodium chloride | 4.5 |
| 1.0 N Sodium hydroxide solution (pH adjustment to 7.0-7.5) | q.s. |
| Water for injection | q.s. ad 1 mL |

| (v) Injection 2 (10 mg/mL) | mg/mL |
|---|---|
| 'Composition X' (free acid form) | 10.0 |
| Monobasic sodium phosphate | 0.3 |
| Dibasic sodium phosphate | 1.1 |
| Polyethylene glycol 400 | 200.0 |
| 0.1 N Sodium hydroxide solution (pH adjustment to 7.0-7.5) | q.s. |
| Water for injection | q.s. ad 1 mL |

| (vi) Aerosol | mg/can |
|---|---|
| 'Composition X' | 20 |
| Oleic acid | 10 |
| Trichloromonofluoromethane | 5,000 |
| Dichlorodifluoromethane | 10,000 |
| Dichlorotetrafluoroethane | 5,000 |

| (vii) Topical Gel 1 | wt. % |
|---|---|
| 'Composition X' | 5% |
| Carbomer 934 | 1.25% |
| Triethanolamine (pH adjustment to 5-7) | q.s. |
| Methyl paraben | 0.2% |
| Purified water | q.s. to 100 g |

| (viii) Topical Gel 2 | wt. % |
|---|---|
| 'Composition X' | 5% |
| Methylcellulose | 2% |
| Methyl paraben | 0.2% |
| Propyl paraben | 0.02% |
| Purified water | q.s. to 100 g |

| (ix) Topical Ointment | wt. % |
|---|---|
| 'Composition X' | 5% |
| Propylene glycol | 1% |
| Anhydrous ointment base | 40% |
| Polysorbate 80 | 2% |
| Methyl paraben | 0.2% |
| Purified water | q.s. to 100 g |

| (x) Topical Cream 1 | wt. % |
|---|---|
| 'Composition X' | 5% |
| White bees wax | 10% |
| Liquid paraffin | 30% |
| Benzyl alcohol | 5% |
| Purified water | q.s. to 100 g |

| (xi) Topical Cream 2 | wt. % |
|---|---|
| 'Composition X' | 5% |
| Stearic acid | 10% |
| Glyceryl monostearate | 3% |
| Polyoxyethylene stearyl ether | 3% |
| Sorbitol | 5% |
| Isopropyl palmitate | 2% |
| Methyl Paraben | 0.2% |
| Purified water | q.s. to 100 g |

These formulations may be prepared by conventional procedures well known in the pharmaceutical art. It will be appreciated that the above pharmaceutical compositions may be varied according to well-known pharmaceutical techniques to accommodate differing amounts and types of active ingredient 'Composition X'. Aerosol formulation (vi) may be used in conjunction with a standard, metered dose aerosol dispenser. Additionally, the specific ingredients and proportions are for illustrative purposes. Ingredients may be exchanged for suitable equivalents and proportions may be varied, according to the desired properties of the dosage form of interest.

While specific embodiments have been described above with reference to the disclosed embodiments and examples, such embodiments are only illustrative and do not limit the scope of the invention. Changes and modifications can be made in accordance with ordinary skill in the art without departing from the invention in its broader aspects as defined in the following claims.

All publications, patents, and patent documents are incorporated by reference herein, as though individually incorporated by reference. No limitations inconsistent with this disclosure are to be understood therefrom. The invention has been described with reference to various specific and preferred embodiments and techniques. However, it should be understood that many variations and modifications may be made while remaining within the spirit and scope of the invention.

What is claimed is:

1. An antibody-drug conjugate comprising:
   a fusion protein comprising an antibody covalently linked to an ADP-ribosyl cyclase protein via a peptide linker moiety;
   a 2'-modified araNAD$^+$ analogue or a 2'-modified araNMN analogue; and
   a payload wherein the 2'-modified araNAD$^+$ analogue or the 2'-modified araNMN analogue is conjugated to the payload to form a functionalized payload, and the functionalized payload is conjugated to the ADP-ribosyl cyclase protein.

2. The antibody-drug conjugate of claim 1 wherein the 2'-modified araNAD$^+$ analogue comprises a chemical group at N6 of an ADP moiety of the 2'-modified araNAD$^+$ analogue, or a chemical group at C2 of an ADP moiety of the 2'-modified araNAD$^+$ analogue, wherein the chemical group optionally comprises an alkyl azide, an alkyne, BCN, or DBCO.

3. The antibody-drug conjugate of claim 2 wherein the 2'-modified araNAD$^+$ analogue comprises 2'-X-araNAD$^+$-N$_3$ wherein X is fluorine, chlorine, or bromine.

4. The antibody-drug conjugate of claim 3 wherein the 2'-modified araNAD$^+$ analogue is Formula I, Formula II, Formula III, Formula IV, Formula V, or Formula VI:

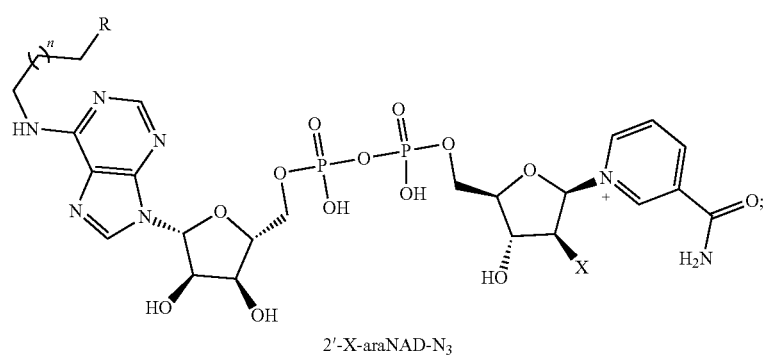

2'-X-araNAD-N$_3$ (I)

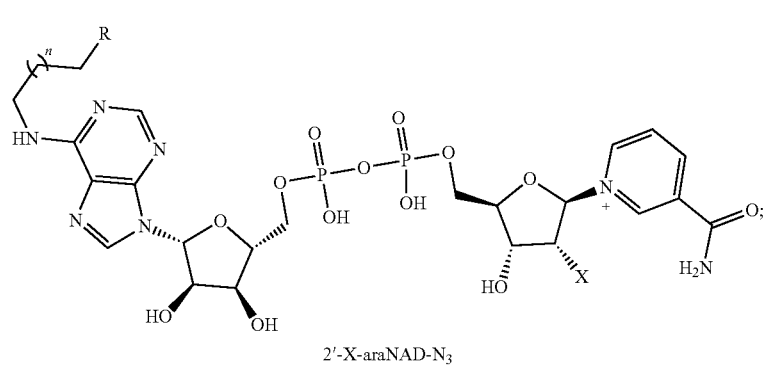

2'-X-araNAD-N$_3$ (II)

-continued
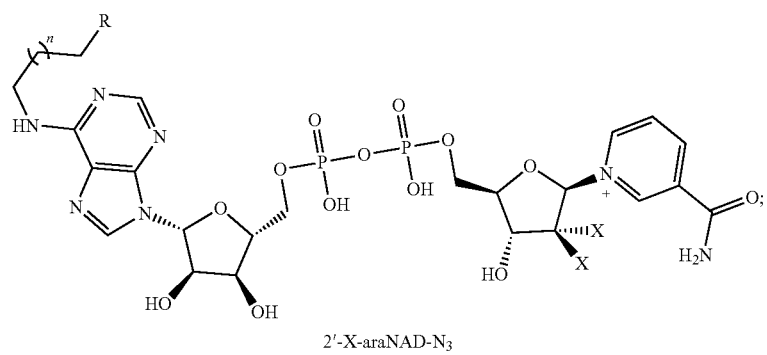
2'-X-araNAD-N₃ (III)
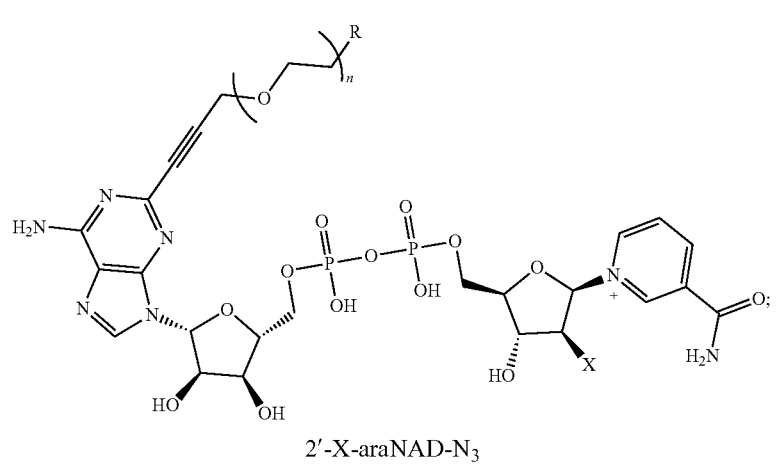
2'-X-araNAD-N₃ (IV)
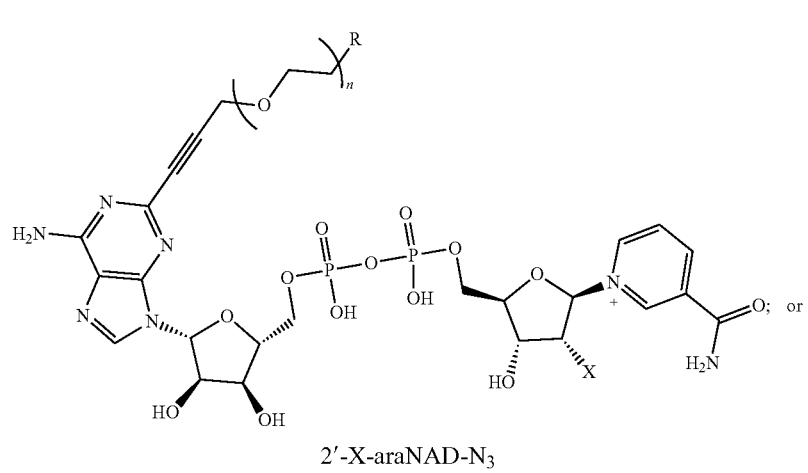
2'-X-araNAD-N₃ (V) or -continued (VI)

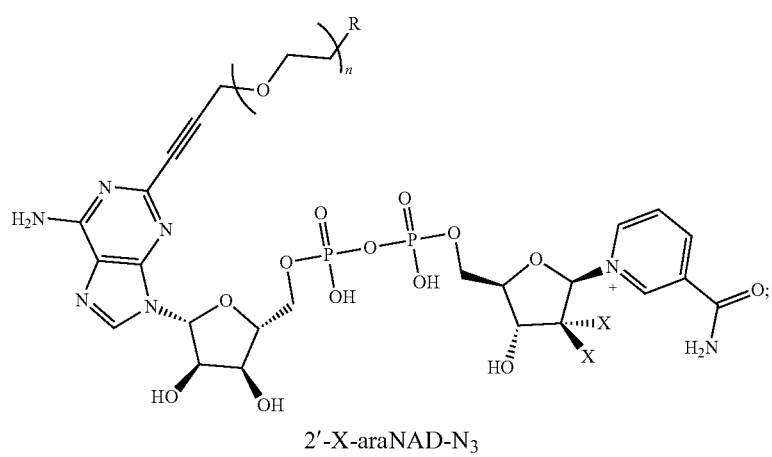

2′-X-araNAD-N₃ wherein R is azido, alkyne, BCN, or DBCO;
X is F, Cl, or Br; and
n is 1-8.

5. The antibody-drug conjugate of claim 1 wherein the 2′-modified araNMN analogue comprises 2′-X-araNMN-PO₄ wherein X is fluorine, chlorine, or bromine.

6. The antibody-drug conjugate of claim 5 wherein the 2′-modified araNMN analogue is a structure selected from:

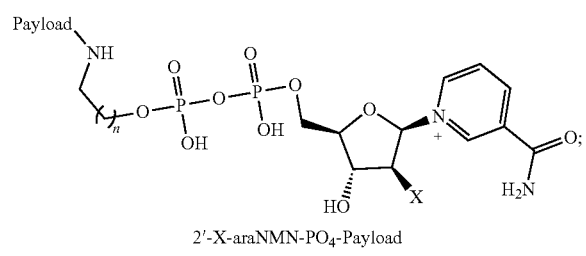

2′-X-araNMN-PO₄-Payload

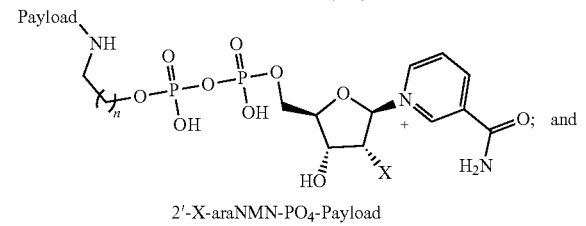

2′-X-araNMN-PO₄-Payload

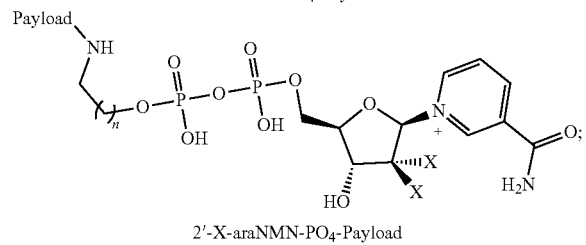

2′-X-araNMN-PO₄-Payload wherein X is F, Cl, or Br; and n is 0-15.

7. The antibody-drug conjugate of claim 1 wherein the payload is a chemotoxic agent or a diagnostic agent.

8. The antibody-drug conjugate of claim 7 wherein the chemotoxic agent is auristatin, calicheamicin, maytansine, duocarmycin, a camptothecin analogue or a benzodiazepine.

9. The antibody-drug conjugate of claim 8 wherein the auristatin is monomethyl auristatin F.

10. The antibody-drug conjugate of claim 7 wherein the diagnostic agent is one or more of a fluorophore, a fluorescent protein, green fluorescence protein (GFP), a resonance energy transfer (RET) donor molecule, a RET acceptor molecule, horseradish peroxidase (HRP), alkaline phosphatase (AP), luciferase, β-galactosidase, chloramphenicol acetyl transferase, glucose oxidase, acetate kinase, xanthine oxidase, and glucose 6-phosphate dehydrogenase.

11. The antibody-drug conjugate of claim 1 wherein the antibody comprises a monoclonal antibody, polyclonal antibody, a single chain Fv, a bispecific antibody, a multispecific antibody, a Fv fragment, a Fab fragment, and a F(ab)₂ fragment.

12. The antibody-drug conjugate of claim 1 wherein the antibody specifically binds to an antigen or epitope of a cancer cell.

13. The antibody-drug conjugate of claim 12 wherein the antigen or epitope is at least a portion of HER2 or a portion of CLL-1.

14. The antibody-drug conjugate of claim 1 wherein the ADP-ribosyl cyclase protein is CD38 or BST1.

15. The antibody-drug conjugate of claim 1 wherein the ADP-ribosyl cyclase protein comprises a full or truncated, wildtype, or mutated catalytic domain of CD38 or BST1, and the payload is conjugated to glutamate 226 of the catalytic domain of CD38 or BST1.

16. The antibody-drug conjugate of claim 1 wherein the ADP-ribosyl cyclase protein is covalently linked to at least one of an N-terminus or a C-terminus of one or more heavy chains or one or more light chains of the antibody.

17. The antibody-drug conjugate of claim 1 wherein the ADP-ribosyl cyclase protein is covalently linked to a C-terminus of a both heavy chains of the antibody or both light chains of the antibody.

18. The antibody-drug conjugate of claim 1 wherein the ADP-ribosyl cyclase protein is covalently linked to a C-terminus of both heavy chains and both light chains of the antibody.

19. The antibody-drug conjugate of claim 1 wherein the peptide linker moiety comprises a (GGS)ₙ peptide (SEQ ID NO: 78), (GGGS)ₙ peptide (SEQ ID NO: 79), or a (GGGGS)ₙ peptide (SEQ ID NO: 80) wherein n is an integer from 1 to 5.

20. The antibody-drug conjugate of claim 1 comprising a drug-to-antibody ratio (DAR) of 2:1 or 4:1.

21. A method of preparing an antibody-drug conjugate comprising:
providing an antibody-peptide linker-ADP-ribosyl cyclase fusion protein;
combining a 2'-modified araNAD⁺ analogue or a 2'-modified araNMN analogue and a payload moiety to form a 2'-modified araNAD⁺ analogue-payload or a 2'-modified araNMN analogue-payload; and
conjugating the antibody-peptide linker-ADP-ribosyl cyclase fusion protein to the 2'-modified araNAD⁺ analogue-payload or the 2'-modified araNMN analogue-payload to form the antibody-drug conjugate.

22. The method of claim 21 wherein the 2'-modified araNAD⁺ analogue is 2'-X-araNAD⁺-N$_3$ wherein X is fluorine, chlorine, or bromine, or wherein the 2'-modified araNMN analogue is 2'-X-araNMN-Pat wherein X is fluorine, chlorine, or bromine.

23. The method of claim 21 wherein the 2'-modified araNAD⁺ analogue-payload is Formula I, Formula II, Formula III, Formula IV, Formula V, or Formula VI:

(I)

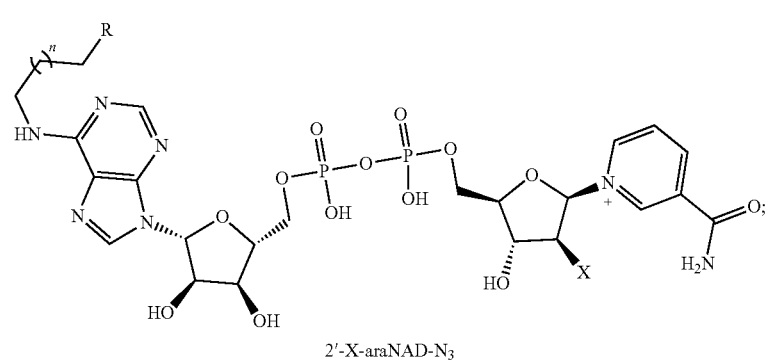

2'-X-araNAD-N$_3$ (II)

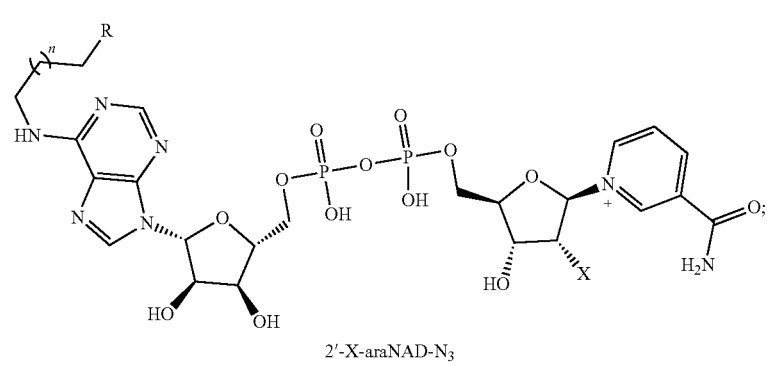

2'-X-araNAD-N$_3$ (III)

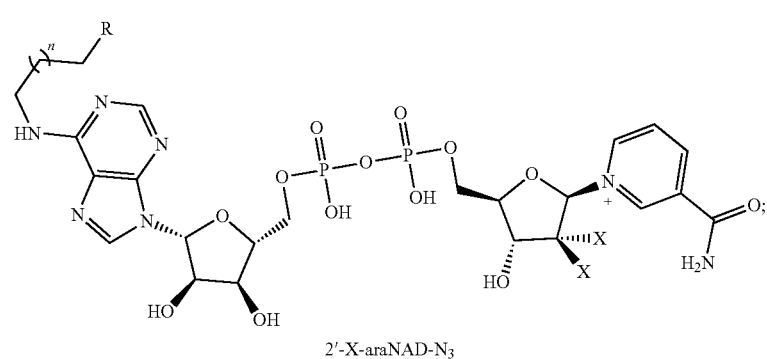

2'-X-araNAD-N$_3$

-continued
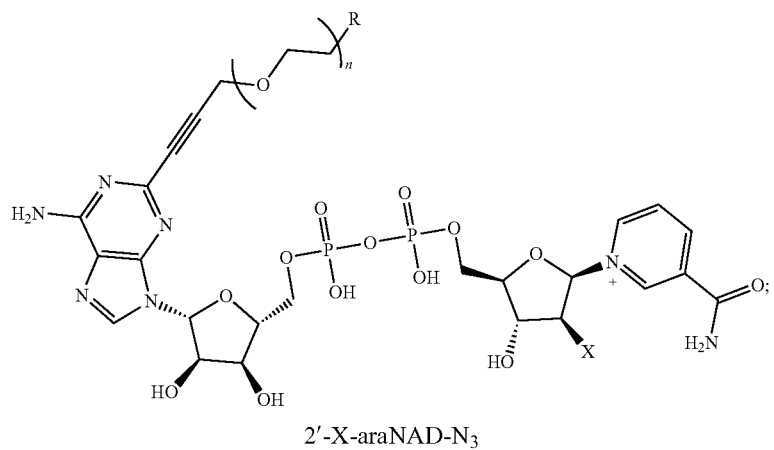
2′-X-araNAD-N₃ (IV)
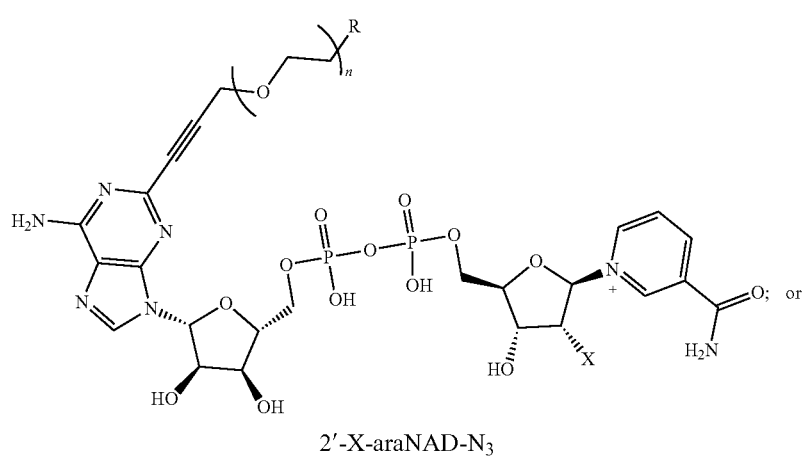
2′-X-araNAD-N₃ (V) or
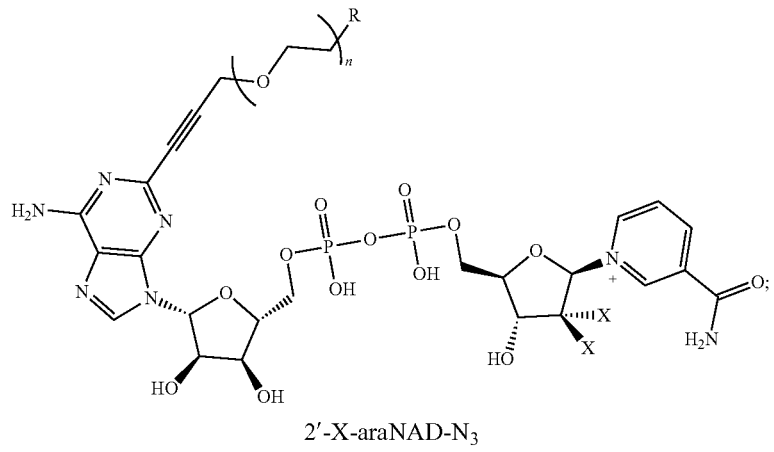
2′-X-araNAD-N₃ (VI)
wherein R is azido, alkyne, BCN, or DBCO;
X is F, Cl, or Br; and
n is 1-8.

24. The method of claim 21 wherein the 2′-modified araNMN analogue-payload is a structure selected from:

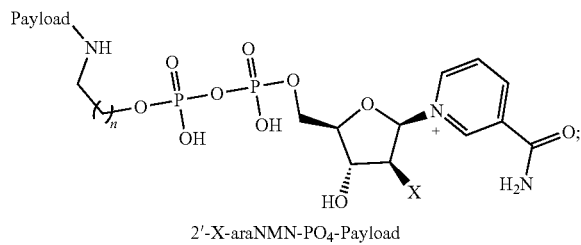

2′-X-araNMN-PO₄-Payload

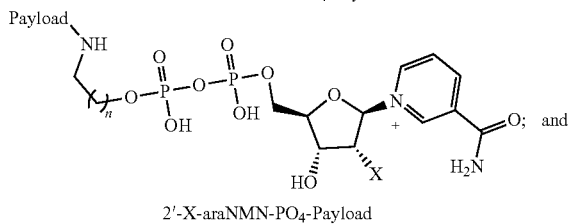

2′-X-araNMN-PO₄-Payload

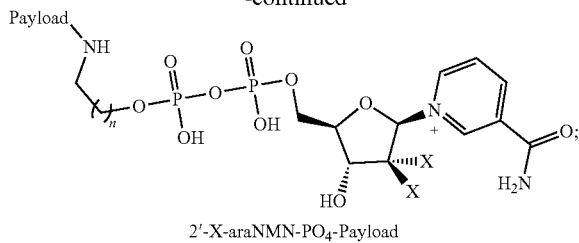

2′-X-araNMN-PO₄-Payload wherein X is F, Cl, or Br; and n is 0-15.

25. A method of treating cancer comprising administering to a subject having cancer or suspected of having cancer a therapeutically effective amount of the antibody-drug conjugate of claim 1, thereby inhibiting the growth of cancer cells or killing cancer cells.

* * * * *

SEQUENCE LISTING

```
<160> NUMBER OF SEQ ID NOS: 81

<210> SEQ ID NO 1
<211> LENGTH: 300
<212> TYPE: PRT
<213> ORGANISM: Homo sapiens

<400> SEQUENCE: 1

Met Ala Asn Cys Glu Phe Ser Pro Val Ser Gly Asp Lys Pro Cys Cys
1               5                   10                  15

Arg Leu Ser Arg Arg Ala Gln Leu Cys Leu Gly Val Ser Ile Leu Val
            20                  25                  30

Leu Ile Leu Val Val Val Leu Ala Val Val Val Pro Arg Trp Arg Gln
        35                  40                  45

Gln Trp Ser Gly Pro Gly Thr Thr Lys Arg Phe Pro Glu Thr Val Leu
    50                  55                  60

Ala Arg Cys Val Lys Tyr Thr Glu Ile His Pro Glu Met Arg His Val
65                  70                  75                  80

Asp Cys Gln Ser Val Trp Asp Ala Phe Lys Gly Ala Phe Ile Ser Lys
                85                  90                  95

His Pro Cys Asn Ile Thr Glu Glu Asp Tyr Gln Pro Leu Met Lys Leu
            100                 105                 110

Gly Thr Gln Thr Val Pro Cys Asn Lys Ile Leu Leu Trp Ser Arg Ile
        115                 120                 125
```

```
Lys Asp Leu Ala His Gln Phe Thr Gln Val Gln Arg Asp Met Phe Thr
130                 135                 140

Leu Glu Asp Thr Leu Leu Gly Tyr Leu Ala Asp Asp Leu Thr Trp Cys
145                 150                 155                 160

Gly Glu Phe Asn Thr Ser Lys Ile Asn Tyr Gln Ser Cys Pro Asp Trp
                165                 170                 175

Arg Lys Asp Cys Ser Asn Asn Pro Val Ser Val Phe Trp Lys Thr Val
            180                 185                 190

Ser Arg Arg Phe Ala Glu Ala Ala Cys Asp Val Val His Val Met Leu
                195                 200                 205

Asn Gly Ser Arg Ser Lys Ile Phe Asp Lys Asn Ser Thr Phe Gly Ser
210                 215                 220

Val Glu Val His Asn Leu Gln Pro Glu Lys Val Gln Thr Leu Glu Ala
225                 230                 235                 240

Trp Val Ile His Gly Gly Arg Glu Asp Ser Arg Asp Leu Cys Gln Asp
                245                 250                 255

Pro Thr Ile Lys Glu Leu Glu Ser Ile Ile Ser Lys Arg Asn Ile Gln
            260                 265                 270

Phe Ser Cys Lys Asn Ile Tyr Arg Pro Asp Lys Phe Leu Gln Cys Val
            275                 280                 285

Lys Asn Pro Glu Asp Ser Ser Cys Thr Ser Glu Ile
290                 295                 300

<210> SEQ ID NO 2
<211> LENGTH: 256
<212> TYPE: PRT
<213> ORGANISM: Homo sapiens

<400> SEQUENCE: 2

Arg Trp Arg Gln Gln Trp Ser Gly Pro Gly Thr Thr Lys Arg Phe Pro
1               5                   10                  15

Glu Thr Val Leu Ala Arg Cys Val Lys Tyr Thr Glu Ile His Pro Glu
                20                  25                  30

Met Arg His Val Asp Cys Gln Ser Val Trp Asp Ala Phe Lys Gly Ala
            35                  40                  45

Phe Ile Ser Lys His Pro Cys Asn Ile Thr Glu Glu Asp Tyr Gln Pro
50                  55                  60

Leu Met Lys Leu Gly Thr Gln Thr Val Pro Cys Asn Lys Ile Leu Leu
65                  70                  75                  80

Trp Ser Arg Ile Lys Asp Leu Ala His Gln Phe Thr Gln Val Gln Arg
                85                  90                  95

Asp Met Phe Thr Leu Glu Asp Thr Leu Leu Gly Tyr Leu Ala Asp Asp
                100                 105                 110

Leu Thr Trp Cys Gly Glu Phe Asn Thr Ser Lys Ile Asn Tyr Gln Ser
            115                 120                 125

Cys Pro Asp Trp Arg Lys Asp Cys Ser Asn Asn Pro Val Ser Val Phe
130                 135                 140

Trp Lys Thr Val Ser Arg Arg Phe Ala Glu Ala Ala Cys Asp Val Val
145                 150                 155                 160

His Val Met Leu Asn Gly Ser Arg Ser Lys Ile Phe Asp Lys Asn Ser
                165                 170                 175

Thr Phe Gly Ser Val Glu Val His Asn Leu Gln Pro Glu Lys Val Gln
            180                 185                 190

Thr Leu Glu Ala Trp Val Ile His Gly Gly Arg Glu Asp Ser Arg Asp
        195                 200                 205
```

Leu Cys Gln Asp Pro Thr Ile Lys Glu Leu Glu Ser Ile Ile Ser Lys
            210                 215                 220

Arg Asn Ile Gln Phe Ser Cys Lys Asn Ile Tyr Arg Pro Asp Lys Phe
225                 230                 235                 240

Leu Gln Cys Val Lys Asn Pro Glu Asp Ser Ser Cys Thr Ser Glu Ile
            245                 250                 255

<210> SEQ ID NO 3
<211> LENGTH: 256
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 3

Arg Trp Arg Gln Gln Trp Ser Gly Pro Gly Thr Thr Lys Arg Phe Pro
1               5                   10                  15

Glu Thr Val Leu Ala Arg Cys Val Lys Tyr Thr Glu Ile His Pro Glu
            20                  25                  30

Met Arg His Val Asp Cys Gln Ser Val Trp Asp Ala Phe Lys Gly Ala
        35                  40                  45

Phe Ile Ser Lys His Pro Cys Asp Ile Thr Glu Glu Asp Tyr Gln Pro
    50                  55                  60

Leu Met Lys Leu Gly Thr Gln Thr Val Pro Cys Asn Lys Ile Leu Leu
65                  70                  75                  80

Trp Ser Arg Ile Lys Asp Leu Ala His Gln Phe Thr Gln Val Gln Arg
                85                  90                  95

Asp Met Phe Thr Leu Glu Asp Thr Leu Leu Gly Tyr Leu Ala Asp Asp
            100                 105                 110

Leu Thr Trp Cys Gly Glu Phe Ala Thr Ser Lys Ile Asn Tyr Gln Ser
        115                 120                 125

Cys Pro Asp Trp Arg Lys Asp Cys Ser Asn Asn Pro Val Ser Val Phe
    130                 135                 140

Trp Lys Thr Val Ser Arg Arg Phe Ala Glu Ala Ala Cys Asp Val Val
145                 150                 155                 160

His Val Met Leu Asp Gly Ser Arg Ser Lys Ile Phe Asp Lys Asp Ser
                165                 170                 175

Thr Phe Gly Ser Val Glu Val His Asn Leu Gln Pro Glu Lys Val Gln
            180                 185                 190

Thr Leu Glu Ala Trp Val Ile His Gly Gly Arg Glu Asp Ser Arg Asp
        195                 200                 205

Leu Cys Gln Asp Pro Thr Ile Lys Glu Leu Glu Ser Ile Ile Ser Lys
    210                 215                 220

Arg Asn Ile Gln Phe Ser Cys Lys Asn Ile Tyr Arg Pro Asp Lys Phe
225                 230                 235                 240

Leu Gln Cys Val Lys Asn Pro Glu Asp Ser Ser Cys Thr Ser Glu Ile
                245                 250                 255

<210> SEQ ID NO 4
<211> LENGTH: 318
<212> TYPE: PRT
<213> ORGANISM: Homo sapiens

<400> SEQUENCE: 4

Met Ala Ala Gln Gly Cys Ala Ala Ser Arg Leu Leu Gln Leu Leu Leu
1               5                   10                  15

Gln Leu Leu Leu Leu Leu Leu Leu Ala Ala Gly Gly Ala Arg Ala
                20                  25                  30

Arg Trp Arg Gly Glu Gly Thr Ser Ala His Leu Arg Asp Ile Phe Leu
            35                  40                  45

Gly Arg Cys Ala Glu Tyr Arg Ala Leu Leu Ser Pro Glu Gln Arg Asn
 50                  55                  60

Lys Asn Cys Thr Ala Ile Trp Glu Ala Phe Lys Val Ala Leu Asp Lys
 65                  70                  75                  80

Asp Pro Cys Ser Val Leu Pro Ser Asp Tyr Asp Leu Phe Ile Asn Leu
                85                  90                  95

Ser Arg His Ser Ile Pro Arg Asp Lys Ser Leu Phe Trp Glu Asn Ser
                100                 105                 110

His Leu Leu Val Asn Ser Phe Ala Asp Asn Thr Arg Arg Phe Met Pro
            115                 120                 125

Leu Ser Asp Val Leu Tyr Gly Arg Val Ala Asp Phe Leu Ser Trp Cys
130                 135                 140

Arg Gln Lys Asn Asp Ser Gly Leu Asp Tyr Gln Ser Cys Pro Thr Ser
145                 150                 155                 160

Glu Asp Cys Glu Asn Asn Pro Val Asp Ser Phe Trp Lys Arg Ala Ser
                165                 170                 175

Ile Gln Tyr Ser Lys Asp Ser Ser Gly Val Ile His Val Met Leu Asn
            180                 185                 190

Gly Ser Glu Pro Thr Gly Ala Tyr Pro Ile Lys Gly Phe Phe Ala Asp
 195                 200                 205

Tyr Glu Ile Pro Asn Leu Gln Lys Glu Lys Ile Thr Arg Ile Glu Ile
210                 215                 220

Trp Val Met His Glu Ile Gly Pro Asn Val Glu Ser Cys Gly Glu
225                 230                 235                 240

Gly Ser Met Lys Val Leu Glu Lys Arg Leu Lys Asp Met Gly Phe Gln
                245                 250                 255

Tyr Ser Cys Ile Asn Asp Tyr Arg Pro Val Lys Leu Leu Gln Cys Val
            260                 265                 270

Asp His Ser Thr His Pro Asp Cys Ala Leu Lys Ser Ala Ala Ala
275                 280                 285

Thr Gln Arg Lys Ala Pro Ser Leu Tyr Thr Glu Gln Arg Ala Gly Leu
            290                 295                 300

Ile Ile Pro Leu Phe Leu Val Leu Ala Ser Arg Thr Gln Leu
305                 310                 315

<210> SEQ ID NO 5
<211> LENGTH: 263
<212> TYPE: PRT
<213> ORGANISM: Homo sapiens

<400> SEQUENCE: 5

Met Ser Glu Glu Val Thr Tyr Ala Asp Gln Phe Gln Asn Ser Ser Glu
1               5                   10                  15

Met Glu Lys Ile Pro Glu Ile Gly Lys Phe Gly Glu Lys Ala Pro Pro
                20                  25                  30

Ala Pro Ser His Val Trp Arg Pro Ala Ala Leu Phe Leu Thr Leu Leu
            35                  40                  45

Cys Leu Leu Leu Leu Ile Gly Leu Gly Val Leu Ala Ser Met Phe His
 50                  55                  60

```
Val Thr Leu Lys Ile Glu Met Lys Lys Met Asn Lys Leu Gln Asn Ile
 65                  70                  75                  80

Ser Glu Glu Leu Gln Arg Asn Ile Ser Leu Gln Leu Met Ser Asn Met
             85                   90                  95

Asn Ile Ser Asn Lys Ile Arg Asn Leu Ser Thr Thr Gln Thr Ile Ala
            100                 105                 110

Thr Lys Leu Cys Arg Glu Leu Tyr Ser Lys Glu Gln Glu His Lys Cys
        115                 120                 125

Lys Pro Cys Pro Arg Arg Trp Ile Trp His Lys Asp Ser Cys Tyr Phe
    130                 135                 140

Leu Ser Asp Asp Val Gln Thr Trp Gln Glu Ser Lys Met Ala Cys Ala
145                 150                 155                 160

Ala Gln Asn Ala Ser Leu Leu Lys Ile Asn Asn Lys Asn Ala Leu Glu
                165                 170                 175

Phe Ile Lys Ser Gln Ser Arg Ser Tyr Asp Tyr Trp Leu Gly Leu Ser
            180                 185                 190

Pro Glu Glu Asp Ser Thr Arg Gly Met Arg Val Asp Asn Ile Ile Asn
        195                 200                 205

Ser Ser Ala Trp Val Ile Arg Asn Ala Pro Asp Leu Asn Asn Met Tyr
210                 215                 220

Cys Gly Tyr Ile Asn Arg Leu Tyr Val Gln Tyr Tyr His Cys Thr Tyr
225                 230                 235                 240

Lys Lys Arg Met Ile Cys Glu Lys Met Ala Asn Pro Val Gln Leu Gly
                245                 250                 255

Ser Thr Tyr Phe Arg Glu Ala
            260

<210> SEQ ID NO 6
<211> LENGTH: 215
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 6

Glu Asn Val Leu Thr Gln Ser Pro Ala Ile Met Ser Ala Ser Pro Gly
 1               5                  10                  15

Glu Lys Val Thr Met Thr Cys Arg Ala Ser Ser Asn Val Ile Ser Ser
             20                  25                  30

Tyr Val His Trp Tyr Gln Gln Arg Ser Gly Ala Ser Pro Lys Leu Trp
         35                  40                  45

Ile Tyr Ser Thr Ser Asn Leu Ala Ser Gly Val Pro Ala Arg Phe Ser
     50                  55                  60

Gly Ser Gly Ser Gly Thr Ser Tyr Ser Leu Thr Ile Ser Ser Val Glu
 65                  70                  75                  80

Ala Glu Asp Ala Ala Thr Tyr Tyr Cys Gln Gln Tyr Ser Gly Tyr Pro
             85                  90                  95

Leu Thr Phe Gly Ala Gly Thr Lys Leu Glu Leu Lys Arg Ala Ala Ala
            100                 105                 110

Ala Pro Ser Val Phe Ile Phe Pro Pro Ser Asp Glu Gln Leu Lys Ser
        115                 120                 125

Gly Thr Ala Ser Val Val Cys Leu Leu Asn Asn Phe Tyr Pro Arg Glu
    130                 135                 140
```

```
Ala Lys Val Gln Trp Lys Val Asp Asn Ala Leu Gln Ser Gly Asn Ser
145                 150                 155                 160

Gln Glu Ser Val Thr Glu Gln Asp Ser Lys Asp Ser Thr Tyr Ser Leu
                165                 170                 175

Ser Ser Thr Leu Thr Leu Ser Lys Ala Asp Tyr Glu Lys His Lys Val
            180                 185                 190

Tyr Ala Cys Glu Val Thr His Gln Gly Leu Ser Ser Pro Val Thr Lys
        195                 200                 205

Ser Phe Asn Arg Gly Glu Cys
    210                 215

<210> SEQ ID NO 7
<211> LENGTH: 645
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 7
gagaacgtgc tcacccaatc ccccgccatt atgtccgcct ccccaggcga aaaggtgaca    60
atgacctgca gggccagctc caacgtgatc agctcttacg tgcactggta ccagcaacgg   120
tccggcgcct ccctaagct gtggatctat agcacaagca acctggcttc cggcgtgcct    180
gcacggttca gcggaagcgg aagcggaaca agttactccc tcaccatttc tagcgttgaa   240
gccgaggatg ccgctacata ctattgtcaa cagtacagcg ataccccct gaccttcgga   300 gccggcacaa aactggagct caagagagca gctgcagctc ccagcgtgtt catttttcct    360
ccctccgacg aacaactgaa aagcggaaca gcctctgtcg tttgcctgtt gaacaatttc   420
taccctaggg aggccaaggt ccagtggaaa gtggataacg ctctgcaaag cggaaattct   480
caggaaagcg ttaccgaaca ggattctaag gactctacat actctctgtc tagcacactc   540
acgctgagca aagcagacta cgagaaacac aaagtctacg cctgcgaagt cacccatcag   600
ggcctgtcct cgcccgtcac aaagagcttc aacaggggag agtgt              645

<210> SEQ ID NO 8
<211> LENGTH: 453
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 8

Asp Ile Gln Leu Gln Glu Ser Gly Pro Gly Leu Val Lys Pro Ser Gln
1               5                   10                  15

Ser Leu Ser Leu Thr Cys Ser Val Thr Gly Tyr Ser Ile Thr Ser Ala
            20                  25                  30

Tyr Tyr Trp Asn Trp Ile Arg Gln Phe Pro Gly Asn Lys Leu Glu Trp
        35                  40                  45

Met Gly Tyr Ile Ser Tyr Asp Gly Arg Asn Asn Tyr Asn Pro Ser Leu
    50                  55                  60

Lys Asn Arg Ile Ser Ile Thr Arg Asp Thr Ser Lys Asn Gln Phe Phe
65                  70                  75                  80

Leu Lys Leu Asn Ser Val Thr Thr Glu Asp Thr Ala Thr Tyr Tyr Cys
                85                  90                  95
```

Ala Lys Glu Gly Asp Tyr Asp Val Gly Asn Tyr Tyr Ala Met Asp Tyr
            100                 105                 110

Trp Gly Gln Gly Thr Ser Val Thr Val Ser Ser Ala Arg Thr Lys Gly
            115                 120                 125

Pro Ser Val Phe Pro Leu Ala Pro Ser Ser Lys Ser Thr Ser Gly Gly
            130                 135                 140

Thr Ala Ala Leu Gly Cys Leu Val Lys Asp Tyr Phe Pro Glu Pro Val
145                 150                 155                 160

Thr Val Ser Trp Asn Ser Gly Ala Leu Thr Ser Gly Val His Thr Phe
                165                 170                 175

Pro Ala Val Leu Gln Ser Ser Gly Leu Tyr Ser Leu Ser Ser Val Val
            180                 185                 190

Thr Val Pro Ser Ser Ser Leu Gly Thr Gln Thr Tyr Ile Cys Asn Val
            195                 200                 205

Asn His Lys Pro Ser Asn Thr Lys Val Asp Lys Lys Val Glu Pro Lys
    210                 215                 220

Ser Cys Asp Lys Thr His Thr Cys Pro Pro Cys Pro Ala Pro Glu Leu
225                 230                 235                 240

Leu Gly Gly Pro Ser Val Phe Leu Phe Pro Pro Lys Pro Lys Asp Thr
                245                 250                 255

Leu Met Ile Ser Arg Thr Pro Glu Val Thr Cys Val Val Val Asp Val
            260                 265                 270

Ser His Glu Asp Pro Glu Val Lys Phe Asn Trp Tyr Val Asp Gly Val
            275                 280                 285

Glu Val His Asn Ala Lys Thr Lys Pro Arg Glu Glu Gln Tyr Asn Ser
            290                 295                 300

Thr Tyr Arg Val Val Ser Val Leu Thr Val Leu His Gln Asp Trp Leu
305                 310                 315                 320

Asn Gly Lys Glu Tyr Lys Cys Lys Val Ser Asn Lys Ala Leu Pro Ala
                325                 330                 335

Pro Ile Glu Lys Thr Ile Ser Lys Ala Lys Gly Gln Pro Arg Glu Pro
            340                 345                 350

Gln Val Tyr Thr Leu Pro Pro Ser Arg Asp Glu Leu Thr Lys Asn Gln
            355                 360                 365

Val Ser Leu Thr Cys Leu Val Lys Gly Phe Tyr Pro Ser Asp Ile Ala
370                 375                 380

Val Glu Trp Glu Ser Asn Gly Gln Pro Glu Asn Asn Tyr Lys Thr Thr
385                 390                 395                 400

Pro Pro Val Leu Asp Ser Asp Gly Ser Phe Phe Leu Tyr Ser Lys Leu
                405                 410                 415

Thr Val Asp Lys Ser Arg Trp Gln Gln Gly Asn Val Phe Ser Cys Ser
            420                 425                 430

Val Met His Glu Ala Leu His Asn His Tyr Thr Gln Lys Ser Leu Ser
            435                 440                 445

Leu Ser Pro Gly Lys
    450

<210> SEQ ID NO 9
<211> LENGTH: 1359
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 9

```
gacatccagc tgcaggagag cggccccggc ctggtgaagc ccagccagag cctgagcctg      60
acctgcagcg tgaccggcta cagcatcacc agcgcctatt actggaactg gatccggcag     120
ttccccggca caagctgga gtggatgggc tacatcagct acgacggccg gaacaactac     180
aacccaagcc tgaagaaccg gatcagcatc acccgggaca ccagcaagaa ccagttttcc    240
ctgaagctga cagcgtgac cacagaggac accgccacct attactgcgc caaggaggga     300
gactacgacg tgggcaacta ctacgccatg gactactggg gccagggcac cagcgtgacc    360
gtgtctagcg ccccggaccaa gggccccagc gtgttccccc tggccccag ctctaagagc    420
accagcggcg gaaccgccgc tctgggctgc ctggtgaagg actacttccc cgagcccgtg   480
accgtgagct ggaacagcgg cgccctgacc agcggcgtgc acaccttccc cgccgtgctg    540
cagagctctg gcctgtacag cctgagcagc gtggttaccg tgcccagttc ttccctgggc    600
acccagacct acatctgcaa cgtgaaccac aagcccagca caccaaggt ggacaagaaa    660
gtggaaccca atcttgcga caaaactcac acatgcccac cgtgcccagc acctgaactc    720
ctgggggac cgtcagtctt cctcttcccc ccaaaaccca aggacaccct catgatctcc    780
cggacccctg aggtcacatg cgtggtggtg acgtgagcc acgaagaccc tgaggtcaag    840
ttcaactggt acgtggacgg cgtggaggtg cataatgcca agacaaagcc gcgggaggag    900
cagtacaaca gcacgtaccg tgtggtcagc gtcctcaccg tcctgcacca ggactggctg    960
aatggcaagg agtacaagtg caaggtctcc aacaaagccc tcccagcccc catcgagaaa    1020
accatctcca agccaaaagg gcagcccga gaaccacagg tgtacaccct gcccccatcc     1080
cgggatgagc tgaccaagaa ccaggtcagc ctgacctgcc tggtcaaagg cttctatccc    1140
agcgacatcg ccgtggagtg ggagagcaat gggcagccgg agaacaacta caagaccacg    1200
cctcccgtgc tggactccga cggctccttc ttcctctaca gcaagctcac cgtggacaag    1260
agcaggtggc agcaggggaa cgtcttctca tgctccgtga tgcatgaggc tctgcacaac    1320
cactacacgc agaagagcct ctccctgtct ccgggtaaa                           1359
```

<210> SEQ ID NO 10
<211> LENGTH: 476
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 10

```
Glu Asn Val Leu Thr Gln Ser Pro Ala Ile Met Ser Ala Ser Pro Gly
1               5                   10                  15

Glu Lys Val Thr Met Thr Cys Arg Ala Ser Ser Asn Val Ile Ser Ser
            20                  25                  30

Tyr Val His Trp Tyr Gln Gln Arg Ser Gly Ala Ser Pro Lys Leu Trp
        35                  40                  45

Ile Tyr Ser Thr Ser Asn Leu Ala Ser Gly Val Pro Ala Arg Phe Ser
    50                  55                  60

Gly Ser Gly Ser Gly Thr Ser Tyr Ser Leu Thr Ile Ser Ser Val Glu
65                  70                  75                  80

Ala Glu Asp Ala Ala Thr Tyr Tyr Cys Gln Gln Tyr Ser Gly Tyr Pro
                85                  90                  95

Leu Thr Phe Gly Ala Gly Thr Lys Leu Glu Leu Lys Arg Ala Ala Ala
            100                 105                 110
```

Ala Pro Ser Val Phe Ile Phe Pro Pro Ser Asp Glu Gln Leu Lys Ser
            115                 120                 125

Gly Thr Ala Ser Val Val Cys Leu Leu Asn Asn Phe Tyr Pro Arg Glu
        130                 135                 140

Ala Lys Val Gln Trp Lys Val Asp Asn Ala Leu Gln Ser Gly Asn Ser
145                 150                 155                 160

Gln Glu Ser Val Thr Glu Gln Asp Ser Lys Asp Ser Thr Tyr Ser Leu
                165                 170                 175

Ser Ser Thr Leu Thr Leu Ser Lys Ala Asp Tyr Glu Lys His Lys Val
            180                 185                 190

Tyr Ala Cys Glu Val Thr His Gln Gly Leu Ser Ser Pro Val Thr Lys
        195                 200                 205

Ser Phe Asn Arg Gly Glu Cys Gly Gly Gly Ser Arg Trp Arg Gln
        210                 215                 220

Gln Trp Ser Gly Pro Gly Thr Thr Lys Arg Phe Pro Glu Thr Val Leu
225                 230                 235                 240

Ala Arg Cys Val Lys Tyr Thr Glu Ile His Pro Glu Met Arg His Val
                245                 250                 255

Asp Cys Gln Ser Val Trp Asp Ala Phe Lys Gly Ala Phe Ile Ser Lys
            260                 265                 270

His Pro Cys Asp Ile Thr Glu Glu Asp Tyr Gln Pro Leu Met Lys Leu
        275                 280                 285

Gly Thr Gln Thr Val Pro Cys Asn Lys Ile Leu Leu Trp Ser Arg Ile
        290                 295                 300

Lys Asp Leu Ala His Gln Phe Thr Gln Val Gln Arg Asp Met Phe Thr
305                 310                 315                 320

Leu Glu Asp Thr Leu Leu Gly Tyr Leu Ala Asp Asp Leu Thr Trp Cys
                325                 330                 335

Gly Glu Phe Ala Thr Ser Lys Ile Asn Tyr Gln Ser Cys Pro Asp Trp
            340                 345                 350

Arg Lys Asp Cys Ser Asn Asn Pro Val Ser Val Phe Trp Lys Thr Val
        355                 360                 365

Ser Arg Arg Phe Ala Glu Ala Ala Cys Asp Val Val His Val Met Leu
        370                 375                 380

Asp Gly Ser Arg Ser Lys Ile Phe Asp Lys Asp Ser Thr Phe Gly Ser
385                 390                 395                 400

Val Glu Val His Asn Leu Gln Pro Glu Lys Val Gln Thr Leu Glu Ala
                405                 410                 415

Trp Val Ile His Gly Gly Arg Glu Asp Ser Arg Asp Leu Cys Gln Asp
            420                 425                 430

Pro Thr Ile Lys Glu Leu Glu Ser Ile Ser Lys Arg Asn Ile Gln
        435                 440                 445

Phe Ser Cys Lys Asn Ile Tyr Arg Pro Asp Lys Phe Leu Gln Cys Val
450                 455                 460

Lys Asn Pro Glu Asp Ser Ser Cys Thr Ser Glu Ile
465                 470                 475

<210> SEQ ID NO 11
<211> LENGTH: 1428
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 11

```
gagaacgtgc tcacccaatc ccccgccatt atgtccgcct ccccaggcga aaaggtgaca      60
atgacctgca gggccagctc caacgtgatc agctcttacg tgcactggta ccagcaacgg     120
tccggcgcct ccactaagct gtggatctat agcacaagca acctggcttc ggcgtgcct     180
gcacggttca gcggaagcgg aagcggaaca agttactccc tcaccatttc tagcgttgaa     240
gccgaggatg ccgctacata ctattgtcaa cagtacagcg atacccct gaccttcgga      300
gccggcacaa aactggagct caagagagca gctgcagctc ccagcgtgtt catttttcct     360
ccctccgacg aacaactgaa agcggaaca gcctctgtcg tttgcctgtt gaacaatttc      420
tacccctaggg aggccaaggt ccagtggaaa gtggataacg ctctgcaaag cggaaattct    480
caggaaagcg ttaccgaaca ggattctaag gactctacat actctctgtc tagcacactc     540
acgctgagca aagcagacta cgagaaacac aaagtctacg cctgcgaagt cacccatcag    600
ggcctgtcct cgcccgtcac aaagagcttc aacaggggag agtgtggggg tggcggaagc    660
agatggaggc aacaatggtc aggccccgga acaacaaaac gatttccaga acggtcctg     720
gcacggtgtg tgaaatatac agaaatacat cccgaaatgc ccatgttga ttgccaatct    780
gtatgggatg ctttcaaagg cgcattcatt agcaagcacc catgcgatat aaccgaggaa    840
gactaccagc ccctgatgaa acttggcaca caaactgtcc cgtgcaataa aatcctgctg    900
tggtcacgga tcaaagacct tgcccatcag tttactcagg ttcagcgaga tatgttcaca    960
cttgaggata cgttgttggg gtacctcgca gatgatctga cctggtgtgg ggagttcgcc   1020
acgtcaaaga taaattacca aagttgtcct gattggagaa aagactgcag taataaccct   1080
gtctctgttt tctggaaaac tgtaagccgc aggttcgctg aagcagcctg cgatgtggtt   1140
cacgttatgc tggatggatc tcggagcaag atttttcgata aagattccac cttcggaagt   1200
gttgaagtac ataacctcca acccgaaaaa gtgcagacac ttgaggcatg ggttattcat   1260
ggaggccgag aggacagccg ggacctgtgc caggaccta ccataaagga acttgagtct    1320
attatctcaa agcgaaatat tcagttttcc tgcaagaata tttatcggcc agataaattt   1380
cttcaatgcg tcaaaaaccc agaggatagt tcatgtacta gtgagatc               1428
```

<210> SEQ ID NO 12
<211> LENGTH: 714
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 12

```
Asp Ile Gln Leu Gln Glu Ser Gly Pro Gly Leu Val Lys Pro Ser Gln
1               5                   10                  15

Ser Leu Ser Leu Thr Cys Ser Val Thr Gly Tyr Ser Ile Thr Ser Ala
            20                  25                  30

Tyr Tyr Trp Asn Trp Ile Arg Gln Phe Pro Gly Asn Lys Leu Glu Trp
        35                  40                  45

Met Gly Tyr Ile Ser Tyr Asp Gly Arg Asn Asn Tyr Asn Pro Ser Leu
    50                  55                  60

Lys Asn Arg Ile Ser Ile Thr Arg Asp Thr Ser Lys Asn Gln Phe Phe
65                  70                  75                  80

Leu Lys Leu Asn Ser Val Thr Thr Glu Asp Thr Ala Thr Tyr Tyr Cys
                85                  90                  95
```

-continued

```
Ala Lys Glu Gly Asp Tyr Asp Val Gly Asn Tyr Tyr Ala Met Asp Tyr
            100                 105                 110

Trp Gly Gln Gly Thr Ser Val Thr Val Ser Ser Ala Arg Thr Lys Gly
        115                 120                 125

Pro Ser Val Phe Pro Leu Ala Pro Ser Ser Lys Ser Thr Ser Gly Gly
    130                 135                 140

Thr Ala Ala Leu Gly Cys Leu Val Lys Asp Tyr Phe Pro Glu Pro Val
145                 150                 155                 160

Thr Val Ser Trp Asn Ser Gly Ala Leu Thr Ser Gly Val His Thr Phe
                165                 170                 175

Pro Ala Val Leu Gln Ser Ser Gly Leu Tyr Ser Leu Ser Ser Val Val
            180                 185                 190

Thr Val Pro Ser Ser Ser Leu Gly Thr Gln Thr Tyr Ile Cys Asn Val
        195                 200                 205

Asn His Lys Pro Ser Asn Thr Lys Val Asp Lys Lys Val Glu Pro Lys
    210                 215                 220

Ser Cys Asp Lys Thr His Thr Cys Pro Pro Cys Pro Ala Pro Glu Leu
225                 230                 235                 240

Leu Gly Gly Pro Ser Val Phe Leu Phe Pro Pro Lys Pro Lys Asp Thr
                245                 250                 255

Leu Met Ile Ser Arg Thr Pro Glu Val Thr Cys Val Val Val Asp Val
            260                 265                 270

Ser His Glu Asp Pro Glu Val Lys Phe Asn Trp Tyr Val Asp Gly Val
        275                 280                 285

Glu Val His Asn Ala Lys Thr Lys Pro Arg Glu Glu Gln Tyr Asn Ser
    290                 295                 300

Thr Tyr Arg Val Val Ser Val Leu Thr Val Leu His Gln Asp Trp Leu
305                 310                 315                 320

Asn Gly Lys Glu Tyr Lys Cys Lys Val Ser Asn Lys Ala Leu Pro Ala
                325                 330                 335

Pro Ile Glu Lys Thr Ile Ser Lys Ala Lys Gly Gln Pro Arg Glu Pro
            340                 345                 350

Gln Val Tyr Thr Leu Pro Pro Ser Arg Asp Glu Leu Thr Lys Asn Gln
        355                 360                 365

Val Ser Leu Thr Cys Leu Val Lys Gly Phe Tyr Pro Ser Asp Ile Ala
    370                 375                 380

Val Glu Trp Glu Ser Asn Gly Gln Pro Glu Asn Asn Tyr Lys Thr Thr
385                 390                 395                 400

Pro Pro Val Leu Asp Ser Asp Gly Ser Phe Phe Leu Tyr Ser Lys Leu
                405                 410                 415

Thr Val Asp Lys Ser Arg Trp Gln Gln Gly Asn Val Phe Ser Cys Ser
            420                 425                 430

Val Met His Glu Ala Leu His Asn His Tyr Thr Gln Lys Ser Leu Ser
        435                 440                 445

Leu Ser Pro Gly Lys Gly Gly Gly Ser Arg Trp Arg Gln Gln Trp
    450                 455                 460

Ser Gly Pro Gly Thr Thr Lys Arg Phe Pro Glu Thr Val Leu Ala Arg
465                 470                 475                 480

Cys Val Lys Tyr Thr Glu Ile His Pro Glu Met Arg His Val Asp Cys
                485                 490                 495

Gln Ser Val Trp Asp Ala Phe Lys Gly Ala Phe Ile Ser Lys His Pro
            500                 505                 510
```

```
Cys Asp Ile Thr Glu Glu Asp Tyr Gln Pro Leu Met Lys Leu Gly Thr
        515                 520                 525

Gln Thr Val Pro Cys Asn Lys Ile Leu Leu Trp Ser Arg Ile Lys Asp
    530                 535                 540

Leu Ala His Gln Phe Thr Gln Val Gln Arg Asp Met Phe Thr Leu Glu
545                 550                 555                 560

Asp Thr Leu Leu Gly Tyr Leu Ala Asp Asp Leu Thr Trp Cys Gly Glu
                565                 570                 575

Phe Ala Thr Ser Lys Ile Asn Tyr Gln Ser Cys Pro Asp Trp Arg Lys
            580                 585                 590

Asp Cys Ser Asn Asn Pro Val Ser Val Phe Trp Lys Thr Val Ser Arg
        595                 600                 605

Arg Phe Ala Glu Ala Ala Cys Asp Val Val His Val Met Leu Asp Gly
    610                 615                 620

Ser Arg Ser Lys Ile Phe Asp Lys Asp Ser Thr Phe Gly Ser Val Glu
625                 630                 635                 640

Val His Asn Leu Gln Pro Glu Lys Val Gln Thr Leu Glu Ala Trp Val
                645                 650                 655

Ile His Gly Gly Arg Glu Asp Ser Arg Asp Leu Cys Gln Asp Pro Thr
            660                 665                 670

Ile Lys Glu Leu Glu Ser Ile Ile Ser Lys Arg Asn Ile Gln Phe Ser
        675                 680                 685

Cys Lys Asn Ile Tyr Arg Pro Asp Lys Phe Leu Gln Cys Val Lys Asn
    690                 695                 700

Pro Glu Asp Ser Ser Cys Thr Ser Glu Ile
705                 710

<210> SEQ ID NO 13
<211> LENGTH: 2142
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 13
gacatccagc tgcaggagag cggccccggc ctggtgaagc ccagccagag cctgagcctg        60
acctgcagcg tgaccggcta cagcatcacc agcgcctatt actggaactg gatccggcag       120
ttccccggca caagctgga gtggatgggc tacatcagct acgacggccg gaacaactac        180
aacccaagcc tgaagaaccg gatcagcatc acccgggaca ccagcaagaa ccagtttttc       240
ctgaagctga acagcgtgac cacagaggac accgccacct attactgcgc caaggaggga       300
gactacgacg tggcaactac tacgccatg gactactggg gccagggcac cagcgtgacc        360
gtgtctagcg cccggaccaa gggccccagc gtgttccccc tggcccccag ctctaagagc       420
accagcggcg gaaccgccgc tctgggctgc ctggtgaagg actacttccc cgagcccgtg       480
accgtgagct ggaacagcgg cgccctgacc agcggcgtgc acaccttccc cgccgtgctg       540
cagagctctg gcctgtacag cctgagcagc gtggttaccg tgcccagttc ttccctgggc       600
acccagacct acatctgcaa cgtgaaccac aagcccagca caccaaggt ggacaagaaa        660 gtggaaccca atcttgcga caaaactcac acatgcccac cgtgcccagc acctgaactc       720
ctggggggac cgtcagtctt cctcttcccc ccaaaaccca aggacaccct catgatctcc       780 cggaccctg aggtcacatg cgtggtggtg gacgtgagcc acgaagaccc tgaggtcaag        840
```

```
ttcaactggt acgtggacgg cgtggaggtg cataatgcca agacaaagcc gcgggaggag    900
cagtacaaca gcacgtaccg tgtggtcagc gtcctcaccg tcctgcacca ggactggctg    960
aatggcaagg agtacaagtg caaggtctcc aacaaagccc tcccagcccc catcgagaaa   1020
accatctcca aagccaaagg gcagccccga gaaccacagg tgtacaccct gcccccatcc   1080
cgggatgagc tgaccaagaa ccaggtcagc ctgacctgcc tggtcaaagg cttctatccc   1140
agcgacatcg ccgtggagtg ggagagcaat gggcagccgg agaacaacta caagaccacg   1200
cctcccgtgc tggactccga cggctccttc ttcctctaca gcaagctcac cgtggacaag   1260
agcaggtggc agcaggggaa cgtcttctca tgctccgtga tgcatgaggc tctgcacaac   1320
cactacacgc agaagagcct ctccctgtct ccgggtaaag ggggtggcgg aagcagatgg   1380
aggcaacaat ggtcaggccc cggaacaaca aaacgatttc agaaacggtt cctggcacgg   1440
tgtgtgaaat atacagaaat acatcccgaa atgcgccatg ttgattgcca atctgtatgg   1500
gatgctttca aggcgcatt cattagcaag cacccatgcg atataaccga ggaagactac   1560
cagcccctga tgaaacttgg cacacaaact gtcccgtgca ataaaatcct gctgtggtca   1620
cggatcaaag accttgccca tcagtttact caggttcagc gagatatgtt cacacttgag   1680
gatacgttgt tggggtacct cgcagatgat ctgacctggt gtggggagtt cgccacgtca   1740
aagataaatt accaaagttg tcctgattgg agaaagact gcagtaataa ccctgtctct   1800
gttttctgga aaactgtaag ccgcaggttc gctgaagcag cctgcgatgt ggttcacgtt   1860
atgctggatg gatctcggag caagatttc gataaagatt ccaccttcgg aagtgttgaa   1920
gtacataacc tccaacccga aaaagtgcag acacttgagg catgggttat tcatggaggc   1980
cgagaggaca gccgggacct gtgccaggac cctaccataa aggaacttga gtctattatc   2040
tcaaagcgaa atattcagtt ttcctgcaag aatatttatc ggccagataa atttcttcaa   2100
tgcgtcaaaa acccagagga tagttcatgt actagtgaga tc                      2142
```

<210> SEQ ID NO 14
<211> LENGTH: 450
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 14

```
Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Asn Ile Lys Asp Thr
            20                  25                  30

Tyr Ile His Trp Val Arg Gln Ala Pro Gly Lys Gly Leu Glu Trp Val
        35                  40                  45

Ala Arg Ile Tyr Pro Thr Asn Gly Tyr Thr Arg Tyr Ala Asp Ser Val
    50                  55                  60

Lys Gly Arg Phe Thr Ile Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Ser Arg Trp Gly Gly Asp Gly Phe Tyr Ala Met Asp Tyr Trp Gly Gln
            100                 105                 110

Gly Thr Leu Val Thr Val Ser Ser Ala Ser Thr Lys Gly Pro Ser Val
        115                 120                 125
```

-continued

```
Phe Pro Leu Ala Pro Ser Ser Lys Ser Thr Ser Gly Gly Thr Ala Ala
    130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Gln Thr Tyr Ile Cys Asn Val Asn His Lys
        195                 200                 205

Pro Ser Asn Thr Lys Val Asp Lys Lys Val Glu Pro Lys Ser Cys Asp
    210                 215                 220

Lys Thr His Thr Cys Pro Pro Cys Pro Ala Pro Glu Leu Leu Gly Gly
225                 230                 235                 240

Pro Ser Val Phe Leu Phe Pro Pro Lys Pro Lys Asp Thr Leu Met Ile
                245                 250                 255

Ser Arg Thr Pro Glu Val Thr Cys Val Val Val Asp Val Ser His Glu
            260                 265                 270

Asp Pro Glu Val Lys Phe Asn Trp Tyr Val Asp Gly Val Glu Val His
        275                 280                 285

Asn Ala Lys Thr Lys Pro Arg Glu Glu Gln Tyr Asn Ser Thr Tyr Arg
    290                 295                 300

Val Val Ser Val Leu Thr Val Leu His Gln Asp Trp Leu Asn Gly Lys
305                 310                 315                 320

Glu Tyr Lys Cys Lys Val Ser Asn Lys Ala Leu Pro Ala Pro Ile Glu
                325                 330                 335

Lys Thr Ile Ser Lys Ala Lys Gly Gln Pro Arg Glu Pro Gln Val Tyr
            340                 345                 350

Thr Leu Pro Pro Ser Arg Glu Glu Met Thr Lys Asn Gln Val Ser Leu
        355                 360                 365

Thr Cys Leu Val Lys Gly Phe Tyr Pro Ser Asp Ile Ala Val Glu Trp
    370                 375                 380

Glu Ser Asn Gly Gln Pro Glu Asn Asn Tyr Lys Thr Thr Pro Pro Val
385                 390                 395                 400

Leu Asp Ser Asp Gly Ser Phe Phe Leu Tyr Ser Lys Leu Thr Val Asp
                405                 410                 415

Lys Ser Arg Trp Gln Gln Gly Asn Val Phe Ser Cys Ser Val Met His
            420                 425                 430

Glu Ala Leu His Asn His Tyr Thr Gln Lys Ser Leu Ser Leu Ser Pro
        435                 440                 445

Gly Lys
    450

<210> SEQ ID NO 15
<211> LENGTH: 214
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 15

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Val Asn Thr Ala
            20                  25                  30
```

Val Ala Trp Tyr Gln Gln Lys Pro Gly Lys Ala Pro Lys Leu Leu Ile
         35                   40                  45

Tyr Ser Ala Ser Phe Leu Tyr Ser Gly Val Pro Ser Arg Phe Ser Gly
         50                  55                  60

Ser Arg Ser Gly Thr Asp Phe Thr Leu Thr Ile Ser Ser Leu Gln Pro
65                  70                  75                  80

Glu Asp Phe Ala Thr Tyr Tyr Cys Gln Gln His Tyr Thr Thr Pro Pro
                 85                  90                  95

Thr Phe Gly Gln Gly Thr Lys Val Glu Ile Lys Arg Thr Val Ala Ala
                100                 105                 110

Pro Ser Val Phe Ile Phe Pro Pro Ser Asp Glu Gln Leu Lys Ser Gly
         115                 120                 125

Thr Ala Ser Val Val Cys Leu Leu Asn Asn Phe Tyr Pro Arg Glu Ala
     130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 16
<211> LENGTH: 475
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 16

Arg Trp Arg Gln Gln Trp Ser Gly Pro Gly Thr Thr Lys Arg Phe Pro
1               5                   10                  15

Glu Thr Val Leu Ala Arg Cys Val Lys Tyr Thr Glu Ile His Pro Glu
            20                  25                  30

Met Arg His Val Asp Cys Gln Ser Val Trp Asp Ala Phe Lys Gly Ala
        35                  40                  45

Phe Ile Ser Lys His Pro Cys Asp Ile Thr Glu Glu Asp Tyr Gln Pro
    50                  55                  60

Leu Met Lys Leu Gly Thr Gln Thr Val Pro Cys Asn Lys Ile Leu Leu
65                  70                  75                  80

Trp Ser Arg Ile Lys Asp Leu Ala His Gln Phe Thr Gln Val Gln Arg
                85                  90                  95

Asp Met Phe Thr Leu Glu Asp Thr Leu Leu Gly Tyr Leu Ala Asp Asp
            100                 105                 110

Leu Thr Trp Cys Gly Glu Phe Ala Thr Ser Lys Ile Asn Tyr Gln Ser
        115                 120                 125

Cys Pro Asp Trp Arg Lys Asp Cys Ser Asn Asn Pro Val Ser Val Phe
    130                 135                 140

Trp Lys Thr Val Ser Arg Arg Phe Ala Glu Ala Ala Cys Asp Val Val
145                 150                 155                 160

His Val Met Leu Asp Gly Ser Arg Ser Lys Ile Phe Asp Lys Asp Ser
                165                 170                 175

Thr Phe Gly Ser Val Glu Val His Asn Leu Gln Pro Glu Lys Val Gln
            180                 185                 190

Thr Leu Glu Ala Trp Val Ile His Gly Gly Arg Glu Asp Ser Arg Asp
        195                 200                 205

Leu Cys Gln Asp Pro Thr Ile Lys Glu Leu Glu Ser Ile Ile Ser Lys
210                 215                 220

Arg Asn Ile Gln Phe Ser Cys Lys Asn Ile Tyr Arg Pro Asp Lys Phe
225                 230                 235                 240

Leu Gln Cys Val Lys Asn Pro Glu Asp Ser Ser Cys Thr Ser Glu Ile
                245                 250                 255

Gly Gly Gly Gly Ser Asp Ile Gln Met Thr Gln Ser Pro Ser Ser Leu
            260                 265                 270

Ser Ala Ser Val Gly Asp Arg Val Thr Ile Thr Cys Arg Ala Ser Gln
        275                 280                 285

Asp Val Asn Thr Ala Val Ala Trp Tyr Gln Gln Lys Pro Gly Lys Ala
290                 295                 300

Pro Lys Leu Leu Ile Tyr Ser Ala Ser Phe Leu Tyr Ser Gly Val Pro
305                 310                 315                 320

Ser Arg Phe Ser Gly Ser Arg Ser Gly Thr Asp Phe Thr Leu Thr Ile
                325                 330                 335

Ser Ser Leu Gln Pro Glu Asp Phe Ala Thr Tyr Tyr Cys Gln Gln His
            340                 345                 350

Tyr Thr Thr Pro Pro Thr Phe Gly Gln Gly Thr Lys Val Glu Ile Lys
        355                 360                 365

Arg Thr Val Ala Ala Pro Ser Val Phe Ile Phe Pro Pro Ser Asp Glu
370                 375                 380

Gln Leu Lys Ser Gly Thr Ala Ser Val Val Cys Leu Leu Asn Asn Phe
385                 390                 395                 400

Tyr Pro Arg Glu Ala Lys Val Gln Trp Lys Val Asp Asn Ala Leu Gln
                405                 410                 415

Ser Gly Asn Ser Gln Glu Ser Val Thr Glu Gln Asp Ser Lys Asp Ser
            420                 425                 430

Thr Tyr Ser Leu Ser Ser Thr Leu Thr Leu Ser Lys Ala Asp Tyr Glu
        435                 440                 445

Lys His Lys Val Tyr Ala Cys Glu Val Thr His Gln Gly Leu Ser Ser
450                 455                 460

Pro Val Thr Lys Ser Phe Asn Arg Gly Glu Cys
465                 470                 475

<210> SEQ ID NO 17
<211> LENGTH: 475
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 17

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Val Asn Thr Ala
            20                  25                  30

-continued

```
Val Ala Trp Tyr Gln Gln Lys Pro Gly Lys Ala Pro Lys Leu Leu Ile
        35                  40                  45

Tyr Ser Ala Ser Phe Leu Tyr Ser Gly Val Pro Ser Arg Phe Ser Gly
        50                  55                  60

Ser Arg Ser Gly Thr Asp Phe Thr Leu Thr Ile Ser Ser Leu Gln Pro
65                  70                  75                  80

Glu Asp Phe Ala Thr Tyr Tyr Cys Gln Gln His Tyr Thr Thr Pro Pro
                    85                  90                  95

Thr Phe Gly Gln Gly Thr Lys Val Glu Ile Lys Arg Thr Val Ala Ala
                100                 105                 110

Pro Ser Val Phe Ile Phe Pro Pro Ser Asp Glu Gln Leu Lys Ser Gly
                115                 120                 125

Thr Ala Ser Val Val Cys Leu Leu Asn Asn Phe Tyr Pro Arg Glu Ala
        130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
                180                 185                 190

Ala Cys Glu Val Thr His Gln Gly Leu Ser Ser Pro Val Thr Lys Ser
        195                 200                 205

Phe Asn Arg Gly Glu Cys Gly Gly Gly Ser Arg Trp Arg Gln Gln
        210                 215                 220

Trp Ser Gly Pro Gly Thr Thr Lys Arg Phe Pro Glu Thr Val Leu Ala
225                 230                 235                 240

Arg Cys Val Lys Tyr Thr Glu Ile His Pro Glu Met Arg His Val Asp
                245                 250                 255

Cys Gln Ser Val Trp Asp Ala Phe Lys Gly Ala Phe Ile Ser Lys His
                260                 265                 270

Pro Cys Asp Ile Thr Glu Glu Asp Tyr Gln Pro Leu Met Lys Leu Gly
        275                 280                 285

Thr Gln Thr Val Pro Cys Asn Lys Ile Leu Leu Trp Ser Arg Ile Lys
        290                 295                 300

Asp Leu Ala His Gln Phe Thr Gln Val Gln Arg Asp Met Phe Thr Leu
305                 310                 315                 320

Glu Asp Thr Leu Leu Gly Tyr Leu Ala Asp Asp Leu Thr Trp Cys Gly
                325                 330                 335

Glu Phe Ala Thr Ser Lys Ile Asn Tyr Gln Ser Cys Pro Asp Trp Arg
                340                 345                 350

Lys Asp Cys Ser Asn Asn Pro Val Ser Val Phe Trp Lys Thr Val Ser
        355                 360                 365

Arg Arg Phe Ala Glu Ala Ala Cys Asp Val Val His Val Met Leu Asp
        370                 375                 380

Gly Ser Arg Ser Lys Ile Phe Asp Lys Asp Ser Thr Phe Gly Ser Val
385                 390                 395                 400

Glu Val His Asn Leu Gln Pro Glu Lys Val Gln Thr Leu Glu Ala Trp
                405                 410                 415

Val Ile His Gly Gly Arg Glu Asp Ser Arg Asp Leu Cys Gln Asp Pro
                420                 425                 430

Thr Ile Lys Glu Leu Glu Ser Ile Ile Ser Lys Arg Asn Ile Gln Phe
        435                 440                 445
```

Ser Cys Lys Asn Ile Tyr Arg Pro Asp Lys Phe Leu Gln Cys Val Lys
    450                 455                 460

Asn Pro Glu Asp Ser Ser Cys Thr Ser Glu Ile
465                 470                 475

<210> SEQ ID NO 18
<211> LENGTH: 711
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 18

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Asn Ile Lys Asp Thr
            20                  25                  30

Tyr Ile His Trp Val Arg Gln Ala Pro Gly Lys Gly Leu Glu Trp Val
        35                  40                  45

Ala Arg Ile Tyr Pro Thr Asn Gly Tyr Thr Arg Tyr Ala Asp Ser Val
    50                  55                  60

Lys Gly Arg Phe Thr Ile Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Ser Arg Trp Gly Gly Asp Gly Phe Tyr Ala Met Asp Tyr Trp Gly Gln
            100                 105                 110

Gly Thr Leu Val Thr Val Ser Ser Ala Ser Thr Lys Gly Pro Ser Val
        115                 120                 125

Phe Pro Leu Ala Pro Ser Ser Lys Ser Thr Ser Gly Gly Thr Ala Ala
    130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Gln Thr Tyr Ile Cys Asn Val Asn His Lys
        195                 200                 205

Pro Ser Asn Thr Lys Val Asp Lys Lys Val Glu Pro Lys Ser Cys Asp
    210                 215                 220

Lys Thr His Thr Cys Pro Pro Cys Pro Ala Pro Glu Leu Leu Gly Gly
225                 230                 235                 240

Pro Ser Val Phe Leu Phe Pro Pro Lys Pro Lys Asp Thr Leu Met Ile
                245                 250                 255

Ser Arg Thr Pro Glu Val Thr Cys Val Val Val Asp Val Ser His Glu
            260                 265                 270

Asp Pro Glu Val Lys Phe Asn Trp Tyr Val Asp Gly Val Glu Val His
        275                 280                 285

Asn Ala Lys Thr Lys Pro Arg Glu Glu Gln Tyr Asn Ser Thr Tyr Arg
    290                 295                 300

Val Val Ser Val Leu Thr Val Leu His Gln Asp Trp Leu Asn Gly Lys
305                 310                 315                 320

Glu Tyr Lys Cys Lys Val Ser Asn Lys Ala Leu Pro Ala Pro Ile Glu
                325                 330                 335

```
Lys Thr Ile Ser Lys Ala Lys Gly Gln Pro Arg Glu Pro Gln Val Tyr
            340                 345                 350

Thr Leu Pro Pro Ser Arg Asp Glu Leu Thr Lys Asn Gln Val Ser Leu
            355                 360                 365

Thr Cys Leu Val Lys Gly Phe Tyr Pro Ser Asp Ile Ala Val Glu Trp
370                 375                 380

Glu Ser Asn Gly Gln Pro Glu Asn Asn Tyr Lys Thr Thr Pro Pro Val
385                 390                 395                 400

Leu Asp Ser Asp Gly Ser Phe Phe Leu Tyr Ser Lys Leu Thr Val Asp
                405                 410                 415

Lys Ser Arg Trp Gln Gln Gly Asn Val Phe Ser Cys Ser Val Met His
            420                 425                 430

Glu Ala Leu His Asn His Tyr Thr Gln Lys Ser Leu Ser Leu Ser Pro
            435                 440                 445

Gly Lys Gly Gly Gly Gly Ser Arg Trp Arg Gln Gln Trp Ser Gly Pro
450                 455                 460

Gly Thr Thr Lys Arg Phe Pro Glu Thr Val Leu Ala Arg Cys Val Lys
465                 470                 475                 480

Tyr Thr Glu Ile His Pro Glu Met Arg His Val Asp Cys Gln Ser Val
                485                 490                 495

Trp Asp Ala Phe Lys Gly Ala Phe Ile Ser Lys His Pro Cys Asp Ile
            500                 505                 510

Thr Glu Glu Asp Tyr Gln Pro Leu Met Lys Leu Gly Thr Gln Thr Val
            515                 520                 525

Pro Cys Asn Lys Ile Leu Leu Trp Ser Arg Ile Lys Asp Leu Ala His
530                 535                 540

Gln Phe Thr Gln Val Gln Arg Asp Met Phe Thr Leu Glu Asp Thr Leu
545                 550                 555                 560

Leu Gly Tyr Leu Ala Asp Asp Leu Thr Trp Cys Gly Glu Phe Ala Thr
                565                 570                 575

Ser Lys Ile Asn Tyr Gln Ser Cys Pro Asp Trp Arg Lys Asp Cys Ser
            580                 585                 590

Asn Asn Pro Val Ser Val Phe Trp Lys Thr Val Ser Arg Arg Phe Ala
            595                 600                 605

Glu Ala Ala Cys Asp Val Val His Val Met Leu Asp Gly Ser Arg Ser
610                 615                 620

Lys Ile Phe Asp Lys Asp Ser Thr Phe Gly Ser Val Glu Val His Asn
625                 630                 635                 640

Leu Gln Pro Glu Lys Val Gln Thr Leu Glu Ala Trp Val Ile His Gly
                645                 650                 655

Gly Arg Glu Asp Ser Arg Asp Leu Cys Gln Asp Pro Thr Ile Lys Glu
            660                 665                 670

Leu Glu Ser Ile Ile Ser Lys Arg Asn Ile Gln Phe Ser Cys Lys Asn
            675                 680                 685

Ile Tyr Arg Pro Asp Lys Phe Leu Gln Cys Val Lys Asn Pro Glu Asp
690                 695                 700

Ser Ser Cys Thr Ser Glu Ile
705                 710

<210> SEQ ID NO 19
<211> LENGTH: 20
<212> TYPE: PRT
<213> ORGANISM: Artificial Sequence
<220> FEATURE:
```

```
<223> OTHER INFORMATION: Description of Artificial Sequence: Synthetic
      peptide
<220> FEATURE:
<221> NAME/KEY: SITE
<222> LOCATION: (1)..(20)
<223> OTHER INFORMATION: This sequence may encompass 1-5 "Gly Gly Gly
      Ser" repeating units

<400> SEQUENCE: 19

Gly Gly Gly Ser Gly Gly Gly Ser Gly Gly Gly Ser Gly Gly Gly Ser
1               5                   10                  15

Gly Gly Gly Ser
            20

<210> SEQ ID NO 20
<211> LENGTH: 25
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: SITE
<222> LOCATION: (1)..(25)
<223> OTHER INFORMATION: This sequence may encompass 1-5 "Gly Gly Gly
      Gly Ser" repeating units

<400> SEQUENCE: 20

Gly Gly Gly Gly Ser Gly Gly Gly Gly Ser Gly Gly Gly Gly Ser Gly
1               5                   10                  15

Gly Gly Gly Ser Gly Gly Gly Gly Ser
            20                  25

<210> SEQ ID NO 21
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 21

Gly Gly Gly Gly Ser
1               5

<210> SEQ ID NO 22
<211> LENGTH: 34
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 22
tcacgaattc gagatggagg caacaatggt cagg                              34

<210> SEQ ID NO 23
<211> LENGTH: 41
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 23
cgccaccccc gatctcacta gtacatgaac tatcctctgg g                      41
```

<210> SEQ ID NO 24
<211> LENGTH: 45
<212> TYPE: DNA
<213> ORGANISM: Artificial Sequence
<220> FEATURE:
<223> OTHER INFORMATION: Description of Artificial Sequence: Synthetic primer

<400> SEQUENCE: 24
tgagatcggg ggtggcggaa gcgacatcca gatgacccag tctcc    45

<210> SEQ ID NO 25
<211> LENGTH: 26
<212> TYPE: DNA
<213> ORGANISM: Artificial Sequence
<220> FEATURE:
<223> OTHER INFORMATION: Description of Artificial Sequence: Synthetic primer

<400> SEQUENCE: 25
cagctagcac ttatcaacac tctccc    26

<210> SEQ ID NO 26
<211> LENGTH: 38
<212> TYPE: DNA
<213> ORGANISM: Artificial Sequence
<220> FEATURE:
<223> OTHER INFORMATION: Description of Artificial Sequence: Synthetic primer

<400> SEQUENCE: 26
gggggtggcg gaagcagatg gaggcaacaa tggtcagg    38

<210> SEQ ID NO 27
<211> LENGTH: 50
<212> TYPE: DNA
<213> ORGANISM: Artificial Sequence
<220> FEATURE:
<223> OTHER INFORMATION: Description of Artificial Sequence: Synthetic primer

<400> SEQUENCE: 27
ccagctagca cttatcagat ctcactagta catgaactat cctctgggtt    50

<210> SEQ ID NO 28
<211> LENGTH: 22
<212> TYPE: DNA
<213> ORGANISM: Artificial Sequence
<220> FEATURE:
<223> OTHER INFORMATION: Description of Artificial Sequence: Synthetic primer

<400> SEQUENCE: 28
cacgaattcg gaggtgcagc tg    22

<210> SEQ ID NO 29
<211> LENGTH: 37
<212> TYPE: DNA
<213> ORGANISM: Artificial Sequence
<220> FEATURE:
<223> OTHER INFORMATION: Description of Artificial Sequence: Synthetic primer

<400> SEQUENCE: 29
gcttccgcca cccccttac ccggagacag ggagagg    37

<210> SEQ ID NO 30

```
<211> LENGTH: 43
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 30
ttcggaagtg ttcaggtaca taacctccaa cccgaaaaag tgc                    43

<210> SEQ ID NO 31
<211> LENGTH: 45
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 31
ggaggttatg tacctgaaca cttccgaagg tggaatcttt atcga                  45

<210> SEQ ID NO 32
<211> LENGTH: 35
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 32
cacgaattcg atcgagatga agaagatgaa caaac                             35

<210> SEQ ID NO 33
<211> LENGTH: 29
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 33
ccagctagca ctcactaatg atgatggtg                                    29

<210> SEQ ID NO 34
<211> LENGTH: 33
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 34
cacgaattcg gagaacgtgc tcacccaatc ccc                               33

<210> SEQ ID NO 35
<211> LENGTH: 45
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 35
ccagctagca cttatcaaca ctctcccctg ttgaagctct ttgtg                  45

<210> SEQ ID NO 36
<211> LENGTH: 32
```

```
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 36
cacgaattcg gacatccagc tgcaggagag cg                              32

<210> SEQ ID NO 37
<211> LENGTH: 44
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 37
cgcaagattt gggttccact ttcttgtcca ccttggtgtt gctg                  44

<210> SEQ ID NO 38
<211> LENGTH: 48
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 38
ggtggacaag aaagtggaac ccaaatcttg cgacaaaact cacacatg              48

<210> SEQ ID NO 39
<211> LENGTH: 40
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 39
ccagctagca cttatcattt acccggagac agggagaggc                      40

<210> SEQ ID NO 40
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 40
gtcacgaatt cggagaacgt gctc                                       24

<210> SEQ ID NO 41
<211> LENGTH: 36
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 41
cgccaccccc acactctccc ctgttgaagc tctttg                          36

<210> SEQ ID NO 42
<211> LENGTH: 24
<212> TYPE: DNA
```

```
<213> ORGANISM: Artificial Sequence
<220> FEATURE:
<223> OTHER INFORMATION: Description of Artificial Sequence: Synthetic
      primer

<400> SEQUENCE: 42
ggagagtgtg ggggtggcgg aagc                                            24

<210> SEQ ID NO 43
<211> LENGTH: 27
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 43
ctggccagct agcacttatc agatctc                                         27

<210> SEQ ID NO 44
<211> LENGTH: 32
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 44
cacgaattcg gacatccagc tgcaggagag cg                                   32

<210> SEQ ID NO 45
<211> LENGTH: 44
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 45
cgcaagattt gggttccact ttcttgtcca ccttggtgtt gctg                      44

<210> SEQ ID NO 46
<211> LENGTH: 48
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 46
ggtggacaag aaagtggaac ccaaatcttg cgacaaaact cacacatg                  48

<210> SEQ ID NO 47
<211> LENGTH: 27
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 47
ctggccagct agcacttatc agatctc                                         27

<210> SEQ ID NO 48
<211> LENGTH: 15
<212> TYPE: PRT
<213> ORGANISM: Artificial Sequence
```

```
<220> FEATURE:
<223> OTHER INFORMATION: Description of Artificial Sequence: Synthetic
      peptide

<400> SEQUENCE: 48

Ser Lys Asn Thr Ala Tyr Leu Gln Met Asn Ser Leu Arg Ala Glu
1               5                   10                  15

<210> SEQ ID NO 49
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 49

Val Ser Val Phe Trp Lys Thr Val Ser Arg Arg Phe Ala Glu Ala
1               5                   10                  15

<210> SEQ ID NO 50
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 50

Asp Val Val His Val Met Leu Asp Gly Ser Arg Ser Lys Ile Phe
1               5                   10                  15

<210> SEQ ID NO 51
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 51

Asn Pro Val Ser Val Phe Trp Lys Thr Val Ser Arg Arg Phe Ala
1               5                   10                  15

<210> SEQ ID NO 52
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 52

Arg Asp Met Phe Thr Leu Glu Asp Thr Leu Leu Gly Tyr Leu Ala
1               5                   10                  15

<210> SEQ ID NO 53
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 53

Gly Gly Ser Leu Arg Leu Ser Cys Ala Ala Ser Gly Phe Asn Ile
1               5                   10                  15
```

<210> SEQ ID NO 54
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 54

Leu Tyr Ser Leu Ser Ser Val Val Thr Val Pro Ser Ser Ser Leu
1               5                   10                  15

<210> SEQ ID NO 55
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 55

Ser Thr Tyr Arg Val Val Ser Val Leu Thr Val Leu His Gln Asp
1               5                   10                  15

<210> SEQ ID NO 56
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 56

Val Lys Phe Asn Trp Tyr Val Asp Gly Val Glu Val His Asn Ala
1               5                   10                  15

<210> SEQ ID NO 57
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 57

Gly Leu Tyr Ser Leu Ser Ser Val Val Thr Val Pro Ser Ser Ser
1               5                   10                  15

<210> SEQ ID NO 58
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 58

Lys Asn Thr Ala Tyr Leu Gln Met Asn Ser Leu Arg Ala Glu Asp
1               5                   10                  15

<210> SEQ ID NO 59
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

```
<400> SEQUENCE: 59

Gly Ser Phe Phe Leu Tyr Ser Lys Leu Thr Val Asp Lys Ser Arg
1               5                   10                  15

<210> SEQ ID NO 60
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 60

Lys Asp Thr Leu Met Ile Ser Arg Thr Pro Glu Val Thr Cys Val
1               5                   10                  15

<210> SEQ ID NO 61
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 61

Asn Asn Pro Val Ser Val Phe Trp Lys Thr Val Ser Arg Arg Phe
1               5                   10                  15

<210> SEQ ID NO 62
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 62

Cys Asn Lys Ile Leu Leu Trp Ser Arg Ile Lys Asp Leu Ala His
1               5                   10                  15

<210> SEQ ID NO 63
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 63

Asn Ser Thr Tyr Arg Val Val Ser Val Leu Thr Val Leu His Gln
1               5                   10                  15

<210> SEQ ID NO 64
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 64

Asn Lys Ile Leu Leu Trp Ser Arg Ile Lys Asp Leu Ala His Gln
1               5                   10                  15

<210> SEQ ID NO 65
<211> LENGTH: 15
<212> TYPE: PRT
```

```
<213> ORGANISM: Artificial Sequence
<220> FEATURE:
<223> OTHER INFORMATION: Description of Artificial Sequence: Synthetic
      peptide

<400> SEQUENCE: 65

Gln Ser Val Trp Asp Ala Phe Lys Gly Ala Phe Ile Ser Lys His
1               5                   10                  15

<210> SEQ ID NO 66
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 66

Val Phe Trp Lys Thr Val Ser Arg Arg Phe Ala Glu Ala Ala Cys
1               5                   10                  15

<210> SEQ ID NO 67
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 67

Ser Lys Ser Thr Ser Gly Gly Thr Ala Ala Leu Gly Cys Leu Val
1               5                   10                  15

<210> SEQ ID NO 68
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 68

Leu Val Glu Ser Gly Gly Gly Leu Val Gln Pro Gly Gly Ser Leu
1               5                   10                  15

<210> SEQ ID NO 69
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 69

Thr Val Ser Trp Asn Ser Gly Ala Leu Thr Ser Gly Val His Thr
1               5                   10                  15

<210> SEQ ID NO 70
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 70

Ser Trp Asn Ser Gly Ala Leu Thr Ser Gly Val His Thr Phe Pro
1               5                   10                  15
```

<210> SEQ ID NO 71
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 71

Gly Val His Thr Phe Pro Ala Val Leu Gln Ser Ser Gly Leu Tyr
1               5                   10                  15

<210> SEQ ID NO 72
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 72

Val Lys Gly Phe Tyr Pro Ser Asp Ile Ala Val Glu Trp Glu Ser
1               5                   10                  15

<210> SEQ ID NO 73
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 73

Leu Glu Asp Thr Leu Leu Gly Tyr Leu Ala Asp Asp Leu Thr Trp
1               5                   10                  15

<210> SEQ ID NO 74
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 74

Pro Glu Val Lys Phe Asn Trp Tyr Val Asp Gly Val Glu Val His
1               5                   10                  15

<210> SEQ ID NO 75
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 75

Ser Val Phe Trp Lys Thr Val Ser Arg Arg Phe Ala Glu Ala Ala
1               5                   10                  15

<210> SEQ ID NO 76
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

```
<400> SEQUENCE: 76

Pro Val Ser Val Phe Trp Lys Thr Val Ser Arg Arg Phe Ala Glu
1               5                   10                  15

<210> SEQ ID NO 77
<211> LENGTH: 6
<212> TYPE: PRT
<213> ORGANISM: Artificial Sequence
<220> FEATURE:
<223> OTHER INFORMATION: Description of Artificial Sequence: Synthetic
      6xHis tag

<400> SEQUENCE: 77

His His His His His His
1               5

<210> SEQ ID NO 78
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: SITE
<222> LOCATION: (1)..(15)
<223> OTHER INFORMATION: This sequence may encompass 0-5 "Gly Gly Ser"
      repeating units

<400> SEQUENCE: 78

Gly Gly Ser Gly Gly Ser Gly Gly Ser Gly Gly Ser Gly Gly Ser
1               5                   10                  15

<210> SEQ ID NO 79
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: SITE
<222> LOCATION: (1)..(20)
<223> OTHER INFORMATION: This sequence may encompass 0-5 "Gly Gly Gly
      Ser" repeating units

<400> SEQUENCE: 79

Gly Gly Gly Ser Gly Gly Gly Ser Gly Gly Gly Ser Gly Gly Gly Ser
1               5                   10                  15

Gly Gly Gly Ser
            20

<210> SEQ ID NO 80
<211> LENGTH: 25
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: SITE
<222> LOCATION: (1)..(25)
<223> OTHER INFORMATION: This sequence may encompass 0-5 "Gly Gly Gly
      Gly Ser" repeating units

<400> SEQUENCE: 80

Gly Gly Gly Gly Ser Gly Gly Gly Gly Ser Gly Gly Gly Gly Ser Gly
1               5                   10                  15
```

```
Gly Gly Gly Ser Gly Gly Gly Gly Ser
            20                  25

<210> SEQ ID NO 81
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 81

Asp Ser Thr Phe Gly Ser Val Glu Val His Asn Leu Gln Pro Glu Lys
1               5                   10                  15
```